US012643858B2

(12) United States Patent
Odingo et al.

(10) Patent No.: US 12,643,858 B2
(45) Date of Patent: Jun. 2, 2026

(54) HSD17B13 INHIBITORS AND USES THEREOF

(71) Applicant: Inipharm, Inc., Bellevue, WA (US)

(72) Inventors: Joshua Odingo, Bothell, WA (US); Heather Kay Webb Hsu, Seattle, WA (US); Vincent Florio, Seattle, WA (US); Subramanyam Janardhan Tantry, Karnataka (IN); Rajendra Kristam, Karnataka (IN); Athisayamani Jeyaraj Duraiswamy, Karnataka (IN)

(73) Assignee: INIPHARM, INC., Bellevue, WA (US)

( * ) Notice: Subject to any disclaimer, the term of this patent is extended or adjusted under 35 U.S.C. 154(b) by 754 days.

(21) Appl. No.: 17/917,096

(22) PCT Filed: Apr. 16, 2021

(86) PCT No.: PCT/US2021/027691

§ 371 (c)(1),
(2) Date: Oct. 5, 2022

(87) PCT Pub. No.: WO2021/211974

PCT Pub. Date: Oct. 21, 2021

(65) Prior Publication Data

US 2023/0150940 A1 May 18, 2023

(30) Foreign Application Priority Data

Apr. 18, 2020 (IN) ............................. 202011016737

(51) Int. Cl.

| | |
|---|---|
| ***C07C 255/54*** | (2006.01) |
| ***C07C 255/59*** | (2006.01) |
| ***C07D 213/64*** | (2006.01) |
| ***C07D 213/643*** | (2006.01) |
| ***C07D 213/647*** | (2006.01) |
| ***C07D 213/70*** | (2006.01) |
| ***C07D 213/74*** | (2006.01) |
| ***C07D 213/82*** | (2006.01) |
| ***C07D 213/84*** | (2006.01) |
| ***C07D 213/85*** | (2006.01) |
| ***C07D 239/34*** | (2006.01) |
| ***C07D 401/04*** | (2006.01) |
| ***C07D 401/12*** | (2006.01) |
| ***C07D 405/04*** | (2006.01) |
| ***C07D 409/04*** | (2006.01) |
| ***C07D 413/04*** | (2006.01) |
| ***C07D 417/04*** | (2006.01) |

(52) U.S. Cl.

CPC .......... *C07D 213/64* (2013.01); *C07C 255/54* (2013.01); *C07C 255/59* (2013.01); *C07D 213/643* (2013.01); *C07D 213/647* (2013.01); *C07D 213/70* (2013.01); *C07D 213/74* (2013.01); *C07D 213/82* (2013.01); *C07D 213/84* (2013.01); *C07D 213/85* (2013.01); *C07D 239/34* (2013.01); *C07D 401/04* (2013.01); *C07D 401/12* (2013.01); *C07D 405/04* (2013.01); *C07D 409/04* (2013.01); *C07D 413/04* (2013.01); *C07D 417/04* (2013.01)

(58) Field of Classification Search

CPC .............. C07D 213/64; C07D 213/643; C07D 213/647; C07D 213/70; C07D 213/74; C07D 213/82; C07D 213/84; C07D 213/85; C07D 239/34; C07D 401/04; C07D 401/12; C07D 405/04; C07D 409/04; C07D 413/04; C07D 417/04; C07D 413/10; C07D 413/12; C07D 417/10; C07D 417/12; C07C 255/54; C07C 255/59

See application file for complete search history.

(56) References Cited

U.S. PATENT DOCUMENTS

| | | | | |
|---|---|---|---|---|
| 6,716,851 | B2 * | 4/2004 | Cai ...................... | C07D 403/04 514/273 |
| 2015/0279654 | A1 | 10/2015 | Kato et al. | |
| 2017/0281622 | A1 * | 10/2017 | Kaloun ................ | A61K 31/165 |

FOREIGN PATENT DOCUMENTS

| | | | | |
|---|---|---|---|---|
| WO | WO-2019222816 | A1 * | 11/2019 | .............. A61P 25/08 |
| WO | WO-2021003295 | A1 | 1/2021 | |
| WO | WO-2021211974 | A1 | 10/2021 | |

OTHER PUBLICATIONS

Chemical Abstracts Registry No. 438249-13-9, indexed in the Registry file on STN CAS Online Jul. 11, 2002. (Year: 2002).*
Braun et al., Structure-based design and profiling of novel 17β-HSD14 inhibitors. Eur J Med Chem. 155:61-76 (2018).
Dahlgren et al., Virtual screening and optimization yield low-nanomolar inhibitors of the tautomerase activity of Plasmodium falciparum macrophage migration inhibitory factor. J Med Chem. 55(22):10148-10159 (2012).
PCT/US2021/027691 International Search Report and Written Opinion dated Sep. 27, 2021.

* cited by examiner

*Primary Examiner* — Laura L Stockton
(74) *Attorney, Agent, or Firm* — WILSON SONSINI GOODRICH & ROSATI

(57) ABSTRACT

Described herein are HSD17B13 inhibitors and pharmaceutical compositions comprising said inhibitors. The subject compounds and compositions are useful for the treatment of liver disease, metabolic disease, or cardiovascular disease, such as NAFLD or NASH, or drug induced liver injury (DILI).

18 Claims, No Drawings

HSD17B13 INHIBITORS AND USES THEREOF

CROSS-REFERENCE

This application is a U.S. National Phase Application of International Application No. PCT/US2021/027691 filed Apr. 16, 2021 which claims the benefit of Indian Application No. 202011016737 filed Apr. 18, 2020 each of which are hereby incorporated by reference in their entirety.

BACKGROUND OF THE INVENTION

Nonalcoholic fatty liver diseases (NAFLDs) including NASH (nonalcoholic steatohepatitis) are considered to be hepatic manifestations of the metabolic syndrome and are characterized by the accumulation of triglycerides in the liver of patients without a history of excessive alcohol consumption. The majority of patients with NAFLD are obese or morbidly obese and have accompanying insulin resistance. The incidence of NAFLD/NASH has been rapidly increasing worldwide consistent with the increased prevalence of obesity, and it is currently the most common chronic liver disease.

NAFLD is classified into simple steatosis, in which only hepatic steatosis is observed, and NASH, in which intralobular inflammation and ballooning degeneration of hepatocytes is observed along with hepatic steatosis. The proportion of patients with NAFLD who have NASH is still not clear but might range from 20-40%. NASH is a progressive disease and may lead to liver cirrhosis and hepatocellular carcinoma. Twenty percent of NASH patients are reported to develop cirrhosis, and 30-40% of patients with NASH cirrhosis experience liver-related death. Recently, NASH has become the third most common indication for liver transplantation in the United States. Currently, the principal treatment for NAFLD/NASH is lifestyle modification by diet and exercise. However, pharmacological therapy is indispensable because obese patients with NAFLD often have difficulty maintaining improved lifestyles.

17β-Hydroxysteroid dehydrogenases (HSD17Bs) comprise a large family of 15 members that are mainly involved in sex hormone metabolism. Some HSD17Bs enzymes also play key roles in cholesterol and fatty acid metabolism. A recent study showed that hydroxysteroid 17β-dehydrogenase 13 (HSD17B13), an enzyme with unknown biological function, is a novel liver-specific lipid droplet (LD)-associated protein in mouse and humans. HSD17B13 expression is markedly upregulated in patients and mice with non-alcoholic fatty liver disease (NAFLD). Hepatic overexpression of HSD17B13 promotes lipid accumulation in the liver. HSD17B13 could also have potential as a biomarker of chronic liver disease, such as alcoholic liver disease (ALD), non-alcoholic fatty liver disease (NAFLD) (for example: steatosis, nonalcoholic steatohepatitis (NASH), NASH-fibrosis, or cirrhosis), steatohepatitis, and liver cancer.

SUMMARY OF THE INVENTION

Provided herein are methods, compounds, and compositions useful for reducing expression or activity of HSD17B13 in a subject in need thereof. Also, provided herein are methods, compounds, and compositions comprising HSD17B13 specific inhibitors, which can be useful in reducing the morbidity of HSD17B13-related diseases or conditions in a subject in need thereof. Such methods, compounds, and compositions can be useful, for example, to treat, prevent, delay or ameliorate liver disease, metabolic disease, or cardiovascular disease.

Disclosed herein are compounds of Formula (I), or a pharmaceutically acceptable salt, solvate, or stereoisomer thereof:

(I)

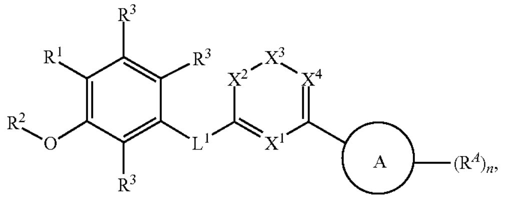

wherein:

$R^1$ is halogen;

$R^2$ is hydrogen, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$C(═O)$OR^b$, cycloalkyl, heterocycloalkyl, aryl, or heteroaryl;

each $R^3$ is independently hydrogen, deuterium, halogen, —CN, —OH, —$OR^a$, —SH, —$SR^a$, —S(═O)$R^a$, —S(═O)$_2R^a$, —$NO_2$, —$NR^cR^d$, —NHS(═O)$_2R^a$, —S(═O)$_2NR^cR^d$, —C(═O)$R^a$, —OC(═O)$R^a$, —C(═O)$OR^b$, —OC(═O)$OR^b$, —C(═O)$NR^cR^d$, —OC(═O)$NR^cR^d$, —$NR^b$C(═O)$NR^cR^d$, —$NR^b$C(═O)$R^a$, —$NR^b$C(═O)$OR^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$C(═O)$OR^b$, cycloalkyl, heterocycloalkyl, aryl, or heteroaryl;

$L^1$ is —O—, —S—, —S(═O)—, —S(═O)$_2$—, or —$NR^{L1}$—;

$R^{L1}$ is hydrogen, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$C(═O)$OR^b$, cycloalkyl, heterocycloalkyl, aryl, or heteroaryl;

$X^1$ is N or C—$R^{X1}$;

$R^{X1}$ is deuterium, halogen, —CN, —OH, —$OR^a$, —SH, —$SR^a$, —S(═O)$R^a$, —S(═O)$_2R^a$, —$NO_2$, —$NR^cR^d$, —NHS(═O)$_2R^a$, —S(═O)$_2NR^cR^d$, —C(═O)$R^a$, —OC(═O)$R^a$, —C(═O)$OR^b$, —OC(═O)$OR^b$, —C(═O)$NR^cR^d$, —OC(═O)$NR^cR^d$, —$NR^b$C(═O)$NR^cR^d$, —$NR^b$C(═O)$R^a$, —$NR^b$C(═O)$OR^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$(═O)$OR^b$, cycloalkyl, heterocycloalkyl, aryl, or heteroaryl;

$X^2$ is N or C—$R^{X2}$;

$R^{X2}$ is hydrogen, deuterium, halogen, —CN, —OH, —$OR^a$, —SH, —$SR^a$, —S(═O)$R^a$, —S(═O)$_2R^a$, —$NO_2$, —$NR^cR^d$, —NHS(═O)$_2R^a$, —S(═O)$_2NR^cR^d$, —C(═O)$R^a$, —OC(═O)$R^a$, —C(═O)$OR^b$, —OC(═O)$OR^b$, —C(═O)$NR^cR^d$, —OC(═O)$NR^cR^d$, —$NR^b$C(═O)$NR^cR^d$, —$NR^b$C(═O)$R^a$, —$NR^b$C(═O)$OR^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$(═O)$OR^b$, cycloalkyl, heterocycloalkyl, aryl, or heteroaryl;

$X^3$ is N or C—$R^{X3}$;

$R^{X3}$ is hydrogen, deuterium, halogen, —CN, —OH, —$OR^a$, —SH, —$SR^a$, —S(═O)$R^a$, —S(═O)$_2R^a$, —$NO_2$, —$NR^cR^d$, —NHS(═O)$_2R^a$, —S(═O)$_2NR^cR^d$, —C(═O)$R^a$, —OC(═O)$R^a$, —C(═O)$OR^b$, —OC(═O)OR$^b$, —C(═O)NR$^c$R$^d$, —OC(═O)NR$^c$R$^d$, —NR$^b$C(═O)NR$^c$R$^d$, —NR$^b$C(═O)R$^a$, —NR$^b$C(═O)OR$^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$C(═O)OR$^b$, cycloalkyl, heterocycloalkyl, aryl, or heteroaryl;

X$^4$ is N or C—R$^{X4}$;

R$^{X4}$ is hydrogen, deuterium, halogen, —CN, —OH, —OR$^a$, —SH, —SR$^a$, —S(═O)R$^a$, —S(═O)$_2$R$^a$, —NO$_2$, —NR$^c$R$^d$, —NHS(═O)$_2$R$^a$, —S(═O)$_2$NR$^c$R$^d$, —C(═O)R$^a$, —OC(═O)R$^a$, —C(═O)OR$^b$, —OC(═O)OR$^b$, —C(═O)NR$^c$R$^d$, —OC(═O)NR$^c$R$^d$, —NR$^b$C(═O)NR$^c$R$^d$, —NR$^b$C(═O)R$^a$, —NR$^b$C(═O)OR$^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$(═O)OR$^b$, cycloalkyl, heterocycloalkyl, aryl, or heteroaryl;

Ring A is aryl, heteroaryl, cycloalkyl, or heterocycloalkyl;

each R$^A$ is independently deuterium, halogen, —Y—CN, —Y—OH, —Y—OR$^a$, —Y—SH, —Y—SR$^a$, —Y—S(═O)R$^a$, —Y—S(═O)$_2$R$^a$, —Y—NO$_2$, —Y—NR$^c$R$^d$, —Y—NR$^b$S(═O)$_2$R$^a$, —Y—NR$^b$S(═O)$_2$NR$^c$R$^d$, —Y—S(═O)$_2$NR$^c$R$^d$, —Y—C(═O)R$^a$, —Y—OC(═O)R$^a$, —Y—C(═O)OR$^b$, —Y—OC(═O)OR$^b$, —Y—C(═O)NR$^c$R$^d$, —Y—OC(═O)NR$^c$R$^d$, —Y—NR$^b$C(═O)NR$^c$R$^d$, —Y—NR$^b$C(═O)R$^a$, —Y—NR$^b$C(═O)OR$^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$(═O)OR$^b$, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three deuterium, oxo, halogen, —CN, —OH, —OMe, —S(═O)Me, —S(═O)$_2$Me, —NH$_2$, —S(═O)$_2$NH$_2$, —C(═O)Me, —C(═O)OH, —C(═O)OMe, $C_1$-$C_6$alkyl, $C_1$-$C_6$haloalkyl, $C_1$-$C_6$hydroxyalkyl, or $C_1$-$C_6$aminoalkyl; or two R$^A$ on the same carbon are taken together to form an oxo;

each Y is independently a bond, $C_1$-$C_6$alkylene, or $C_1$-$C_6$haloalkylene;

n is 0-4;

each R$^a$ is independently $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one, two, or three deuterium, oxo, halogen, —CN, —OH, —OMe, —S(═O)Me, —S(═O)$_2$Me, —NH$_2$, —S(═O)$_2$NH$_2$, —C(═O)Me, —C(═O)OH, —C(═O)OMe, $C_1$-$C_6$alkyl, $C_1$-$C_6$haloalkyl, $C_1$-$C_6$hydroxyalkyl, or $C_1$-$C_6$aminoalkyl;

each R$^b$ is independently hydrogen, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one, two, or three deuterium, oxo, halogen, —CN, —OH, —OMe, —S(═O)Me, —S(═O)$_2$Me, —NH$_2$, —S(═O)$_2$NH$_2$, —C(═O)Me, —C(═O)OH, —C(═O)OMe, $C_1$-$C_6$alkyl, $C_1$-$C_6$haloalkyl, $C_1$-$C_6$hydroxyalkyl, or $C_1$-$C_6$aminoalkyl; and each R$^c$ and R$^d$ are independently hydrogen, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one, two, or three oxo, deuterium, halogen, —CN, —OH, —OMe, —S(═O)Me, —S(═O)$_2$Me, —NH$_2$, —S(═O)$_2$NH$_2$, —C(═O)Me, —C(═O)OH, —C(═O)OMe, $C_1$-$C_6$alkyl, $C_1$-$C_6$haloalkyl, $C_1$-$C_6$hydroxyalkyl, or $C_1$-$C_6$aminoalkyl;

or R$^c$ and R$^d$ are taken together with the atom to which they are attached to form a heterocycloalkyl optionally substituted with one, two, or three oxo, deuterium, halogen, —CN, —OH, —OMe, —S(═O)Me, —S(═O)$_2$Me, —NH$_2$, —S(═O)$_2$NH$_2$, —C(═O)Me, —C(═O)OH, —C(═O)OMe, $C_1$-$C_6$alkyl, $C_1$-$C_6$haloalkyl, $C_1$-$C_6$hydroxyalkyl, or $C_1$-$C_6$aminoalkyl.

Also disclosed herein are compounds of Formula (II), or a pharmaceutically acceptable salt, solvate, or stereoisomer thereof:

(II)

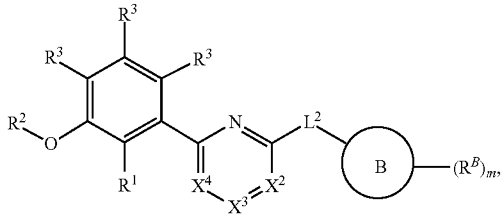

wherein:

R$^1$ is halogen;

R$^2$ is hydrogen, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$C(═O)OR$^b$, cycloalkyl, heterocycloalkyl, aryl, or heteroaryl;

each R$^3$ is independently hydrogen, deuterium, halogen, —CN, —OH, —OR$^a$, —SH, —SR$^a$, —S(═O)R$^a$, —S(═O)$_2$R$^a$, —NO$_2$, —NR$^c$R$^d$, —NHS(═O)$_2$R$^a$, —S(═O)$_2$NR$^c$R$^d$, —C(═O)R$^a$, —OC(═O)R$^a$, —C(═O)OR$^b$, —OC(═O)OR$^b$, —C(═O)NR$^c$R$^d$, —OC(═O)NR$^c$R$^d$, —NR$^b$C(═O)NR$^c$R$^d$, —NR$^b$C(═O)R$^a$, —NR$^b$C(═O)OR$^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$C(═O)OR$^b$, cycloalkyl, heterocycloalkyl, aryl, or heteroaryl;

L$^2$ is —O—, —S—, —S(═O)—, or —S(═O)$_2$—;

X$^2$ is N or C—R$^{X2}$;

R$^{X2}$ is hydrogen, deuterium, halogen, —CN, —OH, —OR$^a$, —SH, —SR$^a$, —S(═O)R$^a$, —S(═O)$_2$R$^a$, —NO$_2$, —NR$^c$R$^d$, —NHS(═O)$_2$R$^a$, —S(═O)$_2$NR$^c$R$^d$, —C(═O)R$^a$, —OC(═O)R$^a$, —C(═O)OR$^b$, —OC(═O)OR$^b$, —C(═O)NR$^c$R$^d$, —OC(═O)NR$^c$R$^d$, —NR$^b$C(═O)NR$^c$R$^d$, —NR$^b$C(═O)R$^a$, —NR$^b$C(═O)OR$^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$C(═O)OR$^b$, cycloalkyl, heterocycloalkyl, aryl, or heteroaryl;

$X^3$ is N or C—$R^{X3}$;

$R^{X3}$ is hydrogen, deuterium, halogen, —CN, —OH, —OR$^a$, —SH, —SR$^a$, —S(═O)R$^a$, —S(═O)$_2$R$^a$, —NO$_2$, —NR$^c$R$^d$, —NHS(═O)$_2$R$^a$, —S(═O)$_2$NR$^c$R$^d$, —C(═O)R$^a$, —OC(═O)R$^a$, —C(═O)OR$^b$, —OC(═O)OR$^b$, —C(═O)NR$^c$R$^d$, —OC(═O)NR$^c$R$^d$, —NR$^b$C(═O)NR$^c$R$^d$, —NR$^b$C(═O)R$^a$, —NR$^b$C(═O)OR$^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$(═O)OR$^b$, cycloalkyl, heterocycloalkyl, aryl, or heteroaryl;

$X^4$ is N or C—$R^{X4}$;

$R^{X4}$ is hydrogen, deuterium, halogen, —CN, —OH, —OR$^a$, —SH, —SR$^a$, —S(═O)R$^a$, —S(═O)$_2$R$^a$, —NO$_2$, —NR$^c$R$^d$, —NHS(═O)$_2$R$^a$, —S(═O)$_2$NR$^c$R$^d$, —C(═O)R$^a$, —OC(═O)R$^a$, —C(═O)OR$^b$, —OC(═O)OR$^b$, —C(═O)NR$^c$R$^d$, —OC(═O)NR$^c$R$^d$, —NR$^b$C(═O)NR$^c$R$^d$, —NR$^b$C(═O)R$^a$, —NR$^b$C(═O)OR$^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$C(═O)OR$^b$, cycloalkyl, heterocycloalkyl, aryl, or heteroaryl;

Ring B is aryl, heteroaryl, cycloalkyl, or heterocycloalkyl;

each $R^B$ is independently deuterium, halogen, —Y—CN, —Y—OH, —Y—OR$^a$, —Y—SH, —Y—SR$^a$, —Y—S(═O)R$^a$, —Y—S(═O)$_2$R$^a$, —Y—NO$_2$, —Y—NR$^c$R$^d$, —Y—NR$^b$S(═O)$_2$R$^a$, —Y—NR$^b$S(═O)$_2$NR$^c$R$^d$, —Y—S(═O)$_2$NR$^c$R$^d$, —Y—C(═O)R$^a$, —Y—OC(═O)R$^a$, —Y—C(═O)OR$^b$, —Y—OC(═O)OR$^b$, —Y—C(═O)NR$^c$R$^d$, —Y—OC(═O)NR$^c$R$^d$, —Y—NR$^b$C(═O)NR$^c$R$^d$, —Y—NR$^b$C(═O)R$^a$, —Y—NR$^b$C(═O)OR$^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$(═O)OR$^b$, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three deuterium, oxo, halogen, —CN, —OH, —OMe, —S(═O)Me, —S(═O)$_2$Me, —NH$_2$, —S(═O)$_2$NH$_2$, —C(═O)Me, —C(═O)OH, —C(═O)OMe, $C_1$-$C_6$alkyl, $C_1$-$C_6$haloalkyl, $C_1$-$C_6$hydroxyalkyl, or $C_1$-$C_6$aminoalkyl; or two $R^B$ on the same carbon are taken together to form an oxo;

each Y is independently a bond, $C_1$-$C_6$alkylene, or $C_1$-$C_6$haloalkylene;

m is 0-4;

each $R^a$ is independently $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one, two, or three deuterium, oxo, halogen, —CN, —OH, —OMe, —S(═O)Me, —S(═O)$_2$Me, —NH$_2$, —S(═O)$_2$NH$_2$, —C(═O)Me, —C(═O)OH, —C(═O)OMe, $C_1$-$C_6$alkyl, $C_1$-$C_6$haloalkyl, $C_1$-$C_6$hydroxyalkyl, or $C_1$-$C_6$aminoalkyl;

each $R^b$ is independently hydrogen, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one, two, or three deuterium, oxo, halogen, —CN, —OH, —OMe, —S(═O)Me, —S(═O)$_2$Me, —NH$_2$, —S(═O)$_2$NH$_2$, —C(═O)Me, —C(═O)OH, —C(═O)OMe, $C_1$-$C_6$alkyl, $C_1$-$C_6$haloalkyl, $C_1$-$C_6$hydroxyalkyl, or $C_1$-$C_6$aminoalkyl; and each $R^c$ and $R^d$ are independently hydrogen, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one, two, or three oxo, deuterium, halogen, —CN, —OH, —OMe, —S(═O)Me, —S(═O)$_2$Me, —NH$_2$, —S(═O)$_2$NH$_2$, —C(═O)Me, —C(═O)OH, —C(═O)OMe, $C_1$-$C_6$alkyl, $C_1$-$C_6$haloalkyl, $C_1$-$C_6$hydroxyalkyl, or $C_1$-$C_6$aminoalkyl;

or $R^c$ and $R^d$ are taken together with the atom to which they are attached to form a heterocycloalkyl optionally substituted with one, two, or three oxo, deuterium, halogen, —CN, —OH, —OMe, —S(═O)Me, —S(═O)$_2$Me, —NH$_2$, —S(═O)$_2$NH$_2$, —C(═O)Me, —C(═O)OH, —C(═O)OMe, $C_1$-$C_6$alkyl, $C_1$-$C_6$haloalkyl, $C_1$-$C_6$hydroxyalkyl, or $C_1$-$C_6$aminoalkyl.

Also disclosed herein is a pharmaceutical composition comprising a compound disclosed herein, or a pharmaceutically acceptable salt, solvate, or stereoisomer thereof, and a pharmaceutically acceptable carrier.

Also disclosed herein is a method of treating a disease in a subject in need thereof, the method comprising administering a pharmaceutically effective amount of a compound disclosed herein, or a pharmaceutically acceptable salt, solvate, or stereoisomer thereof, or a pharmaceutical composition disclosed herein. In some embodiments of a method of treating a disease, the disease is a liver disease, a metabolic disease, or a cardiovascular disease. In some embodiments of a method of treating a disease, the disease is NAFLD. In some embodiments of a method of treating a disease, the disease is NASH. In some embodiments of a method of treating a disease, the disease is drug induced liver injury (DILI). In some embodiments of a method of treating a disease, the disease is associated with HSD17B13. In some embodiments of a method of treating a disease, the diseases is alcoholic liver disease. In some embodiments of a method of treating a disease, the disease is cirrhosis. In some embodiments of a method of treating a disease, the disease is decompensated portal hypertension.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Definitions

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word “comprise” and variations thereof, such as, “comprises” and “comprising” are to be construed in an open, inclusive sense, that is, as “including, but not limited to.” Further, headings provided herein are for convenience only and do not interpret the scope or meaning of the claimed invention.

Reference throughout this specification to “some embodiments” or “an embodiment” means that a particular feature, structure or characteristic described in connection with the embodiment is included in at least one embodiment. Thus, the appearances of the phrases “in one embodiment” or “in an embodiment” in various places throughout this specification are not necessarily all referring to the same embodiment. Furthermore, the particular features, structures, or characteristics may be combined in any suitable manner in one or more embodiments. Also, as used in this specification and the appended claims, the singular forms “a,” “an,” and “the” include plural referents unless the content clearly dictates otherwise. It should also be noted that the term “or” is generally employed in its sense including “and/or” unless the content clearly dictates otherwise.

The terms below, as used herein, have the following meanings, unless indicated otherwise:

“oxo” refers to =O.

“Carboxyl” refers to —COOH.

“Alkyl” refers to a straight-chain, or branched-chain saturated hydrocarbon monoradical having from one to about ten carbon atoms, more preferably one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as “$C_1$-$C_6$ alkyl” or “$C_{1-6}$alkyl”, means that the alkyl group may consist of 1 carbon atom, 2 carbon atoms, 3 carbon atoms, 4 carbon atoms, 5 carbon atoms or 6 carbon atoms, although the present definition also covers the occurrence of the term “alkyl” where no numerical range is designated. In some embodiments, the alkyl is a $C_{1-10}$alkyl. In some embodiments, the alkyl is a $C_{1-6}$alkyl. In some embodiments, the alkyl is a $C_{1-5}$alkyl. In some embodiments, the alkyl is a $C_{1-4}$alkyl. In some embodiments, the alkyl is a $C_{1-3}$alkyl. Unless stated otherwise specifically in the specification, an alkyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkyl is optionally substituted with oxo, halogen, —CN, —COOH, —COOMe, —OH, —OMe, —$NH_2$, or —$NO_2$. In some embodiments, the alkyl is optionally substituted with halogen, —CN, —OH, or —OMe. In some embodiments, the alkyl is optionally substituted with halogen.

“Alkenyl” refers to a straight-chain, or branched-chain hydrocarbon monoradical having one or more carbon-carbon double-bonds and having from two to about ten carbon atoms, more preferably two to about six carbon atoms. The group may be in either the cis or trans conformation about the double bond(s), and should be understood to include both isomers. Examples include, but are not limited to ethenyl (—CH=$CH_2$), 1-propenyl (—$CH_2$CH=$CH_2$), isopropenyl [—C($CH_3$)=$CH_2$], butenyl, 1,3-butadienyl and the like. Whenever it appears herein, a numerical range such as “$C_2$-$C_6$ alkenyl” or “$C_{2-6}$alkenyl”, means that the alkenyl group may consist of 2 carbon atoms, 3 carbon atoms, 4 carbon atoms, 5 carbon atoms or 6 carbon atoms, although the present definition also covers the occurrence of the term “alkenyl” where no numerical range is designated. Unless stated otherwise specifically in the specification, an alkenyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkenyl is optionally substituted with oxo, halogen, —CN, —COOH, —COOMe, —OH, —OMe, —$NH_2$, or —$NO_2$. In some embodiments, the alkenyl is optionally substituted with halogen, —CN, —OH, or —OMe. In some embodiments, the alkenyl is optionally substituted with halogen.

“Alkynyl” refers to a straight-chain or branched-chain hydrocarbon monoradical having one or more carbon-carbon triple-bonds and having from two to about ten carbon atoms, more preferably from two to about six carbon atoms. Examples include, but are not limited to ethynyl, 2-propynyl, 2-butynyl, 1,3-butadiynyl and the like. Whenever it appears herein, a numerical range such as “$C_2$-$C_6$ alkynyl” or “$C_{2-6}$alkynyl”, means that the alkynyl group may consist of 2 carbon atoms, 3 carbon atoms, 4 carbon atoms, 5 carbon atoms or 6 carbon atoms, although the present definition also covers the occurrence of the term “alkynyl” where no numerical range is designated. Unless stated otherwise specifically in the specification, an alkynyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkynyl is optionally substituted with oxo, halogen, —CN, —COOH, COOMe, —OH, —OMe, —$NH_2$, or —$NO_2$. In some embodiments, the alkynyl is optionally substituted with halogen, —CN, —OH, or —OMe. In some embodiments, the alkynyl is optionally substituted with halogen.

“Alkylene” refers to a straight or branched divalent hydrocarbon chain. Unless stated otherwise specifically in the specification, an alkylene group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkylene is optionally substituted with oxo, halogen, —CN, —COOH, COOMe, —OH, —OMe, —$NH_2$, or —$NO_2$. In some embodiments, the alkylene is optionally substituted with halogen, —CN, —OH, or —OMe. In some embodiments, the alkylene is optionally substituted with halogen.

“Alkoxy” refers to a radical of the formula —$OR_a$ where $R_a$ is an alkyl radical as defined. Unless stated otherwise specifically in the specification, an alkoxy group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkoxy is optionally substituted with halogen, —CN, —COOH, COOMe, —OH, —OMe, —$NH_2$, or —$NO_2$. In some embodiments, the alkoxy is optionally substituted with halogen, —CN, —OH, or —OMe. In some embodiments, the alkoxy is optionally substituted with halogen.

"Aryl" refers to a radical derived from a hydrocarbon ring system comprising 6 to 30 carbon atoms and at least one aromatic ring. The aryl radical may be a monocyclic, bicyclic, tricyclic or tetracyclic ring system, which may include fused (when fused with a cycloalkyl or heterocycloalkyl ring, the aryl is bonded through an aromatic ring atom) or bridged ring systems. In some embodiments, the aryl is a 6- to 10-membered aryl. In some embodiments, the aryl is a 6-membered aryl (phenyl). Aryl radicals include, but are not limited to, aryl radicals derived from the hydrocarbon ring systems of anthrylene, naphthylene, phenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl may be optionally substituted, for example, with halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the aryl is optionally substituted with halogen, methyl, ethyl, —CN, —COOH, COOMe, $—CF_3$, —OH, —OMe, $—NH_2$, or $—NO_2$. In some embodiments, the aryl is optionally substituted with halogen, methyl, ethyl, —CN, $—CF_3$, —OH, or —OMe. In some embodiments, the aryl is optionally substituted with halogen.

"Cycloalkyl" refers to a partially or fully saturated, monocyclic or polycyclic carbocyclic ring, which may include fused (when fused with an aryl or a heteroaryl ring, the cycloalkyl is bonded through a non-aromatic ring atom) or bridged ring systems. In some embodiments, the cycloalkyl is fully saturated. Representative cycloalkyls include, but are not limited to, cycloalkyls having from three to fifteen carbon atoms ($C_3$-$C_{15}$ cycloalkyl), from three to ten carbon atoms ($C_3$-$C_{10}$ cycloalkyl), from three to eight carbon atoms ($C_3$-$C_8$ cycloalkyl), from three to six carbon atoms ($C_3$-$C_6$ cycloalkyl), from three to five carbon atoms ($C_3$-$C_5$ cycloalkyl), or three to four carbon atoms ($C_3$-$C_4$ cycloalkyl). In some embodiments, the cycloalkyl is a 3- to 10-membered cycloalkyl. In some embodiments, the cycloalkyl is a 3- to 6-membered cycloalkyl. In some embodiments, the cycloalkyl is a 5- to 6-membered cycloalkyl. Monocyclic cycloalkyls include, for example, cyclopropyl, cyclobutyl, cyclopentyl, cyclohexyl, cycloheptyl, and cyclooctyl. Polycyclic cycloalkyls include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Partially saturated cycloalkyls include, for example cyclopentenyl, cyclohexenyl, cycloheptenyl, and cyclooctenyl. Unless stated otherwise specifically in the specification, a cycloalkyl is optionally substituted, for example, with oxo, halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, a cycloalkyl is optionally substituted with oxo, halogen, methyl, ethyl, —CN, —COOH, COOMe, $—CF_3$, —OH, —OMe, $—NH_2$, or $—NO_2$. In some embodiments, a cycloalkyl is optionally substituted with oxo, halogen, methyl, ethyl, —CN, $—CF_3$, —OH, or —OMe. In some embodiments, the cycloalkyl is optionally substituted with halogen.

"Halo" or "halogen" refers to bromo, chloro, fluoro or iodo. In some embodiments, halogen is fluoro or chloro. In some embodiments, halogen is fluoro.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like.

"Heterocycloalkyl" refers to a 3- to 24-membered partially or fully saturated ring radical comprising 2 to 23 carbon atoms and from one to 8 heteroatoms selected from the group consisting of nitrogen, oxygen, phosphorous and sulfur. In some embodiments, the heterocycloalkyl is fully saturated. In some embodiments, the heterocycloalkyl comprises one to three heteroatoms selected from the group consisting of nitrogen, oxygen, and sulfur. In some embodiments, the heterocycloalkyl comprises one to three heteroatoms selected from the group consisting of nitrogen and oxygen. In some embodiments, the heterocycloalkyl comprises one to three nitrogens. In some embodiments, the heterocycloalkyl comprises one or two nitrogens. In some embodiments, the heterocycloalkyl comprises one nitrogen. In some embodiments, the heterocycloalkyl comprises one nitrogen and one oxygen. Unless stated otherwise specifically in the specification, the heterocycloalkyl radical may be a monocyclic, bicyclic, tricyclic or tetracyclic ring system, which may include fused (when fused with an aryl or a heteroaryl ring, the heterocycloalkyl is bonded through a non-aromatic ring atom) or bridged ring systems; and the nitrogen, carbon, or sulfur atoms in the heterocycloalkyl radical may be optionally oxidized; the nitrogen atom may be optionally quaternized. Representative heterocycloalkyls include, but are not limited to, heterocycloalkyls having from two to fifteen carbon atoms ($C_2$-$C_{15}$ heterocycloalkyl), from two to ten carbon atoms ($C_2$-$C_{10}$ heterocycloalkyl), from two to eight carbon atoms ($C_2$-$C_5$ heterocycloalkyl), from two to seven carbon atoms ($C_2$-$C_7$ heterocycloalkyl), from two to six carbon atoms ($C_2$-$C_6$ heterocycloalkyl), from two to five carbon atoms ($C_2$-$C_5$ heterocycloalkyl), or two to four carbon atoms ($C_2$-$C_4$ heterocycloalkyl). Examples of such heterocycloalkyl radicals include, but are not limited to, aziridinyl, azetidinyl, oxetanyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocycloalkyl also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). In some embodiments, the heterocycloalkyl is a 3- to 8-membered heterocycloalkyl. In some embodiments, the heterocycloalkyl is a 3- to 7-membered heterocycloalkyl. In some embodiments, the heterocycloalkyl is a 3- to 6-membered heterocycloalkyl. In some embodiments, the heterocycloalkyl is a 4- to 6-membered heterocycloalkyl. In some embodiments, the heterocycloalkyl is a 5- to 6-membered heterocycloalkyl. Unless stated otherwise specifically in the specification, a heterocycloalkyl may be optionally substituted as described below, for example, with oxo, halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the heterocycloalkyl is optionally substituted with oxo, halogen, methyl, ethyl, —CN, —COOH, COOMe, —$CF_3$, —OH, —OMe, —$NH_2$, or —$NO_2$. In some embodiments, the heterocycloalkyl is optionally substituted with halogen, methyl, ethyl, —CN, —$CF_3$, —OH, or —OMe. In some embodiments, the heterocycloalkyl is optionally substituted with halogen.

"Heteroaryl" refers to a 5- to 14-membered ring system radical comprising one to thirteen carbon atoms, one to six heteroatoms selected from the group consisting of nitrogen, oxygen, phosphorous, and sulfur, and at least one aromatic ring. In some embodiments, the heteroaryl comprises one to three heteroatoms selected from the group consisting of nitrogen, oxygen, and sulfur. In some embodiments, the heteroaryl comprises one to three heteroatoms selected from the group consisting of nitrogen and oxygen. In some embodiments, the heteroaryl comprises one to three nitrogens. In some embodiments, the heteroaryl comprises one or two nitrogens. In some embodiments, the heteroaryl comprises one nitrogen. The heteroaryl radical may be a monocyclic, bicyclic, tricyclic or tetracyclic ring system, which may include fused (when fused with a cycloalkyl or heterocycloalkyl ring, the heteroaryl is bonded through an aromatic ring atom) or bridged ring systems; and the nitrogen, carbon or sulfur atoms in the heteroaryl radical may be optionally oxidized; the nitrogen atom may be optionally quaternized. In some embodiments, the heteroaryl is a 5- to 10-membered heteroaryl. In some embodiments, the heteroaryl is a 5- to 6-membered heteroaryl. In some embodiments, the heteroaryl is a 6-membered heteroaryl. In some embodiments, the heteroaryl is a 5-membered heteroaryl. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl may be optionally substituted, for example, with halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the heteroaryl is optionally substituted with halogen, methyl, ethyl, —CN, —COOH, COOMe, —$CF_3$, —OH, —OMe, —$NH_2$, or —$NO_2$. In some embodiments, the heteroaryl is optionally substituted with halogen, methyl, ethyl, —CN, —$CF_3$, —OH, or —OMe. In some embodiments, the heteroaryl is optionally substituted with halogen.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined above. Further, an optionally substituted group may be un-substituted (e.g., —$CH_2CH_3$), fully substituted (e.g., —$CF_2CF_3$), mono-substituted (e.g., —$CH_2CH_2F$) or substituted at a level anywhere in-between fully substituted and mono-substituted (e.g., —$CH_2CHF_2$, —$CH_2CF_3$, —$CF_2CH_3$, —$CFHCHF_2$, etc.). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons.

An "effective amount" or "therapeutically effective amount" refers to an amount of a compound administered to a mammalian subject, either as a single dose or as part of a series of doses, which is effective to produce a desired therapeutic effect.

"Treatment" of an individual (e.g. a mammal, such as a human) or a cell is any type of intervention used in an attempt to alter the natural course of the individual or cell. In some embodiments, treatment includes administration of a pharmaceutical composition, subsequent to the initiation of a pathologic event or contact with an etiologic agent and includes stabilization of the condition (e.g., condition does not worsen) or alleviation of the condition. In some embodiments, treatment also includes prophylactic treatment (e.g., administration of a composition described herein when an individual is suspected to be suffering from a liver disease, e.g., NAFLD).

"Synergy" or "synergize" refers to an effect of a combination that is greater than additive of the effects of each component alone at the same doses.

"HSD17B13" means hydroxysteroid 17-beta dehydrogenase 13 and refers to any nucleic acid of HSD17B13. For example, in some embodiments, HSD17B13 includes a DNA sequence encoding HSD17B13, an RNA sequence transcribed from DNA encoding HSD17B13 (including genomic DNA comprising introns and exons). HSD17B13 can also refer to any amino acid sequence of HSD17B13 (may include secondary or tertiary structures of the protein molecule), encoded by a DNA sequence and/or RNA sequence. The target may be referred to in either upper or lower case.

Compounds

Described herein are compounds of Formula (A), (B), (I), or (II) or a pharmaceutically acceptable salt, solvate, or stereoisomer thereof useful in the treatment of liver diseases. In some embodiments, the liver disease is NAFLD.

Disclosed herein is a compound of Formula (A), or a pharmaceutically acceptable salt, solvate, or stereoisomer thereof:

(A)

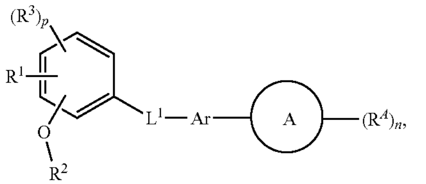

wherein:

$R^1$ is halogen;

$R^2$ is hydrogen, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$C(=O)OR$^b$, cycloalkyl, heterocycloalkyl, aryl, or heteroaryl;

each $R^3$ is independently hydrogen, deuterium, halogen, —CN, —OH, —OR$^a$, —SH, —SR$^a$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$C(=O)OR$^b$, cycloalkyl, heterocycloalkyl, aryl, or heteroaryl; p is 1-3;

$L^1$ is —O—, —S—, —S(=O)—, —S(=O)$_2$—, or —NR$^{L1}$—;

$R^{L1}$ is hydrogen, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$C(=O)OR$^b$, cycloalkyl, heterocycloalkyl, aryl, or heteroaryl;

Ar is

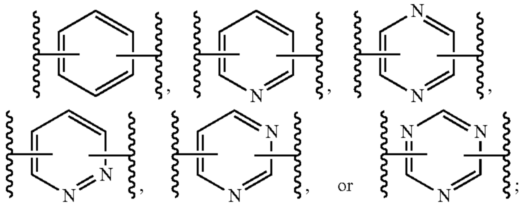

, , , , , or ;

each optionally substituted with one, two, or three deuterium, halogen, —CN, —OH, —OR$^a$, —SH, —SR$^a$, —S(=O)R$^a$, —S(=O)$_2$R$^a$, —NO$_2$, —NR$^c$R$^d$, —NHS(=O)$_2$R$^a$, —S(=O)$_2$NR$^c$R$^d$, —C(=O)R$^a$, —OC(=O)R$^a$, —C(=O)OR$^b$, —OC(=O)OR$^b$, —C(=O)NR$^c$R$^d$, —OC(=O)NR$^c$R$^d$, —NR$^b$C(=O)NR$^c$R$^d$, —NR$^b$C(=O)R$^a$, —NR$^b$C(=O)OR$^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, or —$C_1$-$C_6$C(=O)OR$^b$;

Ring A is aryl, heteroaryl, cycloalkyl, or heterocycloalkyl;

each $R^4$ is independently deuterium, halogen, —Y—CN, —Y—OH, —Y—OR$^a$, —Y—SH, —Y—SR$^a$, —Y—S(=O)R$^a$, —Y—S(=O)$_2$R$^a$, —Y—NO$_2$, —Y—NR$^c$R$^d$, —Y—NR$^b$S(=O)$_2$R$^a$, —Y—NR$^b$S(=O)$_2$NR$^c$R$^d$, —Y—S(=O)$_2$NR$^c$R$^d$, —Y—C(=O)R$^a$, —Y—OC(=O)R$^a$, —Y—C(=O)OR$^b$, —Y—OC(=O)OR$^b$, —Y—C(=O)NR$^c$R$^d$, —Y—OC(=O)NR$^c$R$^d$, —Y—NR$^b$C(=O)NR$^c$R$^d$, —Y—NR$^b$C(=O)R$^a$, —Y—NR$^b$C(=O)OR$^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$(=O)OR$^b$, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three deuterium, oxo, halogen, —CN, —OH, —OMe, —S(=O)Me, —S(=O)$_2$Me, —NH$_2$, —S(=O)$_2$NH$_2$, —C(=O)Me, —C(=O)OH, —C(=O)OMe, $C_1$-$C_6$alkyl, $C_1$-$C_6$haloalkyl, $C_1$-$C_6$hydroxyalkyl, or $C_1$-$C_6$aminoalkyl; or two $R^4$ on the same carbon are taken together to form an oxo;

each Y is independently a bond, $C_1$-$C_6$alkylene, or $C_1$-$C_6$haloalkylene;

n is 0-4;

each $R^a$ is independently $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one, two, or three deuterium, oxo, halogen, —CN, —OH, —OMe, —S(=O)Me, —S(=O)$_2$Me, —NH$_2$, —S(=O)$_2$NH$_2$, —C(=O)Me, —C(=O)OH, —C(=O)OMe, $C_1$-$C_6$alkyl, $C_1$-$C_6$haloalkyl, $C_1$-$C_6$hydroxyalkyl, or $C_1$-$C_6$aminoalkyl;

each $R^b$ is independently hydrogen, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one, two, or three deuterium, oxo, halogen, —CN, —OH, —OMe, —S(=O)Me, —S(=O)$_2$Me, —NH$_2$, —S(=O)$_2$NH$_2$, —C(=O)Me, —C(=O)OH, —C(=O)OMe, $C_1$-$C_6$alkyl, $C_1$-$C_6$haloalkyl, $C_1$-$C_6$hydroxyalkyl, or $C_1$-$C_6$aminoalkyl; and each $R^c$ and $R^d$ are independently hydrogen, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one, two, or three oxo, deuterium, halogen, —CN, —OH, —OMe, —S(=O)Me, —S(=O)$_2$Me, —NH$_2$, —S(=O)$_2$NH$_2$, —C(=O)Me, —C(=O)OH, —C(=O)OMe, $C_1$-$C_6$alkyl, $C_1$-$C_6$haloalkyl, $C_1$-$C_6$hydroxyalkyl, or $C_1$-$C_6$aminoalkyl;

or $R^c$ and $R^d$ are taken together with the atom to which they are attached to form a heterocycloalkyl optionally substituted with one, two, or three oxo, deuterium, halogen, —CN, —OH, —OMe, —S(=O)Me, —S(=O)$_2$Me, —NH$_2$, —S(=O)$_2$NH$_2$, —C(=O)Me, —C(=O)OH, —C(=O)OMe, $C_1$-$C_6$alkyl, $C_1$-$C_6$haloalkyl, $C_1$-$C_6$hydroxyalkyl, or $C_1$-$C_6$aminoalkyl.

Disclosed herein is a compound of Formula (I), or a pharmaceutically acceptable salt, solvate, or stereoisomer thereof:

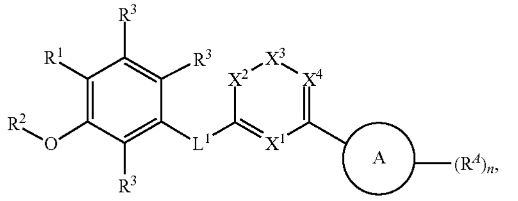

(I)

wherein:

$R^1$ is halogen;

$R^2$ is hydrogen, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$C(═O)OR$^b$, cycloalkyl, heterocycloalkyl, aryl, or heteroaryl;

each $R^3$ is independently hydrogen, deuterium, halogen, —CN, —OH, —OR$^a$, —SH, —SR$^a$, —S(═O)R$^a$, —S(═O)$_2$R$^a$, —NO$_2$, —NR$^c$R$^d$, —NHS(═O)$_2$R$^a$, —S(═O)$_2$NR$^c$R$^d$, —C(═O)R$^a$, —OC(═O)R$^a$, —C(═O)OR$^b$, —OC(═O)OR$^b$, —C(═O)NR$^c$R$^d$, —OC(═O)NR$^c$R$^d$, —NR$^b$C(═O)NR$^c$R$^d$, —NR$^b$C(═O)R$^a$, —NR$^b$C(═O)OR$^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$C(═O)OR$^b$, cycloalkyl, heterocycloalkyl, aryl, or heteroaryl;

$L^1$ is —O—, —S—, —S(═O)—, —S(═O)$_2$—, or —NR$^{L1}$—;

$R^{L1}$ is hydrogen, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$C(═O)OR$^b$, cycloalkyl, heterocycloalkyl, aryl, or heteroaryl;

$X^1$ is N or C—R$^{X1}$;

$R^{X1}$ is deuterium, halogen, —CN, —OH, —OR$^a$, —SH, —SR$^a$, —S(═O)R$^a$, —S(═O)$_2$R$^a$, —NO$_2$, —NR$^c$R$^d$, —NHS(═O)$_2$R$^a$, —S(═O)$_2$NR$^c$R$^d$, —C(═O)R$^a$, —OC(═O)R$^a$, —C(═O)OR$^b$, —OC(═O)OR$^b$, —C(═O)NR$^c$R$^d$, —OC(═O)NR$^c$R$^d$, —NR$^b$C(═O)NR$^c$R$^d$, —NR$^b$C(═O)R$^a$, —NR$^b$C(═O)OR$^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$(═O)OR$^b$, cycloalkyl, heterocycloalkyl, aryl, or heteroaryl;

$X^2$ is N or C—R$^{X2}$;

$R^{X2}$ is hydrogen, deuterium, halogen, —CN, —OH, —OR$^a$, —SH, —SR$^a$, —S(═O)R$^a$, —S(═O)$_2$R$^a$, —NO$_2$, —NR$^c$R$^d$, —NHS(═O)$_2$R$^a$, —S(═O)$_2$NR$^c$R$^d$, —C(═O)R$^a$, —OC(═O)R$^a$, —C(═O)OR$^b$, —OC(═O)OR$^b$, —C(═O)NR$^c$R$^d$, —OC(═O)NR$^c$R$^d$, —NR$^b$C(═O)NR$^c$R$^d$, —NR$^b$C(═O)R$^a$, —NR$^b$C(═O)OR$^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$(═O)OR$^b$, cycloalkyl, heterocycloalkyl, aryl, or heteroaryl;

$X^3$ is N or C—R$^{X3}$;

$R^{X3}$ is hydrogen, deuterium, halogen, —CN, —OH, —OR$^a$, —SH, —SR$^a$, —S(═O)R$^a$, —S(═O)$_2$R$^a$, —NO$_2$, —NR$^c$R$^d$, —NHS(═O)$_2$R$^a$, —S(═O)$_2$NR$^c$R$^d$, —C(═O)R$^a$, —OC(═O)R$^a$, —C(═O)OR$^b$, —OC(═O)OR$^b$, —C(═O)NR$^c$R$^d$, —OC(═O)NR$^c$R$^d$, —NR$^b$C(═O)NR$^c$R$^d$, —NR$^b$C(═O)R$^a$, —NR$^b$C(═O)OR$^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$C(═O)OR$^b$, cycloalkyl, heterocycloalkyl, aryl, or heteroaryl;

$X^4$ is N or C—R$^{X4}$;

$R^{X4}$ is hydrogen, deuterium, halogen, —CN, —OH, —OR$^a$, —SH, —SR$^a$, —S(═O)R$^a$, —S(═O)$_2$R$^a$, —NO$_2$, —NR$^c$R$^d$, —NHS(═O)$_2$R$^a$, —S(═O)$_2$NR$^c$R$^d$, —C(═O)R$^a$, —OC(═O)R$^a$, —C(═O)OR$^b$, —OC(═O)OR$^b$, —C(═O)NR$^c$R$^d$, —OC(═O)NR$^c$R$^d$, —NR$^b$C(═O)NR$^c$R$^d$, —NR$^b$C(═O)R$^a$, —NR$^b$C(═O)OR$^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$(═O)OR$^b$, cycloalkyl, heterocycloalkyl, aryl, or heteroaryl;

Ring A is aryl, heteroaryl, cycloalkyl, or heterocycloalkyl;

each $R^A$ is independently deuterium, halogen, —Y—CN, —Y—OH, —Y—OR$^a$, —Y—SH, —Y—SR$^a$, —Y—S(═O)R$^a$, —Y—S(═O)$_2$R$^a$, —Y—NO$_2$, —Y—NR$^c$R$^d$, —Y—NR$^b$S(═O)$_2$R$^a$, —Y—NR$^b$S(═O)$_2$NR$^c$R$^d$, —Y—S(═O)$_2$NR$^c$R$^d$, —Y—C(═O)R$^a$, —Y—OC(═O)R$^a$, —Y—C(═O)OR$^b$, —Y—OC(═O)OR$^b$, —Y—C(═O)NR$^c$R$^d$, —Y—OC(═O)NR$^c$R$^d$, —Y—NR$^b$C(═O)NR$^c$R$^d$, —Y—NR$^b$C(═O)R$^a$, —Y—NR$^b$C(═O)OR$^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$(═O)OR$^b$, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three deuterium, oxo, halogen, —CN, —OH, —OMe, —S(═O)Me, —S(═O)$_2$Me, —NH$_2$, —S(═O)$_2$NH$_2$, —C(═O)Me, —C(═O)OH, —C(═O)OMe, $C_1$-$C_6$alkyl, $C_1$-$C_6$haloalkyl, $C_1$-$C_6$hydroxyalkyl, or $C_1$-$C_6$aminoalkyl; or two $R^A$ on the same carbon are taken together to form an oxo;

each Y is independently a bond, $C_1$-$C_6$alkylene, or $C_1$-$C_6$haloalkylene;

n is 0-4;

each $R^a$ is independently $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one, two, or three deuterium, oxo, halogen, —CN, —OH, —OMe, —S(═O)Me, —S(═O)$_2$Me, —NH$_2$, —S(═O)$_2$NH$_2$, —C(═O)Me, —C(═O)OH, —C(═O)OMe, $C_1$-$C_6$alkyl, $C_1$-$C_6$haloalkyl, $C_1$-$C_6$hydroxyalkyl, or $C_1$-$C_6$aminoalkyl;

each $R^b$ is independently hydrogen, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one, two, or three deuterium, oxo, halogen, —CN, —OH, —OMe, —S(═O)Me, —S(═O)$_2$Me, —NH$_2$, —S(═O)$_2$NH$_2$, —C(═O)Me, —C(═O)OH, —C(═O)OMe, $C_1$-$C_6$alkyl, $C_1$-$C_6$haloalkyl, $C_1$-$C_6$hydroxyalkyl, or $C_1$-$C_6$aminoalkyl; and each $R^c$ and $R^d$ are independently hydrogen, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one, two, or three oxo, deuterium, halogen, —CN, —OH, —OMe, —S(═O)Me, —S(═O)$_2$Me, —NH$_2$, —S(═O)$_2$NH$_2$, —C(═O)Me, —C(═O)OH, —C(═O)OMe, $C_1$-$C_6$alkyl, $C_1$-$C_6$haloalkyl, $C_1$-$C_6$hydroxyalkyl, or $C_1$-$C_6$aminoalkyl;

or $R^c$ and $R^d$ are taken together with the atom to which they are attached to form a heterocycloalkyl optionally substituted with one, two, or three oxo, deuterium, halogen, —CN, —OH, —OMe, —S(═O)Me, —S(═O)$_2$Me, —NH$_2$, —S(═O)$_2$NH$_2$, —C(═O)Me, —C(═O)OH, —C(═O)OMe, $C_1$-$C_6$alkyl, $C_1$-$C_6$haloalkyl, $C_1$-$C_6$hydroxyalkyl, or $C_1$-$C_6$aminoalkyl.

Also disclosed herein is a compound of Formula (I), or a pharmaceutically acceptable salt, solvate, or stereoisomer thereof:

(I)

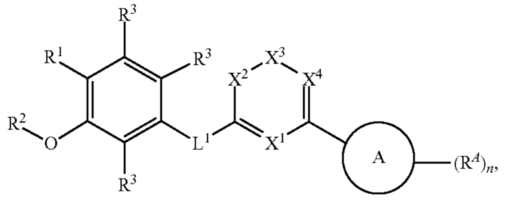

wherein:

$R^1$ is halogen;

$R^2$ is hydrogen, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$C(═O)OR$^b$, cycloalkyl, heterocycloalkyl, aryl, or heteroaryl;

each $R^3$ is independently hydrogen, deuterium, halogen, —CN, —OH, —OR$^a$, —SH, —SR$^a$, —S(═O)R$^a$, —S(═O)$_2$R$^a$, —NO$_2$, —NR$^c$R$^d$, —NHS(═O)$_2$R$^a$, —S(═O)$_2$NR$^c$R$^d$, —C(═O)R$^a$, —OC(═O)R$^a$, —C(═O)OR$^b$, —OC(═O)OR$^b$, —C(═O)NR$^c$R$^d$, —OC(═O)NR$^c$R$^d$, —NR$^b$C(═O)NR$^c$R$^d$, —NR$^b$C(═O)R$^a$, —NR$^b$C(═O)OR$^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, —$C_1$-$C_6$C(═O)OR$^b$, $C_2$-$C_6$alkynyl, —$C_1$-$C_6$C(═O)OR$^b$, cycloalkyl, heterocycloalkyl, aryl, or heteroaryl;

$L^1$ is —O—, —S—, —S(═O)—, —S(═O)$_2$—, or —NR$^{L1}$—;

$R^{L1}$ is hydrogen, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$C(═O)OR$^b$, cycloalkyl, heterocycloalkyl, aryl, or heteroaryl;

$X^1$ is N or C—R$^{X1}$;

$R^{X1}$ is deuterium, halogen, —CN, —OH, —OR$^a$, —SH, —SR$^a$, —S(═O)R$^a$, —S(═O)$_2$R$^a$, —NO$_2$, —NR$^c$R$^d$, —NHS(═O)$_2$R$^a$, —S(═O)$_2$NR$^c$R$^d$, —C(═O)R$^a$, —OC(═O)R$^a$, —C(═O)OR$^b$, —OC(═O)OR$^b$, —C(═O)NR$^c$R$^d$, —OC(═O)NR$^c$R$^d$, —NR$^b$C(═O)NR$^c$R$^d$, —NR$^b$C(═O)R$^a$, —NR$^b$C(═O)OR$^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$(═O)OR$^b$, cycloalkyl, heterocycloalkyl, aryl, or heteroaryl;

$X^2$ is N or C—R$^{X2}$;

$R^{X2}$ is hydrogen, deuterium, halogen, —CN, —OH, —OR$^a$, —SH, —SR$^a$, —S(═O)R$^a$, —S(═O)$_2$R$^a$, —NO$_2$, —NR$^c$R$^d$, —NHS(═O)$_2$R$^a$, —S(═O)$_2$NR$^c$R$^d$, —C(═O)R$^a$, —OC(═O)R$^a$, —C(═O)OR$^b$, —OC(═O)OR$^b$, —C(═O)NR$^c$R$^d$, —OC(═O)NR$^c$R$^d$, —NR$^b$C(═O)NR$^c$R$^d$, —NR$^b$C(═O)R$^a$, —NR$^b$C(═O)OR$^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$C(═O)OR$^b$, cycloalkyl, heterocycloalkyl, aryl, or heteroaryl;

$X^3$ is N or C—R$^{X3}$;

$R^{X3}$ is hydrogen, deuterium, halogen, —CN, —OH, —OR$^a$, —SH, —SR$^a$, —S(═O)R$^a$, —S(═O)$_2$R$^a$, —NO$_2$, —NR$^c$R$^d$, —NHS(═O)$_2$R$^a$, —S(═O)$_2$NR$^c$R$^d$, —C(═O)R$^a$, —OC(═O)R$^a$, —C(═O)OR$^b$, —OC(═O)OR$^b$, —C(═O)NR$^c$R$^d$, —OC(═O)NR$^c$R$^d$, —NR$^b$C(═O)NR$^c$R$^d$, —NR$^b$C(═O)R$^a$, —NR$^b$C(═O)OR$^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$(═O)OR$^b$, cycloalkyl, heterocycloalkyl, aryl, or heteroaryl;

$X^4$ is N or C—R$^{X4}$;

$R^{X4}$ is hydrogen, deuterium, halogen, —CN, —OH, —OR$^a$, —SH, —SR$^a$, —S(═O)R$^a$, —S(═O)$_2$R$^a$, —NO$_2$, —NR$^c$R$^d$, —NHS(═O)$_2$R$^a$, —S(═O)$_2$NR$^c$R$^d$, —C(═O)R$^a$, —OC(═O)R$^a$, —C(═O)OR$^b$, —OC(═O)OR$^b$, —C(═O)NR$^c$R$^d$, —OC(═O)NR$^c$R$^d$, —NR$^b$C(═O)NR$^c$R$^d$, —NR$^b$C(═O)R$^a$, —NR$^b$C(═O)OR$^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$(═O)OR$^b$, cycloalkyl, heterocycloalkyl, aryl, or heteroaryl;

Ring A is aryl, heteroaryl, cycloalkyl, or heterocycloalkyl;

each $R^A$ is independently deuterium, halogen, —Y—CN, —Y—OH, —Y—OR$^a$, —Y—SH, —Y—SR$^a$, —Y—S(═O)R$^a$, —Y—S(═O)$_2$R$^a$, —Y—NO$_2$, —Y—NR$^c$R$^d$, —Y—NR$^b$S(═O)$_2$R$^a$, —Y—NR$^b$S(═O)$_2$NR$^c$R$^d$, —Y—S(═O)$_2$NR$^c$R$^d$, —Y—C(═O)R$^a$, —Y—OC(═O)R$^a$, —Y—C(═O)OR$^b$, —Y—OC(═O)OR$^b$, —Y—C(═O)NR$^c$R$^d$, —Y—OC(═O)NR$^c$R$^d$, —Y—NR$^b$C(═O)NR$^c$R$^d$, —Y—NR$^b$C(═O)R$^a$, —Y—NR$^b$C(═O)OR$^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$(═O)OR$^b$, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three deuterium, oxo, halogen, —CN, —OH, —OMe, —S(═O)Me, —S(═O)$_2$Me, —NH$_2$, —S(═O)$_2$NH$_2$, —C(═O)Me, —C(═O)OH, —C(═O)OMe, $C_1$-$C_6$alkyl, $C_1$-$C_6$haloalkyl, $C_1$-$C_6$hydroxyalkyl, or $C_1$-$C_6$aminoalkyl; or two $R^A$ on the same carbon are taken together to form an oxo;

each Y is independently a bond, $C_1$-$C_6$alkylene, or $C_1$-$C_6$haloalkylene;

n is 0-4;

each $R^a$ is independently $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl);

wherein each alkyl, alkenyl, alkynyl, cycloalkyl, heterocycloalkyl, aryl, and heteroaryl is independently optionally substituted with one, two, or three deuterium, oxo, halogen, —CN, —OH, —OMe, —S(═O)Me, —S(═O)$_2$Me, —NH$_2$, —S(═O)$_2$NH$_2$, —C(═O)Me, —C(═O)OH, —C(═O)OMe, $C_1$-$C_6$alkyl, $C_1$-$C_6$haloalkyl, $C_1$-$C_6$hydroxyalkyl, or $C_1$-$C_6$aminoalkyl;

each $R^b$ is independently hydrogen, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one, two, or three deuterium, oxo, halogen, —CN, —OH, —OMe, —S(═O)Me, —S(═O)$_2$Me, —NH$_2$, —S(═O)$_2$NH$_2$, —C(═O)Me, —C(═O)OH, —C(═O)OMe, $C_1$-$C_6$alkyl, $C_1$-$C_6$haloalkyl, $C_1$-$C_6$hydroxyalkyl, or $C_1$-$C_6$aminoalkyl; and each $R^c$ and $R^d$ are independently hydrogen, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one, two, or three oxo, deuterium, halogen, —CN, —OH, —OMe, —S(═O)Me, —S(═O)$_2$Me, —NH$_2$, —S(═O)$_2$NH$_2$, —C(═O)Me, —C(═O)OH, —C(═O)OMe, $C_1$-$C_6$alkyl, $C_1$-$C_6$haloalkyl, $C_1$-$C_6$hydroxyalkyl, or $C_1$-$C_6$aminoalkyl;

or $R^c$ and $R^d$ are taken together with the atom to which they are attached to form a heterocycloalkyl optionally substituted with one, two, or three oxo, deuterium, halogen, —CN, —OH, —OMe, —S(═O)Me, —S(═O)$_2$Me, —NH$_2$, —S(═O)$_2$NH$_2$, —C(═O)Me, —C(═O)OH, —C(═O)OMe, $C_1$-$C_6$alkyl, $C_1$-$C_6$haloalkyl, $C_1$-$C_6$hydroxyalkyl, or $C_1$-$C_6$aminoalkyl;

provided that the compound of Formula (I) is not OH,

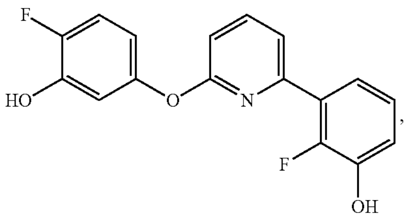

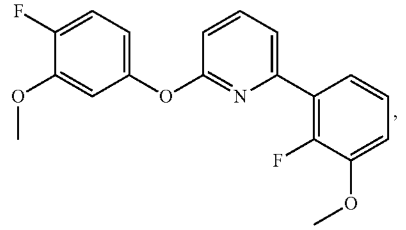

-continued

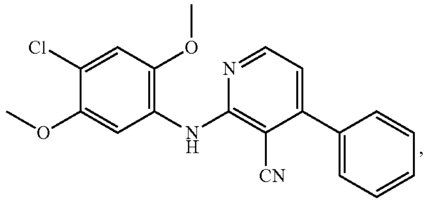

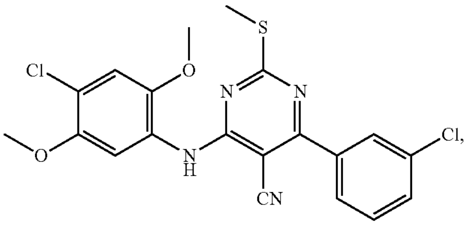

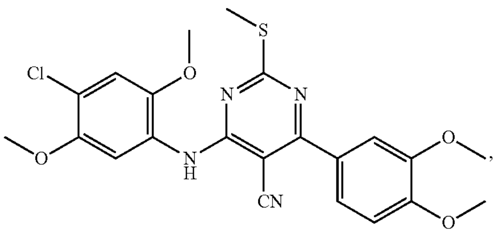

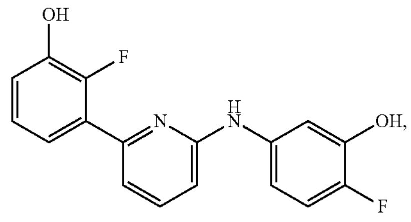

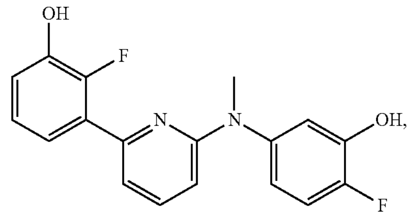

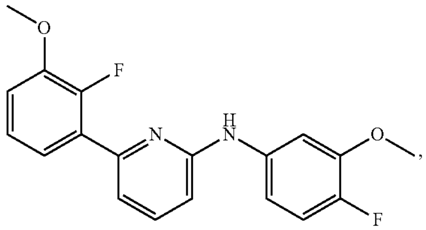

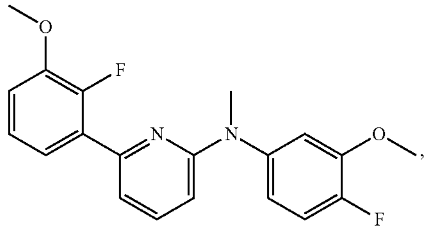

or

-continued

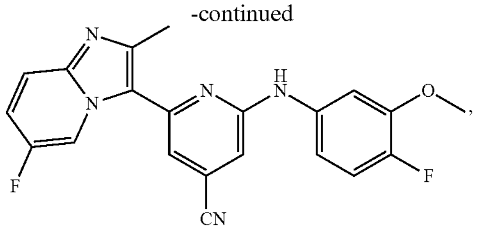

In some embodiments of a compound of Formula (I), or a pharmaceutically acceptable salt, solvate, or stereoisomer thereof, $R^1$ is fluoro. In some embodiments of a compound of Formula (I), or a pharmaceutically acceptable salt, solvate, or stereoisomer thereof, $R^1$ is fluoro or Chloro. In some embodiments of a compound of Formula (I), or a pharmaceutically acceptable salt, solvate, or stereoisomer thereof, $R^1$ is chloro.

In some embodiments of a compound of Formula (I), or a pharmaceutically acceptable salt, solvate, or stereoisomer thereof, $R^2$ is hydrogen or $C_1$-$C_6$alkyl. In some embodiments of a compound of Formula (I), or a pharmaceutically acceptable salt, solvate, or stereoisomer thereof, $R^2$ is hydrogen. In some embodiments of a compound of Formula (I), or a pharmaceutically acceptable salt, solvate, or stereoisomer thereof, $R^2$ is $C_1$-$C_6$alkyl.

In some embodiments of a compound of Formula (I), or a pharmaceutically acceptable salt, solvate, or stereoisomer thereof, each $R^3$ is independently hydrogen, deuterium, halogen, —CN, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$hydroxyalkyl, or $C_1$-$C_6$aminoalkyl. In some embodiments of a compound of Formula (I), or a pharmaceutically acceptable salt, solvate, or stereoisomer thereof, each $R^3$ is independently hydrogen, deuterium, halogen, —OH, —$OR^a$, $C_1$-$C_6$alkyl, or $C_1$-$C_6$haloalkyl. In some embodiments of a compound of Formula (I), or a pharmaceutically acceptable salt, solvate, or stereoisomer thereof, each $R^3$ is independently hydrogen, deuterium, halogen, or $C_1$-$C_6$alkyl. In some embodiments of a compound of Formula (I), or a pharmaceutically acceptable salt, solvate, or stereoisomer thereof, each $R^3$ is hydrogen.

In some embodiments of a compound of Formula (I), or a pharmaceutically acceptable salt, solvate, or stereoisomer thereof, $L^1$ is —O—.

In some embodiments of a compound of Formula (I), or a pharmaceutically acceptable salt, solvate, or stereoisomer thereof, $L^1$ is —S—.

In some embodiments of a compound of Formula (I), or a pharmaceutically acceptable salt, solvate, or stereoisomer thereof, $L^1$ is —S(═O)—.

In some embodiments of a compound of Formula (I), or a pharmaceutically acceptable salt, solvate, or stereoisomer thereof, $L^1$ is —$S(=O)_2$—.

In some embodiments of a compound of Formula (I), or a pharmaceutically acceptable salt, solvate, or stereoisomer thereof, $L^1$ is —$NR^L$—.

In some embodiments of a compound of Formula (I), or a pharmaceutically acceptable salt, solvate, or stereoisomer thereof, $R^{L1}$ is hydrogen or $C_1$-$C_6$alkyl. In some embodiments of a compound of Formula (I), or a pharmaceutically acceptable salt, solvate, or stereoisomer thereof, $R^{L1}$ is hydrogen. In some embodiments of a compound of Formula (I), or a pharmaceutically acceptable salt, solvate, or stereoisomer thereof, $R^{L1}$ is $C_1$-$C_6$alkyl.

In some embodiments of a compound of Formula (I), or a pharmaceutically acceptable salt, solvate, or stereoisomer thereof, $X^1$ is N.

In some embodiments of a compound of Formula (I), or a pharmaceutically acceptable salt, solvate, or stereoisomer thereof, $X^1$ is C—$R^{X1}$.

In some embodiments of a compound of Formula (I), or a pharmaceutically acceptable salt, solvate, or stereoisomer thereof, $R^{X1}$ is deuterium, halogen, —CN, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$hydroxyalkyl, or $C_1$-$C_6$aminoalkyl. In some embodiments of a compound of Formula (I), or a pharmaceutically acceptable salt, solvate, or stereoisomer thereof, $R^{X1}$ is deuterium, halogen, —CN, —OH, —$OR^a$, or $C_1$-$C_6$alkyl. In some embodiments of a compound of Formula (I), or a pharmaceutically acceptable salt, solvate, or stereoisomer thereof, $R^{X1}$ is —CN.

In some embodiments of a compound of Formula (I), or a pharmaceutically acceptable salt, solvate, or stereoisomer thereof, $X^2$ is N.

In some embodiments of a compound of Formula (I), or a pharmaceutically acceptable salt, solvate, or stereoisomer thereof, $X^2$ is C—$R^{X2}$.

In some embodiments of a compound of Formula (I), or a pharmaceutically acceptable salt, solvate, or stereoisomer thereof, $R^{X2}$ is hydrogen, deuterium, halogen, —CN, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$hydroxyalkyl, or $C_1$-$C_6$aminoalkyl. In some embodiments of a compound of Formula (I), or a pharmaceutically acceptable salt, solvate, or stereoisomer thereof, $R^{X2}$ is hydrogen, deuterium, halogen, —CN, —OH, —$OR^a$, or $C_1$-$C_6$alkyl. In some embodiments of a compound of Formula (I), or a pharmaceutically acceptable salt, solvate, or stereoisomer thereof, $R^{X2}$ is hydrogen. In some embodiments of a compound of Formula (I), or a pharmaceutically acceptable salt, solvate, or stereoisomer thereof, $R^{X2}$ is —CN.

In some embodiments of a compound of Formula (I), or a pharmaceutically acceptable salt, solvate, or stereoisomer thereof, $X^3$ is N.

In some embodiments of a compound of Formula (I), or a pharmaceutically acceptable salt, solvate, or stereoisomer thereof, $X^3$ is C—$R^{X3}$.

In some embodiments of a compound of Formula (I), or a pharmaceutically acceptable salt, solvate, or stereoisomer thereof, $R^{X3}$ is hydrogen, deuterium, halogen, —CN, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$hydroxyalkyl, or $C_1$-$C_6$aminoalkyl. In some embodiments of a compound of Formula (I), or a pharmaceutically acceptable salt, solvate, or stereoisomer thereof, $R^{X3}$ is hydrogen, deuterium, halogen, —CN, —OH, —$OR^a$, or $C_1$-$C_6$alkyl. In some embodiments of a compound of Formula (I), or a pharmaceutically acceptable salt, solvate, or stereoisomer thereof, $R^{X3}$ is hydrogen. In some embodiments of a compound of Formula (I), or a pharmaceutically acceptable salt, solvate, or stereoisomer thereof, $R^{X3}$ is —CN.

In some embodiments of a compound of Formula (I), or a pharmaceutically acceptable salt, solvate, or stereoisomer thereof, $X^4$ is N.

In some embodiments of a compound of Formula (I), or a pharmaceutically acceptable salt, solvate, or stereoisomer thereof, $X^4$ is C—$R^{X4}$.

In some embodiments of a compound of Formula (I), or a pharmaceutically acceptable salt, solvate, or stereoisomer thereof, $R^{X4}$ is hydrogen, deuterium, halogen, —CN, —OH, —$OR^a$, —$NR^cR^d$, —C(═O)$R^a$, —C(═O)$OR^b$, —C(═O)

$NR^cR^d$, $C_1$-$C_6$alkyl, $C_1$-$C_6$haloalkyl, $C_1$-$C_6$hydroxyalkyl, or $C_1$-$C_6$aminoalkyl. In some embodiments of a compound of Formula (I), or a pharmaceutically acceptable salt, solvate, or stereoisomer thereof, $R^{X4}$ is hydrogen, deuterium, halogen, —CN, —OH, —$OR^a$, or $C_1$-$C_6$alkyl. In some embodiments of a compound of Formula (I), or a pharmaceutically acceptable salt, solvate, or stereoisomer thereof, $R^{X4}$ is hydrogen. In some embodiments of a compound of Formula (I), or a pharmaceutically acceptable salt, solvate, or stereoisomer thereof, $R^{X4}$ is —CN.

In some embodiments of a compound of Formula (I), or a pharmaceutically acceptable salt, solvate, or stereoisomer thereof, $X^1$ is N and $X^2$ is N. In some embodiments of a compound of Formula (I), or a pharmaceutically acceptable salt, solvate, or stereoisomer thereof, $X^1$ is N and $X^3$ is N. In some embodiments of a compound of Formula (I), or a pharmaceutically acceptable salt, solvate, or stereoisomer thereof, $X^1$ is N and $X^4$ is N.

In some embodiments of a compound of Formula (I), or a pharmaceutically acceptable salt, solvate, or stereoisomer thereof, $X^1$ is C—$R^{X1}$ and $X^2$ is N. In some embodiments of a compound of Formula (I), or a pharmaceutically acceptable salt, solvate, or stereoisomer thereof, $X^1$ is C—$R^{X1}$ and $X^3$ is N. In some embodiments of a compound of Formula (I), or a pharmaceutically acceptable salt, solvate, or stereoisomer thereof, $X^1$ is C—$R^{X1}$ and $X^4$ is N.

In some embodiments of a compound of Formula (I), or a pharmaceutically acceptable salt, solvate, or stereoisomer thereof, Ring A is cycloalkyl or heterocycloalkyl. In some embodiments of a compound of Formula (I), or a pharmaceutically acceptable salt, solvate, or stereoisomer thereof, Ring A is cycloalkyl. In some embodiments of a compound of Formula (I), or a pharmaceutically acceptable salt, solvate, or stereoisomer thereof, Ring A is heterocycloalkyl.

In some embodiments of a compound of Formula (I), or a pharmaceutically acceptable salt, solvate, or stereoisomer thereof, Ring A is aryl or heteroaryl. In some embodiments of a compound of Formula (I), or a pharmaceutically acceptable salt, solvate, or stereoisomer thereof, Ring A is aryl. In some embodiments of a compound of Formula (I), or a pharmaceutically acceptable salt, solvate, or stereoisomer thereof, Ring A is heteroaryl. In some embodiments of a compound of Formula (I), or a pharmaceutically acceptable salt, solvate, or stereoisomer thereof, Ring A is phenyl, pyridyl, pyrimidyl, pyrazinyl, pyridazinyl, thiazolyl, thiophenyl, oxazolyl, imidazolyl, pyrazolyl, triazolyl, tetrazolyl, pyrrolyl, indazolyl, benzimidazolyl, benzoxazolyl, benzothiazolyl, benzothiophenyl, dihydrobenzoxazinyl, dihydrobenzimidazolyl, 1,3-dihydrobenzoisothiazolyl, benzodioxolyl, or dihydropyridinyl. In some embodiments of a compound of Formula (I), or a pharmaceutically acceptable salt, solvate, or stereoisomer thereof, Ring A is phenyl, thiophenyl, oxazolyl, imidazolyl, indazolyl, benzimidazolyl, benzoxazolyl, benzothiazolyl, benzothiophenyl, dihydrobenzoxazinyl, dihydrobenzimidazolyl, 1,3-dihydrobenzoisothiazolyl, benzodioxolyl, or dihydropyridinyl. In some embodiments of a compound of Formula (I), or a pharmaceutically acceptable salt, solvate, or stereoisomer thereof, Ring A is phenyl.

In some embodiments of a compound of Formula (I), or a pharmaceutically acceptable salt, solvate, or stereoisomer thereof, each $R^A$ is independently deuterium, halogen, —Y—CN, —Y—OH, —Y—$OR^a$, —Y—SH, —Y—$SR^a$, —Y—S(=O)$R^a$, —Y—S(=O)$_2R^a$, —Y—$NO_2$, —Y—$NR^cR^d$, —Y—$NR^b$S(=O)$_2R^a$, —Y—$NR^b$S(=O)$_2NR^cR^d$, —Y—S(=O)$_2NR^cR^d$, —Y—C(=O)$R^a$, —Y—OC(=O)$R^a$, —Y—C(=O)$OR^b$, —Y—OC(=O)$OR^b$, —Y—C(=O)$NR^cR^d$, —Y—OC(=O)$NR^cR^d$, —Y—$NR^b$C(=O)$NR^cR^d$, —Y—$NR^b$C(=O)$R^a$, —Y—$NR^b$C(=O)$OR^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$C(=O)$OR^b$, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three deuterium, oxo, halogen, —CN, —OH, —OMe, —S(=O)Me, —S(=O)$_2$Me, —$NH_2$, —S(=O)$_2NH_2$, —C(=O)Me, —C(=O)OH, —C(=O)OMe, $C_1$-$C_6$alkyl, $C_1$-$C_6$haloalkyl, $C_1$-$C_6$hydroxyalkyl, or $C_1$-$C_6$aminoalkyl; or two $R^A$ on the same carbon are taken together to form an oxo.

In some embodiments of a compound of Formula (I), or a pharmaceutically acceptable salt, solvate, or stereoisomer thereof, each $R^A$ is independently deuterium, halogen, —Y—CN, —Y—OH, —Y—$OR^a$, —Y—S(=O)$_2R^a$, —Y—$NR^cR^d$, —Y—$NR^b$S(=O)$_2R^a$, —Y—$NR^b$S(=O)$_2NR^cR^d$, —Y—S(=O)$_2NR^cR^d$, —Y—C(=O)$R^a$, —Y—C(=O)$OR^b$, —Y—C(=O)$NR^cR^d$, —Y—$NR^b$C(=O)$R^a$, $C_1$-$C_6$alkyl, or $C_1$-$C_6$haloalkyl; wherein each alkyl is independently optionally substituted with one, two, or three deuterium, oxo, halogen, —CN, —OH, —OMe, —S(=O)Me, —S(=O)$_2$Me, —$NH_2$, —S(=O)$_2NH_2$, —C(=O)Me, —C(=O)OH, —C(=O)OMe, $C_1$-$C_6$alkyl, $C_1$-$C_6$haloalkyl, $C_1$-$C_6$hydroxyalkyl, or $C_1$-$C_6$aminoalkyl; or two $R^A$ on the same carbon are taken together to form an oxo.

In some embodiments of a compound of Formula (I), or a pharmaceutically acceptable salt, solvate, or stereoisomer thereof, each $R^A$ is independently deuterium, halogen, —Y—CN, —Y—OH, —Y—$OR^a$, —Y—S(=O)$_2R^a$, —Y—$NR^cR^d$, —Y—$NR^b$S(=O)$_2R^a$, —Y—$NR^b$S(=O)$_2NR^cR^d$, —Y—S(=O)$_2NR^cR^d$, —Y—C(=O)$R^a$, —Y—C(=O)$OR^b$, —Y—C(=O)$NR^cR^d$, —Y—$NR^b$C(=O)$R^a$, $C_1$-$C_6$alkyl, or $C_1$-$C_6$haloalkyl; or two $R^A$ on the same carbon are taken together to form an oxo.

In some embodiments of a compound of Formula (I), or a pharmaceutically acceptable salt, solvate, or stereoisomer thereof, each $R^A$ is independently halogen or —Y—OH.

In some embodiments of a compound of Formula (I), or a pharmaceutically acceptable salt, solvate, or stereoisomer thereof, each $R^A$ is independently —Y—$NR^cR^d$.

In some embodiments of a compound of Formula (I), or a pharmaceutically acceptable salt, solvate, or stereoisomer thereof, each $R^A$ is independently deuterium, halogen, —Y—CN, —Y—$OR^a$, —Y—S(=O)$_2R^a$, —Y—$NR^cR^d$, —Y—$NR^b$S(=O)$_2R^a$, —Y—$NR^b$S(=O)$_2NR^cR^d$, —Y—S(=O)$_2NR^cR^d$, —Y—C(=O)$R^a$, —Y—C(=O)$OR^b$, —Y—C(=O)$NR^cR^d$, —Y—$NR^b$C(=O)$R^a$, $C_1$-$C_6$alkyl, or $C_1$-$C_6$haloalkyl; or two $R^A$ on the same carbon are taken together to form an oxo.

In some embodiments of a compound of Formula (I), or a pharmaceutically acceptable salt, solvate, or stereoisomer thereof, each $R^A$ is independently deuterium, —Y—CN, —Y—OH, —Y—$OR^a$, —Y—S(=O)$_2R^a$, —Y—$NR^cR^d$, —Y—$NR^b$S(=O)$_2R^a$, —Y—$NR^b$S(=O)$_2NR^cR^d$, —Y—S(=O)$_2NR^cR^d$, —Y—C(=O)$R^a$, —Y—C(=O)$OR^b$, —Y—C(=O)$NR^cR^d$, —Y—$NR^b$C(=O)$R^a$, $C_1$-$C_6$alkyl, or $C_1$-$C_6$haloalkyl; or two $R^A$ on the same carbon are taken together to form an oxo.

In some embodiments of a compound of Formula (I), or a pharmaceutically acceptable salt, solvate, or stereoisomer thereof, each Y is independently a bond or $C_1$-$C_6$alkylene. In some embodiments of a compound of Formula (I), or a pharmaceutically acceptable salt, solvate, or stereoisomer thereof, each Y is independently a bond or $CH_2$. In some embodiments of a compound of Formula (I), or a pharmaceutically acceptable salt, solvate, or stereoisomer thereof, each Y is a bond. In some embodiments of a compound of Formula (I), or a pharmaceutically acceptable salt, solvate, or stereoisomer thereof, each Y is $CH_2$.

In some embodiments of a compound of Formula (I), or a pharmaceutically acceptable salt, solvate, or stereoisomer thereof, n is 1-3. In some embodiments of a compound of Formula (I), or a pharmaceutically acceptable salt, solvate, or stereoisomer thereof, n is 2 or 3. In some embodiments of a compound of Formula (I), or a pharmaceutically acceptable salt, solvate, or stereoisomer thereof, n is 0 or 1. In some embodiments of a compound of Formula (I), or a pharmaceutically acceptable salt, solvate, or stereoisomer thereof, n is 0-2. In some embodiments of a compound of Formula (I), or a pharmaceutically acceptable salt, solvate, or stereoisomer thereof, n is 1 or 2. In some embodiments of a compound of Formula (I), or a pharmaceutically acceptable salt, solvate, or stereoisomer thereof, n is 1. In some embodiments of a compound of Formula (I), or a pharmaceutically acceptable salt, solvate, or stereoisomer thereof, n is 2. In some embodiments of a compound of Formula (I), or a pharmaceutically acceptable salt, solvate, or stereoisomer thereof, n is 3.

Also disclosed herein is a compound of Formula (B), or a pharmaceutically acceptable salt, solvate, or stereoisomer thereof:

(B)

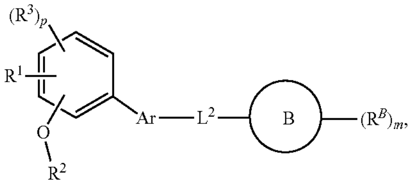

wherein:

$R^1$ is halogen;

$R^2$ is hydrogen, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6C(=O)OR^b$, cycloalkyl, heterocycloalkyl, aryl, or heteroaryl;

each $R^3$ is independently hydrogen, deuterium, halogen, —CN, —OH, —$OR^a$, —SH, —$SR^a$, —$S(=O)R^a$, —$S(=O)_2R^a$, —$NO_2$, —$NR^cR^d$, —$NHS(=O)_2R^a$, —$S(=O)_2NR^cR^d$, —$C(=O)R^a$, —$OC(=O)R^a$, —$C(=O)OR^b$, —$OC(=O)OR^b$, —$C(=O)NR^cR^d$, —$OC(=O)NR^cR^d$, —$NR^bC(=O)NR^cR^d$, —$NR^bC(=O)R^a$, —$NR^bC(=O)OR^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6C(=O)OR^b$, cycloalkyl, heterocycloalkyl, aryl, or heteroaryl; p is 1-3;

$L^2$ is —O—, —S—, —S(=O)—, —$S(=O)_2$—, or —$NR^{L1}$—;

$R^{L2}$ is hydrogen, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6C(=O)OR^b$, cycloalkyl, heterocycloalkyl, aryl, or heteroaryl;

Ar is

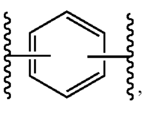, 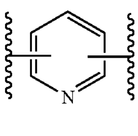, 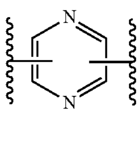,

-continued

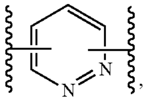, 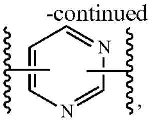, or 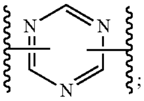;

each optionally substituted with one, two, or three deuterium, halogen, —CN, —OH, —$OR^a$, —SH, —$SR^a$, —$S(=O)R^a$, —$S(=O)_2R^a$, —$NO_2$, —$NR^cR^d$, —$NHS(=O)_2R^a$, —$S(=O)_2NR^cR^d$, —$C(=O)R^a$, —$OC(=O)R^a$, —$C(=O)OR^b$, —$OC(=O)OR^b$, —$C(=O)NR^cR^d$, —$OC(=O)NR^cR^d$, —$NR^bC(=O)NR^cR^d$, —$NR^bC(=O)R^a$, —$NR^bC(=O)OR^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, or —$C_1$-$C_6C(=O)OR^b$;

Ring B is aryl, heteroaryl, cycloalkyl, or heterocycloalkyl;

each $R^B$ is independently deuterium, halogen, —Y—CN, —Y—OH, —Y—$OR^a$, —Y—SH, —Y—$SR^a$, —Y—$S(=O)R^a$, —Y—$S(=O)_2R^a$, —Y—$NO_2$, —Y—$NR^cR^d$, —Y—$NR^bS(=O)_2R^a$, —Y—$NR^bS(=O)_2NR^cR^d$, —Y—$S(=O)_2NR^cR^d$, —Y—$C(=O)R^a$, —Y—$OC(=O)R^a$, —Y—$C(=O)OR^b$, —Y—$OC(=O)OR^b$, —Y—$C(=O)NR^cR^d$, —Y—$OC(=O)NR^cR^d$, —Y—$NR^bC(=O)NR^cR^d$, —Y—$NR^bC(=O)R^a$, —Y—$NR^bC(=O)OR^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6(=O)OR^b$, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three deuterium, oxo, halogen, —CN, —OH, —OMe, —S(=O)Me, —$S(=O)_2$Me, —$NH_2$, —$S(=O)_2NH_2$, —C(=O)Me, —C(=O)OH, —C(=O)OMe, $C_1$-$C_6$alkyl, $C_1$-$C_6$haloalkyl, $C_1$-$C_6$hydroxyalkyl, or $C_1$-$C_6$aminoalkyl; or two $R^B$ on the same carbon are taken together to form an oxo;

each Y is independently a bond, $C_1$-$C_6$alkylene, or $C_1$-$C_6$haloalkylene;

n is 0-4;

each $R^a$ is independently $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one, two, or three deuterium, oxo, halogen, —CN, —OH, —OMe, —S(=O)Me, —$S(=O)_2$Me, —$NH_2$, —$S(=O)_2NH_2$, —C(=O)Me, —C(=O)OH, —C(=O)OMe, $C_1$-$C_6$alkyl, $C_1$-$C_6$haloalkyl, $C_1$-$C_6$hydroxyalkyl, or $C_1$-$C_6$aminoalkyl;

each $R^b$ is independently hydrogen, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one, two, or three deuterium, oxo, halogen, —CN, —OH, —OMe, —S(=O)Me, —$S(=O)_2$Me, —$NH_2$, —$S(=O)_2NH_2$, —C(=O)Me, —C(═O)OH, —C(═O)OMe, $C_1$-$C_6$alkyl, $C_1$-$C_6$haloalkyl, $C_1$-$C_6$hydroxyalkyl, or $C_1$-$C_6$aminoalkyl; and each $R^c$ and $R^d$ are independently hydrogen, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one, two, or three oxo, deuterium, halogen, —CN, —OH, —OMe, —S(═O)Me, —S(═O)$_2$Me, —NH$_2$, —S(═O)$_2$NH$_2$, —C(═O)Me, —C(═O)OH, —C(═O)OMe, $C_1$-$C_6$alkyl, $C_1$-$C_6$haloalkyl, $C_1$-$C_6$hydroxyalkyl, or $C_1$-$C_6$aminoalkyl;

or $R^c$ and $R^d$ are taken together with the atom to which they are attached to form a heterocycloalkyl optionally substituted with one, two, or three oxo, deuterium, halogen, —CN, —OH, —OMe, —S(═O)Me, —S(═O)$_2$Me, —NH$_2$, —S(═O)$_2$NH$_2$, —C(═O)Me, —C(═O)OH, —C(═O)OMe, $C_1$-$C_6$alkyl, $C_1$-$C_6$haloalkyl, $C_1$-$C_6$hydroxyalkyl, or $C_1$-$C_6$aminoalkyl.

Also disclosed herein is a compound of Formula (II), or a pharmaceutically acceptable salt, solvate, or stereoisomer thereof:

(II)

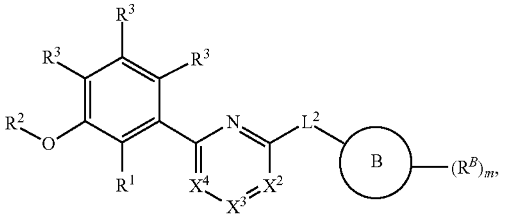

wherein:

$R^1$ is halogen;

$R^2$ is hydrogen, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$C(═O)OR$^b$, cycloalkyl, heterocycloalkyl, aryl, or heteroaryl;

each $R^3$ is independently hydrogen, deuterium, halogen, —CN, —OH, —OR$^a$, —SH, —SR$^a$, —S(═O)R$^a$, —S(═O)$_2$R$^a$, —NO$_2$, —NR$^c$R$^d$, —NHS(═O)$_2$R$^a$, —S(═O)$_2$NR$^c$R$^d$, —C(═O)R$^a$, —OC(═O)R$^a$, —C(═O)OR$^b$, —OC(═O)OR$^b$, —C(═O)NR$^c$R$^d$, —OC(═O)NR$^c$R$^d$, —NR$^b$C(═O)NR$^c$R$^d$, —NR$^b$C(═O)R$^a$, —NR$^b$C(═O)OR$^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$C(═O)OR$^b$, cycloalkyl, heterocycloalkyl, aryl, or heteroaryl;

$L^2$ is —O—, —S—, —S(═O)—, or —S(═O)$_2$—;

$X^2$ is N or C—R$^{X2}$;

$R^{X2}$ is hydrogen, deuterium, halogen, —CN, —OH, —OR$^a$, —SH, —SR$^a$, —S(═O)R$^a$, —S(═O)$_2$R$^a$, —NO$_2$, —NR$^c$R$^d$, —NHS(═O)$_2$R$^a$, —S(═O)$_2$NR$^c$R$^d$, —C(═O)R$^a$, —OC(═O)R$^a$, —C(═O)OR$^b$, —OC(═O)OR$^b$, —C(═O)NR$^c$R$^d$, —OC(═O)NR$^c$R$^d$, —NR$^b$C(═O)NR$^c$R$^d$, —NR$^b$C(═O)R$^a$, —NR$^b$C(═O)OR$^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$(═O)OR$^b$, cycloalkyl, heterocycloalkyl, aryl, or heteroaryl;

$X^3$ is N or C—R$^{X3}$;

$R^{X3}$ is hydrogen, deuterium, halogen, —CN, —OH, —OR$^a$, —SH, —SR$^a$, —S(═O)R$^a$, —S(═O)$_2$R$^a$, —NO$_2$, —NR$^c$R$^d$, —NHS(═O)$_2$R$^a$, —S(═O)$_2$NR$^c$R$^d$, —C(═O)R$^a$, —OC(═O)R$^a$, —C(═O)OR$^b$, —OC(═O)OR$^b$, —C(═O)NR$^c$R$^d$, —OC(═O)NR$^c$R$^d$, —NR$^b$C(═O)NR$^c$R$^d$, —NR$^b$C(═O)R$^a$, —NR$^b$C(═O)OR$^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$C(═O)OR$^b$, cycloalkyl, heterocycloalkyl, aryl, or heteroaryl;

$X^4$ is N or C—R$^{X4}$;

$R^{X4}$ is hydrogen, deuterium, halogen, —CN, —OH, —OR$^a$, —SH, —SR$^a$, —S(═O)R$^a$, —S(═O)$_2$R$^a$, —NO$_2$, —NR$^c$R$^d$, —NHS(═O)$_2$R$^a$, —S(═O)$_2$NR$^c$R$^d$, —C(═O)R$^a$, —OC(═O)R$^a$, —C(═O)OR$^b$, —OC(═O)OR$^b$, —C(═O)NR$^c$R$^d$, —OC(═O)NR$^c$R$^d$, —NR$^b$C(═O)NR$^c$R$^d$, —NR$^b$C(═O)R$^a$, —NR$^b$C(═O)OR$^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$C(═O)OR$^b$, cycloalkyl, heterocycloalkyl, aryl, or heteroaryl;

Ring B is aryl, heteroaryl, cycloalkyl, or heterocycloalkyl;

each $R^B$ is independently deuterium, halogen, —Y—CN, —Y—OH, —Y—OR$^a$, —Y—SH, —Y—SR$^a$, —Y—S(═O)R$^a$, —Y—S(═O)$_2$R$^a$, —Y—NO$_2$, —Y—NR$^c$R$^d$, —Y—NR$^b$S(═O)$_2$R$^a$, —Y—NR$^b$S(═O)$_2$NR$^c$R$^d$, —Y—S(═O)$_2$NR$^c$R$^d$, —Y—C(═O)R$^a$, —Y—OC(═O)R$^a$, —Y—C(═O)OR$^b$, —Y—OC(═O)OR$^b$, —Y—C(═O)NR$^c$R$^d$, —Y—OC(═O)NR$^c$R$^d$, —Y—NR$^b$C(═O)NR$^c$R$^d$, —Y—NR$^b$C(═O)R$^a$, —Y—NR$^b$C(═O)OR$^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$(═O)OR$^b$, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three deuterium, oxo, halogen, —CN, —OH, —OMe, —S(═O)Me, —S(═O)$_2$Me, —NH$_2$, —S(═O)$_2$NH$_2$, —C(═O)Me, —C(═O)OH, —C(═O)OMe, $C_1$-$C_6$alkyl, $C_1$-$C_6$haloalkyl, $C_1$-$C_6$hydroxyalkyl, or $C_1$-$C_6$aminoalkyl; or two $R^B$ on the same carbon are taken together to form an oxo;

each Y is independently a bond, $C_1$-$C_6$alkylene, or $C_1$-$C_6$haloalkylene;

m is 0-4;

each $R^a$ is independently $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one, two, or three deuterium, oxo, halogen, —CN, —OH, —OMe, —S(═O)Me, —S(═O)$_2$Me, —NH$_2$, —S(═O)$_2$NH$_2$, —C(═O)Me, —C(═O)OH, —C(═O)OMe, $C_1$-$C_6$alkyl, $C_1$-$C_6$haloalkyl, $C_1$-$C_6$hydroxyalkyl, or $C_1$-$C_6$aminoalkyl;

each $R^b$ is independently hydrogen, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one, two, or three deuterium, oxo, halogen, —CN, —OH, —OMe, —S(═O)Me, —S(═O)$_2$Me, —NH$_2$, —S(═O)$_2$NH$_2$, —C(═O)Me, —C(═O)OH, —C(═O)OMe, $C_1$-$C_6$alkyl, $C_1$-$C_6$haloalkyl, $C_1$-$C_6$hydroxyalkyl, or $C_1$-$C_6$aminoalkyl; and each $R^c$ and $R^d$ are independently hydrogen, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one, two, or three oxo, deuterium, halogen, —CN, —OH, —OMe, —S(═O)Me, —S(═O)$_2$Me, —NH$_2$, —S(═O)$_2$NH$_2$, —C(═O)Me, —C(═O)OH, —C(═O)OMe, $C_1$-$C_6$alkyl, $C_1$-$C_6$haloalkyl, $C_1$-$C_6$hydroxyalkyl, or $C_1$-$C_6$aminoalkyl;

or $R^c$ and $R^d$ are taken together with the atom to which they are attached to form a heterocycloalkyl optionally substituted with one, two, or three oxo, deuterium, halogen, —CN, —OH, —OMe, —S(═O)Me, —S(═O)$_2$Me, —NH$_2$, —S(═O)$_2$NH$_2$, —C(═O)Me, —C(═O)OH, —C(═O)OMe, $C_1$-$C_6$alkyl, $C_1$-$C_6$haloalkyl, $C_1$-$C_6$hydroxyalkyl, or $C_1$-$C_6$aminoalkyl.

Also disclosed herein is a compound of Formula (II), or a pharmaceutically acceptable salt, solvate, or stereoisomer thereof:

(II)

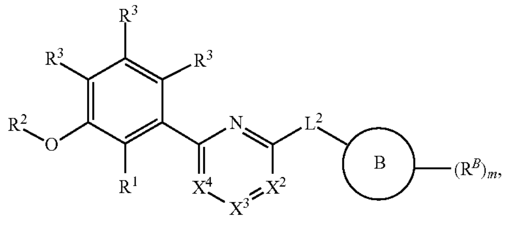

wherein:

$R^1$ is halogen;

$R^2$ is hydrogen, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$C(═O)OR$^b$, cycloalkyl, heterocycloalkyl, aryl, or heteroaryl;

each $R^3$ is independently hydrogen, deuterium, halogen, —CN, —OH, —OR$^a$, —SH, —SR$^a$, —S(═O)R$^a$, —S(═O)$_2$R$^a$, —NO$_2$, —NR$^c$R$^d$, —NHS(═O)$_2$R$^a$, —S(═O)$_2$NR$^c$R$^d$, —C(═O)R$^a$, —OC(═O)R$^a$, —C(═O)OR$^b$, —OC(═O)OR$^b$, —C(═O)NR$^c$R$^d$, —OC(═O)NR$^c$R$^d$, —NR$^b$C(═O)NR$^c$R$^d$, —NR$^b$C(═O)R$^a$, —NR$^b$C(═O)OR$^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$C(═O)OR$^b$, cycloalkyl, heterocycloalkyl, aryl, or heteroaryl;

$L^2$ is —O—, —S—, —S(═O)—, or —S(═O)$_2$—;

$X^2$ is N or C—R$^{X2}$;

$R^{X2}$ is hydrogen, deuterium, halogen, —CN, —OH, —OR$^a$, —SH, —SR$^a$, —S(═O)R$^a$, —S(═O)$_2$R$^a$, —NO$_2$, —NR$^c$R$^d$, —NHS(═O)$_2$R$^a$, —S(═O)$_2$NR$^c$R$^d$, —C(═O)R$^a$, —OC(═O)R$^a$, —C(═O)OR$^b$, —OC(═O)OR$^b$, —C(═O)NR$^c$R$^d$, —OC(═O)NR$^c$R$^d$, —NR$^b$C(═O)NR$^c$R$^d$, —NR$^b$C(═O)R$^a$, —NR$^b$C(═O)OR$^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$(═O)OR$^b$, cycloalkyl, heterocycloalkyl, aryl, or heteroaryl;

$X^3$ is N or C—R$^{X3}$;

$R^{X3}$ is hydrogen, deuterium, halogen, —CN, —OH, —OR$^a$, —SH, —SR$^a$, —S(═O)R$^a$, —S(═O)$_2$R$^a$, —NO$_2$, —NR$^c$R$^d$, —NHS(═O)$_2$R$^a$, —S(═O)$_2$NR$^c$R$^d$, —C(═O)R$^a$, —OC(═O)R$^a$, —C(═O)OR$^b$, —OC(═O)OR$^b$, —C(═O)NR$^c$R$^d$, —OC(═O)NR$^c$R$^d$, —NR$^b$C(═O)NR$^c$R$^d$, —NR$^b$C(═O)R$^a$, —NR$^b$C(═O)OR$^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$C(═O)OR$^b$, cycloalkyl, heterocycloalkyl, aryl, or heteroaryl;

$X^4$ is N or C—R$^{X4}$;

$R^{X4}$ is hydrogen, deuterium, halogen, —CN, —OH, —OR$^a$, —SH, —SR$^a$, —S(═O)R$^a$, —S(═O)$_2$R$^a$, —NO$_2$, —NR$^c$R$^d$, —NHS(═O)$_2$R$^a$, —S(═O)$_2$NR$^c$R$^d$, —C(═O)R$^a$, —OC(═O)R$^a$, —C(═O)OR$^b$, —OC(═O)OR$^b$, —C(═O)NR$^c$R$^d$, —OC(═O)NR$^c$R$^d$, —NR$^b$C(═O)NR$^c$R$^d$, —NR$^b$C(═O)R$^a$, —NR$^b$C(═O)OR$^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$C(═O)OR$^b$, cycloalkyl, heterocycloalkyl, aryl, or heteroaryl;

Ring B is aryl, heteroaryl, cycloalkyl, or heterocycloalkyl;

each $R^B$ is independently deuterium, halogen, —Y—CN, —Y—OH, —Y—OR$^a$, —Y—SH, —Y—SR$^a$, —Y—S(═O)R$^a$, —Y—S(═O)$_2$R$^a$, —Y—NO$_2$, —Y—NR$^c$R$^d$, —Y—NR$^b$S(═O)$_2$R$^a$, —Y—NR$^b$S(═O)$_2$NR$^c$R$^d$, —Y—S(═O)$_2$NR$^c$R$^d$, —Y—C(═O)R$^a$, —Y—OC(═O)R$^a$, —Y—C(═O)OR$^b$, —Y—OC(═O)OR$^b$, —Y—C(═O)NR$^c$R$^d$, —Y—OC(═O)NR$^c$R$^d$, —Y—NR$^b$C(═O)NR$^c$R$^d$, —Y—NR$^b$C(═O)R$^a$, —Y—NR$^b$C(═O)OR$^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$(═O)OR$^b$, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three deuterium, oxo, halogen, —CN, —OH, —OMe, —S(═O)Me, —S(═O)$_2$Me, —NH$_2$, —S(═O)$_2$NH$_2$, —C(═O)Me, —C(═O)OH, —C(═O)OMe, $C_1$-$C_6$alkyl, $C_1$-$C_6$haloalkyl, $C_1$-$C_6$hydroxyalkyl, or $C_1$-$C_6$aminoalkyl; or two $R^B$ on the same carbon are taken together to form an oxo;

each Y is independently a bond, $C_1$-$C_6$alkylene, or $C_1$-$C_6$haloalkylene;

m is 0-4;

each $R^a$ is independently $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one, two, or three deuterium, oxo, halogen, —CN, —OH, —OMe, —S(═O)Me, —S(═O)$_2$Me, —NH$_2$, —S(═O)$_2$NH$_2$, —C(═O)Me, —C(═O)OH, —C(═O)OMe, $C_1$-$C_6$alkyl, $C_1$-$C_6$haloalkyl, $C_1$-$C_6$hydroxyalkyl, or $C_1$-$C_6$aminoalkyl;

each $R^b$ is independently hydrogen, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one, two, or three deuterium, oxo, halogen, —CN, —OH, —OMe, —S(═O)Me, —S(═O)$_2$Me, —NH$_2$, —S(═O)$_2$NH$_2$, —C(═O)Me, —C(═O)OH, —C(═O)OMe, $C_1$-$C_6$alkyl, $C_1$-$C_6$haloalkyl, $C_1$-$C_6$hydroxyalkyl, or $C_1$-$C_6$aminoalkyl; and each $R^c$ and $R^d$ are independently hydrogen, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one, two, or three oxo, deuterium, halogen, —CN, —OH, —OMe, —S(═O)Me, —S(═O)$_2$Me, —NH$_2$, —S(═O)$_2$NH$_2$, —C(═O)Me, —C(═O)OH, —C(═O)OMe, $C_1$-$C_6$alkyl, $C_1$-$C_6$haloalkyl, $C_1$-$C_6$hydroxyalkyl, or $C_1$-$C_6$aminoalkyl;

or $R^c$ and $R^d$ are taken together with the atom to which they are attached to form a heterocycloalkyl optionally substituted with one, two, or three oxo, deuterium, halogen, —CN, —OH, —OMe, —S(═O)Me, —S(═O)$_2$Me, —NH$_2$, —S(═O)$_2$NH$_2$, —C(═O)Me, —C(═O)OH, —C(═O)OMe, $C_1$-$C_6$alkyl, $C_1$-$C_6$haloalkyl, $C_1$-$C_6$hydroxyalkyl, or $C_1$-$C_6$aminoalkyl;

provided that the compound of Formula (II) is not

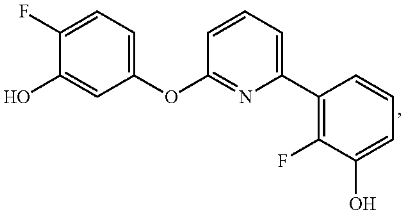

,

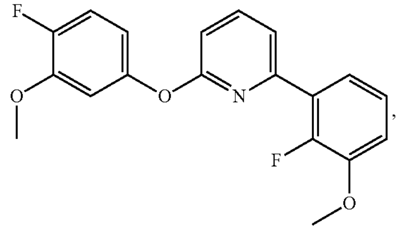

,

-continued

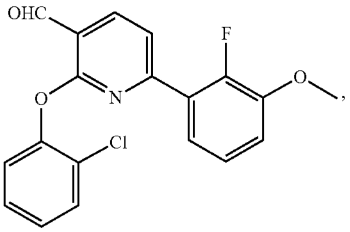

,

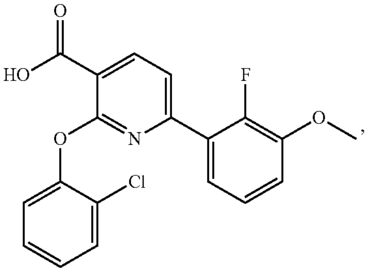

,

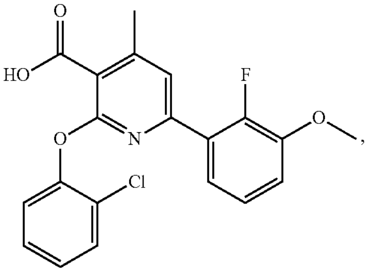

,

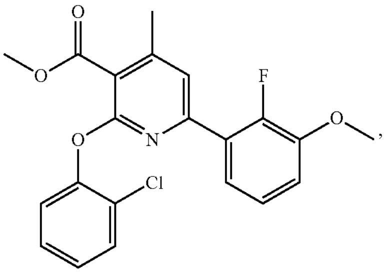

,

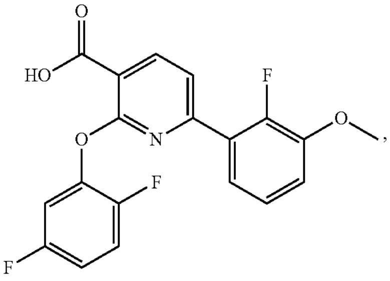

,

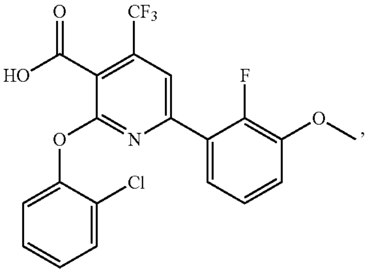

,

-continued

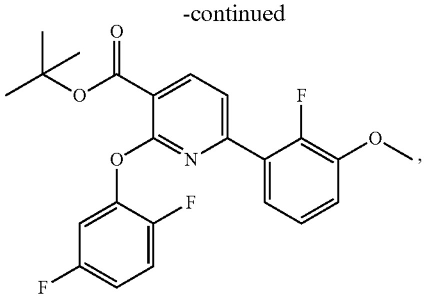

, or

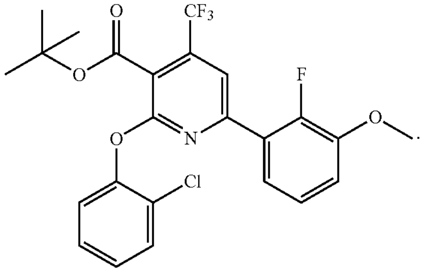

.

In some embodiments of a compound of Formula (II), or a pharmaceutically acceptable salt, solvate, or stereoisomer thereof, $R^1$ is fluoro. In some embodiments of a compound of Formula (II), or a pharmaceutically acceptable salt, solvate, or stereoisomer thereof, $R^1$ is fluoro or Chloro. In some embodiments of a compound of Formula (II), or a pharmaceutically acceptable salt, solvate, or stereoisomer thereof, $R^1$ is chloro.

In some embodiments of a compound of Formula (II), or a pharmaceutically acceptable salt, solvate, or stereoisomer thereof, $R^2$ is hydrogen or $C_1$-$C_6$alkyl. In some embodiments of a compound of Formula (II), or a pharmaceutically acceptable salt, solvate, or stereoisomer thereof, $R^2$ is hydrogen. In some embodiments of a compound of Formula (II), or a pharmaceutically acceptable salt, solvate, or stereoisomer thereof, $R^2$ is $C_1$-$C_6$alkyl.

In some embodiments of a compound of Formula (II), or a pharmaceutically acceptable salt, solvate, or stereoisomer thereof, each $R^3$ is independently hydrogen, deuterium, halogen, —CN, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$hydroxyalkyl, or $C_1$-$C_6$aminoalkyl. In some embodiments of a compound of Formula (II), or a pharmaceutically acceptable salt, solvate, or stereoisomer thereof, each $R^3$ is independently hydrogen, deuterium, halogen, —OH, —$OR^a$, $C_1$-$C_6$alkyl, or $C_1$-$C_6$haloalkyl. In some embodiments of a compound of Formula (II), or a pharmaceutically acceptable salt, solvate, or stereoisomer thereof, each $R^3$ is independently hydrogen, deuterium, halogen, or $C_1$-$C_6$alkyl. In some embodiments of a compound of Formula (II), or a pharmaceutically acceptable salt, solvate, or stereoisomer thereof, each $R^3$ is hydrogen.

In some embodiments of a compound of Formula (II), or a pharmaceutically acceptable salt, solvate, or stereoisomer thereof, $L^2$ is —O—.

In some embodiments of a compound of Formula (II), or a pharmaceutically acceptable salt, solvate, or stereoisomer thereof, $L^2$ is —S—.

In some embodiments of a compound of Formula (II), or a pharmaceutically acceptable salt, solvate, or stereoisomer thereof, $L^2$ is —S(═O)—.

In some embodiments of a compound of Formula (II), or a pharmaceutically acceptable salt, solvate, or stereoisomer thereof, $L^2$ is —S(═O)$_2$—.

In some embodiments of a compound of Formula (II), or a pharmaceutically acceptable salt, solvate, or stereoisomer thereof, $X^2$ is N.

In some embodiments of a compound of Formula (II), or a pharmaceutically acceptable salt, solvate, or stereoisomer thereof, $X^2$ is C—$R^{X2}$.

In some embodiments of a compound of Formula (II), or a pharmaceutically acceptable salt, solvate, or stereoisomer thereof, $R^{X2}$ is hydrogen, deuterium, halogen, —CN, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$hydroxyalkyl, or $C_1$-$C_6$aminoalkyl. In some embodiments of a compound of Formula (II), or a pharmaceutically acceptable salt, solvate, or stereoisomer thereof, $R^{X2}$ is hydrogen, deuterium, halogen, —CN, —OH, —$OR^a$, or $C_1$-$C_6$alkyl. In some embodiments of a compound of Formula (II), or a pharmaceutically acceptable salt, solvate, or stereoisomer thereof, $R^{X2}$ is hydrogen. In some embodiments of a compound of Formula (II), or a pharmaceutically acceptable salt, solvate, or stereoisomer thereof, $R^{X2}$ is —CN.

In some embodiments of a compound of Formula (II), or a pharmaceutically acceptable salt, solvate, or stereoisomer thereof, $X^3$ is N.

In some embodiments of a compound of Formula (II), or a pharmaceutically acceptable salt, solvate, or stereoisomer thereof, $X^3$ is C—$R^{X3}$.

In some embodiments of a compound of Formula (II), or a pharmaceutically acceptable salt, solvate, or stereoisomer thereof, $R^{X3}$ is hydrogen, deuterium, halogen, —CN, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$hydroxyalkyl, or $C_1$-$C_6$aminoalkyl. In some embodiments of a compound of Formula (II), or a pharmaceutically acceptable salt, solvate, or stereoisomer thereof, $R^{X3}$ is hydrogen, deuterium, halogen, —CN, —OH, —$OR^a$, or $C_1$-$C_6$alkyl. In some embodiments of a compound of Formula (II), or a pharmaceutically acceptable salt, solvate, or stereoisomer thereof, $R^{X3}$ is hydrogen. In some embodiments of a compound of Formula (II), or a pharmaceutically acceptable salt, solvate, or stereoisomer thereof, $R^{X3}$ is —CN.

In some embodiments of a compound of Formula (II), or a pharmaceutically acceptable salt, solvate, or stereoisomer thereof, $X^4$ is N.

In some embodiments of a compound of Formula (II), or a pharmaceutically acceptable salt, solvate, or stereoisomer thereof, $X^4$ is C—$R^{X4}$.

In some embodiments of a compound of Formula (II), or a pharmaceutically acceptable salt, solvate, or stereoisomer thereof, $R^{X4}$ is hydrogen, deuterium, halogen, —CN, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$hydroxyalkyl, or $C_1$-$C_6$aminoalkyl. In some embodiments of a compound of Formula (II), or a pharmaceutically acceptable salt, solvate, or stereoisomer thereof, $R^{X4}$ is hydrogen, deuterium, halogen, —CN, —OH, —$OR^a$, or $C_1$-$C_6$alkyl. In some embodiments of a compound of Formula (II), or a pharmaceutically acceptable salt, solvate, or stereoisomer thereof, $R^{X4}$ is hydrogen. In some embodiments of a compound of Formula (II), or a pharmaceutically acceptable salt, solvate, or stereoisomer thereof, $R^{X4}$ is —CN.

In some embodiments of a compound of Formula (II), or a pharmaceutically acceptable salt, solvate, or stereoisomer thereof, Ring B is cycloalkyl or heterocycloalkyl. In some embodiments of a compound of Formula (II), or a pharmaceutically acceptable salt, solvate, or stereoisomer thereof, Ring B is cycloalkyl. In some embodiments of a compound of Formula (II), or a pharmaceutically acceptable salt, solvate, or stereoisomer thereof, Ring B is heterocycloalkyl.

In some embodiments of a compound of Formula (II), or a pharmaceutically acceptable salt, solvate, or stereoisomer thereof, Ring B is aryl or heteroaryl. In some embodiments of a compound of Formula (II), or a pharmaceutically acceptable salt, solvate, or stereoisomer thereof, Ring B is aryl. In some embodiments of a compound of Formula (II), or a pharmaceutically acceptable salt, solvate, or stereoisomer thereof, Ring B is heteroaryl. In some embodiments of a compound of Formula (II), or a pharmaceutically acceptable salt, solvate, or stereoisomer thereof, Ring B is phenyl, pyridyl, pyrimidyl, pyrazinyl, pyridazinyl, thiazolyl, thiophenyl, oxazolyl, imidazolyl, pyrazolyl, triazolyl, tetrazolyl, pyrrolyl, indazolyl, benzimidazolyl, benzoxazolyl, benzothiazolyl, benzothiophenyl, dihydrobenzoxazinyl, dihydrobenzimidazolyl, 1,3-dihydrobenzoisothiazolyl, benzodioxolyl, or dihydropyridinyl. In some embodiments of a compound of Formula (II), or a pharmaceutically acceptable salt, solvate, or stereoisomer thereof, Ring B is phenyl, thiophenyl, oxazolyl, imidazolyl, indazolyl, benzimidazolyl, benzoxazolyl, benzothiazolyl, benzothiophenyl, dihydrobenzoxazinyl, dihydrobenzimidazolyl, 1,3-dihydrobenzoisothiazolyl, benzodioxolyl, or dihydropyridinyl. In some embodiments of a compound of Formula (II), or a pharmaceutically acceptable salt, solvate, or stereoisomer thereof, Ring B is phenyl.

In some embodiments of a compound of Formula (II), or a pharmaceutically acceptable salt, solvate, or stereoisomer thereof, each $R^B$ is independently deuterium, halogen, —Y—CN, —Y—OH, —Y—$OR^a$, —Y—SH, —Y—$SR^a$, —Y—S(=O)$R^a$, —Y—S(=O)$_2R^a$, —Y—$NO_2$, —Y—$NR^cR^d$, —Y—$NR^b$S(=O)$_2R^a$, —Y—$NR^b$S(=O)$_2NR^cR^d$, —Y—S(=O)$_2NR^cR^d$, —Y—C(=O)$R^a$, —Y—OC(=O)$R^a$, —Y—C(=O)$OR^b$, —Y—OC(=O)$OR^b$, —Y—C(=O)$NR^cR^d$, —Y—OC(=O)$NR^cR^d$, —Y—$NR^b$C(=O)$NR^cR^d$, —Y—$NR^b$C(=O)$R^a$, —Y—$NR^b$C(=O)$OR^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three deuterium, oxo, halogen, —CN, —OH, —OMe, —S(=O)Me, —S(=O)$_2$Me, —$NH_2$, —S(=O)$_2NH_2$, —C(=O)Me, —C(=O)OH, —C(=O)OMe, $C_1$-$C_6$alkyl, $C_1$-$C_6$haloalkyl, $C_1$-$C_6$hydroxyalkyl, or $C_1$-$C_6$aminoalkyl; or two $R^A$ on the same carbon are taken together to form an oxo.

In some embodiments of a compound of Formula (II), or a pharmaceutically acceptable salt, solvate, or stereoisomer thereof, each $R^B$ is independently deuterium, halogen, —Y—CN, —Y—OH, —Y—$OR^a$, —Y—S(=O)$_2R^a$, —Y—$NR^cR^d$, —Y—$NR^b$S(=O)$_2R^a$, —Y—$NR^b$S(=O)$_2NR^cR^d$, —Y—S(=O)$_2NR^cR^d$, —Y—C(=O)$R^a$, —Y—C(=O)$OR^b$, —Y—C(=O)$NR^cR^d$, —Y—$NR^b$C(=O)$R^a$, $C_1$-$C_6$alkyl, or $C_1$-$C_6$haloalkyl; wherein each alkyl is independently optionally substituted with one, two, or three deuterium, oxo, halogen, —CN, —OH, —OMe, —S(=O)Me, —S(=O)$_2$Me, —$NH_2$, —S(=O)$_2NH_2$, —C(=O)Me, —C(=O)OH, —C(=O)OMe, $C_1$-$C_6$alkyl, $C_1$-$C_6$haloalkyl, $C_1$-$C_6$hydroxyalkyl, or $C_1$-$C_6$aminoalkyl; or two $R^A$ on the same carbon are taken together to form an oxo.

In some embodiments of a compound of Formula (II), or a pharmaceutically acceptable salt, solvate, or stereoisomer thereof, each $R^B$ is independently deuterium, halogen, —Y—CN, —Y—OH, —Y—$OR^a$, —Y—S(=O)$_2R^a$, —Y—$NR^cR^d$, —Y—$NR^b$S(=O)$_2R^a$, —Y—$NR^b$S(=O)$_2NR^cR^d$, —Y—S(=O)$_2NR^cR^d$, —Y—C(=O)$R^a$, —Y—C(=O)$OR^b$, —Y—C(=O)$NR^cR^d$, —Y—$NR^b$C(=O)$R^a$, $C_1$-$C_6$alkyl, or $C_1$-$C_6$haloalkyl; or two $R^A$ on the same carbon are taken together to form an oxo.

In some embodiments of a compound of Formula (II), or a pharmaceutically acceptable salt, solvate, or stereoisomer thereof, each $R^B$ is independently halogen or —Y—OH.

In some embodiments of a compound of Formula (II), or a pharmaceutically acceptable salt, solvate, or stereoisomer thereof, each $R^B$ is independently —Y—$NR^cR^d$.

In some embodiments of a compound of Formula (II), or a pharmaceutically acceptable salt, solvate, or stereoisomer thereof, each $R^B$ is independently deuterium, halogen, —Y—CN, —Y—$OR^a$, —Y—S(=O)$_2R^a$, —Y—$NR^cR^d$, —Y—$NR^b$S(=O)$_2R^a$, —Y—$NR^b$S(=O)$_2NR^cR^d$, —Y—S(=O)$_2NR^cR^d$, —Y—C(=O)$R^a$, —Y—C(=O)$OR^b$, —Y—C(=O)$NR^cR^d$, —Y—$NR^b$C(=O)$R^a$, $C_1$-$C_6$alkyl, or $C_1$-$C_6$haloalkyl; or two $R^A$ on the same carbon are taken together to form an oxo.

In some embodiments of a compound of Formula (II), or a pharmaceutically acceptable salt, solvate, or stereoisomer thereof, each $R^B$ is independently deuterium, —Y—CN, —Y—OH, —Y—$OR^a$, —Y—S(=O)$_2R^a$, —Y—$NR^cR^d$, —Y—$NR^b$S(=O)$_2R^a$, —Y—$NR^b$S(=O)$_2NR^cR^d$, —Y—S(=O)$_2NR^cR^d$, —Y—C(=O)$R^a$, —Y—C(=O)$OR^b$, —Y—C(=O)$NR^cR^d$, —Y—$NR^b$C(=O)$R^a$, $C_1$-$C_6$alkyl, or $C_1$-$C_6$haloalkyl; or two $R^A$ on the same carbon are taken together to form an oxo.

In some embodiments of a compound of Formula (II), or a pharmaceutically acceptable salt, solvate, or stereoisomer thereof, each Y is independently a bond or $C_1$-$C_6$alkylene. In some embodiments of a compound of Formula (II), or a pharmaceutically acceptable salt, solvate, or stereoisomer thereof, each Y is independently a bond or $CH_2$. In some embodiments of a compound of Formula (II), or a pharmaceutically acceptable salt, solvate, or stereoisomer thereof, each Y is $CH_2$. In some embodiments of a compound of Formula (II), or a pharmaceutically acceptable salt, solvate, or stereoisomer thereof, each Y is a bond.

In some embodiments of a compound of Formula (II), or a pharmaceutically acceptable salt, solvate, or stereoisomer thereof, m is 1-3. In some embodiments of a compound of Formula (II), or a pharmaceutically acceptable salt, solvate, or stereoisomer thereof, m is 2 or 3. In some embodiments of a compound of Formula (II), or a pharmaceutically acceptable salt, solvate, or stereoisomer thereof, m is 0 or 1. In some embodiments of a compound of Formula (II), or a pharmaceutically acceptable salt, solvate, or stereoisomer thereof, m is 0-2. In some embodiments of a compound of Formula (II), or a pharmaceutically acceptable salt, solvate, or stereoisomer thereof, m is 1 or 2. In some embodiments of a compound of Formula (II), or a pharmaceutically acceptable salt, solvate, or stereoisomer thereof, m is 1. In some embodiments of a compound of Formula (II), or a pharmaceutically acceptable salt, solvate, or stereoisomer thereof, m is 2. In some embodiments of a compound of Formula (II), or a pharmaceutically acceptable salt, solvate, or stereoisomer thereof, m is 3.

In some embodiments of a compound of Formula (I) or (II), or a pharmaceutically acceptable salt, solvate, or stereoisomer thereof, each $R^a$ is independently $C_1$-$C_6$alkyl, $C_1$-$C_6$haloalkyl, $C_1$-$C_6$hydroxyalkyl, $C_1$-$C_6$aminoalkyl, cycloalkyl, heterocycloalkyl, aryl, or heteroaryl. In some embodiments of a compound of Formula (I) or (II), or a pharmaceutically acceptable salt, solvate, or stereoisomer thereof, each $R^a$ is independently $C_1$-$C_6$alkyl, $C_1$-$C_6$haloalkyl, cycloalkyl, or heterocycloalkyl. In some embodiments of a compound of Formula (I) or (II), or a pharmaceutically acceptable salt, solvate, or stereoisomer thereof, each $R^a$ is independently $C_1$-$C_6$alkyl, $C_1$-$C_6$haloalkyl, or cycloalkyl. In some embodiments of a compound of Formula (I) or (II), or a pharmaceutically acceptable salt, solvate, or stereoisomer thereof, each $R^a$ is independently $C_1$-$C_6$alkyl or $C_1$-$C_6$haloalkyl. In some embodiments of a compound of Formula (I) or (II), or a pharmaceutically acceptable salt, solvate, or stereoisomer thereof, each $R^a$ is independently $C_1$-$C_6$alkyl.

In some embodiments of a compound of Formula (I) or (II), or a pharmaceutically acceptable salt, solvate, or stereoisomer thereof, each $R^b$ is independently hydrogen, $C_1$-$C_6$alkyl, $C_1$-$C_6$haloalkyl, $C_1$-$C_6$hydroxyalkyl, $C_1$-$C_6$aminoalkyl, cycloalkyl, heterocycloalkyl, aryl, or heteroaryl. In some embodiments of a compound of Formula (I) or (II), or a pharmaceutically acceptable salt, solvate, or stereoisomer thereof, each $R^b$ is independently hydrogen, $C_1$-$C_6$alkyl, $C_1$-$C_6$haloalkyl, cycloalkyl, or heterocycloalkyl. In some embodiments of a compound of Formula (I) or (II), or a pharmaceutically acceptable salt, solvate, or stereoisomer thereof, each $R^b$ is independently hydrogen, $C_1$-$C_6$alkyl, $C_1$-$C_6$haloalkyl, or cycloalkyl. In some embodiments of a compound of Formula (I) or (II), or a pharmaceutically acceptable salt, solvate, or stereoisomer thereof, each $R^b$ is independently hydrogen, $C_1$-$C_6$alkyl, or $C_1$-$C_6$haloalkyl. In some embodiments of a compound of Formula (I) or (II), or a pharmaceutically acceptable salt, solvate, or stereoisomer thereof, each $R^b$ is independently hydrogen or $C_1$-$C_6$alkyl. In some embodiments of a compound of Formula (I) or (II), or a pharmaceutically acceptable salt, solvate, or stereoisomer thereof, each $R^b$ is hydrogen. In some embodiments of a compound of Formula (I) or (II), or a pharmaceutically acceptable salt, solvate, or stereoisomer thereof, each $R^b$ is independently $C_1$-$C_6$alkyl.

In some embodiments of a compound of Formula (I) or (II), or a pharmaceutically acceptable salt, solvate, or stereoisomer thereof, each $R^c$ and $R^d$ is independently hydrogen, $C_1$-$C_6$alkyl, $C_1$-$C_6$haloalkyl, $C_1$-$C_6$hydroxyalkyl, $C_1$-$C_6$aminoalkyl, cycloalkyl, heterocycloalkyl, aryl, or heteroaryl. In some embodiments of a compound of Formula (I) or (II), or a pharmaceutically acceptable salt, solvate, or stereoisomer thereof, each $R^c$ and $R^d$ is independently hydrogen, $C_1$-$C_6$alkyl, $C_1$-$C_6$haloalkyl, cycloalkyl, or heterocycloalkyl. In some embodiments of a compound of Formula (I) or (II), or a pharmaceutically acceptable salt, solvate, or stereoisomer thereof, each $R^c$ and $R^d$ is independently hydrogen, $C_1$-$C_6$alkyl, $C_1$-$C_6$haloalkyl, or cycloalkyl. In some embodiments of a compound of Formula (I) or (II), or a pharmaceutically acceptable salt, solvate, or stereoisomer thereof, each $R^c$ and $R^d$ is independently hydrogen, $C_1$-$C_6$alkyl, or $C_1$-$C_6$haloalkyl. In some embodiments of a compound of Formula (I) or (II), or a pharmaceutically acceptable salt, solvate, or stereoisomer thereof, each $R^c$ and $R^d$ is independently hydrogen or $C_1$-$C_6$alkyl. In some embodiments of a compound of Formula (I) or (II), or a pharmaceutically acceptable salt, solvate, or stereoisomer thereof, each $R^c$ and $R^d$ is hydrogen.

In some embodiments of a compound of Formula (I) or (II), or a pharmaceutically acceptable salt, solvate, or stereoisomer thereof, $R^c$ and $R^d$ are taken together with the atom to which they are attached to form a heterocycloalkyl optionally substituted with one, two, or three halogen, $C_1$-$C_6$alkyl, or $C_1$-$C_6$haloalkyl.

Any combination of the groups described above for the various variables is contemplated herein. Throughout the specification, groups and substituents thereof are chosen by one skilled in the field to provide stable moieties and compounds.

Described herein is a compound of Formula (I) or (II), or a pharmaceutically acceptable salt, solvate, or stereoisomer thereof, selected from a compound in Table 1.

TABLE 1

| Exemplary compounds | | |
|---|---|---|
| Ex. | Structure | Name |
| 1 | 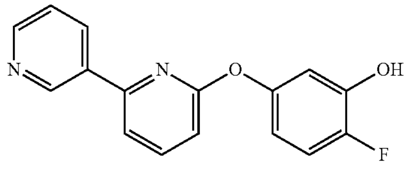 [SMILES: Oc1cc(Oc2cccc(-c3cccnc3)n2)ccc1F] | 5-([2,3'-bipyridin]-6-yloxy)-2-fluorophenol |
| 2 | 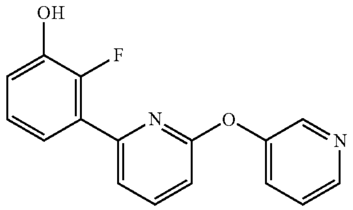 [SMILES: Oc1cccc(-c2cccc(Oc3cccnc3)n2)c1F] | 2-fluoro-3-(6-(pyridin-3-yloxy)pyridin-2-yl) phenol |
| 3 | 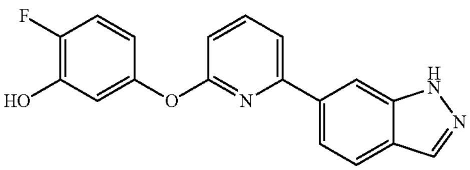 [SMILES: Oc1cc(Oc2cccc(-c3ccc4cn[nH]c4c3)n2)ccc1F] | 5-((6-(1H-indazol-6-yl)pyridin-2-yl)oxy)-2-fluorophenol |

TABLE 1-continued

| Ex. | Structure | Name |
|---|---|---|
| | Exemplary compounds | |
| 4 | 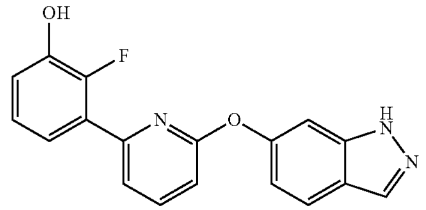 [SMILES: Oc1cccc(-c2cccc(Oc3ccc4cn[nH]c4c3)n2)c1F] | 6-((6-(2-fluoro-3-methoxyphenyl)pyridin-2-yl) oxy)-1H-indazole and 3-(6-((1H-indazol-6-yl)oxy)pyridin-2-yl)-2 fluorophenol |
| 5 | 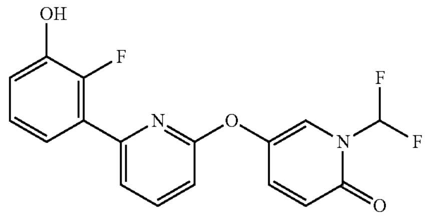 [SMILES: O=c1ccc(Oc2cccc(-c3cccc(O)c3F)n2)cn1C(F)F] | 1-(difluoromethyl)-5-((6-(2-fluoro-3-hydroxyphenyl)pyridin-2-yl)oxy)pyridin-2(1H)-one |
| 6 | 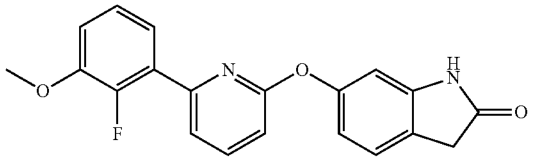 [SMILES: COc1cccc(-c2cccc(Oc3ccc4c(c3)NC(=O)C4)n2)c1F] | 6-{[6-(2-fluoro-3-methoxyphenyl)pyridin-2-yl]oxy}-2,3-dihydro-1H-indol-2-one |
| 7 | 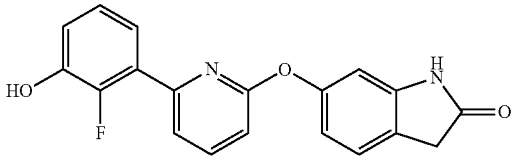 [SMILES: O=C1Cc2ccc(Oc3cccc(-c4cccc(O)c4F)n3)cc2N1] | 6-{[6-(2-fluoro-3-methoxyphenyl)pyridin-2-yl]oxy}-2,3-dihydro-1H-indol-2-one |
| 8 | 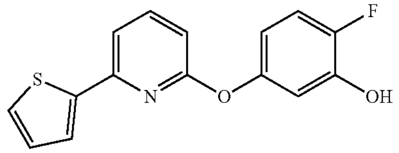 [SMILES: Oc1cc(Oc2cccc(-c3cccs3)n2)ccc1F] | 2-fluoro-5-((6-(thiophen-2-yl)pyridin-2-yl)oxy) phenol |
| 9 | 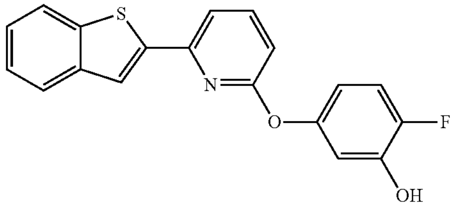 [SMILES: Oc1cc(Oc2cccc(-c3cc4ccccc4s3)n2)ccc1F] | 5-((6-(benzo[b]thiophen-2-yl)pyridin-2-yl)oxy)-2-fluorophenol |
| 10 | 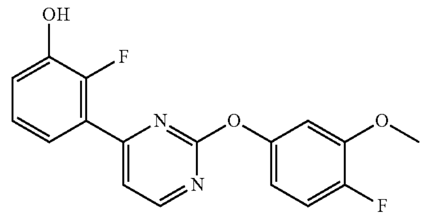 [SMILES: COc1cc(Oc2nccc(-c3cccc(O)c3F)n2)ccc1F] | 2-fluoro-3-[2-(4-fluoro-3-methoxyphenoxy)pyrimidin-4-yl]phenol |

TABLE 1-continued

| Exemplary compounds | | |
|---|---|---|
| Ex. | Structure | Name |
| 11 | 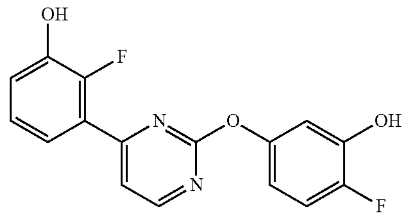 [SMILES: Oc1cc(Oc2nccc(-c3cccc(O)c3F)n2)ccc1F] | 2-fluoro-3-[2-(4-fluoro-3-hydroxyphenoxy)pyrimidin-4-yl]phenol |
| 12 | 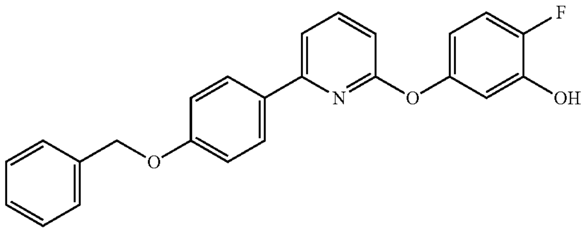 [SMILES: Oc1cc(Oc2cccc(-c3ccc(OCc4ccccc4)cc3)n2)ccc1F] | 5-((6-(4-(benzyloxy)phenyl)pyridin-2-yl)oxy)-2-fluorophenol |
| 13 | 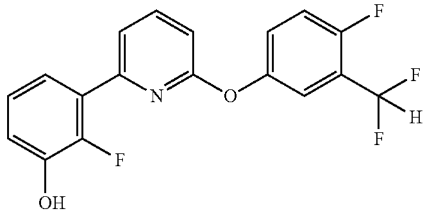 [SMILES: Oc1cccc(-c2cccc(Oc3ccc(F)c(C(F)F)c3)n2)c1F] | 3-{6-[3-(difluoromethyl)-4-fluorophenoxy]pyridin-2-yl}-2-fluorophenol |
| 14 | 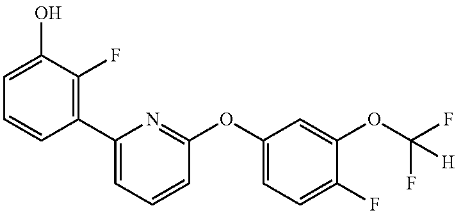 [SMILES: Oc1cccc(-c2cccc(Oc3ccc(F)c(OC(F)F)c3)n2)c1F] | 3-{6-[3-(difluoromethoxy)-4-fluorophenoxy]pyridin-2-yl}-2-fluorophenol |
| 15 | 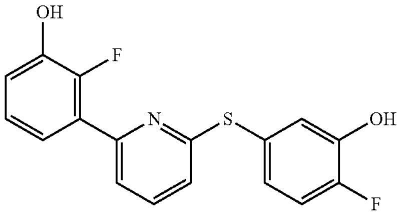 [SMILES: Oc1cc(Sc2cccc(-c3cccc(O)c3F)n2)ccc1F] | 2-fluoro-3-(6-((4-fluoro-3-hydroxyphenyl)thio)pyridin-2-yl)phenol |
| 16 | 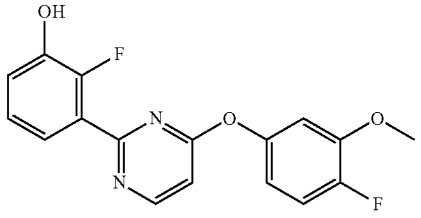 | 2-fluoro-3-[4-(4-fluoro-3-methoxyphenoxy)pyrimidin-2-yl]phenol |

TABLE 1-continued

| Exemplary compounds | | |
|---|---|---|
| Ex. | Structure | Name |
| 17 | 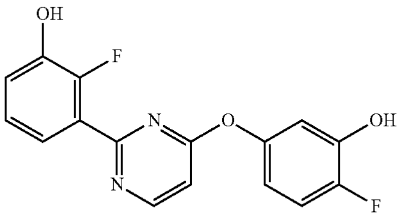 [SMILES: Oc1cc(Oc2ccnc(-c3cccc(O)c3F)n2)ccc1F] | 2-fluoro-3-[4-(4-fluoro-3-hydroxyphenoxy)pyrimidin-2-yl]phenol |
| 18 | 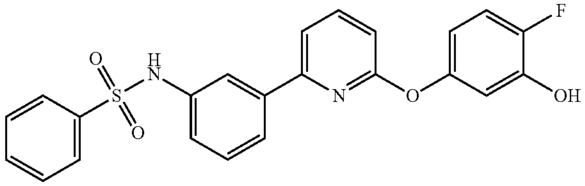 [SMILES: O=S(=O)(Nc1cccc(-c2cccc(Oc3ccc(F)c(O)c3)n2)c1)c1ccccc1] | N-(3-(6-(4-fluoro-3-hydroxyphenoxy)pyridin-2-yl)phenyl) benzenesulfonamide |
| 19 | 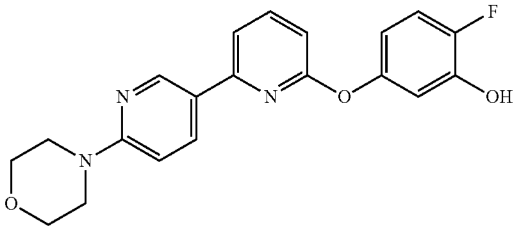 [SMILES: Oc1cc(Oc2cccc(-c3ccc(N4CCOCC4)nc3)n2)ccc1F] | 2-fluoro-5-((6'-morpholino-[2,3'-bipyridin]-6-yl) oxy)phenol |
| 20 | 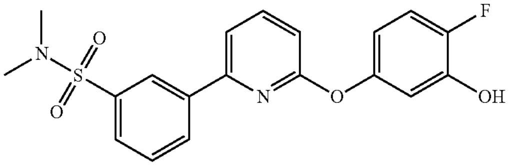 [SMILES: CN(C)S(=O)(=O)c1cccc(-c2cccc(Oc3ccc(F)c(O)c3)n2)c1] | 3-(6-(4-fluoro-3-hydroxyphenoxy)pyridin-2-yl)-N,N-dimethylbenzenesulfonamide |
| 21 | 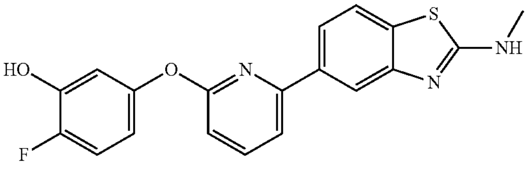 [SMILES: CNc1nc2cc(-c3cccc(Oc4ccc(F)c(O)c4)n3)ccc2s1] | 5-((6-(2-aminobenzo[d]thiazol-5-yl)pyridin-2-yl)oxy)-2-fluorophenol |
| 22 | 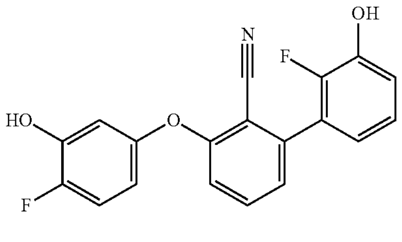 [SMILES: N#Cc1c(Oc2ccc(F)c(O)c2)cccc1-c1cccc(O)c1F] | 2'-fluoro-3-(4-fluoro-3-hydroxyphenoxy)-3'-hydroxy-[1,1'-biphenyl]-2-carbonitrile |
| 23 | 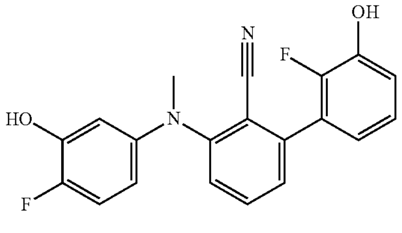 [SMILES: CN(c1ccc(F)c(O)c1)c1cccc(-c2cccc(O)c2F)c1C#N] | 2'-fluoro-3-((4-fluoro-3-hydroxyphenyl)(methyl) amino)-3'-hydroxy-1,1'-biphenyl]-2-carbonitrile |

TABLE 1-continued

| Exemplary compounds | | |
|---|---|---|
| Ex. | Structure | Name |
| 25 | 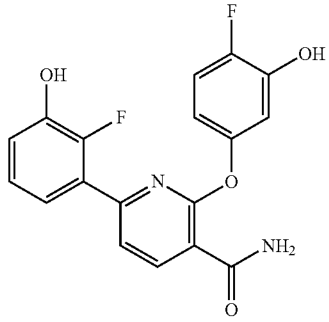 [SMILES: NC(=O)c1ccc(-c2cccc(O)c2F)nc1Oc1ccc(F)c(O)c1] | 2-(4-fluoro-3-hydroxyphenoxy)-6-(2-fluoro-3-hydroxyphenyl)pyridine-3-carboxamide |
| 26 | 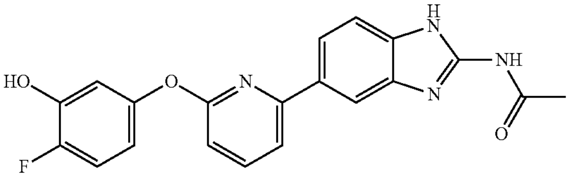 [SMILES: CC(=O)Nc1nc2cc(-c3cccc(Oc4ccc(F)c(O)c4)n3)ccc2[nH]1] | N-(5-(6-(4-fluoro-3-hydroxyphenoxy)pyridin-2-yl)-1H-benzo [d]imidazol-2-yl)acetamide |
| 27 | 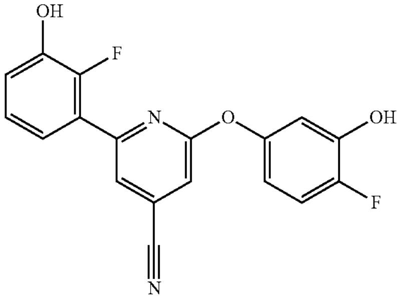 [SMILES: N#Cc1cc(Oc2ccc(F)c(O)c2)nc(-c2cccc(O)c2F)c1] | 2-(4-fluoro-3-hydroxyphenoxy)-6-(2-fluoro-3-hydroxyphenyl) pyridine-4-carbonitrile |
| 28 | 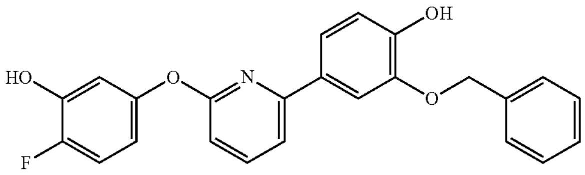 [SMILES: Oc1cc(Oc2cccc(-c3ccc(O)c(OCc4ccccc4)c3)n2)ccc1F] | 2-(benzyloxy)-4-[6-(4-fluoro-3-hydroxyphenoxy) pyridin-2-yl] phenol |
| 29 | 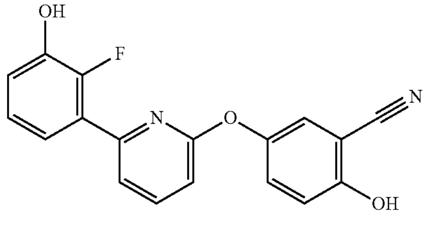 [SMILES: N#Cc1cc(Oc2cccc(-c3cccc(O)c3F)n2)ccc1O] | 4-{[6-(2-fluoro-3-hydroxyphenyl)pyridin-2-yl]oxy}-2-hydroxybenzonitrile |
| 30 | 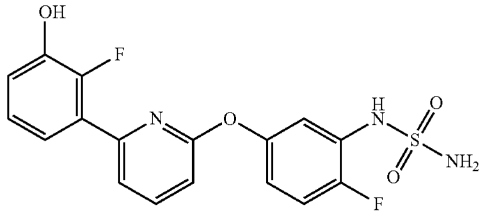 [SMILES: NS(=O)(=O)Nc1cc(Oc2cccc(-c3cccc(O)c3F)n2)ccc1F] | N-(2-fluoro-5-{[6-(2-fluoro-3-hydroxyphenyl)pyridin-2-yl]oxy}phenyl)aminosulfonamide |

TABLE 1-continued

| Exemplary compounds | | |
|---|---|---|
| Ex. | Structure | Name |
| 31 | 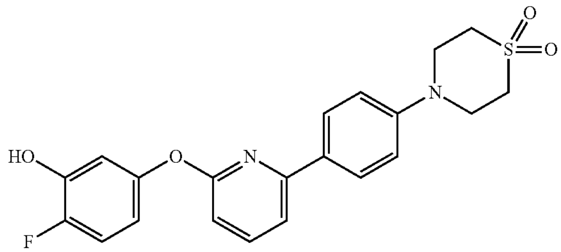 [SMILES: O=S1(=O)CCN(c2ccc(-c3cccc(Oc4ccc(F)c(O)c4)n3)cc2)CC1] | 4-(4-(6-(4-fluoro-3-hydroxyphenoxy)pyridin-2-yl)phenyl)thiomorpholine 1,1-dioxide |
| 32 | 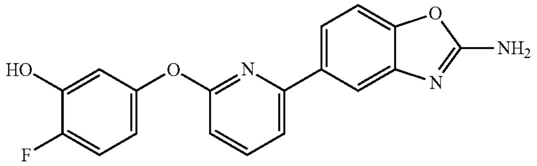 [SMILES: Nc1nc2cc(-c3cccc(Oc4ccc(F)c(O)c4)n3)ccc2o1] | 5-{[6-(2-amino-1,3-benzoxazol-5-yl)pyridin-2-yl]oxy}-2-fluorophenol |
| 33 | 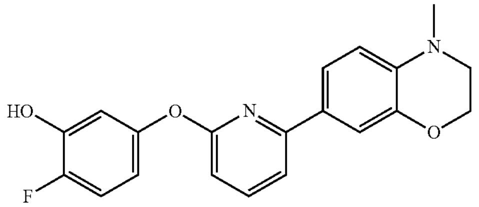 [SMILES: CN1CCOc2cc(-c3cccc(Oc4ccc(F)c(O)c4)n3)ccc21] | 2-fluoro-5-((6-(4-methyl-3,4-dihydro-2H-benzo[b][1,4]oxazin-7-yl)pyridin-2-yl)oxy)phenol |
| 34 | 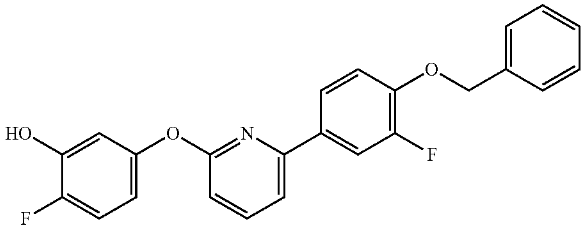 [SMILES: Oc1cc(Oc2cccc(-c3ccc(OCc4ccccc4)c(F)c3)n2)ccc1F] | 5-({6-[4-(benzyloxy)-3-fluorophenyl]pyridin-2-yl}oxy)-2-fluorophenol |
| 35 | 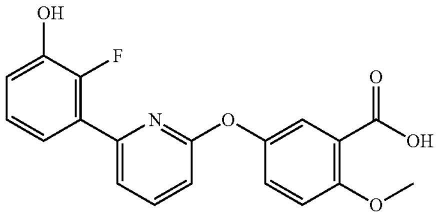 [SMILES: COc1ccc(Oc2cccc(-c3cccc(O)c3F)n2)cc1C(=O)O] | 5-((6-(2-fluoro-3-hydroxyphenyl)pyridin-2-yl)oxy)-2-methoxybenzoic acid |
| 36 | 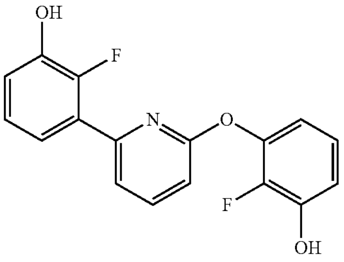 [SMILES: Oc1cccc(Oc2cccc(-c3cccc(O)c3F)n2)c1F] | 2-fluoro-3-(6-(2-fluoro-3-hydroxyphenoxy)pyridin-2-yl)phenol |

TABLE 1-continued

| Exemplary compounds | | |
|---|---|---|
| Ex. | Structure | Name |
| 37 | 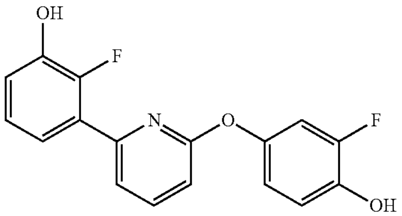 [SMILES: Oc1ccc(Oc2cccc(-c3cccc(O)c3F)n2)cc1F] | 2-fluoro-3-[6-(3-fluoro-4-hydroxyphenoxy) pyridin-2-yl] phenol |
| 38 | 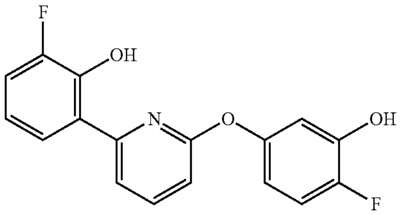 [SMILES: Oc1cc(Oc2cccc(-c3cccc(F)c3O)n2)ccc1F] | 2-fluoro-5-((6-(3-fluoro-2-hydroxyphenyl)pyridin-2-yl)oxy)phenol |
| 39 | 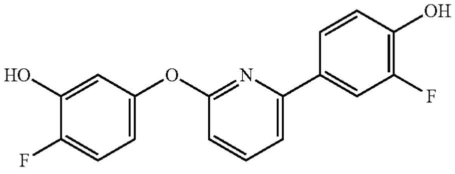 [SMILES: Oc1cc(Oc2cccc(-c3ccc(O)c(F)c3)n2)ccc1F] | 2-fluoro-4-(6-(4-fluoro-3-hydroxyphenoxy)pyridin-2-yl)phenol |
| 40 | 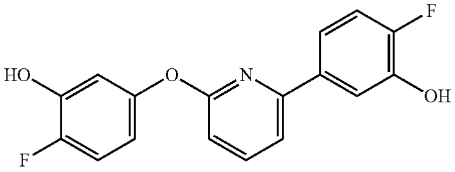 [SMILES: Oc1cc(Oc2cccc(-c3ccc(F)c(O)c3)n2)ccc1F] | 2-fluoro-5-(6-(4-fluoro-3-hydroxyphenoxy)pyridin-2-yl)phenol |
| 41 | 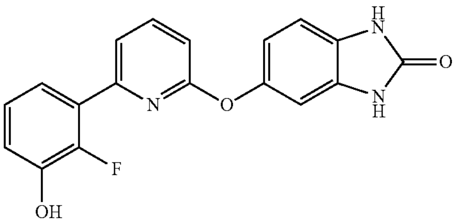 [SMILES: O=c1[nH]c2ccc(Oc3cccc(-c4cccc(O)c4F)n3)cc2[nH]1] | 5-((6-(2-fluoro-3-hydroxyphenyl)pyridin-2-yl)oxy)-1,3-dihydro-2H-benzo[d]imidazol-2-one |
| 42 | 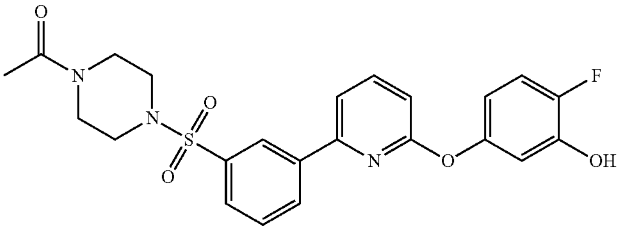 [SMILES: CC(=O)N1CCN(S(=O)(=O)c2cccc(-c3cccc(Oc4ccc(F)c(O)c4)n3)c2)CC1] | 1-(4-{3-[6-(4-fluoro-3-hydroxyphenoxy)pyridin-2-yl]benzenesulfonyl} piperazin-1-yl)ethan-1-one |
| 43 | 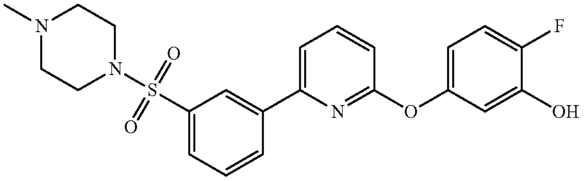 [SMILES: CN1CCN(S(=O)(=O)c2cccc(-c3cccc(Oc4ccc(F)c(O)c4)n3)c2)CC1] | 2-fluoro-5-((6-(3-((4-methylpiperazin-1-yl)sulfonyl)phenyl)pyridin-2-yl)oxy)phenol |

TABLE 1-continued

| Ex. | Structure | Name |
|---|---|---|
| | Exemplary compounds | |
| 44 | 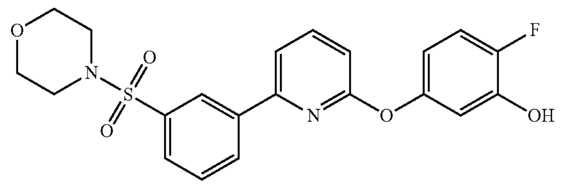 [SMILES: O=S(=O)(c1cccc(-c2cccc(Oc3ccc(F)c(O)c3)n2)c1)N1CCOCC1] | 2-fluoro-5-((6-(3-(morpholinosulfonyl)phenyl)pyridin-2-yl) oxy)phenol |
| 45 | 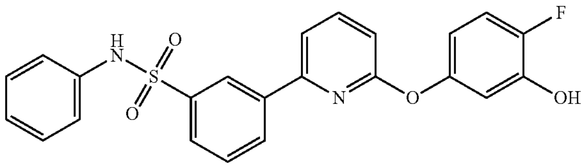 [SMILES: O=S(=O)(Nc1ccccc1)c1cccc(-c2cccc(Oc3ccc(F)c(O)c3)n2)c1] | 3-(6-(4-fluoro-3-hydroxyphenoxy)pyridin-2-yl)-N-phenylbenzene sulfonamide |
| 46 | 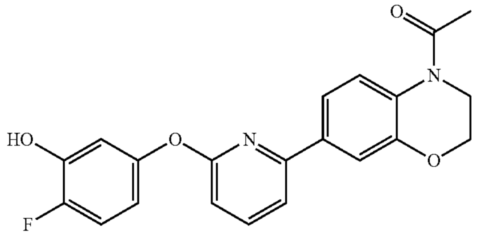 [SMILES: CC(=O)N1CCOc2cc(-c3cccc(Oc4ccc(F)c(O)c4)n3)ccc21] | 1-{7-[6-(4-fluoro-3-hydroxyphenoxy)pyridin-2-yl]-3,4-dihydro-2H-1,4-benzoxazin-4-yl}ethan-1-one |
| 47 | 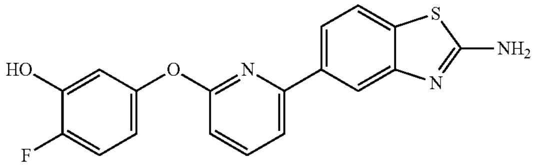 [SMILES: Nc1nc2cc(-c3cccc(Oc4ccc(F)c(O)c4)n3)ccc2s1] | 5-((6-(2-aminobenzo[d]thiazol-5-yl)pyridin-2-yl)oxy)-2-fluorophenol |
| 48 | 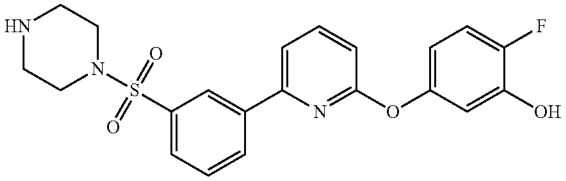 [SMILES: O=S(=O)(c1cccc(-c2cccc(Oc3ccc(F)c(O)c3)n2)c1)N1CCNCC1] | 2-fluoro-5-((6-(3-(piperazin-1-ylsulfonyl)phenyl)pyridin-2-yl)oxy) phenol |
| 49 | 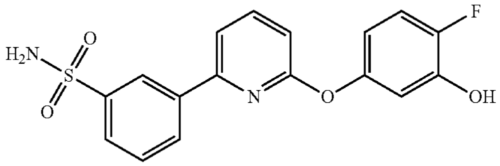 [SMILES: NS(=O)(=O)c1cccc(-c2cccc(Oc3ccc(F)c(O)c3)n2)c1] | 3-[6-(4-fluoro-3-hydroxyphenoxy)pyridin-2-yl]benzene-1-sulfonamide |
| 50 | 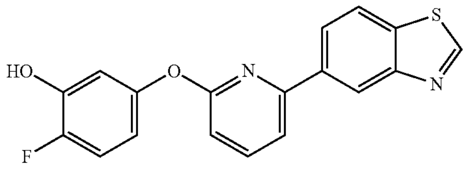 [SMILES: Oc1cc(Oc2cccc(-c3ccc4scnc4c3)n2)ccc1F] | 5-{[6-(1,3-benzothiazol-5-yl)pyridin-2-yl]oxy}-2-fluorophenol |
| 51 | 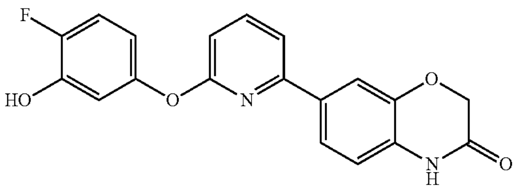 [SMILES: O=C1COc2cc(-c3cccc(Oc4ccc(F)c(O)c4)n3)ccc2N1] | 7-(6-(4-fluoro-3-hydroxyphenoxy)pyridin-2-yl)-2H-benzo[b][1,4]oxazin-3(4H)-one |

TABLE 1-continued

| Exemplary compounds | | |
|---|---|---|
| Ex. | Structure | Name |
| 52 | 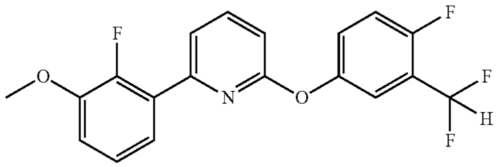 [SMILES: COc1cccc(-c2cccc(Oc3ccc(F)c(C(F)F)c3)n2)c1F] | 2-[3-(difluoromethyl)-4-fluorophenoxy]-6-(2-fluoro-3-methoxyphenyl) pyridine |
| 53 | 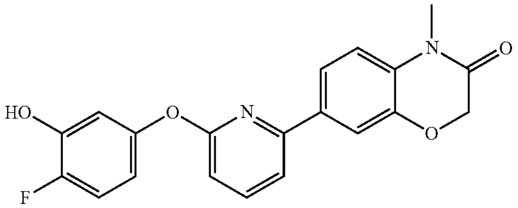 [SMILES: CN1C(=O)COc2cc(-c3cccc(Oc4ccc(F)c(O)c4)n3)ccc21] | 7-(6-(4-fluoro-3-hydroxyphenoxy)pyridin-2-yl)-4-methyl-2H-benzo[b][1,4]oxazin-3(4H)-one |
| 54 | 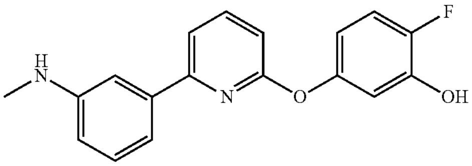 [SMILES: CNc1cccc(-c2cccc(Oc3ccc(F)c(O)c3)n2)c1] | 2-fluoro-5-({6-[3-(methylamino)phenyl]pyridin-2-yl}oxy)phenol |
| 55 | 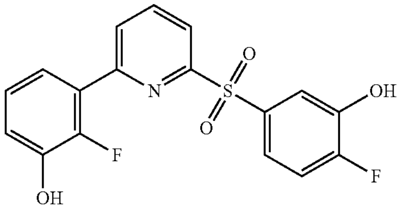 [SMILES: O=S(=O)(c1ccc(F)c(O)c1)c1cccc(-c2cccc(O)c2F)n1] | 2-fluoro-3-[6-(4-fluoro-3-hydroxybenzenesulfonyl)pyridin-2-yl]phenol |
| 56 | 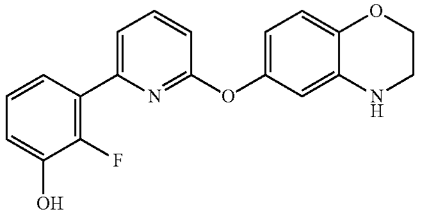 [SMILES: Oc1cccc(-c2cccc(Oc3ccc4c(c3)NCCO4)n2)c1F] | 3-[6-(3,4-dihydro-2H-1,4-benzoxazin-6-yloxy)pyridin-2-yl]-2-fluorophenol |
| 57 | 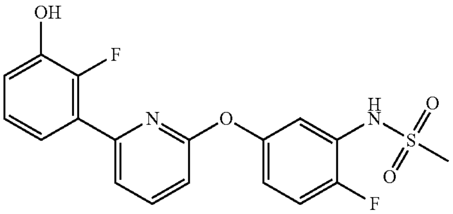 [SMILES: CS(=O)(=O)Nc1cc(Oc2cccc(-c3cccc(O)c3F)n2)ccc1F] | N-(2-fluoro-5-{[6-(2-fluoro-3-hydroxyphenyl)pyridin-2-yl]oxy}phenyl)methane-sulfonamide |
| 58 | 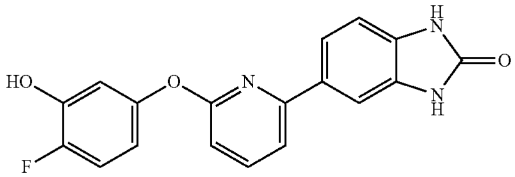 [SMILES: O=c1[nH]c2ccc(-c3cccc(Oc4ccc(F)c(O)c4)n3)cc2[nH]1] | 5-(6-(4-fluoro-3-hydroxyphenoxy)pyridin-2-yl)-1,3-dihydro-2H-benzo[d]imidazol-2-one |

TABLE 1-continued

| Exemplary compounds | | |
|---|---|---|
| Ex. | Structure | Name |
| 59 | 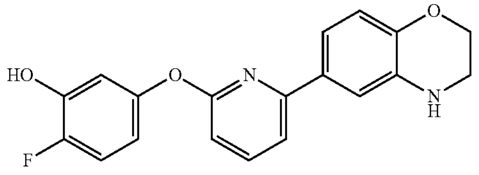 [SMILES: Oc1cc(Oc2cccc(-c3ccc4c(c3)NCCO4)n2)ccc1F] | 5-((6-(3,4-dihydro-2H-benzo[b][1,4]oxazin-6-yl) pyridin-2-yl)oxy)-2-fluorophenol |
| 60 | 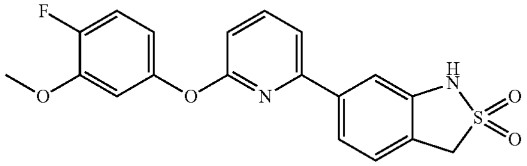 [SMILES: COc1cc(Oc2cccc(-c3ccc4c(c3)NS(=O)(=O)C4)n2)ccc1F] | 6-(6-(4-fluoro-3-methoxyphenoxy)pyridin-2-yl)-1,3-dihydrobenzo[c]isothiazole 2,2-dioxide |
| 61 | 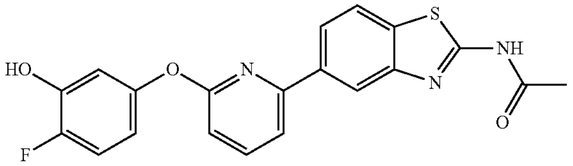 [SMILES: CC(=O)Nc1nc2cc(-c3cccc(Oc4ccc(F)c(O)c4)n3)ccc2s1] | N-(5-(6-(4-fluoro-3-hydroxyphenoxy)pyridin-2-yl)benzo[d]thiazol-2-yl) acetamide |
| 62 | 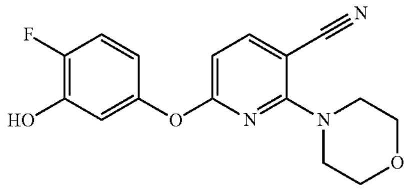 [SMILES: N#Cc1ccc(Oc2ccc(F)c(O)c2)nc1N1CCOCC1] | 6-(4-fluoro-3-hydroxyphenoxy)-2-(morpholin-4-yl)pyridine-3-carbonitrile |
| 63 | 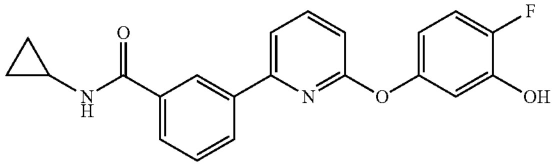 [SMILES: O=C(NC1CC1)c1cccc(-c2cccc(Oc3ccc(F)c(O)c3)n2)c1] | N-cyclopropyl-3-(6-(4-fluoro-3-hydroxyphenoxy)pyridin-2-yl)benzamide |
| 64 | 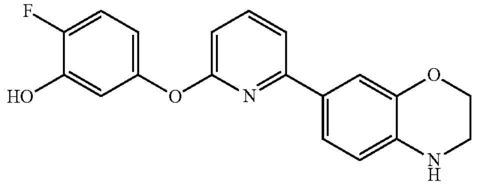 [SMILES: Oc1cc(Oc2cccc(-c3ccc4c(c3)OCCN4)n2)ccc1F] | 5-{[6-(3,4-dihydro-2H-1,4-benzoxazin-7-yl)pyridin-2-yl]oxy}-2-fluorophenol |
| 65 | 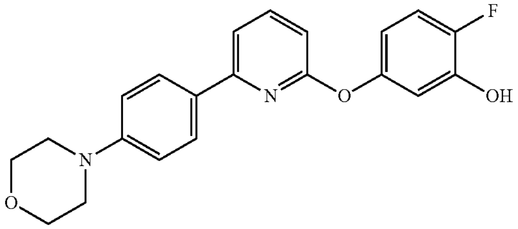 | 2-fluoro-5-((6-(4-morpholinophenyl)pyridin-2-yl)oxy)phenol |
| 66 | 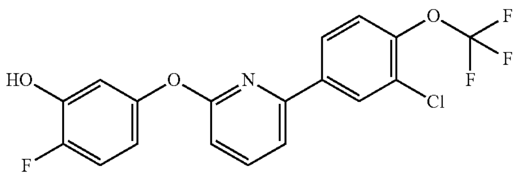 [SMILES: Oc1cc(Oc2cccc(-c3ccc(OC(F)(F)F)c(Cl)c3)n2)ccc1F] | 5-((6-(3-chloro-4-(trifluoromethoxy)phenyl)pyridin-2-yl)oxy)-2-fluorophenol |

TABLE 1-continued

| Exemplary compounds | | |
|---|---|---|
| Ex. | Structure | Name |
| 67 | 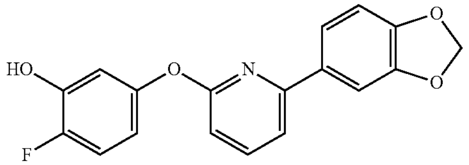 [SMILES: Oc1cc(Oc2cccc(-c3ccc4c(c3)OCO4)n2)ccc1F] | 5-((6-(benzo[d][1,3]dioxol-5-yl)pyridin-2-yl)oxy)-2-fluorophenol |
| 68 | 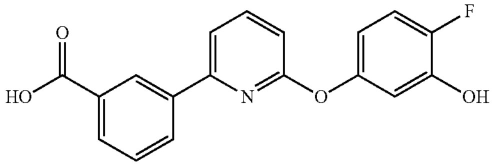 [SMILES: O=C(O)c1cccc(-c2cccc(Oc3ccc(F)c(O)c3)n2)c1] | 3-(6-(4-fluoro-3-hydroxyphenoxy)pyridin-2-yl)benzoic acid |
| 69 | 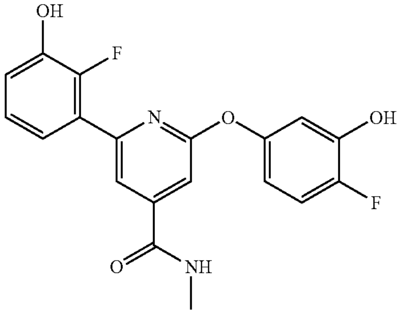 [SMILES: CNC(=O)c1cc(Oc2ccc(F)c(O)c2)nc(-c2cccc(O)c2F)c1] | 2-(4-fluoro-3-hydroxyphenoxy)-6-(2-fluoro-3-hydroxyphenyl)-N-methylpyridine-4-carboxamide |
| 70 | 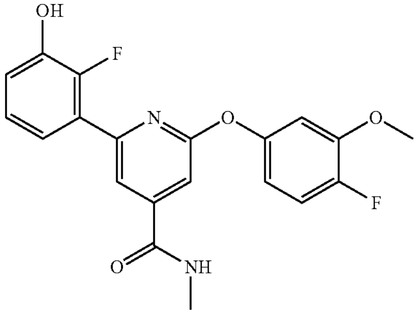 [SMILES: CNC(=O)c1cc(Oc2ccc(F)c(OC)c2)nc(-c2cccc(O)c2F)c1] | 2-(2-fluoro-3-hydroxyphenyl)-6-(4-fluoro-3-methoxyphenoxy)-N-methylpyridine-4-carboxamide |
| 71 | 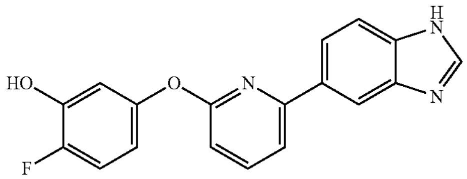 [SMILES: Oc1cc(Oc2cccc(-c3ccc4[nH]cnc4c3)n2)ccc1F] | 4-{[6-(1H-1,3-benzodiazol-5-yl)pyridin-2-yl]oxy}-2-fluorophenol |
| 72 | 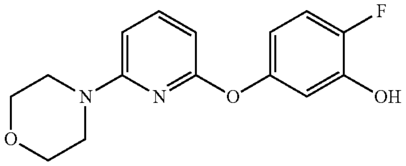 [SMILES: Oc1cc(Oc2cccc(N3CCOCC3)n2)ccc1F] | 2-fluoro-5-{[6-(morpholin-4-yl)pyridin-2-yl]oxy}phenol |
| 73 | 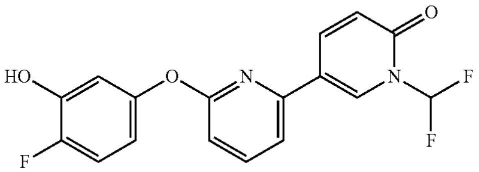 [SMILES: O=c1ccc(-c2cccc(Oc3ccc(F)c(O)c3)n2)cn1C(F)F] | 1'-(difluoromethyl)-6-(4-fluoro-3-hydroxyphenoxy)-[2,3'-bipyridin]-6'(1'H)-one |

TABLE 1-continued

| Exemplary compounds | | |
|---|---|---|
| Ex. | Structure | Name |
| 74 | 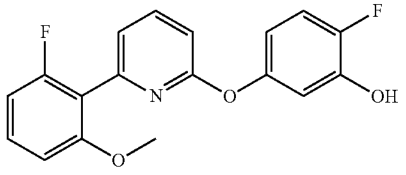 [SMILES: COc1cccc(F)c1-c1cccc(Oc2ccc(F)c(O)c2)n1] | 2-fluoro-5-((6-(2-fluoro-6-methoxyphenyl)pyridin-2-yl)oxy)phenol |
| 75 | 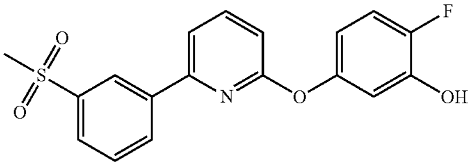 [SMILES: CS(=O)(=O)c1cccc(-c2cccc(Oc3ccc(F)c(O)c3)n2)c1] | 2-fluoro-5-((6-(3-(methylsulfonyl)phenyl)pyridin-2-yl)oxy)phenol |
| 76 | 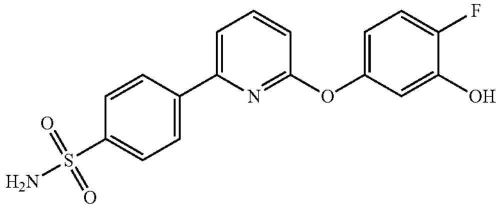 [SMILES: NS(=O)(=O)c1ccc(-c2cccc(Oc3ccc(F)c(O)c3)n2)cc1] | 4-(6-(4-fluoro-3-hydroxyphenoxy)pyridin-2-yl)benzene sulfonamide |
| 77 | 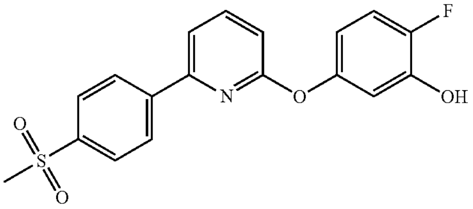 [SMILES: CS(=O)(=O)c1ccc(-c2cccc(Oc3ccc(F)c(O)c3)n2)cc1] | 2-fluoro-5-((6-(4-(methylsulfonyl)phenyl)pyridin-2-yl)oxy)phenol |
| 78 | 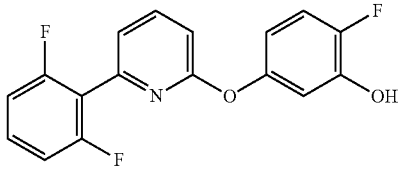 [SMILES: Oc1cc(Oc2cccc(-c3c(F)cccc3F)n2)ccc1F] | 5-((6-(2,6-difluorophenyl)pyridin-2-yl)oxy)-2-fluorophenol |
| 79 | 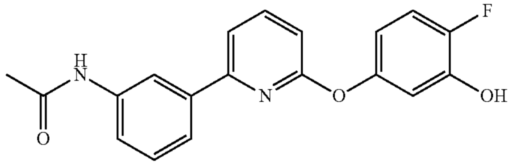 [SMILES: CC(=O)Nc1cccc(-c2cccc(Oc3ccc(F)c(O)c3)n2)c1] | N-(3-(6-(4-fluoro-3-hydroxyphenoxy)pyridin-2-yl)phenyl)acetamide |
| 80 | 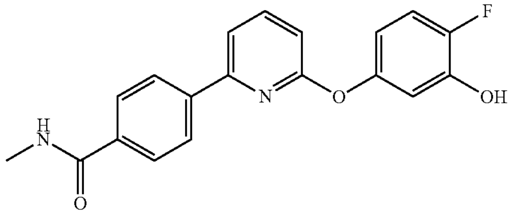 [SMILES: CNC(=O)c1ccc(-c2cccc(Oc3ccc(F)c(O)c3)n2)cc1] | 4-(6-(4-fluoro-3-hydroxyphenoxy)pyridin-2-yl)-N-methylbenzamide |
| 81 | 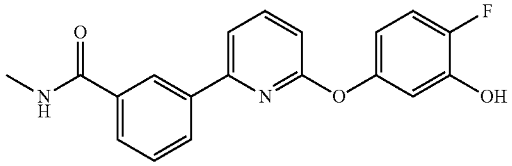 [SMILES: CNC(=O)c1cccc(-c2cccc(Oc3ccc(F)c(O)c3)n2)c1] | 3-(6-(4-fluoro-3-hydroxyphenoxy)pyridin-2-yl)-N-methylbenzamide |

TABLE 1-continued

| Ex. | Structure | Name |
|---|---|---|
| | Exemplary compounds | |
| 82 | 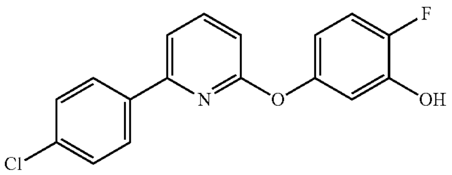 [SMILES: Oc1cc(Oc2cccc(-c3ccc(Cl)cc3)n2)ccc1F] | 5-{[6-(4-chlorophenyl)pyridin-2-yl]oxy}-2-fluorophenol |
| 83 | 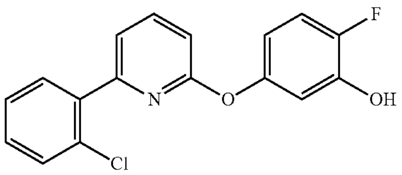 [SMILES: Oc1cc(Oc2cccc(-c3ccccc3Cl)n2)ccc1F] | 5-{[6-(2-chlorophenyl)pyridin-2-yl]oxy}-2-fluorophenol |
| 84 | 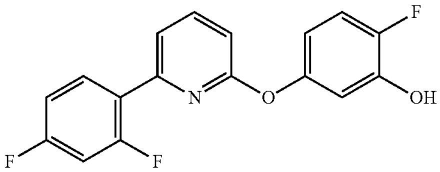 [SMILES: Oc1cc(Oc2cccc(-c3ccc(F)cc3F)n2)ccc1F] | 5-{[6-(2,4-difluorophenyl)pyridin-2-yl]oxy}-2-fluorophenol |
| 85 | 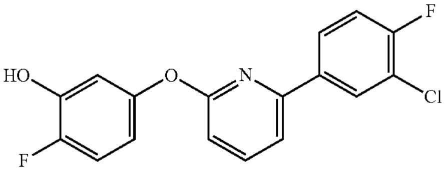 [SMILES: Oc1cc(Oc2cccc(-c3ccc(F)c(Cl)c3)n2)ccc1F] | 5-{[6-(3-chloro-4-fluorophenyl)pyridin-2-yl]oxy}-2-fluorophenol |
| 86 | 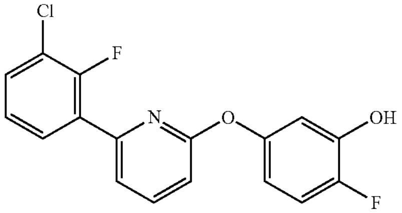 [SMILES: Oc1cc(Oc2cccc(-c3cccc(Cl)c3F)n2)ccc1F] | 5-{[6-(3-chloro-2-fluorophenyl)pyridin-2-yl]oxy}-2-fluorophenol |
| 87 | 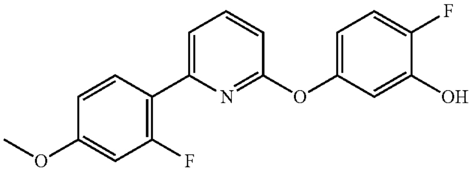 [SMILES: COc1ccc(-c2cccc(Oc3ccc(F)c(O)c3)n2)c(F)c1] | 2-fluoro-5-{[6-(2-fluoro-4-methoxyphenyl)pyridin-2-yl]oxy}phenol |
| 88 | 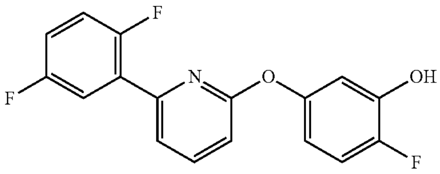 [SMILES: Oc1cc(Oc2cccc(-c3cc(F)ccc3F)n2)ccc1F] | 5-{[6-(2,5-difluorophenyl)pyridin-2-yl]oxy}-2-fluorophenol |
| 89 | 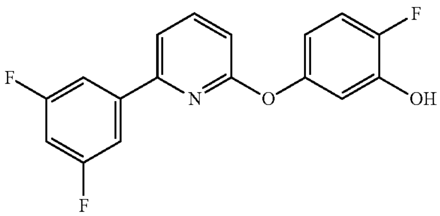 [SMILES: Oc1cc(Oc2cccc(-c3cc(F)cc(F)c3)n2)ccc1F] | 5-{[6-(3,5-difluorophenyl)pyridin-2-yl]oxy}-2-fluorophenol |

TABLE 1-continued

| Exemplary compounds | | |
|---|---|---|
| Ex. | Structure | Name |
| 90 | 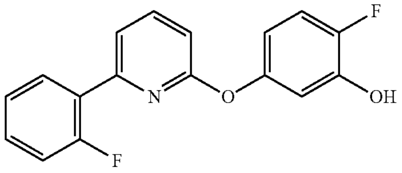 [SMILES: Oc1cc(Oc2cccc(-c3ccccc3F)n2)ccc1F] | 2-fluoro-5-((6-(2-fluorophenyl)pyridin-2-yl)oxy)phenol |
| 91 | 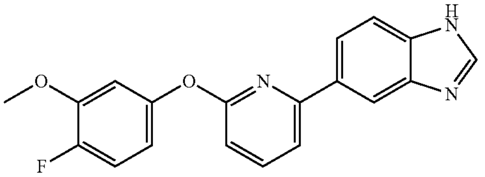 [SMILES: COc1cc(Oc2cccc(-c3ccc4[nH]cnc4c3)n2)ccc1F] | 5-[6-(3-fluoro-4-methoxyphenoxy)pyridin-2-yl]-1H-1,3-benzodiazole |
| 92 | 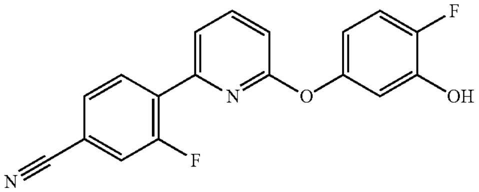 [SMILES: N#Cc1ccc(-c2cccc(Oc3ccc(F)c(O)c3)n2)c(F)c1] | 3-fluoro-4-(6-(4-fluoro-3-hydroxyphenoxy)pyridin-2-yl)benzonitrile |
| 93 | 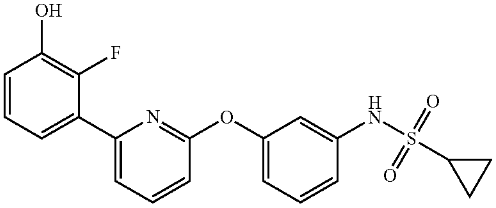 [SMILES: O=S(=O)(Nc1cccc(Oc2cccc(-c3cccc(O)c3F)n2)c1)C1CC1] | N-(3-{[6-(2-fluoro-3-hydroxyphenyl)pyridin-2-yl]oxy}phenyl)cyclopropane-sulfonamide |
| 94 | 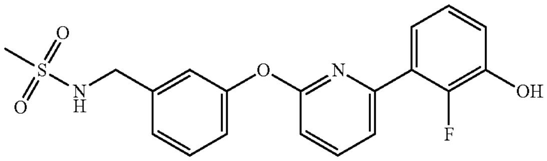 [SMILES: CS(=O)(=O)NCc1cccc(Oc2cccc(-c3cccc(O)c3F)n2)c1] | N-[(3-{[6-(2-fluoro-3-hydroxyphenyl)pyridin-2-yl]oxy}phenyl)methyl]methane-sulfonamide |
| 95 | 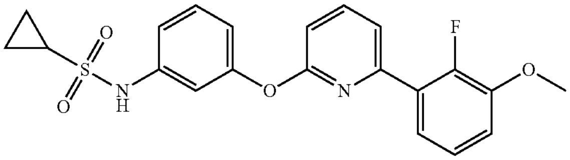 [SMILES: COc1cccc(-c2cccc(Oc3cccc(NS(=O)(=O)C4CC4)c3)n2)c1F] | N-(3-{[6-(2-fluoro-3-methoxyphenyl)pyridin-2-yl]oxy}phenyl)cyclopropane-sulfonamide |
| 96 | 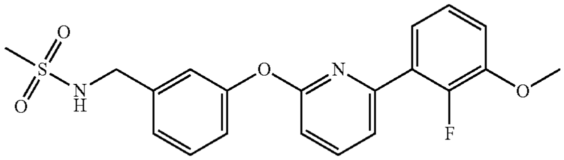 | N-[(3-{[6-(2-fluoro-3-methoxyphenyl)pyridin-2-yl]oxy}phenyl)methyl]methane-sulfonamide |
| 97 | 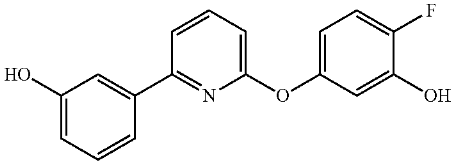 [SMILES: Oc1cccc(-c2cccc(Oc3ccc(F)c(O)c3)n2)c1] | 2-fluoro-5-{[6-(3-hydroxyphenyl)pyridin-2-yl]oxy}phenol |

TABLE 1-continued

| Exemplary compounds | | |
|---|---|---|
| Ex. | Structure | Name |
| 98 | 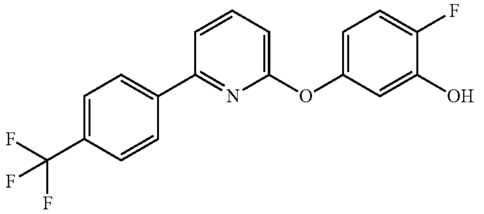 [SMILES: Oc1cc(Oc2cccc(-c3ccc(C(F)(F)F)cc3)n2)ccc1F] | 2-fluoro-5-((6-(4-(trifluoromethyl)phenyl)pyridin-2-yl)oxy)phenol |
| 99 | 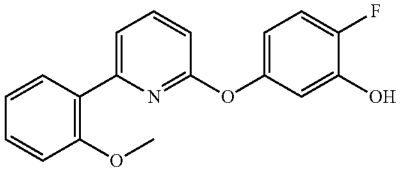 [SMILES: COc1ccccc1-c1cccc(Oc2ccc(F)c(O)c2)n1] | 2-fluoro-5-((6-(2-methoxyphenyl)pyridin-2-yl)oxy)phenol |
| 100 | 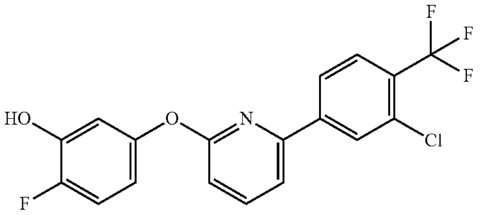 [SMILES: Oc1cc(Oc2cccc(-c3ccc(C(F)(F)F)c(Cl)c3)n2)ccc1F] | 5-((6-(3-chloro-4-(trifluoromethyl)phenyl)pyridin-2-yl)oxy)-2-fluorophenol |
| 101 | 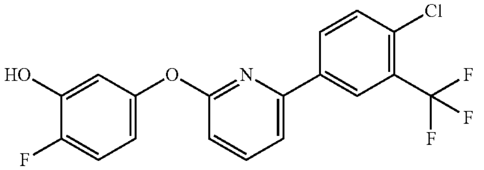 [SMILES: Oc1cc(Oc2cccc(-c3ccc(Cl)c(C(F)(F)F)c3)n2)ccc1F] | 5-((6-(4-chloro-3-(trifluoromethyl)phenyl)pyridin-2-yl)oxy)-2-fluorophenol |
| 102 | 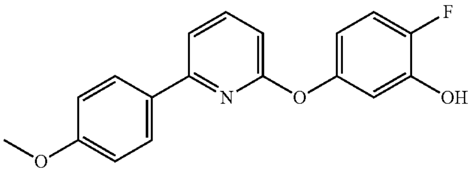 [SMILES: COc1ccc(-c2cccc(Oc3ccc(F)c(O)c3)n2)cc1] | 2-fluoro-5-((6-(4-methoxyphenyl)pyridin-2-yl)oxy)phenol |
| 103 | 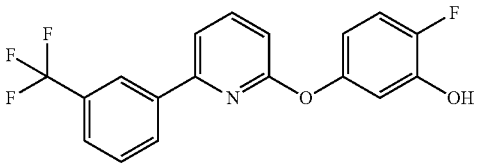 [SMILES: Oc1cc(Oc2cccc(-c3cccc(C(F)(F)F)c3)n2)ccc1F] | 2-fluoro-5-((6-(3-(trifluoromethyl)phenyl)pyridin-2-yl)oxy)phenol |
| 104 | 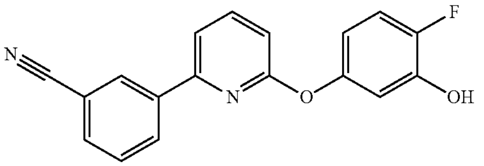 [SMILES: N#Cc1cccc(-c2cccc(Oc3ccc(F)c(O)c3)n2)c1] | 3-(6-(4-fluoro-3-hydroxyphenoxy)pyridin-2-yl)benzonitrile |
| 105 | 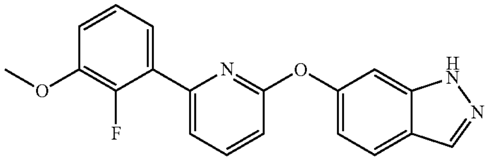 [SMILES: COc1cccc(-c2cccc(Oc3ccc4cn[nH]c4c3)n2)c1F] | 6-{[6-(2-fluoro-3-methoxyphenyl)pyridin-2-yl]oxy}-1H-indazole |

TABLE 1-continued

| Exemplary compounds | | |
|---|---|---|
| Ex. | Structure | Name |
| 106 | 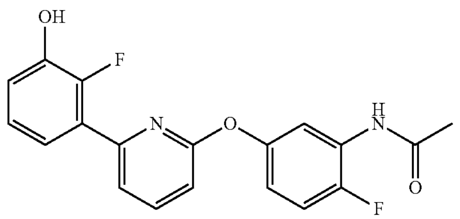 [SMILES: CC(=O)Nc1cc(Oc2cccc(-c3cccc(O)c3F)n2)ccc1F] | N-(2-fluoro-5-{[6-(2-fluoro-3-hydroxyphenyl)pyridin-2-yl]oxy}phenyl)acetamide |
| 107 | 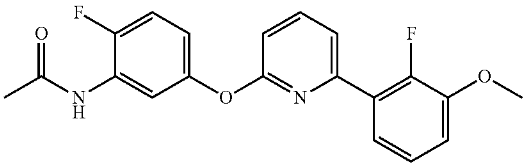 [SMILES: COc1cccc(-c2cccc(Oc3ccc(F)c(NC(C)=O)c3)n2)c1F] | N-(2-fluoro-5-{[6-(2-fluoro-3-methoxyphenyl)pyridin-2-yl]oxy}phenyl)acetamide |
| 108 | 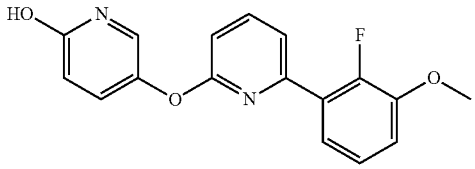 [SMILES: COc1cccc(-c2cccc(Oc3ccc(O)nc3)n2)c1F] | 5-{[6-(2-fluoro-3-methoxyphenyl)pyridin-2-yl]oxy}-1,2-dihydropyridin-2-one |
| 109 | 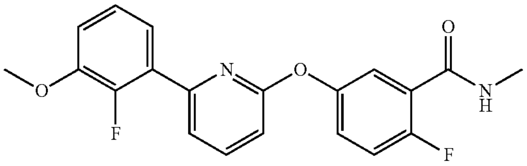 | 2-fluoro-5-{[6-(2-fluoro-3-methoxyphenyl)pyridin-2-yl]oxy}-N-methylbenzamide |
| 110 | 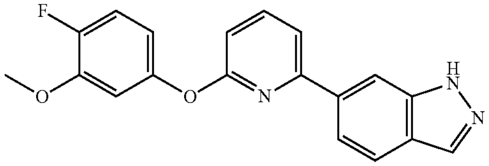 [SMILES: COc1cc(Oc2cccc(-c3ccc4cn[nH]c4c3)n2)ccc1F] | 6-[6-(4-fluoro-3-methoxyphenoxy)pyridin-2-yl]-2H-indazole |
| 111 | 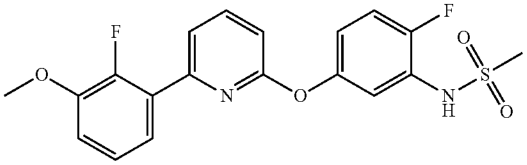 | N-(2-fluoro-5-((6-(2-fluoro-3-methoxyphenyl)pyridin-2-yl)oxy)phenyl) methanesulfonamide |
| 112 | 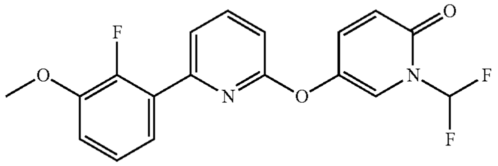 [SMILES: COc1cccc(-c2cccc(Oc3ccc(=O)n(C(F)F)c3)n2)c1F] | 1-(difluoromethyl)-5-((6-(2-fluoro-3-methoxyphenyl)pyridin-2-yl)oxy)pyridin-2(1H)-one |
| 113 | 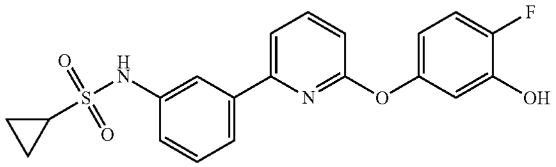 [SMILES: O=S(=O)(Nc1cccc(-c2cccc(Oc3ccc(F)c(O)c3)n2)c1)C1CC1] | N-(3-(6-(4-fluoro-3-hydroxyphenoxy)pyridin-2-yl)phenyl) cyclopropanesulfonamide |

TABLE 1-continued

Exemplary compounds

| Ex. | Structure | Name |
| --- | --- | --- |
| 114 | 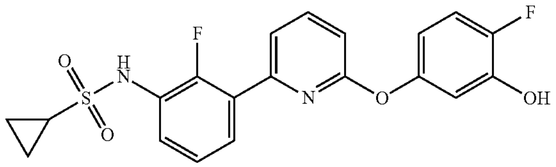 [SMILES: O=S(=O)(Nc1cccc(-c2cccc(Oc3ccc(F)c(O)c3)n2)c1F)C1CC1] | N-{2-fluoro-3-[6-(4-fluoro-3-hydroxyphenoxy)pyridin-2-yl]phenyl}cyclopropanesulfonamide |
| 115 | 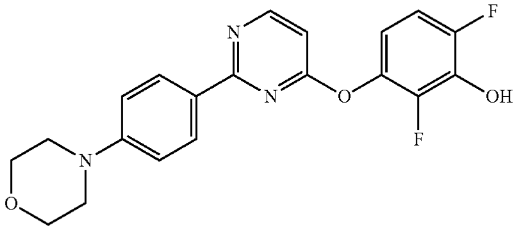 [SMILES: Oc1c(F)ccc(Oc2ccnc(-c3ccc(N4CCOCC4)cc3)n2)c1F] | 2,6-difluoro-3-((2-(4-morpholinophenyl)pyrimidin-4-yl)oxy)phenol |
| 116 | 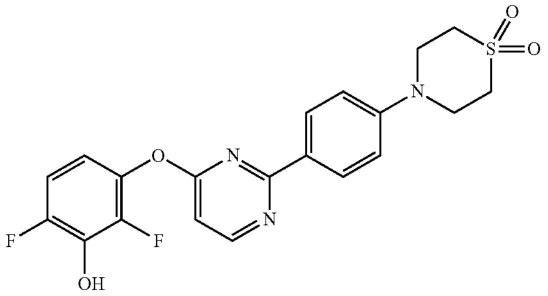 [SMILES: O=S1(=O)CCN(c2ccc(-c3nccc(Oc4ccc(F)c(O)c4F)n3)cc2)CC1] | 4-(4-(4-(2,4-difluoro-3-hydroxyphenoxy)pyrimidin-2-yl)phenyl)thiomorpholine 1,1-dioxide |
| 117 | 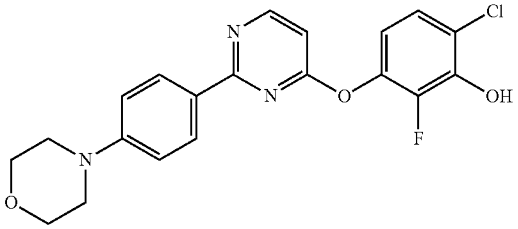 | 6-chloro-2-fluoro-3-((2-(4-morpholinophenyl)pyrimidin-4-yl)oxy)phenol |
| 118 | 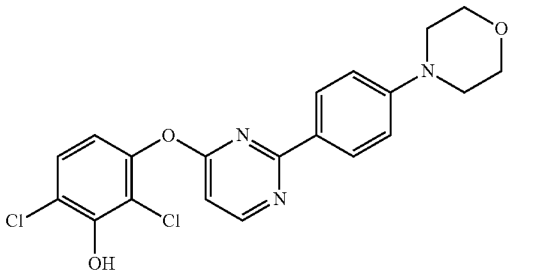 [SMILES: Oc1c(Cl)ccc(Oc2ccnc(-c3ccc(N4CCOCC4)cc3)n2)c1Cl] | 2,6-dichloro-3-((2-(4-morpholinophenyl)pyrimidin-4-yl)oxy)pheno |

Further Forms of Compounds Disclosed Herein

Isomers/Stereoisomers

In some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred. In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds disclosed herein include isotopes of hydrogen, carbon, nitrogen, oxygen, phosphorous, sulfur, fluorine and chloride, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, and the pharmaceutically acceptable salts, solvates, or stereoisomers thereof which contain the aforementioned isotopes and/or other isotopes of other atoms are within the scope of this invention. Certain isotopically-labeled compounds, for example those into which radioactive isotopes such as $^{3}H$ and $^{14}C$ are incorporated, are useful in drug and/or substrate tissue distribution assays. Tritiated, i.e., $^{3}H$ and carbon-14, i.e., $^{14}C$, isotopes are particularly preferred for their ease of preparation and detectability. Further, substitution with heavy isotopes such as deuterium, i.e., $^{2}H$, produces certain therapeutic advantages resulting from greater metabolic stability, for example increased in vivo half-life or reduced dosage requirements.

In some embodiments, the compounds described herein are labeled by other means, including, but not limited to, the use of chromophores or fluorescent moieties, bioluminescent labels, or chemiluminescent labels.

In some embodiments, the labeled compounds described herein are used for measuring in vitro and in vivo binding of unlabeled HSD17B13 inhibitors.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds disclosed herein, or a solvate, or stereoisomer thereof, or by separately reacting a purified compound in its free form with a suitable acid or base, and isolating the salt thus formed.

Examples of pharmaceutically acceptable salts include those salts prepared by reaction of the compounds described herein with a mineral, organic acid or inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylateundeconate and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid and muconic acid. In some embodiments, other acids, such as oxalic, while not in themselves pharmaceutically acceptable, are employed in the preparation of salts useful as intermediates in obtaining the compounds disclosed herein, solvate, or stereoisomer thereof and their pharmaceutically acceptable acid addition salts.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N^{+}(C_{1-4}\ alkyl)_4$, and the like.

Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they contain. In some embodiments, water or oil-soluble or dispersible products are obtained by such quaternization.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared by recrystallization from an aqueous/organic solvent mixture, using organic solvents including, but not limited to, dioxane, tetrahydrofuran or methanol. In addition, the compounds provided herein can exist in unsolvated as well as solvated forms. In general, the solvated forms are considered equivalent to the unsolvated forms for the purposes of the compounds and methods provided herein.

Tautomers

In some situations, compounds exist as tautomers. The compounds described herein include all possible tautomers within the formulas described herein. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH.

Method of Treatment

Provided herein are methods of inhibiting HSD17B13 expression or activity, which can be useful for treating, preventing, or ameliorating a disease associated with HSD17B13 in a subject in need thereof, such as NAFLD or NASH, by administration of a compound that targets HSD17B13, or a pharmaceutically acceptable salt, solvate, or stereoisomer thereof.

Provided herein are methods of inhibiting expression or activity of HSD17B13 in a cell comprising contacting the cell with a HSD17B13 inhibitor disclosed or a pharmaceutically acceptable salt, solvate, or stereoisomer thereof, thereby inhibiting expression or activity of HSD17B13 in the cell. In some embodiments, the cell is a hepatocyte cell. In some embodiments, the cell is in the liver. In some embodiments, the cell is in the liver of a subject who has, or is at risk of having a disease, disorder, condition, symptom, or physiological marker associated with a liver disease, metabolic disease, or cardiovascular disease or disorder. In some embodiments, the cells is the adipocyte or monocyte from a subject who has or is at risk of having a disease. In some embodiments, the liver disease, metabolic disease, or cardiovascular disease or disorder is metabolic syndrome, fatty liver disease, chronic liver disease, liver cirrhosis, hepatic steatosis, steatohepatitis, nonalcoholic fatty liver disease (NAFLD), alcoholic liver disease, nonalcoholic steatohepatitis (NASH), Fulminant Wilson's disease, rapidly fibrosising hepatitis C viral injury, and decompensated portal vein hypertension. In some embodiments, the liver disease, metabolic disease, or cardiovascular disease or disorder is NASH.

In some embodiments, the liver disease is primary biliary cirrhosis and primary sclerosing cholangitis.

Provided herein are methods of treating, preventing, delaying the onset, slowing the progression, or ameliorating one or more diseases, disorders, conditions, symptoms, or physiological markers associated with HSD17B13 comprising administering to a subject in need thereof a compound disclosed herein, or a pharmaceutically acceptable salt, solvate, or stereoisomer thereof. In some embodiments, the subject in need thereof is identified as having, or at risk of having, the disease, disorder, condition, symptom or physiological marker. In some embodiments, the liver disease, metabolic disease, or cardiovascular disease or disorder is metabolic syndrome, liver disease, fatty liver disease, chronic liver disease, liver cirrhosis, hepatic steatosis, steatohepatitis, alcoholic liver disease, nonalcoholic fatty liver disease (NAFLD), and nonalcoholic steatohepatitis (NASH). In some embodiments, the liver disease, metabolic disease, or cardiovascular disease or disorder is NASH.

Provided herein are methods of reducing, improving, or regulating hepatic steatosis, liver fibrosis, triglyceride synthesis, lipid levels, hepatic lipids, ALT levels, NAFLD Activity Score (NAS), cholesterol levels, or triglyceride levels, or a combination thereof, in a subject in need thereof comprising administering to the subject a compound disclosed herein, or a pharmaceutically acceptable salt, solvate, or stereoisomer thereof. In some embodiments, the compound disclosed herein, or a pharmaceutically acceptable salt, solvate, or stereoisomer thereof, is provided for use in reducing, improving, or regulating hepatic steatosis in the individual. In some embodiments, the compound disclosed herein, or a pharmaceutically acceptable salt, solvate, or stereoisomer thereof, is provided for use in reducing, improving, or regulating liver fibrosis in the individual. In some embodiments, the compound disclosed herein, or a pharmaceutically acceptable salt, solvate, or stereoisomer thereof, is provided for use in reducing, improving, or regulating triglyceride synthesis in the individual. In some embodiments, the compound disclosed herein, or a pharmaceutically acceptable salt, solvate, or stereoisomer thereof, is provided for use in reducing, improving, or regulating lipid levels in the individual. In some embodiments, the compound disclosed herein, or a pharmaceutically acceptable salt, solvate, or stereoisomer thereof, is provided for use in reducing, improving, or regulating hepatic lipids in the individual. In some embodiments, the compound disclosed herein, or a pharmaceutically acceptable salt, solvate, or stereoisomer thereof, is provided for use in reducing, improving, or regulating ALT levels in the individual. In some embodiments, the compound disclosed herein, or a pharmaceutically acceptable salt, solvate, or stereoisomer thereof, is provided for use in reducing, improving, or regulating NAFLD Activity Score in the individual. In some embodiments, the compound disclosed herein, or a pharmaceutically acceptable salt, solvate, or stereoisomer thereof, is provided for use in reducing, improving, or regulating cholesterol levels in the individual. In some embodiments, the compound disclosed herein, or a pharmaceutically acceptable salt, solvate, or stereoisomer thereof, is provided for use in reducing, improving, or regulating triglyceride levels in the individual. In some embodiments, the subject is identified as having, or at risk of having a disease, disorder, condition, symptom, or physiological marker associated with a liver disease, metabolic disease, or cardiovascular disease or disorder. In some embodiments, the liver disease, metabolic disease, or cardiovascular disease or disorder is metabolic syndrome, liver disease, fatty liver disease, chronic liver disease, liver cirrhosis, hepatic steatosis, steatohepatitis, nonalcoholic fatty liver disease (NAFLD), and nonalcoholic steatohepatitis (NASH). In some embodiments, the liver disease, metabolic disease, or cardiovascular disease or disorder is NASH.

Provided herein are methods for treating, preventing, or delaying onset drug induced liver injury (DILI) in a subject in need thereof. In some embodiments, the liver injury is steatohepatitis. Also Provided herein are methods for treating, preventing, or delaying onset drug induced steatohepatitis (DISH) in a subject in need thereof. In some embodiments, the subject in need thereof is receiving chemotherapy for treating cancer. In some embodiments, the subject in need thereof is receiving a treatment for a cardiovascular disease. In some embodiments, the subject in need thereof is receiving treatment for a psychiatric disease/condition. In some embodiments, the subject in need thereof is receiving treatment for pain. In some embodiments, the subject in need thereof is receiving treatment for arthritis. In some embodiments, the chemotherapy is tamoxifen, toremifene, irinotecan, methotrexate, fluorouracil (5-FU), or any combination thereof. In some embodiments, the subject in need thereof is receiving amiodarone, perhexiline, propranolol, or any combination thereof. In some embodiments, the subject in need thereof is receiving amitriptyline, clozapine, or any combination thereof. In some embodiments, the subject in need thereof is receiving methotrexate, pirprofen, or any combinations thereof.

Dosing

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of or risk factor for the disease being treated and is currently in remission, a pharmaceutical composition comprising a compound described herein, or a pharmaceutically acceptable salt thereof, in order to prevent a return of the symptoms of the disease or condition. In one aspect, prophylactic treatments include administering to a mammal having patatin-like phospholipase domain-containing 3 (PNPLA3) polymorphism, a pharmaceutical composition comprising a compound described herein, or a pharmaceutically acceptable salt thereof, in order to prevent liver damages. The 148 Isoleucine to Methionine protein variant (I148M) of patatin-like phospholipase domain-containing 3 (PNPLA3), a protein is expressed in the liver and is involved in lipid metabolism, has recently been identified as a major determinant of liver fat content. Several studies confirmed that the I148M variant predisposes towards the full spectrum of liver damage associated with fatty liver: from simple steatosis to steatohepatitis and progressive fibrosis. Furthermore, the I148M variant represents a major determinant of progression of alcohol related steatohepatitis to cirrhosis, and to influence fibrogenesis and related clinical outcomes in chronic hepatitis C virus hepatitis, and possibly chronic hepatitis B virus hepatitis, hereditary hemochromatosis and primary sclerosing cholangitis. In some embodiments, PNPLA3 polymorphism is used to predict liver disease progression.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered is temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent or daily treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound described herein, or a pharmaceutically acceptable salt thereof, are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{10}$ and the $ED_{90}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once a day; or (ii) the compound is administered to the mammal multiple times over the span of one day.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the subject every 12 hours; (v) the compound is administered to the subject every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

Pharmaceutical Compositions/Formulations

The compounds described herein are administered to a subject in need thereof, either alone or in combination with pharmaceutically acceptable carriers, excipients or diluents, in a pharmaceutical composition, according to standard pharmaceutical practice. In one embodiment, the compounds of this invention may be administered to animals. The compounds can be administered orally or parenterally, including the intravenous, intramuscular, intraperitoneal, subcutaneous, rectal and topical routes of administration.

In another aspect, provided herein are pharmaceutical compositions comprising a compound described herein, or a pharmaceutically acceptable salt, solvate, or stereoisomer thereof, and at least one pharmaceutically acceptable excipient. Pharmaceutical compositions are formulated in a conventional manner using one or more pharmaceutically acceptable excipients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the pharmaceutically acceptable excipient is selected from carriers, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, and any combinations thereof.

The pharmaceutical compositions described herein are administered to a subject by appropriate administration routes, including, but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, liquids, gels, syrups, elixirs, slurries, suspensions, self-emulsifying dispersions, solid solutions, liposomal dispersions, aerosols, solid oral dosage forms, powders, immediate release formulations, controlled release formulations, fast melt formulations, tablets, capsules, pills, powders, dragees, effervescent formulations, lyophilized formulations, delayed release formulations, extended release formulations, pulsatile release formulations, multiparticulate formulations, and mixed immediate and controlled release formulations.

Pharmaceutical compositions including compounds described herein, or a pharmaceutically acceptable salt, solvate, or stereoisomer thereof are manufactured in a conventional manner, such as, by way of example only, by means of conventional mixing, dissolving, granulating, dragee-making, levigating, emulsifying, encapsulating, entrapping, or compression processes.

Pharmaceutical compositions for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as polyvinylpyrrolidone (PVP or povidone) or calcium phosphate. If desired, disintegrating agents are added, such as the cross-linked croscarmellose sodium, polyvinylpyrrolidone, agar, or alginic acid or a salt thereof such as sodium alginate. In some embodiments, dyestuffs or pigments are added to the tablets or dragee coatings for identification or to characterize different combinations of active compound doses.

Pharmaceutical compositions that are administered orally include push-fit capsules made of gelatin, as well as soft, sealed capsules made of gelatin and a plasticizer, such as glycerol or sorbitol. The push-fit capsules contain the active ingredients in admixture with filler such as lactose, binders such as starches, and/or lubricants such as talc or magnesium stearate and, optionally, stabilizers. In soft capsules, the active compounds are dissolved or suspended in suitable liquids, such as fatty oils, liquid paraffin, or liquid polyethylene glycols. In some embodiments, stabilizers are added.

Pharmaceutical compositions for parental use are formulated as infusions or injections. In some embodiments, the pharmaceutical composition suitable for injection or infusion includes sterile aqueous solutions, or dispersions, or sterile powders comprising a compound described herein, or a pharmaceutically acceptable salt, solvate, or stereoisomer thereof. In some embodiments, the pharmaceutical composition comprises a liquid carrier. In some embodiments, the liquid carrier is a solvent or liquid dispersion medium comprising, for example, water, saline, ethanol, a polyol (for example, glycerol, propylene glycol, liquid polyethylene glycols, and the like), vegetable oils, nontoxic glyceryl esters, and any combinations thereof. In some embodiments, the pharmaceutical compositions further comprise a preservative to prevent growth of microorganisms.

Combination

Disclosed herein are method of treating a liver disease, metabolic disease, or cardiovascular disease using a compound disclosed herein, or a pharmaceutically acceptable salt, solvate, or stereoisomer thereof, in combination with an additional therapeutic agent.

In some embodiments, the additional therapeutic agent is used for the treatment of diabetes or diabetes related disorder or conditions.

In some instances, the additional therapeutic agent comprises a statin, an insulin sensitizing drug, an insulin secretagogue, an alpha-glucosidase inhibitor, a GLP agonist, a GIP agonist, a THR beta agonist, a PDE inhibitor, a DPP-4 inhibitor (such as sitagliptin, vildagliptin, saxagliptin, linagliptin, anaglptin, teneligliptin, alogliptin, gemiglptin, or dutoglpitin), a catecholamine (such as epinephrine, norepinephrine, or dopamine), peroxisome proliferator-activated receptor (PPAR)-gamma agonist (e.g., a thiazolidinedione (TZD) [such as pioglitazone, rosiglitazone, rivoglitazone, or troglitazone], aleglitazar, farglitazar, muraglitazar, or tesaglitazar), peroxisome proliferator-activated receptor (PPAR)-alpha agonist, peroxisome proliferator-activated receptor (PPAR)-delta agonist, a farnesoid X receptor (FXR) agonist (e.g., obeticholic acid), or a combination thereof. In some cases, the statin is a HMG-CoA reductase inhibitor. In other instances, additional therapeutic agents include fish oil, fibrate, vitamins such as niacin, retinoic acid (e.g., 9 cis-retinoic acid), nicotinamide ribonucleoside or its analogs thereof, or combinations thereof. In other instances, additional therapeutic agents include ACC inhibitors, FGF19 and FGF21 mimics, CCR2/CCR5 antagonists, or combinations thereof.

In some embodiments, the additional therapeutic agent is vivitrol.

In some embodiments, the additional therapeutic agent is a statin such as a HMG-CoA reductase inhibitor, fish oil, fibrate, niacin or a combination thereof. In other instances, the additional therapeutic agent is a dyslipidemia drug that prevent lipid absorption such as orlistat.

In some embodiments, the additional therapeutic agent is a vitamin such as retinoic acid or tocopheryl acetate for the treatment of diabetes and diabetes related disorder or condition such as lowering elevated body weight and/or lowering elevated blood glucose from food intake.

In some embodiments, the additional therapeutic agent is a glucose-lowering agent. In some embodiments, the additional therapeutic agent is an anti-obesity agent. In some embodiments, the additional therapeutic agent is selected from among a peroxisome proliferator activated receptor (PPAR) agonist (gamma, dual, or pan), a dipeptidyl peptidase (IV) inhibitor, a glucagon-like peptide-1 (GLP-1) analog, insulin or an insulin analog, an insulin secretagogue, a sodium glucose co-transporter 2 (SGLT2) inhibitor, a glucophage, a human amylin analog, a biguanide, an alpha-glucosidase inhibitor, a meglitinide, a thiazolidinedione, and sulfonylurea. In some embodiments, the additional therapeutic agent is metformin, sitagliptin, saxaglitpin, repaglinide, nateglinide, exenatide, liraglutide, insulin lispro, insulin aspart, insulin glargine, insulin detemir, insulin isophane, and glucagon-like peptide 1, or any combination thereof. In some embodiments, the additional therapeutic agent is a lipid-lowering agent.

In some embodiments, the additional therapeutic agent is an antioxidant, corticosteroid such as budesonide, anti-tumor necrosis factor (TNF), or a combination thereof.

In some embodiments, the additional therapeutic agent is administered at the same time as the compound disclosed herein. In some embodiments, the additional therapeutic agent and the compound disclosed herein are administered sequentially. In some embodiments, the additional therapeutic agent is administered less frequently than the compound disclosed herein. In some embodiments, the additional therapeutic agent is administered more frequently than the compound disclosed herein. In some embodiments, the additional therapeutic agent is administered prior than the administration of the compound disclosed herein. In some embodiments, the additional therapeutic agent is administered after the administration of the compound disclosed herein.

EXAMPLE

Intermediate 1: 5-((6-bromopyridin-2-yl)oxy)-2-fluorophenol

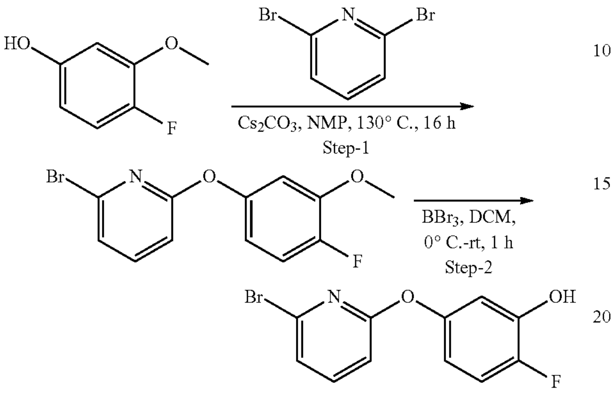

Step 1: Synthesis of 2-bromo-6-(4-fluoro-3-methoxyphenoxy)pyridine

To a stirred solution of 4-fluoro-3-methoxyphenol (3.00 g, 21.1 mmol) in NMP (50.0 mL) was added 2,6-dibromopyridine (7.50 g, 31.7 mmol) and cesium carbonate (13.8 g, 42.2 mmol) at room temperature. The reaction mixture was stirred at 130° C. for 16 h. After completion of the reaction, the reaction mixture was quenched with ice-cold water (70 mL) and extracted with ethyl acetate (2×50 mL). The organic layer was washed with water (100 mL), brine solution (100 mL), dried over anhydrous sodium sulphate, filtered and evaporated in vacuo to obtain crude 2-bromo-6-(4-fluoro-3-methoxyphenoxy)pyridine. This was purified by flash chromatography to afford pure 2-bromo-6-(4-fluoro-3-methoxyphenoxy)pyridine (4.80 g, 76.2%), LC-MS m/z calcd for C12H9BrFNO2, 296.98; found 298.1 [M+H]+.

Step 2: Synthesis of 5-((6-bromopyridin-2-yl)oxy)-2-fluorophenol

To a stirred solution of 2-bromo-6-(4-fluoro-3-methoxyphenoxy)pyridine (4.50 g, 15.1 mmol) in dichloromethane (50.0 mL) was slowly added boron tribromide (1.72 mL, 1.2 eq., 18.1 mmol) at 0° C. The reaction mixture stirred at 0° C. for 1 h. After completion of the reaction, the reaction mixture was quenched with ice-cold sodium bicarbonate solution (50 mL) and extracted with dichloromethane (2×100 mL). The organic layer was washed with brine solution (100 mL), dried over anhydrous sodium sulphate, filtered and evaporated in vacuo to obtain crude product. This was purified by flash chromatography to afford pure 5-[(6-bromopyridin-2-yl)oxy]-2-fluorophenol (3.14 g, 73.2%), LCMS m/z calcd for C11H7BrFNO2, 282.9; found 284.1; $^{1}$H NMR (400 MHz, DMSO-d6) δ 10.15 (s, 1H), 7.76 (t, J=7.9 Hz, 1H), 7.36 (d, J=7.6 Hz, 1H), 7.17 (dd, J=11.0, 8.8 Hz, 1H), 6.98 (d, J=8.1 Hz, 1H), 6.70 (dd, J=7.5, 2.9 Hz, 1H), 6.56 (dt, J=8.9, 3.3 Hz, 1H).

Intermediate 2: 2-bromo-6-(2-fluoro-3-methoxyphenyl)pyridine

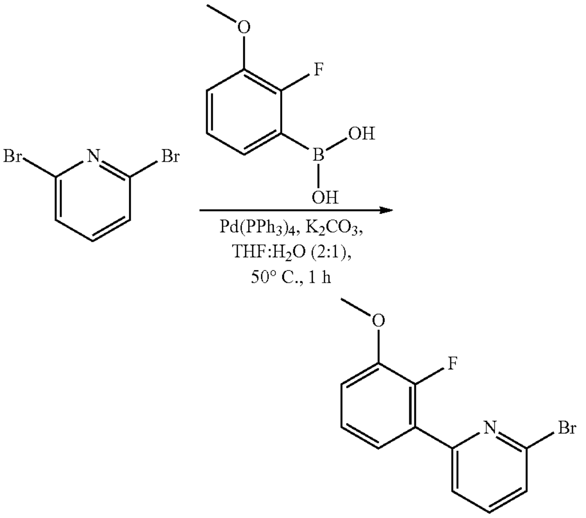

To a stirred solution of 2,6-dibromopyridine (1.0 g, 4.25 mmol) and (2-fluoro-3-methoxyphenyl)boronic acid (0.54 g, 3.19 mmol) in tetrahydrofuran (2 mL) and water (1 mL) was added potassium carbonate (1.76 g, 12.25 mmol) and purged with argon for 10 min. To this, Tetrakis(triphenylphosphine) palladium(0) (0.05 g, 0.04 mmol) was added and the reaction mixture was stirred at 50° C. for 1 h. After completion of the reaction, the reaction mixture was poured into water (40 mL) and extracted with ethyl acetate (2×40 mL). The organic phase was washed with water, brine, dried over anhydrous sodium sulfate, filtered and concentrated in vacuo to get crude product. The crude material was purified by flash chromatography to afford 2-bromo-6-(2-fluoro-3-methoxyphenyl)pyridine as a white solid (0.55 g, 46%), LCMS m/z calcd for C12H9BrFNO, 280.99; found 282.3; (M+H).

Example 1: Synthesis of 5-([2,3'-bipyridin]-6-yloxy)-2-fluorophenol

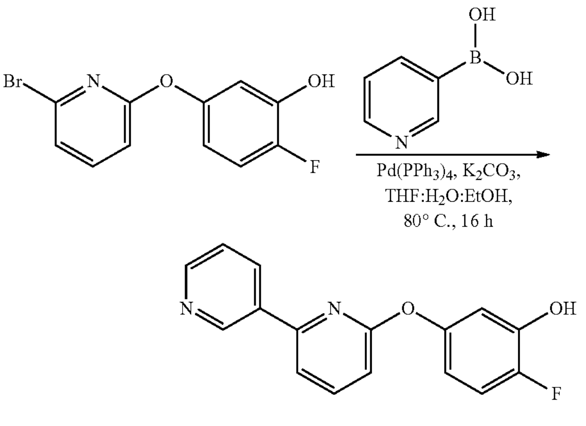

To a stirred solution of 5-((6-bromopyridin-2-yl)oxy)-2-fluorophenol (0.1 g, 0.34 mmol) and (4-methoxyphenyl)

boronic acid (0.064 g, 0.52 mmol) in tetrahydrofuran, water and ethanol mixture (5 mL, 4:0.5:0.5) was added potassium carbonate (0.14 g, 1.04 mmol). Then the reaction mixture was purged with argon for 10 minutes. This was followed by the addition of tetrakis(triphenylphosphine)palladium(0) (0.04 mg, 0.034 mmol) and the reaction mixture was heated to 80° C. and stirred for 16 hours. After completion of the reaction, the reaction mixture was poured into water (20 ml) and extracted with ethyl acetate (3×10 mL). The organic phase was washed with water, brine solution, dried over anhydrous sodium sulfate, and concentrated in vacuo to result in crude product. The crude material was purified by flash column chromatography to afford pure 2-fluoro-5-((6-(4-methoxyphenyl)pyridin-2-yl)oxy)phenol as a white solid (0.065 g, 66%); LCMS m/z calcd for C16H11FN2O2, 282.08; found 283.0; $^1$H NMR (400 MHz, DMSO-$d_6$) δ 10.06 (s, 1H), 9.07 (s, 1H), 8.57 (d, J=4.7 Hz, 1H), 8.23 (d, J=8.5 Hz, 1H), 7.94 (td, J=7.9, 2.2 Hz, 1H), 7.77 (d, J=7.7 Hz, 1H), 7.45 (dd, J=8.2, 4.6 Hz, 1H), 7.16 (t, J=10.2 Hz, 1H), 6.97 (dd, J=8.2, 2.3 Hz, 1H), 6.77 (dd, J=7.4, 3.1 Hz, 1H), 6.60 (dd, J=9.2, 3.5 Hz, 1H).

Example 2: Synthesis of 2-fluoro-3-(6-(pyridin-3-yloxy)pyridin-2-yl) phenol

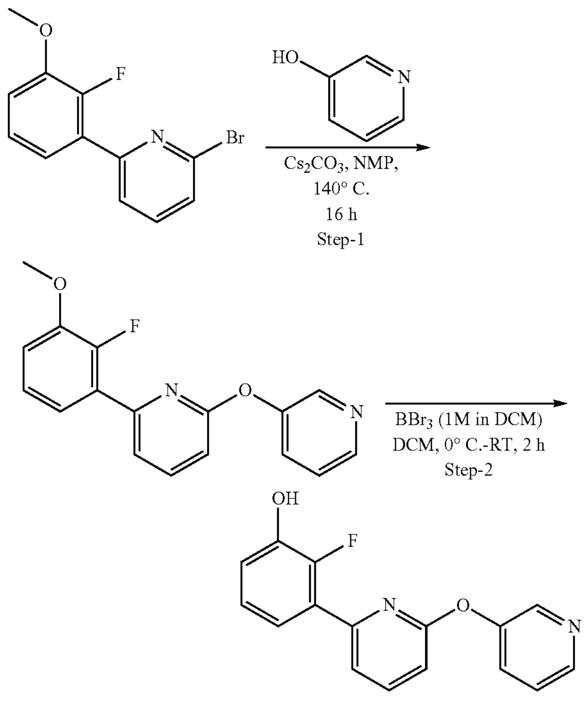

Step-1: Synthesis of 2-(2-fluoro-3-methoxyphenyl)-6-(pyridin-3-yloxy)pyridine

To a stirred solution of 2-bromo-6-(2-fluoro-3-methoxyphenyl)pyridine (0.12 g, 0.53 mmol) in 1-Methyl-2-pyrrolidone (3 mL) were added cesium carbonate (0.17 g, 0.53 mmol) and 4-pyridin-3-ol (0.06 g, 0.53 mmol) and the mixture was allowed to stir at 140° C. for 16 h. After completion of the reaction, the reaction mixture was poured into water (30 mL) and extracted with ethyl acetate (2×30 mL). The organic phase was washed with water, brine, dried over anhydrous sodium sulfate, filtered and concentrated in vacuo to give crude product. The crude material was purified by flash column chromatography to afford 2-(2-fluoro-3-methoxyphenyl)-6-(pyridin-3-yloxy)pyridine as a yellow solid (0.12 g, 76%); LCMS (ES) m/z calcd. for C17H13FN2O2, 296.1; found, 297.1 (M+H)

Step-2: Synthesis of 2-fluoro-3-(6-(pyridin-3-yloxy)pyridin-2-yl)phenol

To a stirred solution of 2-(2-fluoro-3-methoxyphenyl)-6-(pyridin-3-yloxy)pyridine (0.12 g, 0.40 mmol) in dichloromethane (3 mL) at 0° C. was added boron tribromide (1.2 mL, 1.21 mmol) and the reaction mixture was allowed stirred at room temperature for 2 h. The reaction mixture was poured into ice-water (40 mL), extracted into dichloromethane (2×30 mL). The organic phase was washed with water, brine and dried over anhydrous sodium sulfate, filtered and concentrated in vacuo to result in crude product. The crude material was purified by flash column chromatography to afford 2-fluoro-3-(6-(pyridin-3-yloxy)pyridin-2-yl)phenol as off-white solid (0.05 g, 45%); LCMS (ES) m/z calcd. for C16H11FN2O2, 282.08; found, 283.0 (M+H); 1HNMR (400 MHz, DMSO-$d_6$): δ 9.91 (s, 1H), 8.51 (d, J=2.4 Hz, 1H), 8.41 (d, J=4.0 Hz, 1H), 7.96 (t, J=7.2 Hz, 1H), 7.69 (d, J=8.4 Hz, 1H), 7.52 (d, J=6.0 Hz, 1H), 7.45-7.48 (m, 1H), 7.11 (d, J=8.0 Hz, 1H), 6.92-6.97 (m, 3H).

Example 3: Synthesis of 5-((6-(1H-indazol-6-yl)pyridin-2-yl)oxy)-2-fluorophenol

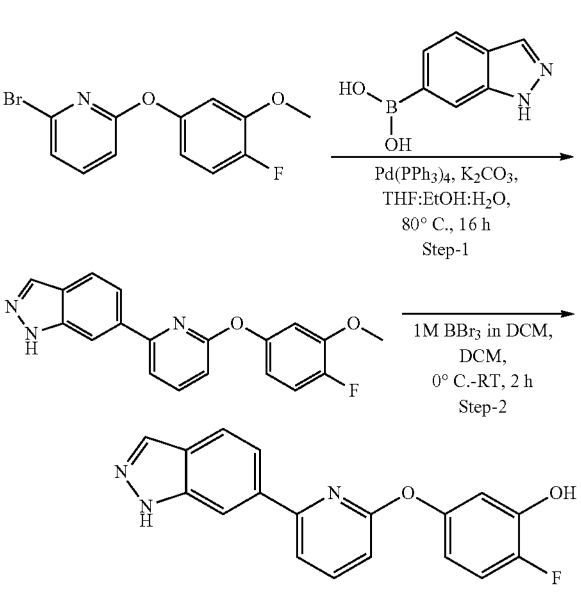

Step:1: synthesis of 6-(6-(4-fluoro-3-methoxyphenoxy)pyridin-2-yl)-1H-indazole

To a stirred solution of 2-bromo-6-(4-fluoro-3-methoxyphenoxy)pyridine (0.15 g, 0.50 mmol) and (1H-indazol-6-yl)boronic acid (0.16 g, 1.01 mmol) in tetrahydrofuran, water and ethanol mixture (5 mL, 4:0.5:0.5) was added potassium carbonate (0.21 g, 1.51 mmol). Then the reaction mixture was degassed under argon gas for 10 minutes. This was followed by the addition of Tetrakis(triphenylphosphine)palladium(0) (0.06 g, 0.05 mmol) and the reaction mixture was heated to 80° C. for 16 hours. After completion of the reaction, the reaction mixture was poured into water (20 ml) and extracted with ethyl acetate (2×20 mL). The organic phase was washed with water, brine solution and dried over anhydrous sodium sulfate, concentrated in vacuo. The crude material was purified by flash column chromatography to afford 6-(6-(4-fluoro-3-methoxyphenoxy)pyridin-2-yl)-1H-indazole as a White solid (0.03 g, 18%); LCMS (ES) m/z calcd. for C19H14FN3O2, 335.3; found, 336.3 (M+H).

Step-2: Synthesis of 5-((6-(1H-indazol-6-yl)pyridin-2-yl)oxy)-2-fluorophenol

To a stirred solution of 6-(6-(4-fluoro-3-methoxyphenoxy)pyridin-2-yl)-1H-indazole (0.03 g, 0.089 mmol) in dichloromethane at 0° C. (2.00 mL) was added 1M boron tribromide in dichloromethane (0.0467 mL, 0.89 mmol) and the reaction mixture was stirred at room temperature for 1 h. The reaction mixture was poured into ice-water (20 mL), extracted into dichloromethane (2×20 mL). The organic phase was washed with brine solution (20 mL) and dried over anhydrous sodium sulphate, filtered and evaporated in vacuo. The crude material was purified by flash column chromatography to afford 5-((6-(1H-indazol-6-yl)pyridin-2-yl)oxy)-2-fluorophenol (0.01 g, 35%); LCMS (ES) m/z calcd. for C18H12FN3O2, 321.3; found, 322.0 (M+H); $^1$H NMR (400 MHz, DMSO-$d_6$) δ 13.19 (s, 1H), 10.09 (s, 1H), 8.06 (d, J=9.8 Hz, 2H), 7.93 (t, J=7.8 Hz, 1H), 7.79 (d, J=7.8 Hz, 2H), 7.69 (d, J=8.5 Hz, 1H), 7.20 (dd, J=11.1, 8.8 Hz, 1H), 6.93 (d, J=8.0 Hz, 1H), 6.78 (dd, J=7.4, 2.9 Hz, 1H), 6.63 (d, J=8.5 Hz, 1H), Example 4: Synthesis of 6-((6-(2-fluoro-3-methoxyphenyl)pyridin-2-yl) oxy)-1H-indazole and 3-(6-((1H-indazol-6-yl)oxy)pyridin-2-yl)-2 fluorophenol

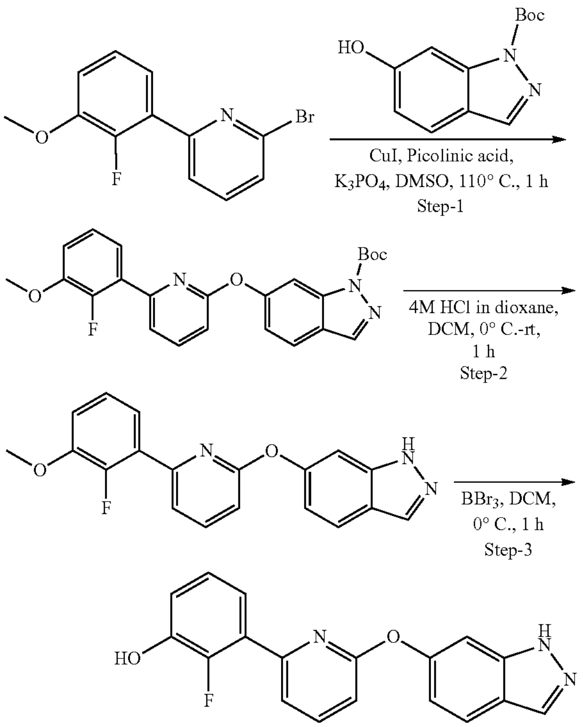

Step 1: Synthesis of tert-butyl 6-((6-(2-fluoro-3-methoxyphenyl)pyridin-2-yl)oxy)-1H-indazole-1-carboxylate To a solution of 2-bromo-6-(2-fluoro-3-methoxyphenyl) pyridine (300 mg, 1.06 mmol) in DMSO (10.0 mL) was added tert-butyl 6-hydroxy-1H-indazole-1-carboxylate (498 mg, 2.13 mmol), copper iodide (33.7 mg, 0.106 mmol), picolinic acid (26.2 mg, 0.213 mmol) and tripotassium phosphate (458 mg, 2.13 mmol) at room temperature and the reaction mixture was allowed to stir at 110° C. for 1 hours. After completion, the reaction mixture was quenched with ice cold water (30 mL) and extracted with ethyl acetate (30 mL). The organic phase was washed with water (30 mL), brine solution (30 mL) and dried over anhydrous sodium sulfate, filtered and concentrated to obtain crude product. The crude was purified by flash chromatography. Pure fractions were collected and concentrated in vacuo to afford pure tert-butyl 6-{[6-(2-fluoro-3-methoxyphenyl)pyridin-2-yl]oxy}-1H-indazole-1-carboxylate (537 mg). LCMS (ES) m/z calcd. for C24H22FN3O4, 435.1; found, 436.0 (M+H)

Step 2: Synthesis of 6-((6-(2-fluoro-3-methoxyphenyl)pyridin-2-yl)oxy)-1H-indazole To a solution of tert-butyl 6-{[6-(2-fluoro-3-methoxyphenyl)pyridin-2-yl]oxy}-1H-indazole-1-carboxylate (537 mg, 1.23 mmol) in dichloromethane (10.0 mL) at 0° C. was slowly added 4 M HCl in 1,4-dioxane (1.54 mL, 6.17 mmol). The reaction mixture was stirred at room temperature for 16 h. After completion of the reaction, the reaction mixture was diluted with DCM (30 mL) and washed with sodium bicarbonate solution (30 mL). The organic phase was washed with water, brine, dried over anhydrous sodium sulphate, filtered and concentrated in vacuo to afford crude product which was purified by flash chromatography. Pure fractions were concentrated in vacuo to afford 6-{[6-(2-fluoro-3-methoxyphenyl)pyridin-2-yl]oxy}-1H-indazole as off-white solid (93.0 mg, 22.5%). LCMS (ES) m/z calcd. for C19H14FN3O2, 335.1; found, 336.1 (M+H). $^1$H NMR (400 MHz, DMSO-$d_6$) δ 13.01 (s, 1H), 8.05 (s, 1H), 7.95 (t, J=7.9 Hz, 1H), 7.77 (d, J=8.8 Hz, 1H), 7.53 (d, J=7.6 Hz, 1H), 7.29 (s, 1H), 7.17 (t, J=7.5 Hz, 2H), 7.12 (d, J=7.4 Hz, 1H), 7.04 (d, J=8.2 Hz, 1H), 6.95 (d, J=8.8 Hz, 1H), 3.83 (s, 2H).

Step 3: Synthesis of 3-(6-((1H-indazol-6-yl)oxy) pyridin-2-yl)-2-fluorophenol

To a stirred solution of 6-{[6-(2-fluoro-3-methoxyphenyl) pyridin-2-yl]oxy}-1H-indazole (75.0 mg, 0.224 mmol) in dichloromethane (2.00 mL) was added boron tribromide (0.5 mL, 0.492 mmol) at 0° C. The reaction mixture was stirred at 0° C. for 1 h. The reaction mixture was quenched with ice-cold sodium bicarbonate solution (5 mL) and extracted with dichloromethane (10 mL). Organic layer was washed brine solution (20 mL) and dried over anhydrous sodium sulphate, filtered and evaporated in vacuo to obtain crude product. The crude was purified using flash chromatography. Pure fractions were concentrated in vacuo to afford 2-fluoro-3-[6-(1H-indazol-6-yloxy)pyridin-2-yl]phenol (16.0 mg, 22.2%), LCMS (ES) m/z calcd. for C18H12FN3O2, 321.09; found, 322.0 (M+H). $^1$H NMR (400 MHz, DMSO-$d_6$) δ 13.00 (s, 1H), 9.94 (s, 1H), 8.05 (s, 1H), 7.94 (t, J=7.9 Hz, 1H), 7.77 (d, J=8.7 Hz, 1H), 7.51 (dd, J=7.6, 2.0 Hz, 1H), 7.28 (s, 1H), 7.06-6.99 (m, 2H), 6.99-6.89 (m, 3H).

Example 5: Synthesis of 1-(difluoromethyl)-5-((6-(2-fluoro-3-hydroxyphenyl)pyridin-2-yl)oxy)pyridin-2(1H)-one

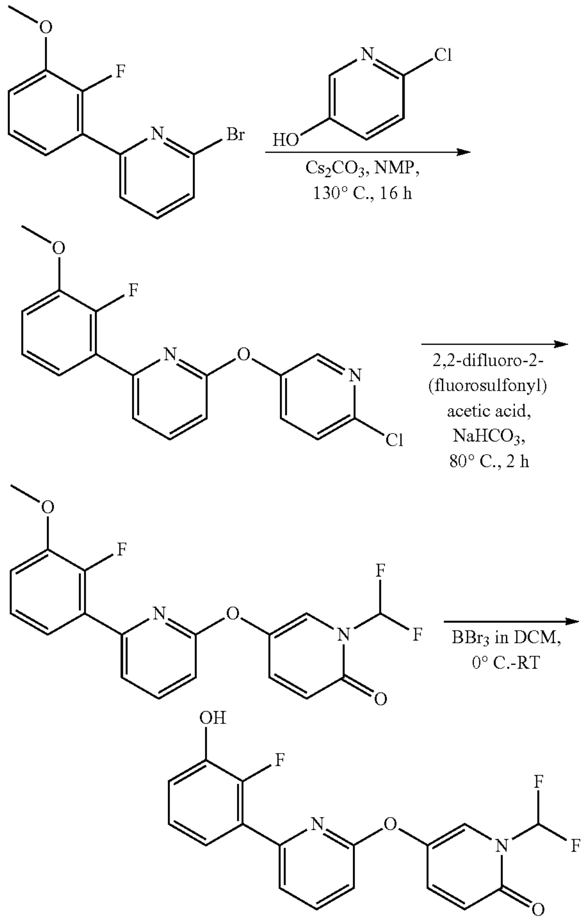

Step 1: 2-chloro-5-((6-(2-fluoro-3-methoxyphenyl) pyridin-2-yl)oxy)pyridine

To a solution of 2-bromo-6-(2-fluoro-3-methoxyphenyl) pyridine (0.2 g, 0.71 mmol) and 6-chloropyridin-3-ol (0.082 g, 0.64 mmol) in NMP (5 mL) was added cesium carbonate (0.46 g, 1.42 mmol) and the solution was stirred at 110° C. for 16 hours. The reaction mixture was cooled to room temperature and partitioned between ethyl acetate and water. The organic layer was washed with water, anhydrous sodium sulfate, filtered and concentrated in vacuo to give crude product. The crude product was purified by flash column chromatography. Purification afforded 2-[(6-chloropyridin-3-yl)oxy]-6-(2-fluoro-3-methoxyphenyl)pyridine as off-white solid (0.06 g, 26%); LCMS (ES) m/z calcd. for C17H12ClFN2O2, 330.06; found, 331.1 (M+H).

Step-2: 1-(difluoromethyl)-5-((6-(2-fluoro-3-methoxyphenyl)pyridin-2-yl) oxy)pyridin-2(1H)-one To a stirred solution of 2-[(6-chloropyridin-3-yl)oxy]-6-(2-fluoro-3-methoxyphenyl)pyridine (60.0 mg, 0.18 mmol) in acetonitrile (5 mL) was added sodium bicarbonate (23.1 mg, 0.27 mmol) and 2,2-difluoro-2-(fluorosulfonyl) acetic acid (194 mg, 1.09 mmol). The resulting reaction mixture was heated to 80° C. for 2 h. After completion of reaction, the reaction mixture was cooled to room temperature and partitioned between ethyl acetate and water. The organic layer was washed with water, anhydrous sodium sulfate, filtered and concentrated in vacuo. The resulting crude material was purified by flash column chromatography. Purification afforded 1-(difluoromethyl)-5-{[6-(2-fluoro-3-methoxyphenyl)pyridin-2-yl]oxy}-1,2-dihydropyridin-2-one as an off-white solid (0.032 g, 49%); LCMS (ES) m/z calcd. for C18H13F3N2O3, 362.09; found, 363.3; 1H NMR (400 MHz, DMSO-d6): δ 7.96 (t, J=8.0 Hz, 1H), 7.89 (d, J=2.8 Hz, 1H), 7.83 (s, 1H), 7.66-7.69 (m, 1H), 7.54 (d, J=6.8 Hz, 1H), 7.15-7.25 (m, 3H), 7.13 (d, J=8.4 Hz, 1H), 6.57 (d, J=10 Hz, 1H), 3.85 (s, 3H).

Step-3: Synthesis of 1-(difluoromethyl)-5-((6-(2-fluoro-3-hydroxyphenyl) pyridin-2-yl)oxy)pyridin-2 (1H)-one To a stirred solution of 1-(difluoromethyl)-5-{[6-(2-fluoro-3-methoxyphenyl)pyridin-2-yl]oxy}-1,2-dihydro-pyridin-2-one (25.0 mg, 69.0 μmol) in dichloromethane (1 mL) was added 1M boron tribromide in dichloromethane (0.13 mL, 0.13 mmol) at 0° C. and then stirred at room temperature for 30 min. The progress of the reaction was monitored by TLC. After completion of reaction, the reaction mixture was partitioned between dichloromethane and water. The organic layer was washed with water, anhydrous sodium sulfate, filtered and concentrated in vacuo. The crude material was purified by flash column chromatography. Purification afforded 1-(difluoromethyl)-5-{[6-(2-fluoro-3-hydroxyphenyl)pyridin-2-yl]oxy}-1,2-dihydro-pyridin-2-one as white solid (0.01 g, 42%); LCMS (ES) m/z calcd. for C17H11F3N2O3, 348.07; found, 349.0; 1H NMR (400 MHz, DMSO-d6): δ 9.97 (s, 1H), 7.90-7.99 (m, 2H), 7.84 (s, 1H), 7.66-7.69 (m, 1H), 7.52 (d, J=6.8 Hz, 1H), 6.94-7.03 (m, 4H), 6.57 (d, J=10.0 Hz, 1H).

Example 6: Synthesis of 6-{[6-(2-fluoro-3-methoxyphenyl)pyridin-2-yl]oxy}-2,3-dihydro-1H-indol-2-one

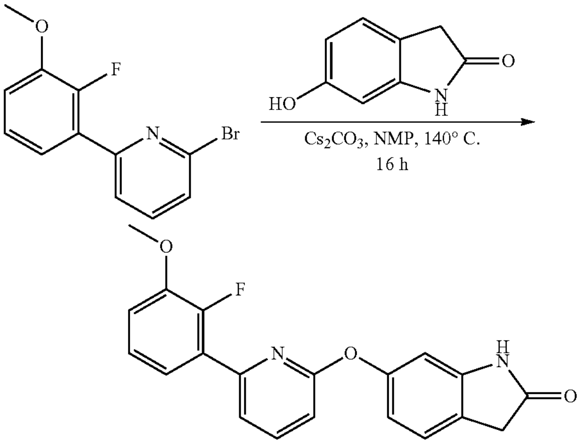

To a stirred solution of 2-bromo-6-(2-fluoro-3-methoxyphenyl)pyridine (0.2 g, 0.70 mmol) in 1-methyl-2-pyrrolidone (4 mL) were added cesium carbonate (0.23 g, 0.70 mmol) and 6-hydroxyindolin-2-one (0.10 g, 0.70 mmol) and allowed to stir at 130° C. for 16 h. After completion, the reaction mixture was poured onto water (40 mL) and extracted with ethyl acetate (2×40 mL). The organic phase was washed with water, brine, dried over anhydrous sodium sulfate, filtered and concentrated in vacuo. The resulting crude material was purified by flash column chromatography using ethyl acetate-hexane (product elutes at 18% ethyl acetate). The compound was further purified by reverse phase preparative HPLC. Pure fraction was collected and freeze dried. Purification afforded 6-{[6-(2-fluoro-3-methoxyphenyl)pyridin-2-yl]oxy}-2,3-dihydro-1H-indol-2-one as off-white solid (0.03 g, 12%); LCMS (ES) m/z calcd. for C20H15FN2O3, 350.1; found, 351.2 (M+H). 1HNMR (400 MHz, DMSO-$d_6$): δ 10.38 (s, 1H), 7.93 (t, J=8.0 Hz, 1H), 7.50 (d, J=6.4 Hz, 1H), 7.13-7.21 (m, 4H), 6.99 (d, J=8.0 Hz, 1H), 6.70-6.73 (m, 1H), 6.60 (s, 1H), 3.84 (s, 3H), 3.45 (s, 2H).

Example 7: Synthesis of 6-{[6-(2-fluoro-3-methoxyphenyl)pyridin-2-yl]oxy}-2,3-dihydro-1H-indol-2-one

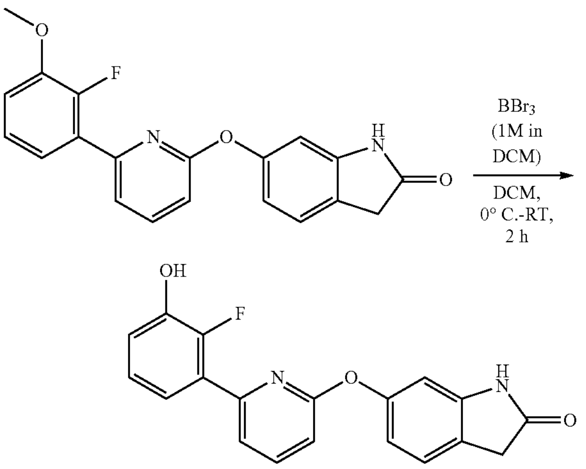

To a stirred solution of 6-{[6-(2-fluoro-3-methoxyphenyl) pyridin-2-yl]oxy}-2,3-dihydro-1H-indol-2-one (0.04 g, 0.11 mmol) in dichloromethane (3 mL) at 0° C. was added 1M boron tribromide in dichloromethane (0.4 mL, 0.4 mmol) and reaction mixture was allowed to stir at room temperature for 2 h. After completion, the reaction mixture was poured into ice-water (40 mL) and extracted into dichloromethane (2×30 mL). The organic layer was washed with water, brine, dried over anhydrous sodium sulfate, filtered and concentrated in vacuo. The resulting crude material was purified by flash column chromatography. The compound was further purified by reverse phase preparative HPLC and the pure fraction was collected and freeze dried. Purification resulted in 6-{[6-(2-fluoro-3-hydroxyphenyl)pyridin-2-yl]oxy}-2,3-dihydro-1H-indol-2-one as white solid (0.02 g, 52%); LCMS (ES) m/z calcd. for C19H13FN2O3, 336.09; found, 337.1 (M+H). 1HNMR (400 MHz, DMSO-$d_6$): δ 10.37 (s, 1H), 9.95 (s, 1H), 7.92 (t, J=9.6 Hz, 1H), 7.32 (d, J=6.0 Hz, 1H), 7.20 (d, J=8.0 Hz, 1H), 6.94-7.07 (m, 4H), 6.70 (d, J=1.6 Hz, 1H), 6.60 (d, J=1.6 Hz, 1H), 3.45 (s, 2H). LCMS (ES) m/z=337.1 [M+H].

Example 8: Synthesis of 2-fluoro-5-((6-(thiophen-2-yl)pyridin-2-yl)oxy) phenol

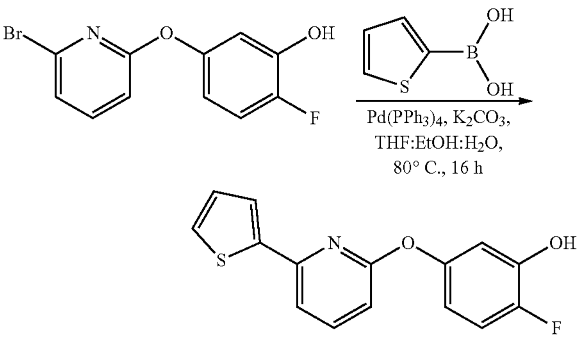

To a stirred solution of 5-((6-bromopyridin-2-yl)oxy)-2-fluorophenol (0.2 g, 0.70 mmol) and (thiophen-2-yl)boronic acid (0.13 g, 1.06 mmol) in tetrahydrofuran, water and ethanol mixture (5 mL, 4:0.5:0.5) was added potassium carbonate (0.21 g, 1.51 mmol). Then the reaction mixture was degassed under argon gas for 10 minutes. This was followed by the addition of Tetrakis(triphenylphosphine) palladium(0) (0.16 g, 0.14 mmol) and the reaction mixture was heated to 80° C. for 16 hours. After completion of the reaction, the reaction mixture was poured into water (20 ml) and extracted with ethyl acetate (2×20 ml). The organic phase was washed with water, brine solution and dried over anhydrous sodium sulfate, concentrated under vacuo. The crude material was purified by flash column chromatography to afford 2-fluoro-5-((6-(thiophen-2-yl)pyridin-2-yl)oxy) phenol as a White solid (0.2 g, 98%); LCMS (ES) m/z calcd. for C15H10FNO2S, 287.3; found, 288.3 (M+H); $^1$H NMR (400 MHz, DMSO-$d_6$) δ 10.07 (s, 1H), 7.83 (t, J=7.9 Hz, 1H), 7.72 (d, J=3.8 Hz, 1H), 7.59 (dd, J=10.6, 6.4 Hz, 2H), 7.21-7.10 (m, 1H), 7.11 (d, J=4.3 Hz, 1H), 6.80-6.71 (m, 2H), 6.59 (dt, J=9.1, 3.2 Hz, 1H).

Example 9: Synthesis of 5-((6-(benzo[b]thiophen-2-yl)pyridin-2-yl)oxy)-2-fluorophenol

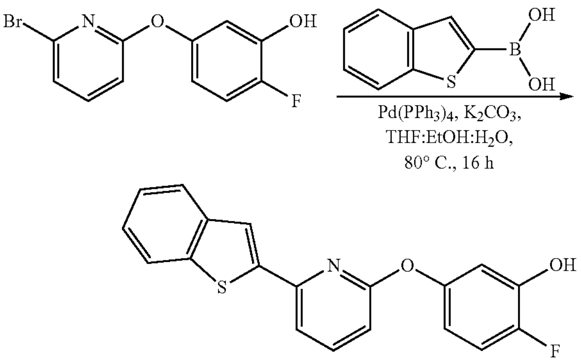

To a stirred solution of 5-((6-bromopyridin-2-yl)oxy)-2-fluorophenol (0.2 g, 0.70 mmol) and benzo[b]thiophen-2-ylboronic acid (0.18 g, 1.06 mmol) in tetrahydrofuran, water and ethanol mixture (5 mL, 4:0.5:0.5) was added potassium carbonate (0.14 g, 1.51 mmol). Then the reaction mixture was degassed under argon gas for 10 minutes. This was followed by the addition of Tetrakis(triphenylphosphine) palladium(0) (0.16 g, 0.14 mmol) and the reaction mixture was heated to 80° C. for 16 hours. After completion of the reaction, the reaction mixture was poured into water (20 ml) and extracted with ethyl acetate (2×30 ml). The organic phase was washed with water, brine solution and dried over anhydrous sodium sulfate, concentrated in vacuo. The crude material was purified by flash column chromatography to afford 5-((6-(benzo[b]thiophen-2-yl)pyridin-2-yl)oxy)-2-fluorophenol as a white solid (0.2 g, 84%); LCMS (ES) m/z calcd. for C19H12FNO2S, 3378.3; found, 338.0 (M+H); $^{1}$H NMR (400 MHz, DMSO-$d_6$) δ 10.11 (s, 1H), 8.10 (s, 1H), 7.98-7.87 (m, 2H), 7.82 (dd, J=16.0, 7.3 Hz, 2H), 7.41-7.30 (m, 2H), 7.20 (t, J=10.0 Hz, 1H), 6.88 (d, J=8.1 Hz, 1H), 6.81-6.74 (m, 1H), 6.63 (d, J=8.8 Hz, 1H).

Example 10: Synthesis of 2-fluoro-3-[2-(4-fluoro-3-methoxyphenoxy)pyrimidin-4-yl]phenol

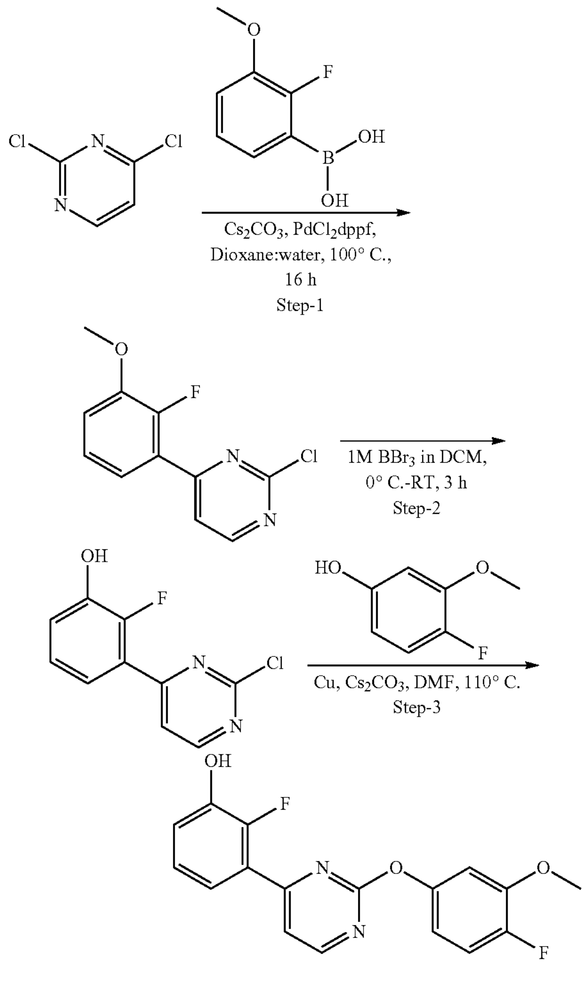

Step-1: Synthesis of 2-chloro-4-(2-fluoro-3-methoxyphenyl)pyrimidine

To a stirred solution of 2,4-dichloropyrimidine (300 mg, 2.01 mmol) and (2-fluoro-3-methoxyphenyl)boronic acid (205 mg, 1.21 mmol) in 1,4-dioxane (5.00 mL) water (1.00 mL) was added cesium carbonate (825 mg, 2.52 mmol). The reaction mixture was purged with argon for 5 min and added $PdCl_2$(dppf) (53.6 mg, 0.1 eq., 0.100.1 mmol). The reaction mixture was heated at 85° C. for 4 h. The reaction mixture was monitored by TLC and LCMS. After completion of the reaction, the organic layer was washed with brine, dried over sodium sulfate and concentrated under vacuum. The crude was purified by flash chromatography. Pure fraction was collected and concentrated in vacuo. The obtained solid was further triturated with diethyl ether, pentane, filtered and dried to result in pure title compound 3-(2-chloropyrimidin-4-yl)-2-fluorophenol (220 mg, 67%) as white solid. LCMS (ES) m/z calcd. for C11H8ClFN2O, 238.0; found, 239.08.142 [M+H]

Step-2: Synthesis of 3-(2-chloropyrimidin-4-yl)-2-fluorophenol

To a stirred solution of 2-chloro-4-(2-fluoro-3-methoxyphenyl)pyrimidine (220 mg, 1.47 mmol) in dichloromethane (5 mL) maintained at 0° C. was added drop-wise a 1M solution of boron tribromide in dichloromethane (368 mg, 2.93 mmol). The mixture was stirred at room temperature for 3 h. Progress of reaction was monitored by TLC and LCMS. After completion of the reaction, the reaction mixture was cooled to 0° C. and quenched with saturated sodium bicarbonate and extracted with ethyl acetate. The organic layer was washed with brine, dried over sodium sulfate and concentrated in vacuo. The crude was purified by flash chromatography. The pure fraction was collected and evaporated under reduced pressure. The obtained solid was further triturated with diethyl ether, pentane, filtered and dried to give the title compound 3-(2-chloropyrimidin-4-yl)-2-fluorophenol (220 mg, 67%) as white solid. LCMS (ES) m/z calcd. for C10H6ClFN2O, 224.0; found, 225.1

Step-3: Synthesis of 2-fluoro-3-[2-(4-fluoro-3-methoxyphenoxy)pyrimidin-4-yl]phenol To a stirred solution of 3-(2-chloropyrimidin-4-yl)-2-fluorophenol (220 mg, 2.23 mmol) and 4-fluoro-3-methoxyphenol (316 mg, 2.23 mmol) in N,N-dimethylformamide (5.0 mL) was added copper (14.1 mg, 0.222 mmol), cesium carbonate (1.82 g, 5.56 mmol). The reaction mixture was stirred at 110° C. for 6 h. The reaction progress was monitored by TLC and LCMS. After completion, the reaction mixture was quenched with water (10 mL) and extracted with ethyl acetate (2×10 mL). The combined organic layer was washed with water (2×30 mL). The organic layer was dried over anhydrous sodium sulphate, filtered and evaporated under reduced pressure to get crude product. The crude product was purified by reverse phase preparative HPLC to give 2-fluoro-3-[2-(4-fluoro-3-methoxyphenoxy)pyrimidin-4-yl]phenol (380 mg, 56%) as white solid. LCMS (ES) m/z calcd. for C17H12F2N2O3, 330.08; found, 331.15 $[M+H]^+$; $^{1}$H NMR (400 MHz, DMSO-$d_6$) δ 10.17 (s, 1H), 8.72 (d, J=5.2 Hz, 1H), 7.61, (dd, J=4.8 Hz, J=1.6 Hz, 1H), 7.29-7.24 (m, 2H), 7.17, (dd, J=7.6 Hz, J=2.8 Hz, 1H), 7.14-7.09 (m, 2H), 6.84-6.80 (m, 1H), 3.81 (s, 3H).

Example 11: Synthesis of 2-fluoro-3-[2-(4-fluoro-3-hydroxyphenoxy)pyrimidin-4-yl]phenol

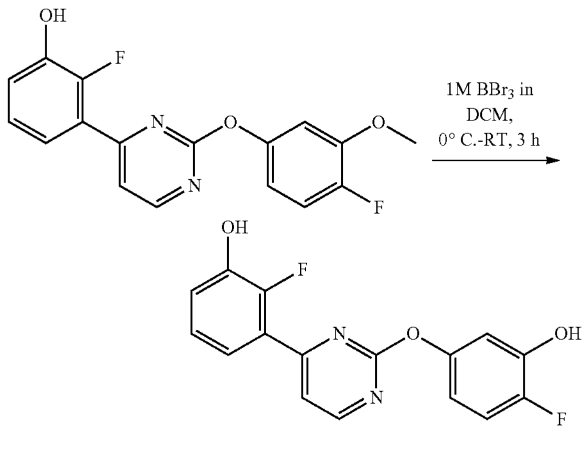

To a stirred solution of 2-fluoro-3-[2-(4-fluoro-3-methoxyphenoxy)pyrimidin-4-yl]phenol (220 mg, 666 μmol) in dichloromethane (5 mL), 1M solution of boron tribromide (368 mg, 2.93 mmol) in dichloromethane was added drop-wise at 0° C. The reaction mixture was stirred at room temperature. Progress of reaction was monitored by TLC and LCMS. Saturated sodium bicarbonate was added into the reaction mixture and the residue was extracted with ethyl acetate (2×20 mL). The combined organic layer was washed with brine, dried over sodium sulfate. and evaporated under reduced pressure to obtain crude. The crude was purified by flash chromatography. Pure fractions were collected and the residue was further triturated with diethyl ether, pentane, filtered and dried to give title compound, 2-fluoro-3-[2-(4-fluoro-3-hydroxyphenoxy)pyrimidin-4-yl]phenol (48 mg, 23%) as off-white solid. LCMS (ES) m/z calcd. for C16H10F2N2O3, 316.07; found, 317.09 [M+H]+; $^1$H NMR (400 MHz, DMSO-$d_6$) δ 10.17 (s, 1H), 10.11 (s, 1H),), 8.70 (d, J=5.16 Hz, 1H), 7.61, (dd, J=2.08 Hz, J=5.16 Hz, 1H), 7.30-7.26 (m, 2H), 7.21-7.10 (m, 3H), 6.82 (d, J=2.8 Hz, J=7.52 Hz, 1H), 6.68-6.64 (m, 1H), 3.81 (s, 3H).

Example 12: Synthesis of 5-((6-(4-(benzyloxy)phenyl)pyridin-2-yl)oxy)-2-fluorophenol

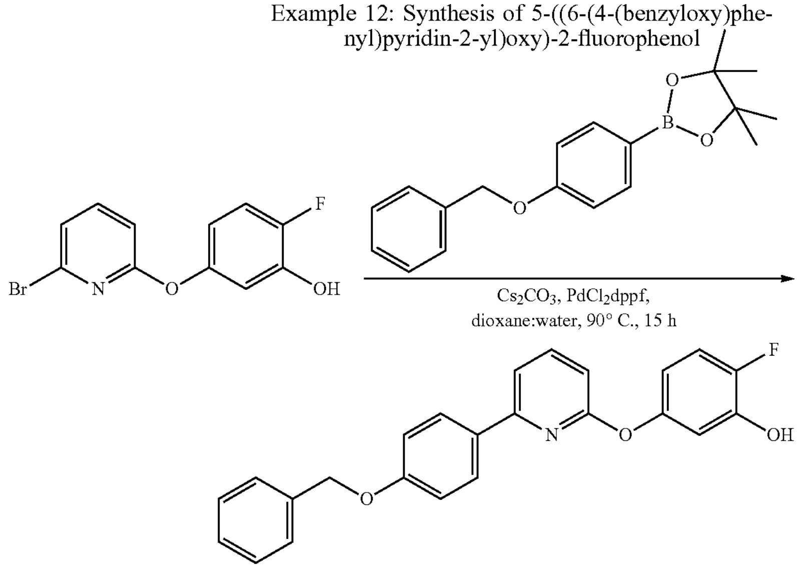

To a stirred solution of 2-[4-(benzyloxy)phenyl]-4,4,5,5-tetramethyl-1,3,2-dioxaborolane (164 mg, 0.528 mmol), 5-[(6-bromopyridin-2-yl)oxy]-2-fluorophenol (100 mg, 0.352 mmol) in 1,4-dioxane (0.4 mL) and water (0.4 mL) in a sealed tube, was added cesium carbonate (0.346 g, 1.06 mmol) and purged with nitrogen for 15 min and $Pdcl_2$(dppf) (25.7 mg, 0.0352 mmol) was added. The reaction mixture was heated at 90° C. for 15 h. The progress of reaction was monitored by LCMS and TLC. After completion, the reaction mixture was quenched with water (10 mL) and extracted with dichloromethane (2×10 mL). The combined organic layer was washed with water (10 mL). The organic layer was dried over anhydrous sodium sulphate, filtered and evaporated under reduced pressure to get crude product. The crude product was purified by flash chromatography over silica gel using ethyl acetate-hexane (product eluted at 40% ethyl acetate). Pure fractions were collected and evaporated to give 6-(2-fluoro-3-methoxyphenyl)pyridin-2-amine (70 g g, 52%) as a white solid. LCMS (ES) m/z calcd. for C24H18FNO3, 387.13; found, 388.20 $[M+H]^+$; $^1$H-NMR (400 MHz, DMSO-d6)-δ 10.13 (brs, 1H) 7.87-7.84 (m, 3H) 7.64 (d, J=7.6 Hz, 1H) 7.46 (d, J=7.2 Hz, 2H) 7.39 (t, J=7.08 Hz, J=7.2 Hz, 2H) 7.34-7.32 (d, J=6.8 Hz, 1H) 7.20-7.15 (m, 1H) 7.08 (d, J=8.8 Hz, 2H) 6.85 (d, J=8.4 Hz, 1H), 6.77 (dd, J=7.2 Hz, J=2.8 Hz, 1H) 6.62-6.58 (m, 1H) 5.14 (s, 2H).

Example 13: Synthesis of 3-{6-[3-(difluoromethyl)-4-fluorophenoxy]pyridin-2-yl}-2-fluorophenol

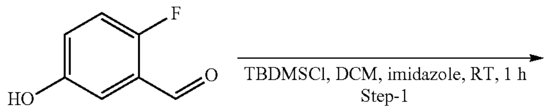

-continued

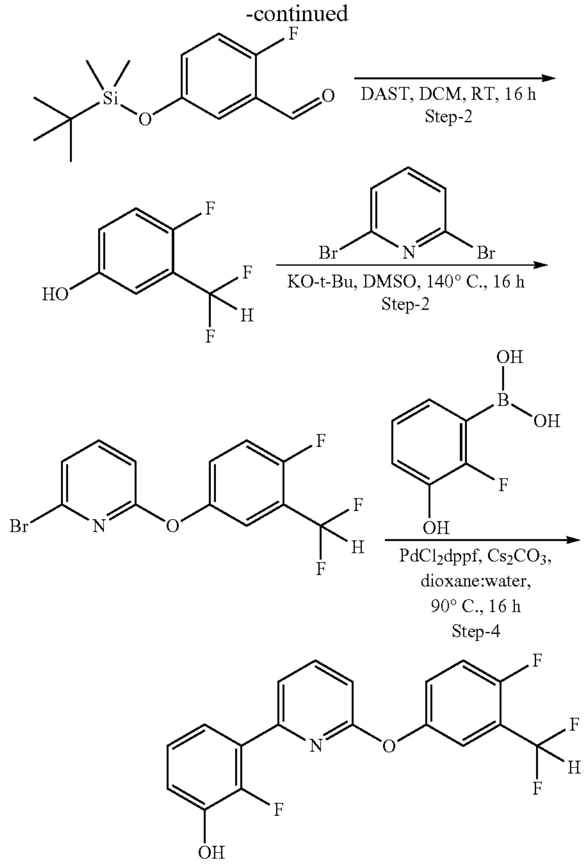

Step-1: Synthesis of 5-[(tert-butyldimethylsilyl)oxy]-2-fluorobenzaldehyde

To a stirred solution of 2-fluoro-5-hydroxybenzaldehyde (2 g, 14.3 mmol) in dichloromethane (50 mL), was added 1H-imidazole (3.89 g, 57.1 mmol) at 0° C. The reaction mixture stirred for 15 min then tert-butyl(chloro)dimethylsilane (4.30 g, 28.5 mmol) was added at 0° C. The reaction mixture was stirred for 30 min. at room temperature. The progress of reaction was monitored by TLC. After complete consumption of starting material, the reaction mixture was quenched with water and extracted with dichloromethane (2×50 mL). The organic layer was washed with aq. $NaHCO_3$ solution and dried under reduced pressure to get title compound 5-[(tert-butyldimethylsilyl)oxy]-2-fluorobenzaldehyde (2.0 g, 90%) as yellow colored liquid. The crude product was taken for next step.

Step-2: Synthesis of 3-(difluoromethyl)-4-fluorophenol

To a stirred solution of 5-[(tert-butyldimethylsilyl)oxy]-2-fluorobenzaldehyde (1.8 g, 7.08 mmol) in dichloromethane (20 mL) maintained at 0° C., was slowly added DAST (5.70 g, 35.4 mmol) at 0° C. The reaction mixture was stirred for 12 h at room temperature. The progress of reaction was monitored by TLC and LCMS. After complete consumption of starting material, the reaction mixture was quenched with aq. $NaHCO_3$ solution and extracted with DCM (3×75 mL). The organic layer was dried over sodium sulphate and evaporated under reduced pressure to get title crude compound 3-(difluoromethyl)-4-fluorophenol (1.2 g, 82.64%) as yellow liquid. LCMS (ES) m/z calcd. for C7H5F30, 162.03; found, 160.93 $[M-H]^-$ Step-3: Synthesis of 2-bromo-6-[3-(difluoromethyl)-4-fluorophenoxy] pyridine To a stirred solution of 3-(difluoromethyl)-4-fluorophenol (1 g, 6.17 mmol) in dimethylsulfoxide (10 mL) was added 2,6-dibromopyridine (1.17 g, 4.93 mmol) and potassium 2-methylpropan-2-olate (698 mg, 6.17 mmol). The reaction mixture was stirred for 16 h at 140° C. The progress of reaction was monitored by TLC and LCMS. After complete consumption of starting material, reaction mixture was quenched with water and extracted with ethyl acetate (2×50 mL). The organic layer was dried over sodium sulphate and concentrated under reduced pressure to give 2-bromo-6-[3-(difluoromethyl)-4-fluorophenoxy]pyridine (600.0 mg 88.48%) as a yellow gummy mass. LCMS (ES) m/z calcd. for C12H7BrF3NO, 318.9; found, 320 $[M+H]^+$.

Step-4: Synthesis of 3-{6-[3-(difluoromethyl)-4-fluorophenoxy]pyridin-2-yl}-2-fluorophenol To a stirred solution of 2-bromo-6-[3-(difluoromethyl)-4-fluorophenoxy]pyridine (200 mg, 0.629 mmol), (2-fluoro-3-hydroxyphenyl)boronic acid (98 mg, 0.629 mmol) and cesium carbonate (215 mg, 1.57 mmol) in 1,4-dioxane (8.00 mL), was added water (2.00 mL) and then purged with argon for 5 min. To this reaction mixture was added $PdCl_2$(dppf) (46 mg, 0.062.9 mmol) and stirred at 85° C. for 16 h. The progress of reaction was monitored by TLC and LCMS. The organic layer was washed with brine and dried over sodium sulfate. Evaporation of solvent resulted in crude product which was purified by flash chromatography on combi Flash chromatography. The residue was further triturated with diethyl ether, pentane, filtered and dried to give pure title compound 3-{6-[3-(difluoromethyl)-4-fluorophenoxy]pyridin-2-yl}-2-fluorophenol (40 mg, 18.21%) as light brown semi solid. LCMS (ES) m/z calcd. for C18H11F4NO2, 349.07; found, 350.09 $[M+H]^+$. $^1$H NMR (400 MHz, DMSO-$d_6$) δ 9.96 (s, 1H), 8.00 (t, J=8 Hz, J=15.6 Hz 1H), 7.55-7.42, (m, 4H), 7.34-6.94 (m, 5H).

Example 14: Synthesis of 3-{6-[3-(difluoromethoxy)-4-fluorophenoxy]pyridin-2-yl}-2-fluorophenol

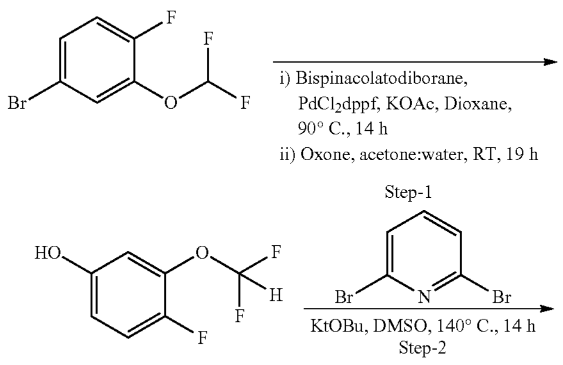

-continued

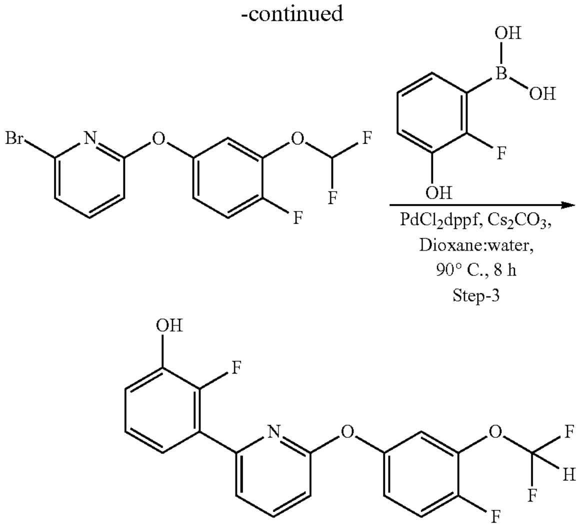

Step 1: Synthesis of 3-(difluoromethoxy)-4-fluorophenol

A stirred solution of 4-bromo-2-(difluoromethoxy)-1-fluorobenzene (2.00 g, 8.30 mmol), potassium acetate (1.65 g, 16.6 mmol) and 4,4,5,5-tetramethyl-2-(4,4,5,5-tetramethyl-1,3,2-dioxaborolan-2-yl)-1,3,2-dioxaborolane (2.53 g, 9.96 mmol) in 1,4-dioxane was purged with argon gas for 20 min at ambient temperature and then added 1,1'-Bis(diphenylphosphino) ferrocene]dichloropalladium(II) (677 mg, 0.830 mmol). The reaction mixture was stirred for 3 h at 85° C. Progress of reaction was monitored by TLC. After consumption of starting material, the reaction mixture was passed through celite bed, washed with ethyl acetate and concentrated under vacuum to obtain crude. The crude product was dissolved in propan-2-one (30.0 mL), cooled to 0° C. and a solution of oxone (1.53 g, 9.96 mmol) in water (28.0 mL) was added. The reaction mixture was stirred at 0° C. for 2 hr. The progress of reaction was monitored by TLC. After completion of reaction, the reaction was quenched with water (50.0 mL) and extracted with ethyl acetate (2×50.0 mL). The combined organic layer was dried over anhydrous sodium sulphate and evaporated under reduced pressure. Crude was purified by flash column chromatography using ethyl acetate-hexane (product elutes at 10% ethyl acetate) to afford 3-(difluoromethoxy)-4-fluorophenol (1.20 g, 6.74 mmol) as brown oil. LCMS (ES) m/z calcd. for C7H5F302, 178.02; found, 177.1 [M−H]

Step 2: Synthesis of 2-bromo-6-[3-(difluoromethoxy)-4-fluorophenoxy] pyridine

In a dry round-bottomed flask, 3-(difluoromethoxy)-4-fluorophenol (500 mg, 2.81 mmol) and 2,6-dibromopyridine (665 mg, 2.81 mmol) dissolved in dimethyl sulfoxide (5.00 mL) was placed. To this solution potassium 2-methylpropan-2-olate (318 mg, 2.81 mmol) was added. The reaction mixture was stirred at 140° C. for 14 h. Progress of reaction was monitored by TLC and LCMS. After completion of the reaction, the reaction mixture was cooled to room temperature and quenched with water (50.0 mL), extracted with ethyl acetate (3×30.0 mL). The organic layer was washed with brine (50.0 mL) and dried over anhydrous sodium sulphate, filtered and concentrated under vacuum to give (0.600 g, 64%) as a yellow solid. LCMS (ES) m/z calcd. for C12H7BrF3NO2, 332.9; found, 334.1 $[M+H]^+$ Step 3: Synthesis of 3-{6-[3-(difluoromethoxy)-4-fluorophenoxy]pyridin-2-yl}-2-fluorophenol To a stirred solution of 2-bromo-6-[3-(difluoromethoxy) phenoxy]pyridine (600 mg, 1.90 mmol) and (2-fluoro-3-hydroxyphenyl)boronic acid (355 mg, 2.28 mmol) in 1,4-dioxane (8.00 mL) and water (2.00 mL) was added cesium carbonate (1.10 g, 5.69 mmol). The reaction mixture was purged with argon gas for 10 min and added [1,1'-Bis (diphenylphosphino) ferrocene]dichloropalladium(II) (139 mg, 0.190 mmol). The reaction mixture was heated at 95° C. for 16 h. The progress of reaction was monitored by TLC. After completion of reaction, the reaction mixture was cooled to room temperature, quenched with water (50.0 mL) and extracted with ethyl acetate (2×50.0 mL). The organic layer was dried over anhydrous sodium sulfate and evaporated under reduced pressure. The crude was purified by column chromatography to afford 3-{6-[3-(difluoromethoxy)-4-fluorophenoxy]pyridin-2-yl}-2-fluorophenol (240 mg, 34.6%) as off-white solid. LCMS (ES) m/z calcd. for C18H11F4NO3, 365.07; found, 366.11 [M+H]; $^1$H NMR (400 MHz, DMSO-$d_6$) δ 9.96 (s, 1H), 7.97 (t, J=8 Hz, 1H), 7.55 (dd, J=2 Hz, J=7.6 Hz, 1H), 7.49-7.10 (m, 4H), 7.08-7.04 (m, 2H), 7.01-6.9 (m, 2H).

Example 15: Synthesis of 2-fluoro-3-(6-((4-fluoro-3-hydroxyphenyl)thio)pyridin-2-yl) phenol

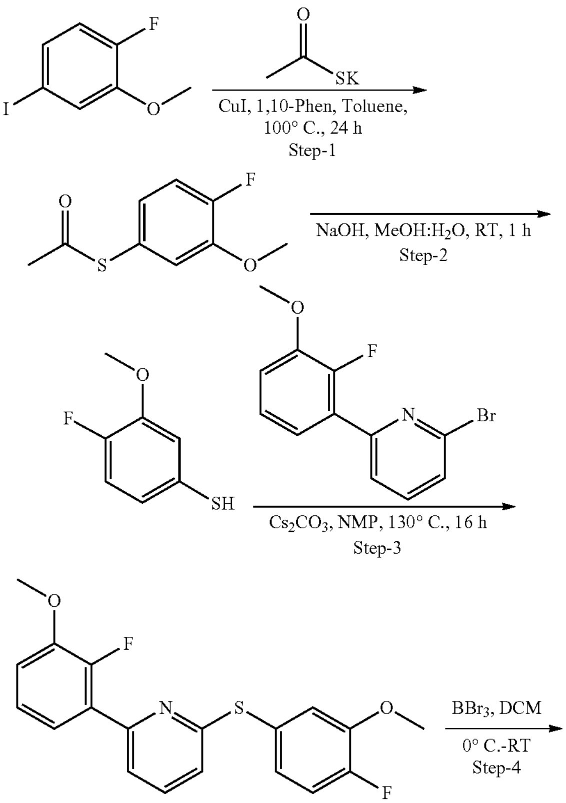

-continued

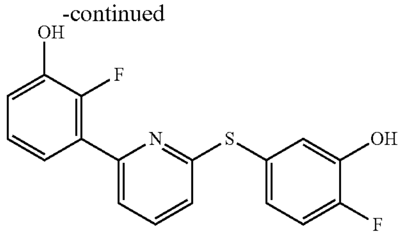

Step-1: Synthesis of (4-fluoro-3-methoxyphenyl) ethanethioate (1)

To a stirred solution of 1-fluoro-4-iodo-2-methoxybenzene (0.5 g, 1.98 mmol) and Potassium thioacetate (0.68 g, 5.95 mmol) in toluene (3 mL) was added Copper(I) iodide (0.038 g, 0.19 mmol) and 1,10-Phenanthroline (0.071 g, 0.39 mmol) at room temperature under nitrogen atmosphere. The resulting reaction mixture was heated to 100° C. for 16 h. The reaction was cooled to ambient temperature, diluted with ethyl acetate and water. The organic layer was separated, washed with brine, dried over anhydrous sodium sulfate, filtered and concentrated in vacuo. The crude material was purified using flash chromatography using ethyl acetate-hexane (product elutes at 3% ethyl acetate) to provide (4-fluoro-3-methoxyphenyl) ethanethioate as light yellow liquid (0.38 g, 95%) $^{1}$H NMR (400 MHz, Chloroform-d) δ 7.26 (s, 1H), 6.95-7.26 (m, 2H), 3.90 (s, 3H), 2.51 (s, 3H)

Step-2: Synthesis of 4-fluoro-3-methoxybenzenethiol

To a solution of (4-fluoro-3-methoxyphenyl) ethanethioate (0.38 g, 1.9 mmol) in methanol:water (8 mL:2 mL) was added sodium hydroxide (0.28 g, 5.70 mmol) and the solution stirred at room temperature for 30 minutes. The progress of the reaction was monitored by TLC. The reaction mixture was concentrated in vacuo. The obtained residue was dissolved in water and acidified with dilute hydrochloric acid and the aqueous layer was extracted with ethyl acetate. The organic layer was dried over sodium sulphate, filtered and concentrated in vacuo to provide 4-fluoro-3-methoxybenzenethiol as a colorless viscous liquid (0.38 g, crude).

Step-3: 2-(2-fluoro-3-methoxyphenyl)-6-((4-fluoro-3-methoxyphenyl)thio) pyridine To a stirred solution of 4-fluoro-3-methoxybenzenethiol (0.38 g, 2.40 mmol) and 2-bromo-6-(2-fluoro-3-methoxyphenyl)pyridine (0.67 g, 2.40 mmol) in N-methylmorpholine (5 mL) was added Cesium carbonate (1.58 g, 4.80 mmol) at room temperature. The reaction mass was then heated to 130° C. for 16 h. After completion, the reaction mixture was cooled to ambient temperature and diluted with ethyl acetate and water. The organic layers were washed with brine, dried over anhydrous sodium sulfate, filtered and concentrated in vacuo. The crude material was purified by using flash chromatography. Purification resulted in 2-(2-fluoro-3-methoxyphenyl)-6-((4-fluoro-3-methoxyphenyl) thio)pyridine as an off-white solid (0.45 g, 52% yield): LCMS (ES) m/z calcd. for C19H15F2NO2S, 359.08; found, 360.1 $[M+H]^+$ Step-4: Synthesis of 2-fluoro-3-(6-((4-fluoro-3-hydroxyphenyl)thio)pyridin-2-yl)phenol To a stirred solution of 2-(2-fluoro-3-methoxyphenyl)-6-((4-fluoro-3-methoxyphenyl)thio) pyridine (0.1 g, 0.278 mmol) in dichloromethane (2 mL) was added 1M boron tribromide in dichloromethane (1.4 mL, 1.39 mmol) at 0° C. The resulting reaction mixture was stirred at 0° C. to room temperature for 2 h. The reaction mixture was poured into ice-water (40 mL) and extracted with dichloromethane (2×30 mL). The organic phase was washed with water, brine and dried over anhydrous sodium sulfate, filtered and concentrated in vacuo. The crude material was purified by flash column chromatography. Purification afforded 2-fluoro-3-(6-((4-fluoro-3-hydroxyphenyl) thio)pyridin-2-yl)phenol as a white solid (0.02 g, 22%); LCMS (ES) m/z calcd. for C17H11F2NO2S, 331.05; found, 332.0 (M+H); $^{1}$H NMR (400 MHz, DMSO-$d_6$) δ 10.29 (s, 1H), 9.97 (s, 1H), 7.73 (t, J=7.9 Hz, 1H), 7.48 (dd, J=7.8, 2.2 Hz, 1H), 7.28 (dd, J=11.3, 8.4 Hz, 1H), 7.15 (ddd, J=16.8, 7.5, 2.1 Hz, 2H), 7.09-6.95 (m, 3H), 6.88 (d, J=8.0 Hz, 1H).

Example 16: Synthesis of 2-fluoro-3-[4-(4-fluoro-3-methoxyphenoxy)pyrimidin-2-yl]phenol

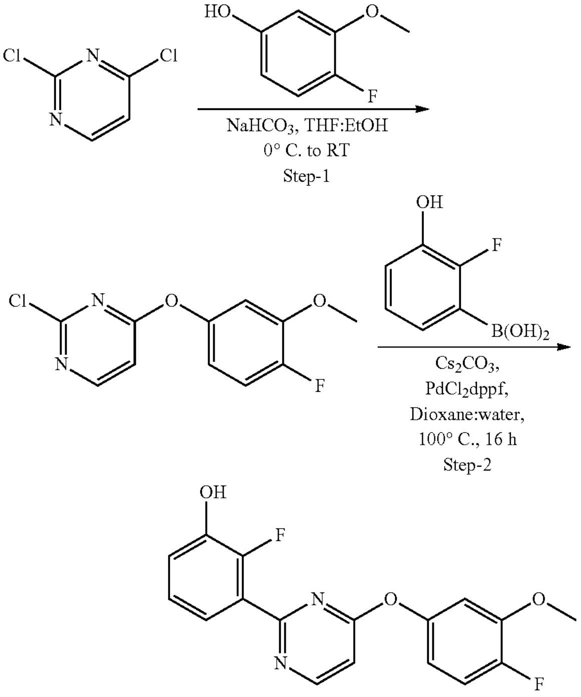

Step-1: Synthesis of 2-chloro-4-(4-fluoro-3-methoxyphenoxy)pyrimidine

To a stirred solution of 2,4-dichloropyrimidine (500 mg, 3.36 mmol), 4-fluoro-3-methoxyphenol (382 mg, 2.69 mmol) in tetrahydrofuran (2 mL), ethanol (4 mL), was added sodium hydrogen carbonate (713 mg, 8.39 mmol) and stirred for 6 h at room temperature. The progress of reaction mixture was monitored by TLC and LCMS. After completion, the reaction mixture was quenched by water and extracted with ethyl acetate, and the organic layer was dried under reduced pressure. The resulting crude was purified by column chromatography using ethyl acetate-hexane (product elutes at 20% ethyl acetate). Purification resulted in pure 2-chloro-4-(4-fluoro-3-methoxyphenoxy) pyrimidine as white solid (350 mg, 41%). LCMS (ES) m/z calcd. for C11H8ClFN2O2, 254.3; found, 255.19 [M+H]

Step-2: Synthesis of 2-fluoro-3-[4-(4-fluoro-3-methoxyphenoxy)pyrimidin-2-yl]phenol To a stirred solution of 2-chloro-4-(4-fluoro-3-methoxyphenoxy)pyrimidine (150 mg, 0.589 mmol), (2-fluoro-3-hydroxyphenyl)boronic acid (91.8 mg, 0.589 mmol), cesium carbonate (483 mg, 1.47 mmol), in 1,4-dioxane (3.00 mL) water (1.00 mL) and then purged with argon for 5 min. To the reaction was added $PdCl_2$(dppf) (43.1 mg, 0.058 mmol) and the solution was stirred at 100° C. for 16 h. The progress of reaction was monitored by TLC and LCMS. The reaction was quenched with water and extracted with ethyl acetate. The organic layer was washed with brine, dried over sodium sulfate and concentrated under vacuum. The crude was purified by flash chromatography. Concentration of pure fractions resulted in residue which was further triturated with diethyl ether, pentane, filtered and dried to result in title compound 2-fluoro-3-[4-(4-fluoro-3-methoxyphenoxy)pyrimidin-2-yl]phenol as white solid (90 mg, 46%). LCMS (ES) m/z calcd. for C17H12F2N2O3, 330.08; found, 331.12 $[M+H]^+$; $^1H$ NMR (400 MHz, DMSO-$d_6$) δ 9.95 (s, 1H), 8.79 (d, J=5.6 Hz, 1H), 7.30-7.18 (m, 3H), 7.06-7.03 (m, 3H) 6.86-6.83 (m, 1H), 3.82 (s, 3H).

Example 17: Synthesis of 2-fluoro-3-[4-(4-fluoro-3-hydroxyphenoxy)pyrimidin-2-yl]phenol

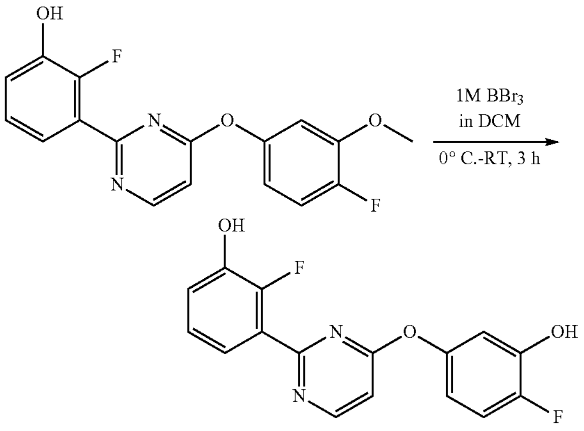

To a stirred solution of 2-fluoro-3-[4-(4-fluoro-3-methoxyphenoxy)pyrimidin-2-yl]phenol (150 mg, 1.0 eq., 454 μmol) in DCM (2 mL) was added drop-wise 1M tribromoborane in dichloromethane (569 mg, 2.27 mmol) at 0° C. The reaction mixture was then stirred at room temperature. Progress of reaction was monitored by TLC and LCMS. After completion, saturated sodium bicarbonate was added into the reaction mixture and the residue was extracted with ethyl acetate (2×20 mL). The organic layer was washed with brine, dried over sodium sulfate and evaporated to obtain crude. The crude was purified by reverse phase preparative HPLC to give title compound 2-fluoro-3-[4-(4-fluoro-3-hydroxyphenoxy)pyrimidin-2-yl] phenol Example (10 mg, 7%) as white solid. LCMS (ES) m/z calcd. for C16H10F2N2O3, 316.07; found, 317.13 $[M+H]^+$; $^1H$ NMR (400 MHz, DMSO-$d_6$) δ 10.20 (s, 1H), 9.95 (s, 1H), 8.78 (d, J=5.6 Hz, 1H), 7.25-7.19 (m, 2H), 7.07-7.01 (m, 3H), 6.83 (dd, J=2.8 Hz, J=7.2 Hz, 1H), 6.71-6.69, (m, 1H).

Example 18: Synthesis of N-(3-(6-(4-fluoro-3-hydroxyphenoxy)pyridin-2-yl)phenyl) benzenesulfonamide

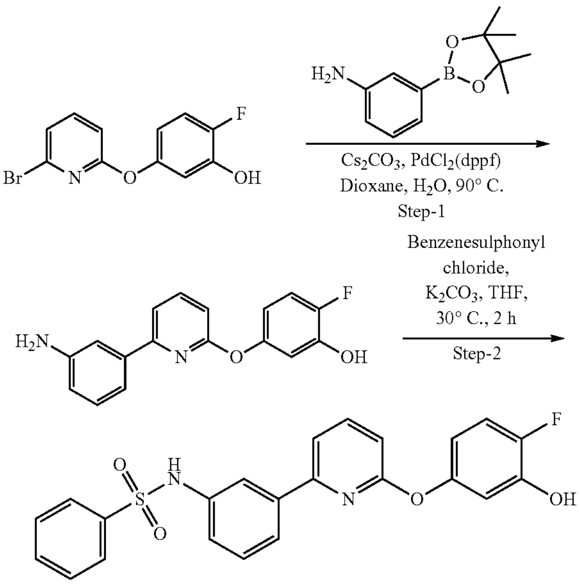

Step-1: Synthesis of 5-((6-(3-aminophenyl)pyridin-2-yl)oxy)-2-fluorophenol

To a stirred solution of 5-[(6-bromopyridin-2-yl)oxy]-2-fluorophenol (1.00 g, 3.52 mmol) in 1,4-dioxane (5.00 mL) and water (1.00 mL) was added cesium carbonate (2.86 g, 8.80 mmol), and (3-aminophenyl)boronic acid (482 mg, 3.52 mmol). This reaction mass was purged with argon gas for 30 minute and then $PdCl_2$dppf (257 mg, 0.352 mmol) was added. The reaction vial was sealed and heated at 90° C. for 12 hr. Progress of reaction was monitored by LCMS and TLC. After completion, the reaction mixture was quenched with water (50 mL) and extracted with ethyl acetate (3×50 mL). The combined organic layer was washed with water (50 mL). The organic layer was dried over anhydrous sodium sulphate, filtered and evaporated under reduced pressure to get crude. The crude mass was purified by flash chromatography over silica gel eluted using ethyl acetate-hexane (product elutes at 20% ethyl acetate) to give title compound as off-white solid. LCMS (ES) m/z calcd. for C17H13FN2O2, 296.1; found, 297.0 [M+H]+

Step-2: Synthesis of N-{3-[6-(4-fluoro-3-hydroxyphenoxy)pyridin-2-yl] phenyl}benzene sulfonamide To a stirred solution of 5-{[6-(3-aminophenyl)pyridin-2-yl]oxy}-2-fluorophenol (90.0 mg, 0.304 mmol) tetrahydrofuran (5.00 mL) was added Potassium carbonate (85.2 mg, 0.607 mmol), followed by addition of benzenesulfonyl chloride (59.0 mg, 0.334 mmol). The reaction mass stirred for 2 h at 30° C. Progress of reaction was monitored by LCMS and TLC. After completion, the reaction mixture was quenched with water (50 mL) and extracted with ethyl acetate (3×50 mL). The combined organic layer was washed with water (50 mL), dried over anhydrous sodium sulphate, filtered and evaporated under reduced pressure to get crude product. The crude mass was purified by flash chromatography over silica gel using ethyl acetate-hexane (product eluted in 20% ethyl acetate) to get title compound N-{3-[6-(4-fluoro-3-hydroxyphenoxy) pyridin-2-yl] phenyl}benzenesulfonamide (18 mg, 13.5%) as yellow solid. LCMS (ES) m/z calcd. for C23H17FN2O4S, 436.09; found, 347.06 $[M+H]^+$; $^1H$ NMR (400 MHz, DMSO-$d_6$) δ 10.40 (s, 1H) 10.07 (s, 1H) 7.92 (t, J=8.0 Hz, 1H) 7.73-7.70 (m, 3H) 7.59-7.48 (m, 5H) 7.30-7.28 (t, J=8.0 Hz, 1H) 7.21-7.16 (m, 1H) 7.10 (d, J=9.2 Hz, 1H), 6.92-6.90 (d, J=8.4 Hz, 1H), 6.75 (dd, J=7.6 Hz, J=2.8 Hz, 1H), 6.63-6.59 (m, 1H).

Example 19: Synthesis of 2-fluoro-5-((6'-morpholino-[2,3'-bipyridin]-6-yl) oxy)phenol

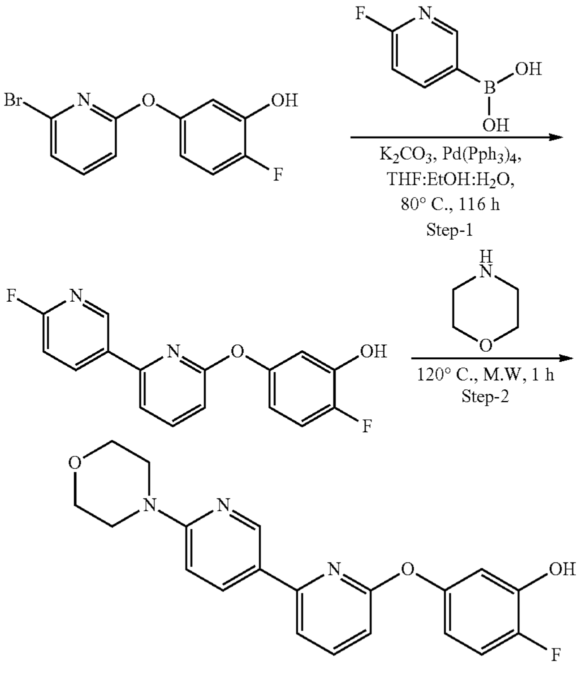

Step 1: Synthesis of 2-fluoro-5-((6'-fluoro-[2,3'-bipyridin]-6-yl)oxy)phenol

To a stirred solution of 5-[(6-bromopyridin-2-yl)oxy]-2-fluorophenol (0.15 g, 0.528 mmol) and (6-fluoropyridin-3-yl)boronic acid (0.11 g, 0.792 mmol) in tetrahydrofuran, water and ethanol mixture (5 mL, 4:0.5:0.5) was added potassium carbonate (0.15 g, 1.06 mmol). Then the reaction mixture was degassed under argon gas for 10 minutes. This was followed by the addition of Tetrakis(triphenylphosphine)palladium(0) (0.061 g, 0.053 mmol) and the reaction mixture was heated to 80° C. for 16 hours. After completion of the reaction, the reaction mixture was poured into water (20 mL) and extracted with ethyl acetate (2×20 mL). The organic phase was washed with water, brine solution and dried over anhydrous sodium sulfate, concentrated in vacuo. The crude material was purified by flash column chromatography to afford 2-fluoro-5-({6'-fluoro-[2,3'-bipyridin]-6-yl}oxy)phenol as a yellow solid (0.15 g, 38%); LCMS (ES) m/z calcd. for C16H10F2N2O2, 300.2; found, 301.0 (M+H).

Step 2: Synthesis of 2-fluoro-5-((6'-fluoro-[2,3'-bipyridin]-6-yl)oxy)phenol

The solution of 2-fluoro-5-({6'-fluoro-[2,3'-bipyridin]-6-yl}oxy)phenol (10.0 mg, 0.033 mmol) in morpholine (0.014 mL, 0.17 mmol) was subjected to microwave irradiation at 120° C. for 1 h. After completion of the reaction, the reaction mixture was poured into water (10 ml) and extracted with ethyl acetate (2×10 ml). The organic phase was washed with water, brine solution and dried over anhydrous sodium sulfate, concentrated under vacuo. The crude material was purified by flash column chromatography to afford 2-fluoro-5-{[6'-(morpholin-4-yl)-[2,3'-bipyridin]-6-yl]oxy}phenol as white solid (0.012 g, 98%); LCMS (ES) m/z calcd. for C20H18FN3O3, 367.3; found, 368.1 (M+H); $^1H$ NMR (400 MHz, DMSO-$d_6$) δ 10.03 (s, 1H), 8.67 (d, J=2.5 Hz, 1H), 8.02 (dd, J=9.0, 2.5 Hz, 1H), 7.83 (t, J=7.9 Hz, 1H), 7.59 (d, J=7.6 Hz, 1H), 7.16 (t, J=10.0 Hz, 1H), 6.87 (d, J=9.0 Hz, 1H), 6.84-6.72 (m, 2H), 6.59 (dt, J=8.9, 3.1 Hz, 1H), 3.67 (t, J=4.8 Hz, 4H), 3.50 (t, J=4.8 Hz, 4H).

Example 20: Synthesis of 3-(6-(4-fluoro-3-hydroxyphenoxy)pyridin-2-yl)-N,N-dimethylbenzenesulfonamide

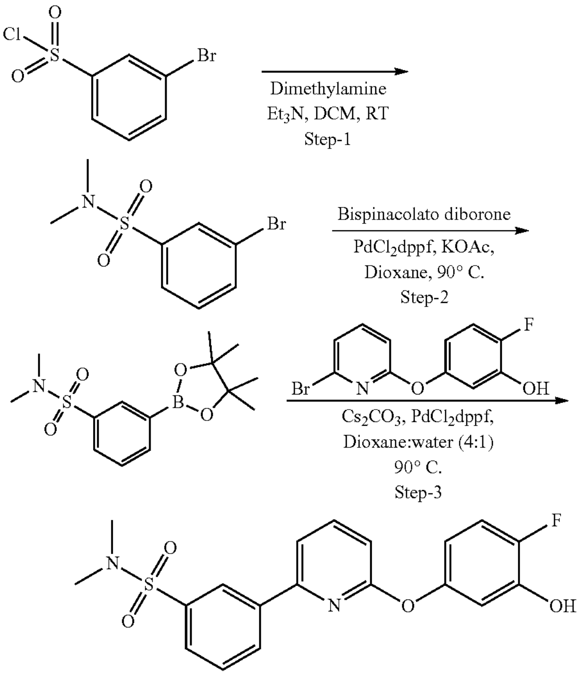

Step 1: Synthesis of 3-bromo-N, N-dimethylbenzenesulfonamide

To a stirred solution of 3-bromobenzene-1-sulfonyl chloride (0.500 g, 1.96 mmol) in dichloromethane at 0° C. was added 2M dimethylamine in THF (1.66 mL, 3.33 mmol) and triethylamine (0.39 mL, 2.94 mmol). This was stirred at RT for 2 h. The reaction mixture was poured into ice-water (20 mL), extracted into dichloromethane (2×20 mL). The organic phase was washed with brine solution (20 mL) and dried over anhydrous sodium sulphate, filtered and evaporated in vacuo. The crude material was purified by flash column chromatography to afford 3-bromo-N, N-dimethyl-benzenesulfonamide as an off-white solid (0.4 g, 77%); LCMS (ES) m/z calcd. for C8H10BrNO2S, 264.1; found, 265.9 (M+H); The crude material was used as such for the next step without column purification.

Step 2: Synthesis of N, N-dimethyl-3-(4,4,5,5-tetramethyl-1,3,2-dioxaborolan-2-yl)benzenesulfonamide To a stirred solution of 3-bromo-N,N-dimethylbenzene-1-sulfonamide (0.350 g, 1.33 mmol) and 4,4,5,5-tetramethyl-2-(4,4,5,5-tetramethyl-1,3,2-dioxaborolan-2-yl)-1,3,2-dioxaborolane (0.505 g, 1.99 mmol) in 1,4-dioxane (5 mL) was added potassium acetate (0.263 g, 2.65 mmol). Then the reaction mixture was degassed under argon gas for 10 minutes. This was followed by the addition of [1,1'-Bis (diphenylphosphino)ferrocene]dichloropalladium(II) (0.097 g, 0.133 mmol) and the reaction mixture was heated to 90° C. for 12 hours. After completion of the reaction, the reaction mixture was poured into water (20 ml) and extracted with ethyl acetate (2×20 ml). The organic phase was washed with water, brine solution and dried over anhydrous sodium sulfate, concentrated in vacuo to afford N, N-dimethyl-3-(4,4,5,5-tetramethyl-1,3,2-dioxaborolan-2-yl)benzenes sulfonamide as a brown solid (0.2 g, crude); The crude material was used as such for next step without column purification.

Step 3: Synthesis of 3-(6-(4-fluoro-3-hydroxyphenoxy)pyridin-2-yl)-N,N-dimethylbenzene sulfonamide To a stirred solution of N,N-dimethyl-3-(4,4,5,5-tetramethyl-1,3,2-dioxaborolan-2-yl)benzene-1-sulfonamide (0.2 g, 0.643 mmol) and 5-[(6-bromopyridin-2-yl)oxy]-2-fluorophenol (0.183 mg, 0.643 mmol) in 1,4-dioxane and water (4 mL, 1:1) was added cesium carbonate (0.312 g, 1.61 mmol). Then the reaction mixture was degassed under argon gas for 10 minutes. This was followed by the addition of [1,1'-Bis (diphenylphosphino)ferrocene]dichloropalladium(II) (0.047 g, 0.064 g mmol) and the reaction mixture was heated to 90° C. for 18 hours. After completion of the reaction, the reaction mixture was poured into water (20 ml) and extracted with ethyl acetate (2×20 ml). The organic phase was washed with water, brine solution and dried over anhydrous sodium sulfate, concentrated under vacuo. The crude material was purified by flash column chromatography to afford 3-(6-(4-fluoro-3-hydroxyphenoxy)pyridin-2-yl)-N, N-dimethyl benzene sulfonamide (0.1 g, 40%) as a white solid; LCMS (ES) m/z calcd. for C19H17FN2O4S, 388.4; found, 389.0 (M+H); $^1$H NMR (400 MHz, DMSO-$d_6$): δ 10.09 (s, 1H), 8.27 (d, J=7.6 Hz, 1H), 8.17 (s, 1H), 7.98 (t, J=7.8 Hz 1H), 7.83 (d, J=7.2 Hz, 1H), 7.783-7.70 (m 2H), 7.18 (dd, J=11.0 Hz and 8.8 Hz, 1H), 7.02 (d, J=8.0 Hz, 1H), 6.77 (dd, J=7.6 Hz and 2.8 Hz, 1H), 6.70 (m, 1H), 2.56 (m, 6H).

Example 21: Synthesis of 5-((6-(2-aminobenzo[d]thiazol-5-yl)pyridin-2-yl)oxy)-2-fluorophenol

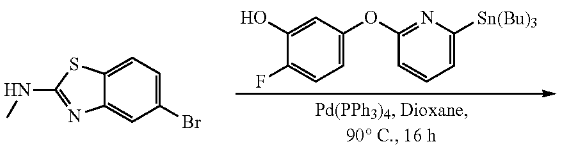

-continued

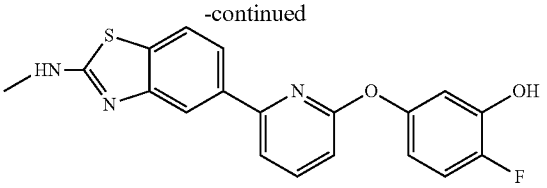

To a stirred solution of 5-bromo-N-methyl-1,3-benzothiazol-2-amine (0.2 g, 0.82 mmol) and 2-fluoro-5-{[6-(tributylstannyl)pyridin-2-yl]oxy}phenol (0.47 g, 0.905 mmol) in 1,4-dioxane (6 mL). Then the reaction mixture was degassed under argon gas for 10 minutes. This was followed by the addition of Tetrakis(triphenylphosphine)palladium(0) (0.09 g, 0.08 mmol) and the reaction mixture was heated to 100° C. for 16 hours. After completion of the reaction, the reaction mixture was poured into water (20 ml) and extracted with ethyl acetate (2×20 ml). The organic phase was washed with water, brine solution and dried over anhydrous sodium sulfate, concentrated under vacuo. The crude material was purified by flash column chromatography to afford 2-fluoro-5-({6-[2-(methylamino)-1,3-benzothiazol-5-yl]pyridin-2-yl}oxy)phenol as a white solid (0.1 g, 36.73%); LCMS (ES) m/z calcd. for C19H14FN3O2S, 367.4; found, 368.0 (M+H)+; $^1$HNMR (400 MHz, DMSO-d6) δ 10.10 (s, 1H), 8.04-8.00 (m, 1H), 7.91 (s, 1H), 7.89 (d, J=8.0 Hz, 1H), 7.74-7.70 (dd, J=10.0 Hz, J=7.6 Hz, 2H), 7.60-7.58 (dd, J=8.0 Hz, J=1.2 Hz, 1H), 7.22-7.17 (dd, J=10.8 Hz, J=8.8 Hz, 1H), 6.92 (d, J=8 Hz, 1H), 6.78 (dd, J=7.6 Hz, J=2.8 Hz, 1H), 6.64-6.61 (m, 1H), 2.95 (d, J=4.4 Hz, 3H).

Example 22: Synthesis of 2'-fluoro-3-(4-fluoro-3-hydroxyphenoxy)-3'-hydroxy-[1,1'-biphenyl]-2-carbonitrile

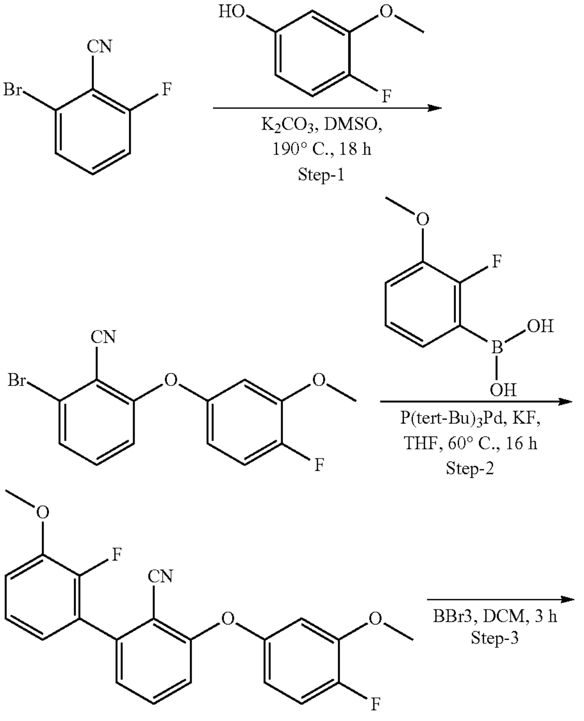

-continued

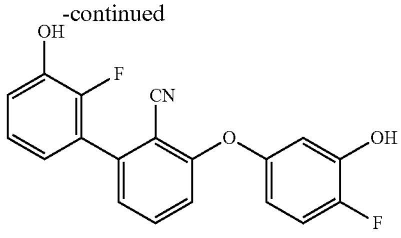

Step 1: Synthesis of 2-bromo-6-(4-fluoro-3-methoxyphenoxy)benzonitrile

To a stirred solution of 2-bromo-6-fluorobenzonitrile (0.4 g, 2.00 mmol) and 4-fluoro-3-methoxyphenol (0.28 g, 2.00 mmol) in DMSO (10.0 mL) was added potassium carbonate (0.69 g, 5.00 mmol). The reaction mixture was heated to 190° C. for 4 h. After completion of the reaction, the reaction mixture was cooled to ambient temperature and quenched with water (50.0 mL), extracted with ethyl acetate (2×50.0 mL). The organic phase was washed with water, brine solution and dried over anhydrous sodium sulfate, concentrated in vacuo. The crude material was purified by flash column chromatography to afford 2-bromo-6-(4-fluoro-3-methoxyphenoxy)benzonitrile as yellow solid (0.26 g, 40%). $^1$H NMR (400 MHz, DMSO-$d_6$) δ 7.61-7.52 (m, 2H), 7.34-7.29 (1H), 7.17-7.15 (m, 1H), 6.91-6.87 (m, 1H), 6.79-6.76 (m, 1H), 3.83 (s, 3H).

Step 2: Synthesis of 2'-fluoro-3-(4-fluoro-3-methoxyphenoxy)-3'-methoxy-[1,1'-biphenyl]-2-carbonitrile To a stirred solution of 2-bromo-6-(4-fluoro-3-methoxyphenoxy)benzonitrile (0.3 g, 0.93 mmol) and (2-fluoro-3-methoxyphenyl)boronic acid (0.19 g, 1.12 mmol) in tetrahydrofuran (7 mL) was added potassium fluoride (0.17 g, 3.07 mmol). Then the reaction mixture was degassed under argon gas for 10 minutes. This was followed by the addition of bis(tri-t-butylphosphine)palladium(0) (0.023 g, 0.046 mmol) and the reaction mixture was heated to 85° C. for 16 hours. After completion of the reaction, the reaction mixture was poured into water (20 ml) and extracted with ethyl acetate (2×20 ml). The organic phase was washed with water, brine solution and dried over anhydrous sodium sulfate, concentrated in vacuo. The crude material was purified by flash column chromatography to afford 2'-fluoro-3-(4-fluoro-3-methoxyphenoxy)-3'-methoxy-[1,1'-biphenyl]-2-carbonitrile as on off white solid (0.3 g, 88%). LCMS (ES) m/z calcd. for C21H15F2NO3, 367.3; found, 366.19 $[M-H]^+$ Step 3: Synthesis of 2'-fluoro-3-(4-fluoro-3-hydroxyphenoxy)-3'-hydroxy-[1,1'-biphenyl]-2-carbonitrile To a stirred solution of 2'-fluoro-3-(4-fluoro-3-methoxyphenoxy)-3'-methoxy-[1,1'-biphenyl]-2-carbonitrile (300 mg, 817 μmol) in dichloromethane at 0° C. (2.00 mL) was added 1M boron tribromide in dichloromethane (8.17 mL, 8.17 mmol) and the reaction mixture was allowed stirred at room temperature for 3 h. The reaction mixture was poured into ice-water (20 mL), extracted into dichloromethane (2×20 mL). The organic phase was washed with brine solution (20 mL) and dried over anhydrous sodium sulphate, filtered and evaporated in vacuo. The crude material was purified by flash column chromatography to afford 2'-fluoro-3-(4-fluoro-3-hydroxyphenoxy)-3'-hydroxy-[1,1'-biphenyl]-2-carbonitrile as off white solid (0.05 g, 20%) LCMS (ES) m/z calcd. for C19H11F2NO3, 339.3; found, 337.97 $[M-H]^+$ $^1$H NMR (400 MHz, DMSO-$d_6$) δ 10.30 (s, 1H), 10.16 (s, 1H), 7.70 (t, J=8.4 Hz, 1H), 7.27-7.21 (m, 2H), 7.15-7.06 (m, 2H), 7.01-6.99 (d, J=8.4 Hz, 1H), 6.89-6.85 (m, 1H), 6.76-6.74 (m, 1H), 6.65-6.61 (m, 1H).

Example 23: Synthesis of 2'-fluoro-3-((4-fluoro-3-hydroxyphenyl)(methyl) amino)-3'-hydroxy-[1,1'-biphenyl]-2-carbonitrile

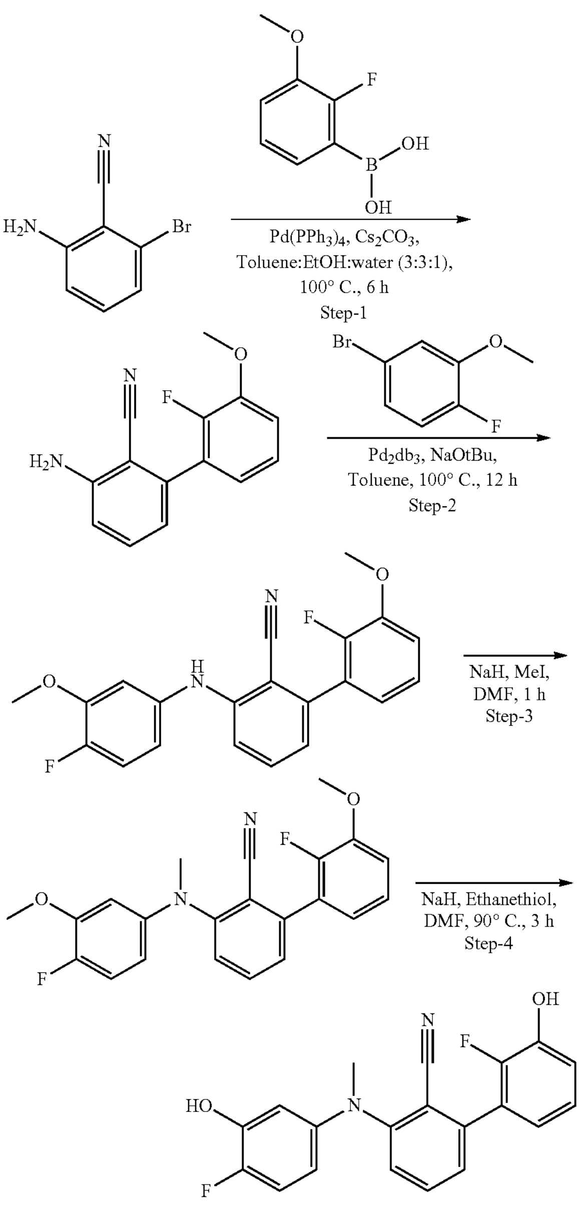

Step 1: Synthesis of 3-amino-2'-fluoro-3'-methoxy-[1,1'-biphenyl]-2-carbonitrile To a stirred solution of 2-amino-6-bromobenzonitrile (0.5 g, 2.54 mmol) and (2-fluoro-3-methoxyphenyl)boronic acid (0.54 g, 3.17 mmol) in toluene, ethanol and water mixture (5 mL, 4:0.5:0.5) was added cesium carbonate (1.66 g, 5.08 mmol). Then the reaction mixture was degassed under argon gas for 10 minutes. This was followed by the addition of Tetrakis(triphenylphosphine)palladium(0) (0.24 g, 0.21 mmol) and the reaction mixture was allowed to stirred at 100° C. for 12 h. After completion of the reaction, the reaction mixture was poured into water (20 ml) and extracted with ethyl acetate (2×20 ml). The organic phase was washed with water, brine solution and dried over anhydrous sodium sulfate, concentrated in vacuo. The crude material was purified by flash column chromatography to afford 3-amino-2'-fluoro-3'-methoxy-[1,1'-biphenyl]-2-carbonitrile as off white solid (0.5 g, 81%). 1HNMR (400 MHz, DMSO-$d_6$): δ 7.35 (t, J=8.0 Hz, 1H), 7.33-7.19 (m, 2H), 6.92-6.90 (m, 1H), 6.83 (d, J=8.4 Hz, 1H), 6.55 (d, J=7.3 Hz, 1H), 6.14 (br s, 2H), 3.88 (s, 3H)

Step 2: Synthesis of 2'-fluoro-3-((4-fluoro-3-methoxyphenyl)amino)-3'-methoxy-[1,1'-biphenyl]-2-carbonitrile To a stirred solution of 3-amino-2'-fluoro-3'-methoxy-[1,1'-biphenyl]-2-carbonitrile (0.35 g, 1.44 mmol) and 4-bromo-1-fluoro-2-methoxybenzene (0.88 g, 4.33 mmol) in toluene (15.0 mL) was added sodium tert-butoxide (0.21 g, 2.17 mmol). Then the reaction mixture was degassed under argon gas for 10 minutes. This was followed by the addition of [2'-(diphenylphosphanyl)-[1,1'-binaphthalen]-2-yl]diphenylphosphane (0.09 g, 0.144 mmol), Tris(dibenzylideneacetone)dipalladium(0) (0.066 g, 0.072 mmol) and the reaction mixture was heated to 100° C. for 16 hours. After completion of the reaction, the reaction mixture was poured into water (50 ml) and extracted with ethyl acetate (2×50 ml). The organic phase was washed with water, brine solution and dried over anhydrous sodium sulfate, concentrated under vacuo. The crude material was purified by flash column chromatography to afford 2'-fluoro-3-((4-fluoro-3-methoxyphenyl)amino)-3'-methoxy-[1,1'-biphenyl]-2-carbonitrile as a light yellow solid (0.33 g, 62%); LCMS (ES) m/z calcd. for C21H16F2N2O2, 366.3; found, 367.30 $[M+H]^+$ Step 3: Synthesis of 2'-fluoro-3-((4-fluoro-3-methoxyphenyl)(methyl) amino)-3'-methoxy-[1,1'-biphenyl]-2-carbonitrile To the stirred solution of 2'-fluoro-3-[(4-fluoro-3-methoxyphenyl)amino]-3'-methoxy-[1,1'-biphenyl]-2-carbonitrile (0.25 g, 0.68 mmol) in N,N-dimethylformamide (2.0 mL) at 0° C. was added sodium hydride (0.024 g, 1.02 mmol). After 10 minutes, iodomethane (0.19 g, 1.36 mmol) was added at 0° C. and then reaction mixture was stirred at room temperature for 1 h. The reaction mixture was quenched with ice water (50 mL), extracted with ethyl acetate (2×50 mL). The organic phase was washed with water, brine solution and dried over anhydrous sodium sulfate, concentrated in vacuo. The crude material was purified by flash column chromatography to afford 2'-fluoro-3-[(4-fluoro-3-methoxy phenyl)(methyl)amino]-3'-methoxy-[1,1'-biphenyl]-2-carbonitrile as viscous liquid (0.2 g, 77%) $^1$HNMR (400 MHz, DMSO-$d_6$): δ 7.76 (t, J=8.0 Hz, 1H), 7.43 (d, J=8.4 Hz, 1H), 7.28-7.23 (m, 3H), 7.11-7.05 (m, 1H), 7.0-6.97 (m, 1H), 6.67-6.65 (m, 1H), 6.37-6.35 (m, 1H), 3.88 (s, 3H), 3.76 (s, 3H), 3.36 (s, 3H).

Step 4: Synthesis of 2'-fluoro-3-((4-fluoro-3-hydroxyphenyl)(methyl)amino)-3'-hydroxy-[1,1'-biphenyl]-2-carbonitrile To a suspended solution of sodium hydride (60% dispersion in mineral oil) (0.15 g, 4.10 mmol) in dry DMF (1.5 ml) at 0° C. was added ethanethiol (0.21 g, 3.42 mmol) in dry DMF (1.5 mL) under nitrogen atmosphere. After 15 minutes, 2'-fluoro-3-[(4-fluoro-3-methoxyphenyl)(methyl) amino]-3'-methoxy-[1,1'-biphenyl]-2-carbonitrile (0.13 g, 0.34 mmol) in dry DMF (1.5 mL) was added to the above stirred solution at 0° C. and the reaction mixture was heated to 90° for 3 h. After completion of the reaction, the reaction mixture was poured into water (20 ml) and extracted with ethyl acetate (2×20 ml). The organic phase was washed with water, brine solution and dried over anhydrous sodium sulfate, concentrated under vacuo. The crude material was purified by reverse phase HPLC to afford 2'-fluoro-3-[(4-fluoro-3-hydroxyphenyl)(methyl)amino]-3'-hydroxy-[1,1'-biphenyl]-2-carbonitrile as a grey solid (0.02 g, 16%) LCMS (ES) m/z calcd. for C20H14F2N2O2, 352.3; found, 353.8 $[M+H]^+$ $^1$H NMR (400 MHz, DMSO-$d_6$): δ 10.07 (s, 1H), 9.70 (s, 1H), 7.75 (t, J=8.0 Hz, 1H), 7.41 (d, J=8.0 Hz, 1H), 7.29 (d, J=7.6 Hz, 1H), 7.11-6.98 (m, 3H), 6.84-6.80 (m, 1H), 6.42 (dd, J=10.4 & 2.8 Hz, 1H), 6.28-6.24 (m, 1H), 3.27 (s, 3H).

Example 25: Synthesis of 2-(4-fluoro-3-hydroxyphenoxy)-6-(2-fluoro-3-hydroxyphenyl)pyridine-3-carboxamide

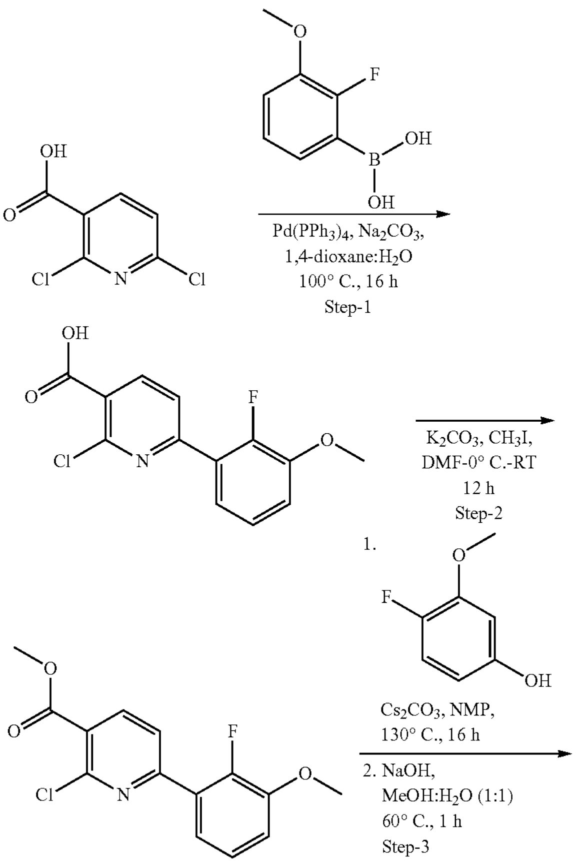

-continued

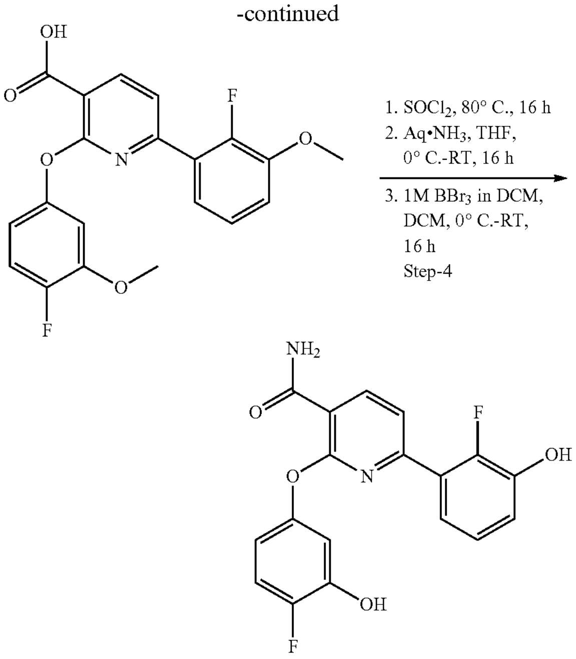

Step 1: Synthesis of 2-chloro-6-(2-fluoro-3-methoxyphenyl)pyridine-3-carboxylic acid To a stirred solution of 2,6-dichloropyridine-3-carboxylic acid (2.00 g, 10.4 mmol) and (2-fluoro-3-methoxyphenyl) boronic acid (2.12 g, 12.5 mmol) in 1,4-dioxane and water (15:2 mL) was added sodium carbonate (3.31 g, 31.3 mmol). Then the reaction mixture was degassed under argon gas for 10 minutes. This was followed by the addition of Tetrakis (triphenylphosphine)palladium(0) (1.20 g, 1.04 mmol) and the reaction mixture was heated to 80° C. for 16 hours. Then the reaction mixture was poured into water (200 ml) and extracted with ethyl acetate (3×100 ml). The organic phase was washed with water, brine solution and dried over anhydrous sodium sulfate, concentrated in vacuo to afford crude 2-chloro-6-(2-fluoro-3-methoxyphenyl)pyridine-3-carboxylic acid as a brown solid (5 g, crude); LCMS (ES) m/z calcd. for C13H9ClFNO3, 281.6; found, 282.2 [M+H].

Step 2: Synthesis of methyl 2-chloro-6-(2-fluoro-3-methoxyphenyl)pyridine-3-carboxylate To a stirred solution of 2-chloro-6-(2-fluoro-3-methoxyphenyl)pyridine-3-carboxylic acid (5 g, 17.74 mmol) in N,N-dimethylformamide (15.0 mL) at 0° C. was added potassium carbonate (7.46 g, 53.24 mmol) and iodomethane (5.52 mL, 88.7 mmol). Then reaction mixture was stirred at room temperature for 16 h. Then the reaction mixture was quenched with ice-water (300 ml) and extracted with ethyl acetate (3×100 ml). The organic phase was washed with water, brine solution and dried over anhydrous sodium sulfate, concentrated under vacuo. The crude material was purified by flash column chromatography to afford methyl 2-chloro-6-(2-fluoro-3-methoxyphenyl)pyridine-3-carboxylate as a white solid (4.80 g, 91%); LCMS (ES) m/z calcd. for C14H11ClFNO3, 295.6; found, 296.1 (M+1).

Step 3: Synthesis of 2-(4-fluoro-3-methoxyphenoxy)-6-(2-fluoro-3-methoxyphenyl)pyridine-3-carboxylic acid To a stirred solution of methyl 2-chloro-6-(2-fluoro-3-methoxyphenyl)pyridine-3-carboxylate (2.50 g, 8.45 mmol) and 4-fluoro-3-methoxyphenol (1.44 g, 10.16 mmol) in 1-methylpyrrolidin-2-one (20.0 mL) was added cesium carbonate (5.54 g, 16.9 mmol) and then reaction mixture was heated to 130° C. for 16 h. After completion of the reaction, the reaction mixture was poured into water (200 ml) and extracted with ethyl acetate (2×150 ml). The organic phase was washed with water, brine solution and dried over anhydrous sodium sulfate, concentrated in vacuo. The crude material was purified by flash column chromatography to afford methyl 2-(4-fluoro-3-methoxyphenoxy)-6-(2-fluoro-3-methoxyphenyl)pyridine-3-carboxylate as a brown solid (1 g, 74%); LCMS (ES) m/z calcd. for C21H17F2NO5, 401.3; found, 402.3 (M+1).

To a stirred solution of methyl 2-(4-fluoro-3-methoxyphenoxy)-6-(2-fluoro-3-methoxyphenyl)pyridine-3-carboxylate (1.00 g, 2.49 mmol) in methanol and water mixture (20.0 ml) was added sodium hydroxide (306 mg, 7.47 mmol) and heated to 60° C. for 1 h. After completion reaction mixture was distilled to remove methanol and poured into water (30 ml) and aqueous layer was extracted with ethyl acetate (200 ml). The obtained aqueous layer was acidified using 1.5 N Hydrochloric acid until pH-4. Precipitated solid was filtered and was washed with water (50 ml), hexane (100 ml) and dried in vacuo to afford 2-(4-fluoro-3-methoxyphenoxy)-6-(2-fluoro-3-methoxyphenyl)pyridine-3-carboxylic acid as a white solid (0.85 g, 88%): LCMS (ES) m/z calcd. for C20H15F2NO5, 387.3; found, 388.1 (M+H).

Step 4: Synthesis of 2-(4-fluoro-3-hydroxyphenoxy)-6-(2-fluoro-3-hydroxyphenyl)pyridine-3-carboxamide To a stirred solution of 2-(4-fluoro-3-methoxyphenoxy)-6-(2-fluoro-3-methoxyphenyl)pyridine-3-carboxylic acid (850 mg, 1.1 eq., 2.19 mmol) in thionyl chloride (15.0 mL) was added N,N-dimethylformamide (1.00 mL) and heated to 80° C. for 8 h. The reaction mixture was concentrated in vacuo to remove excess thionyl chloride and afford crude 2-(4-fluoro-3-methoxyphenoxy)-6-(2-fluoro-3-methoxyphenyl)pyridine-3-carbonyl chloride. Obtained residue was dissolved in tetrahydrofuran (10 mL) and cooled to 0° C. This was then purged with ammonia gas for 30 min and stirred at room temperature for 1 h. After completion of the reaction, the reaction mixture was poured into water (100 ml) and extracted with ethyl acetate (2×100 ml). The organic phase was washed with water, brine solution and dried over anhydrous sodium sulfate, concentrated in vacuo. The crude material was purified by flash column chromatography 2-(4-fluoro-3-methoxyphenoxy)-6-(2-fluoro-3-methoxyphenyl) pyridine-3-carboxamide as a white solid (0.075 g, 10%); LCMS (ES) m/z calcd. for C20H16F2N2O4, 386.3; found, 387.3 (M+1). To a stirred solution of 2-(4-fluoro-3-methoxyphenoxy)-6-(2-fluoro-3-methoxyphenyl)pyridine-3-carboxamide (75.0 mg, 0.194 mmol) in dichloromethane (5 mL) at 0° C. was added 1M boron tribromide in dichloromethane (0.971 mL, 0.971 mmol)) and the reaction mixture was stirred at room temperature for 1 h. The reaction mixture was poured into ice-water (10 mL), extracted into dichloromethane (2×20 mL). The organic phase was washed with brine solution (10 mL) and dried over anhydrous sodium sulphate, filtered and evaporated in vacuo. The crude material was purified by flash column chromatography to afford 2-(4-fluoro-3-hydroxyphenoxy)-6-(2-fluoro-3-hydroxyphenyl)pyridine-3-carboxamide as an off-white solid (0.002 g, 3%); LCMS (ES) m/z calcd. for C18H12F2N2O4, 358.3; found, 359.1 (M+H). $^1$H NMR (400 MHz, DMSO $d_6$) δ=9.9 (s, 2H), 8.22 (d, J=7.6 Hz, 1H), 7.75 (d, J=14.0 Hz, 2H), 7.57 (d, J=7.6 Hz, 1H), 7.15 (t, J=9.6 Hz, 2H), 6.98 (s, 2H), 6.81 (d, J=7.2 Hz, 1H), 6.66 (s, 1H).

Example 26: Synthesis of N-(5-(6-(4-fluoro-3-hydroxyphenoxy)pyridin-2-yl)-1H-benzo [d]imidazol-2-yl)acetamide

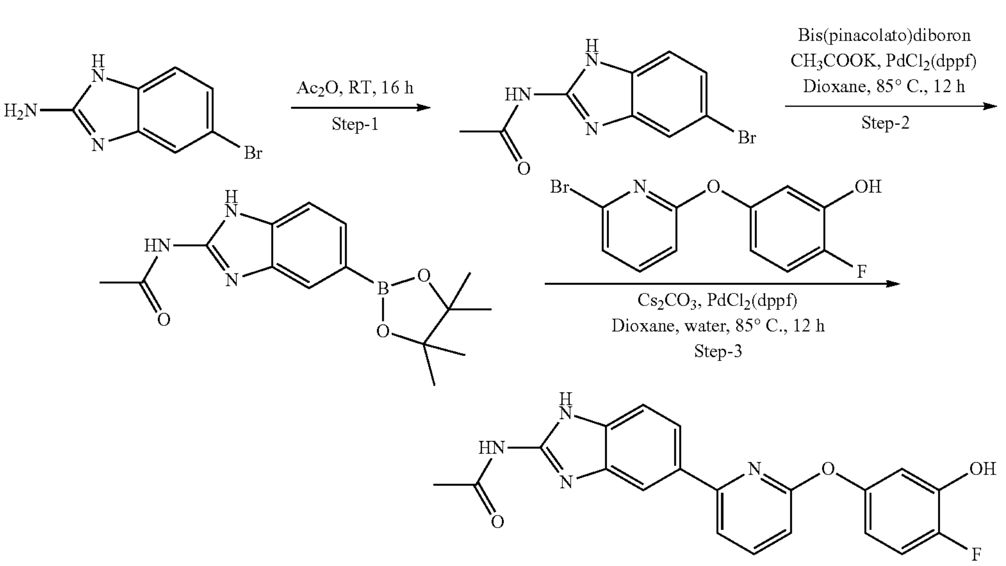

Step-1: Synthesis of N-(5-bromo-1H-benzo[d]imidazol-2-yl)acetamide 5-bromo-1H-1,3-benzodiazol-2-amine (100 mg, 0.472 mmol) and acetic anhydride (481 mg, 4.72 mmol) was taken up in 10 mL reaction vial and stirred at room temperature for 16 h. The progress of reaction was monitored by LCMS and TLC. After completion, the reaction mixture was quenched with water (10 mL) and extracted with ethyl acetate (2×50 mL). The combined organic layer was washed with water (50 mL). The organic layer was dried over anhydrous sodium sulphate, filtered and evaporated under reduced pressure to get crude product. This was purified by flash chromatography over silica gel using ethyl acetate-hexane (product eluted at 20% ethyl acetate). Purification resulted in the title compound N-(5-bromo-1H-benzo[d]imidazol-2-yl) acetamide as brown solid (50.0 mg, 41%). LCMS (ES) m/z calcd. for C9H8BrN3O, 252.9, found, 253.8 $[M+H]^+$.

Step-2: Synthesis of N-(5-(4,4,5,5-tetramethyl-1,3,2-dioxaborolan-2-yl)-1H-benzo[d]imidazol-2-yl) acetamide To a stirred solution of N-(5-bromo-1H-1,3-benzodiazol-2-yl)acetamide (50.0 mg, 0.197 mmol) 1,4-dioxane (5.00 mL), was added bis(pinacolato)diboron (80.0 mg, 0.315 mmol), and potassium acetate (48.3 mg, 0.492 mmol). The reaction mass was purged with argon gas for 30 minute and then $PdCl_2$(dppf) (14.4 mg, 0.1 eq., 0.0197 mmol) was added. The reaction mass was heated to 85° C. and stirred for 12 h. The progress of reaction was monitored by LCMS and TLC. After completion of the reaction, the reaction mixture was quenched with water (10 mL) and extracted with ethyl acetate (2×50 mL). The combined organic layer was washed with water (50 mL), dried over anhydrous sodium sulphate, filtered and evaporated under reduced pressure to get N-(5-(4,4,5,5-tetramethyl-1,3,2-dioxaborolan-2-yl)-1H-benzo[d]imidazol-2-yl)acetamide (50 mg) as gummy solid. LCMS (ES) m/z calcd. for C15H20BN3O3, 301.1, found, 302.3 $[M+H]^+$, Step-3: Synthesis of N-(5-(6-(4-fluoro-3-hydroxyphenoxy)pyridin-2-yl)-1H-benzo[d]imidazole-2-yl) acetamide To a stirred solution of N-[5-(4,4,5,5-tetramethyl-1,3,2-dioxaborolan-2-yl)-1H-1,3-benzodiazol-2-yl]acetamide (50.0 mg, 0.166 mmol) and 5-[(6-bromopyridin-2-yl)oxy]-2-fluorophenol (47.2 mg, 0.166 mmol) 1,4-dioxane (6.00 mL) in water (0.2 mL), was added cesium carbonate (80.5 mg, 0.415 mmol). The reaction mass was purged with argon gas for 45 minutes and then [1,1'-Bis(diphenylphosphino) ferrocene] dichloropalladium(II) (12.1 mg, 0.0166 mmol) was added. The reaction mass was heated to 85° C. and stirred for 12 h. The progress of reaction was monitored by LCMS and TLC. The reaction mixture was quenched with water (10 mL) and extracted with ethyl acetate (2×50 mL). The combined organic layer was washed with water (50 mL), dried over anhydrous sodium sulphate, filtered and evaporated under reduced pressure to get crude product. The crude mass was purified by flash chromatography over silica gel using ethyl acetate-hexane (product eluted at 40% ethyl acetate) to give title compound N-(5-(6-(4-fluoro-3-hydroxyphenoxy)pyridin-2-yl)-1H-benzo[d]imidazol-2-yl) (11 mg, 17.5%) as a white solid. LCMS (ES) m/z calcd. for C20H15FN4O3, 378.11, found, 379.07 $[M+H]^+$, $^1H$ NMR (400 MHz, DMSO-$d_6$) δ 12.14 (s, 1H) 11.56 (s, 1H) 10.06 (s, 1H) 8.04-7.97 (bs, 1H) 7.89-7.85 (t, J=8.8 Hz, 1H) 7.71-7.69 (m, 2H), 7.48-7.43 (m, 1H), 7.21-7.16 (dd, J=10.8 Hz, J=8.8 Hz, 1H), 6.84-6.82 (d, J=8.0 Hz, 1H), 6.77 (s, 1H), 6.63-6.60 (m, 1H), 2.16 (s, 3H).

Example 27: Synthesis of 2-(4-fluoro-3-hydroxy-phenoxy)-6-(2-fluoro-3-hydroxyphenyl) pyridine-4-carbonitrile

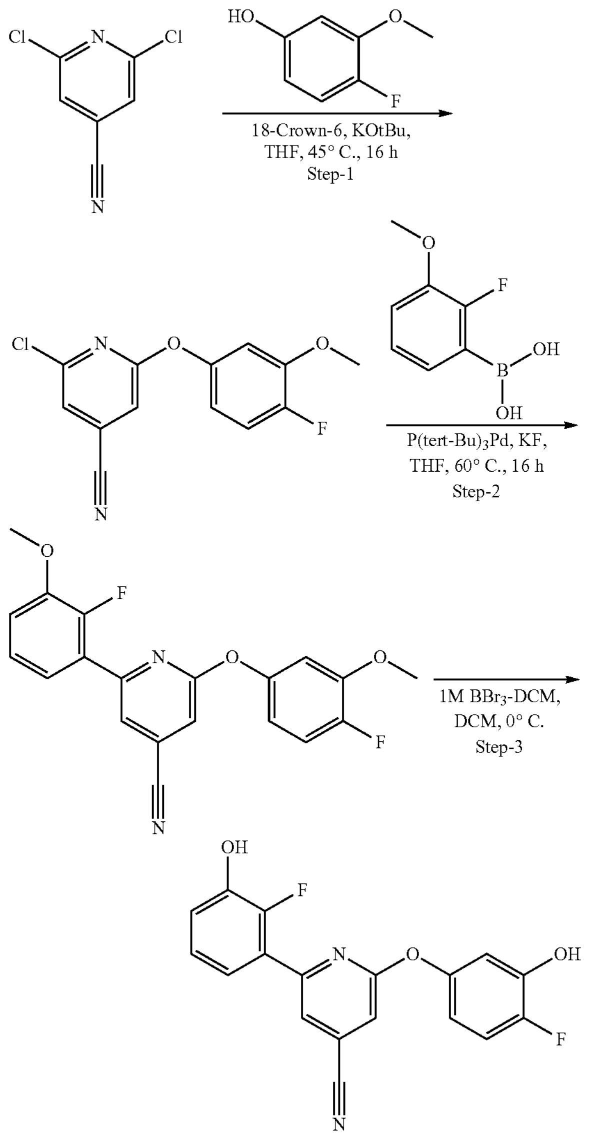

Step 1: Synthesis of 2-chloro-6-(4-fluoro-3-methoxyphenoxy)pyridine-4-carbonitrile To a stirred solution of 2,6-dichloropyridine-4-carbonitrile (500 mg, 2.89 mmol), 4-fluoro-3-methoxyphenol (411 mg, 2.89 mmol) and 1,4,7,10,13,16-hexaoxacyclooctadecane (153 mg, 0.578 mmol) in tetrahydrofuran (20.0 mL), was added 3.47 mmol) at room temperature under nitrogen atmosphere. The reaction mixture was stirred at 45° C. for 16 h. The progress of reaction was monitored by TLC. The reaction was cooled to room temperature and quenched with water (50.0 mL), extracted with ethyl acetate (2×50.0 mL). The organic layer was dried over anhydrous sodium sulfate, concentrated under reduced pressure to give crude. The crude was purified by column chromatography by using ethyl acetate-hexane (product elutes at 40% ethyl acetate) to give 2-chloro-6-(4-fluoro-3-methoxyphenoxy)pyridine-4-carbonitrile (300 mg, 37.3%) as pale yellow solid. Product was confirmed by 1H-NMR. $^{1}$H NMR (400 MHz, DMSO-$d_6$): δ 7.85 (s, 1H), 7.65 (s, 1H), 7.29 (dd, J=12 Hz, J=8.8 Hz, 1H), 7.11 (dd, J=7.6 Hz, J=2.8 Hz, 1H), 6.76-6.80 (m, 1H), 3.8 (s, 3H).

Step 2: Synthesis of 2-(4-fluoro-3-methoxyphenoxy)-6-(2-fluoro-3-methoxy phenyl)pyridine-4-carbonitrile To a stirred solution of 2-chloro-6-(4-fluoro-3-methoxy-phenoxy)pyridine-4-carbonitrile (150 mg, 0.538 mmol) and (2-fluoro-3-methoxyphenyl)boronic acid (119 mg, 0.700 mmol) in tetrahydrofuran (10.0 mL), was added potassium fluoride (103 mg, 1.78 mmol). Reaction mixture was purged with Argon for 5 min and then added P(tert-Bu)$_3$Pd (13.8 mg, 0.0269 mmol). The reaction mass heated at 60° C. for 16 h. After completion, reaction mixture was quenched with water (50.0 mL) and extracted by ethyl acetate (2×50.0 mL). Organic layer was dried over anhydrous sodium sulfate and evaporated under reduced pressure to get crude. The crude was purified by column chromatography by to afford 2-(4-fluoro-3-methoxyphenoxy)-6-(2-fluoro-3-methoxyphenyl) pyridine-4-carbonitrile (110 mg, 55.5%) as off-white solid. Product was confirmed by 1H-NMR. $^{1}$H NMR (400 MHz, DMSO-$d_6$): δ 7.90 (s, 1H), 7.63 (s, 1H), 7.30-7.14 (m, 5H), 6.80 (m, 1H), 3.87 (s, 3H), 3.81 (s, 3H).

Step 3: Synthesis of 2-(4-fluoro-3-hydroxyphenoxy)-6-(2-fluoro-3-hydroxy phenyl)pyridine-4-carbonitrile To a solution of 2-(4-fluoro-3-methoxyphenoxy)-6-(2-fluoro-3-methoxyphenyl)pyridine-4-carbonitrile (110 mg, 0.299 mmol) in dichloromethane (20.0 mL), was added 1M boron tribromide in dichloromethane (2.99 mL, 2.99 mmol) at room temperature, under nitrogen atmosphere. Reaction mixture was stirred for 4 h at room temperature. The progress of reaction was monitored by TLC. The reaction mixture was quenched with cold aqueous $NaHCO_3$ solution (50.0 mL), extracted with 5% methanol in dichloromethane (2×50.0 mL). The organic layer was dried over anhydrous sodium sulphate, filtered and concentrated under vacuum. The resulting crude was purified by reverse phase chromatography preparative HPLC (Mobile phase A: 5 mM $NH_4OAc$ in water, Mobile phase B: ACN) Pure fraction was collected and freeze dried to afford 2-(4-fluoro-3-hydroxy-phenoxy)-6-(2-fluoro-3-hydroxyphenyl) pyridine-4-carbonitrile (30.0 mg, 29.5%) as off-white solid. LCMS (ES) m/z calcd. for C18H10F2N2O3, 340.07, found, 341.07 (M+H)*; $^{1}$H NMR (400 MHz, DMSO-$d_6$): δ 10.14 (s, 1H), 10.09 (s, 1H), 7.85 (s, 1H), 7.57 (d, J=0.8 Hz, 1H), 7.22 (dd, J=11.2 Hz, J=8.8 Hz, 1H), 7.07-7.00 (m, 3H), 6.81 (dd, J=7.6 Hz, J=2.8 Hz, 1H), 6.67-6.63 (m, 1H).

Examples 28-114: Example 28-114 were Synthesized as Described for Examples 1-27

| Ex. | Spectral data |
|---|---|
| 28 | $^1$H NMR (400 MHz, DMSO-$d_6$): δ 10.08 (s, 1H), 9.41 (s, 1H), 7.82 (t, J = 7.6 Hz, 1H), 7.58-7.57 (m, 2H), 7.44-7.28 (m, 6H), 7.20 (dd, J = 11.2 & 8.8 Hz, 1H), 6.85-6.79 (m, 3H), 6.63-6.60 (m, 1H), 5.06 (s, 2H); LCMS (ES) m/z = 404.11 $[M + H]^+$ |
| 29 | 1H NMR (400 MHz, DMSO-d6) δ 11.21 (s, 1H), 9.95 (s, 1H), 8.00 (t, J = 7.9 Hz, 1H), 7.61 (dd, J = 12.4, 8.3 Hz, 2H), 7.15-6.94 (m, 4H), 6.72 (d, J = 7.3 Hz, 2H); LCMS (ES) m/z = 323.2 [M + H]. |
| 30 | 1H NMR (400 MHz, DMSO-$d_6$): δ 9.87 (s, 1H), 9.30 (s, 1H), 7.91 (s, 1H), 7.49 (s, 1H), 7.30 (s, 1H), 7.14-7.24 (m, 3H), 7.08 (s, 1H), 6.91-6.97 (m, 4H). LCMS (ES) m/z = 394.1 [M + H]. |
| 31 | $^1$H NMR (400 MHz, DMSO-$d_6$) δ 10.01 (s, 1H), 7.80 (d, J = 8.9 Hz, 3H), 7.58 (d, J = 8.4 Hz, 1H), 7.15 (d, J = 9.3 Hz, 1H), 7.05 (d, J = 9.2 Hz, 2H), 6.79 (d, J = 7.9 Hz, 1H), 6.73 (s, 1H), 6.57 (s, 1H), 3.83 (s, 4H), 3.07 (s, 4H). LC-MS (ES) m/z = 415.3 $[M + H]^+$ |
| 32 | $^1$H-NMR (400 MHz, DMSO-d6):- δ 10.07 (s, 1H), 7.87 (t, J = 8 Hz, 1H), 7.72 (d, J = 1.6 Hz, 1H), 7.69 (d, J = 8 Hz, 1H), 7.58-7.56 (dd, J = 1.6 Hz, J = 8.4 Hz, 1H), 7.46 (s, 2H), 7.35 (d, J = 8.4 Hz, 1H), 7.21 (dd, J = 8.8 Hz, J = 10.8 Hz, 1H), 6.87 (d, J = 8.0 Hz, 1H), 6.79-6.76 (dd, J = 7.2 Hz, J = 2.8 Hz, 1H) 6.63-6.59 (m, 1H); LCMS (ES) m/z 338.07 $[M + H]^+$ |
| 33 | $^1$H-NMR (400 MHz, DMSO-d6)- δ 10.05 (s, 1H), 7.78 (t, J = 8 Hz, 1H), 7.53 (d, J = 7.6 Hz, 1H), 7.40 (dd, 8.4 Hz, J = 2.0 Hz, 1H), 7.22 (d, J = 2.0 Hz, 1H), 7.17 (dd, J = 10.8 Hz, J = 8.8 Hz, 1H), 6.76-6.69 (m, 3H), 6.60-6.56 (m, 1H), 4.21 (t, J = 4.0 Hz, 2H), 3.27 (t, J = 4.4 Hz, 2H), 2.86 (s, 3H); LCMS (ES) m/z 353.4$[M + H]^+$ |
| 34 | $^1$H NMR (400 MHz, DMSO-$d_6$) δ 9.83 (s, 1H), 7.91 (t, J = 7.84 Hz, 1H), 7.78 (dd, J = 1.88 Hz, J = 1.84 Hz, 1H), 7.73 (d, J = 7.56 Hz, 1H), 7.56-7.52 (m, 1H), 7.43-7.33 (m, 5H), 7.31-7.26 (m, 1H), 7.23-7.18 (m, 1H), 6.93 (d, J = 8.08 Hz, 1H), 6.84 (dd, J = 2.8 Hz, J = 7.56 Hz, 1H), 6.65-6.61 (m, 1H), 5.16 (s, 2H); LCMS (ES) m/z = 406.06[M + H] + |
| 35 | $^1$H NMR (400 MHz, DMSO-$d_6$): δ 12.733 (s, 1H), 9.94 (s, 1H), 7.92 (t, J = 7.6 Hz, 1H), 7.47-7.34 (m, 2H), 7.35 (d, J = 8.8 Hz, 1H), 7.04 (d, J = 7.6 Hz, 1H), 7.00-6.97 (m, 4H), 3.81 (s, 3H), LCMS (ES) m/z: 356.1 (M + H). |
| 36 | $^1$H NMR (400 MHz, DMSO $d_6$) δ = 10.03 (s, 4H), 9.95 (s, 1H), 7.93 (t, J = 8.0 Hz, 1H), 7.49 (d, J = 6.4 Hz, 1H), 6.98 (s, 1H), 6.96-6.82 (m, 4H), 6.80 (d, J = 7.6 Hz, 1H), 6.70 (d J = 7.2 Hz, 1H); LCMS (ES) m/z 316.1 $[M + H]^+$ |
| 37 | $^1$H NMR (400 MHz, DMSO $d_6$) δ = 9.94 (s, 1H), 9.75 (s, 1H), 7.89 (t, J = 7.6 Hz, 1H), 7.46 (d, J = 6.8 Hz, 1H), 7.10-6.93 (m, 6H), 6.85 (s, 1H); MS (ES) m/z: 316.1 (M + H) |
| 38 | $^1$H NMR (400 MHz, DMSO-$d_6$) δ 12.35 (s, 1H), 10.18 (s, 1H), 8.05 (t, J = 8.0 Hz, 1H), 7.89 (d, J = 7.8 Hz, 1H), 7.77 (d, J = 8.2 Hz, 1H), 7.30-7.17 (m, 2H), 7.10 (d, J = 8.2 Hz, 1H), 6.85 (td, J = 8.1, 5.0 Hz, 1H), 6.79 (dd, J = 7.5, 2.9 Hz, 1H), 6.67 (dt, J = 9.0, 3.2 Hz, 1H). LC-MS (ES) m/z = 316.2 $[M + H]^+$ |
| 39 | $^1$H NMR (400 MHz, DMSO-$d_6$) δ 10.11 (s, 2H), 7.84 (t, J = 7.9 Hz, 1H), 7.69-7.56 (m, 3H), 7.18 (t, J = 10.1 Hz, 1H), 6.97 (t, J = 8.9 Hz, 1H), 6.83 (d, J = 8.2 Hz, 1H), 6.78-6.71 (m, 1H), 6.62-6.55 (m, 1H). LC-MS (ES) m/z = 316.2 $[M + H]^+$ |
| 40 | $^1$H NMR (400 MHz, DMSO-$d_6$) δ 10.08 (s, 1H), 10.01 (s, 1H), 7.87 (t, J = 7.9 Hz, 1H), 7.59 (d, J = 7.6 Hz, 1H), 7.50 (dd, J = 8.7, 2.3 Hz, 1H), 7.39-7.31 (m, 1H), 7.17 (dd, J = 11.7, 8.6, 4.0 Hz, 2H), 6.88 (d, J = 8.1 Hz, 1H), 6.73 (dd, J = 7.6, 2.9 Hz, 1H), 6.59 (dt, J = 8.9, 3.2 Hz, 1H). LC-MS (ES) m/z = 316.2 $[M + H]^+$ |
| 41 | $^1$H NMR (400 MHz, DMSO-$d_6$) δ 10.63 (d, J = 9.9 Hz, 2H), 9.94 (s, 1H), 7.89 (t, J = 7.9 Hz, 1H), 7.45 (d, J = 7.5 Hz, 2H), 7.07-6.87 (m, 4H), 6.74 (d, J = 7.9 Hz, 2H). LC-MS (ES) m/z = 338.2 $[M + H]^+$ |
| 42 | $^1$H NMR (400 MHz, DMSO-$d_6$) δ 10.13 (s, 1H), 8.28 (t, J = 2.0 Hz, 1H), 8.15 (s, 1H), 7.97 (t, J = 7.6 Hz, 1H), 7.83 (d, J = 7.2 Hz, 1H), 7.74-7.70 (m, 2H), 7.21 (dd, J = 10.8 Hz, J = 8.8 Hz, 1H), 7.03 (d, J = 8.0 Hz, 1H), 6.79-6.77 (m, 1H), 6.66-6.62 (m, 1H), 3.49-3.48 (m, 4H), 2.85-2.79 (m, 4H), 1.92 (s, 3H); LCMS (ES) m/z = 472.05 [M + H] + |
| 43 | $^1$H NMR (400 MHz, DMSO-$d_6$): δ 10.10 (s, 1H), 8.29-8.26 (m, 1H), 8.13 (s, 1H), 7.98 (t, J = 7.6 Hz, 1H), 7.83 (d, J = 7.6 Hz, 1H), 7.74-7.70 (m, 2H), 7.19 (dd, J = 10.8 Hz & 8.8 Hz, 1H), 7.04 (d, J = 8.4 Hz, 1H), 6.77 (dd, J = 7.6 Hz & 2.8 Hz, 1H), 6.65-6.61 (m, 1H), 2.80 (brs, 4H), 2.35-2.32 (m, 4H), 2.12 (s, 3H); LC-MS (ES) m/z = 444.06 $[M + H]^+$ |
| 44 | $^1$H NMR (400 MHz, DMSO-$d_6$): δ 10.04 (bs, 1H), 8.31-8.28 (m, 1H), 8.14 (s, 1H), 8.00-7.96 (m, 1H), 7.83 (d, J = 7.6 Hz, 1H), 7.76-7.72 (m, 2H), 7.20 (dd, J = 11.0 Hz and 8.8 Hz, 1H), 7.04 (d, J = 8.1 Hz, 1H), 6.78 (dd, J = 7.6 Hz and 2.8 Hz, 1H), 6.65-6.62 (m, 1H), 3.62 (t, J = 4.8 Hz 4H), 2.79 (t, J = 4.4 Hz, 4H); LC-MS (ES) m/z = 431 $[M + H]^+$ |
| 45 | $^1$H NMR (400 MHz, DMSO-$d_6$): δ 10.11 (bs, 2H), 8.34 (t, J = 1.6 Hz, 1H), 8.13 (d, J = 8.0 Hz, 1H), 7.97 (t, J = 7.8 Hz, 1H), 7.75 (d, J = 6.8 Hz, 1H), 7.71 (d, J = 7.5 Hz, 1H), 7.61 (t, J = 7.8 Hz, 1H), 7.20 (m, 3H), 7.07 (m, 2H), 7.00 (m, 1H), 6.95 (m, 1H), 6.76 (dd, J = 7.6 Hz and 2.9 Hz, 1H), 6.63 (m, 1H); LC-MS (ES) m/z = 437 $[M + H]^+$ |
| 46 | $^1$H NMR (400 MHz, DMSO-$d_6$) δ 10.08 (s, 1H), 7.90 (t, J = 8 Hz, 1H), 7.68 (d, J = 7.2 Hz, 1H), 7.46 (dd, J = 1.6 Hz, J = 8.8 Hz, 1H), 7.40 (s, |

-continued

| Ex. | Spectral data |
|---|---|
| | 1H), 7.21-7.16 (m, 1H), 6.91 (d, J = 8.4 Hz, 1H), 6.77 (dd, J = 2.8 Hz, J = 7.6 Hz, 1H), 6.62-6.58 (m, 1H), 4.28 (t, J = 4 Hz, 2H), 3.86 (t, J = 4.4 Hz, 2H), 2.25 (s, 3H); LCMS (ES) m/z = 381.05 $[M + H]^+$ |
| 47 | $^1$H NMR (400 MHz, DMSO-$d_6$) δ 10.06 (s, 1H), 7.89 (t, J = 7.6 Hz, 1H), 7.85-7.84 (d, J = 1.2 Hz, 1H), 7.70 (t, J = 8.0 Hz, 2H), 7.60-7.56 (m, 3H), 7.22-7.17 (dd, J = 10.8 Hz, J = 8.8 Hz, 1H), 6.91 (d, J = 8.0 Hz, 1H), 6.79-6.77 (dd, J = 7.6 Hz, J = 2.8 Hz, 1H), 6.64-6.60 (m, 1H); LCMS (ES) m/z = 354.37$[M + H]^+$ |
| 48 | $^1$H NMR (400 MHz, DMSO-$d_6$): δ 10.14 (bs, 1H), 8.28-8.26 (m, 1H), 8.12 (s, 1H), 7.98 (t, J = 7.6 Hz, 1H), 7.83 (d, J = 7.6 Hz, 1H), 7.73 (d, J = 4.8 Hz, 2H), 7.21-7.16 (m, 1H), 7.04(d, J = 8, 1H), 6.78 (dd, J = 7.6 Hz & 2.8 Hz, 1H), 6.65- 6.62 (m, 1H), 2.67 (m, 6H), 2.21 (m, 2H); LC-MS (ES) m/z = 430.02 $[M + H]^+$ |
| 49 | $^1$H NMR (400 MHz, DMSO-$d_6$) δ 10.03 (s, 1H), 8.42 (s, 1H), 8.14 (d, J = 8.0 Hz, 1H), 7.98 (t, J = 7.2 Hz, 1H), 7.86 (d, J = 8.0 Hz, 1H), 7.78 (d, J = 7.6 Hz, 1H), 7.66 (t, J = 7.6 Hz, 1H), 7.42 (bs, 2H), 7.19 (dd, J = 10.8 Hz, J = 9.2 Hz, 1H), 6.95 (d, J = 8.0 Hz, 1H), 6.77-6.75 (m, 1H), 6.64-6.61 (m, 1H); LCMS (ES) m/z = 360.99 $[M + H]^+$ |
| 50 | $^1$H NMR (400 MHz, DMSO-$d_6$) δ 10.10 (d, J = 6.5 Hz, 1H), 9.59-9.05 (m, 1H), 8.59 (d, J = 4.9 Hz, 1H), 8.22 (d, J = 8.5 Hz, 1H), 8.05 (d, J = 7.3 Hz, 1H), 7.94 (dt, J = 9.7, 6.1 Hz, 1H), 7.88 (d, J = 6.8 Hz, 1H), 7.19 (d, J = 9.9 Hz, 1H), 6.96 (t, J = 7.3 Hz, 1H), 6.81 (dd, J = 7.6, 3.4 Hz, 1H), 6.70-6.54 (m, 1H). LC-MS (ES) m/z = 339.0 $[M + H]^+$ |
| 51 | $^1$H NMR (400 MHz, DMSO-$d_6$) δ 10.85 (s, 1H), 10.08 (s, 1H), 7.86 (t, J = 7.8 Hz, 1H), 7.64 (d, J = 7.56 Hz, 1H), 7.55 (dd, J1 = 8.24 Hz, J2 = 1.84 Hz, 1H), 7.46 (d, J = 1.88 Hz, 1H), 7.21-7.16 (m, 1H), 6.90 (d, J = 8.08 Hz, 1H), 6.87 (d, J = 8.08 Hz, 1H) 6.76 (dd, J1 = 7.56 Hz, J2 = 2.84 Hz, 1H), 6.62-6.58 (m, 1H), 4.59 (s, 2H); LC-MS (ES) m/z = 353.1 [M + H] + |
| 52 | $^1$H NMR (400 MHz, DMSO-$d_6$) δ 7.99 (t, J = 7.6 Hz, J = 15.6 Hz 1H), 7.57 (dd, J = 2.0 Hz, J = 7.6 Hz 1H), ), 7.52-7.07 H(m, 8H), 3.85, (s, 3H); LCMS (ES) m/z = 364.03 $[M + H]^+$ |
| 53 | $^1$H NMR (400 MHz, DMSO-$d_6$) δ 10.09 (s, 1H), 7.88 (t, J = 7.8 Hz, 1H), 7.70 (d, J = 7.5 Hz, 1H), 7.65 (dd, $J_1$ = 8.44 Hz, $J_2$ = 1.92 Hz, 1H), 7.51 (d, J = 1.88 Hz, 1H), 7.23-7.17 (m, 2H), 6.90 (d, J = 8.08 Hz, 1H), 6.76 (dd, $J_1$ = 7.56 Hz, $J_2$ = 1.92 Hz, 1H), 6.63-6.59 (m, 1H), 4.68 (s, 2H), 3.32 (s, 3H). LC-MS (ES) m/z = 367.0 $[M + H]^+$ |
| 54 | $^1$H NMR (400 MHz, DMSO-$d_6$) δ 10.05 (s, 1H), 7.86 (t, J = 7.6 Hz, 1H), 7.60, (d, J = 7.2 Hz, 1H), 7.20-7.06 (m, 4H), 6.86 (d, J = 8.0 Hz, 1H), 6.77(dd, J = 7.6 Hz & 2.8 Hz, 1H), 6.63-6.56 (m, 2H), 5.73-5.69 (m, 1H), 2.66 (d, J = 4.8 Hz, 3H), LCMS (ES) m/z = 311.16 $[M + H]^+$ |
| 55 | $^1$H NMR (400 MHz, DMSO-$d_6$) δ 10.82 (s, 1H), 10.11 (s, 1H), 8.21 (t, J = 7.9 Hz, 1H), 8.13 (d, J = 7.7 Hz, 1H), 8.01 (d, J = 7.8 Hz, 1H), 7.57 (dd, J = 7.9, 2.1 Hz, 1H), 7.49-7.37 (m, 2H), 7.12 (s, 1H), 7.12-7.01 (m, 2H); LCMS (ES) m/z = 364.0 [M + H] |
| 56 | 1HNMR (400 MHz, DMSO-$d_6$): δ 9.93 (s, 1H), 7.85 (t, J = 7.6 Hz, 1H), 7.42 (d, J = 7.2 Hz, 1H), 7.10 (t, J = 6.0 Hz, 1H), 6.94-7.03 (m, 2H), 6.82 (d, J = 8.4 Hz, 1H), 6.63 (d, J = 8.4 Hz, 1H), 6.33 (d, J = 2.0 Hz, 1H), 6.24 (t, J = 8.0 Hz, 1H), 5.91 (s, 1H), 4.08 (s, 2H), 3.26 (s, 2H). LCMS (ES) m/z = 339.1 [M + H] |
| 57 | 1HNMR (400 MHz, DMSO-$d_6$): δ 8.13 (d, J = 8.4 Hz, 1H), 8.06 (d, J = 4.4 Hz, 2H), 7.56 (s, 4H), 7.18-7.25 (m, 2H), 6.99 (d, J = 5.6 Hz, 1H), 6.59 (d, J = 8.8 Hz, 1H), 3.80 (s, 3H). LCMS (ES) m/z = 393.0 [M + H] |
| 58 | $^1$H NMR (400 MHz, DMSO-$d_6$) δ 10.70 (s, 2H), 10.04 (s, 1H), 7.84 (t, J = 7.9 Hz, 1H), 7.61 (d, J = 7.6 Hz, 1H), 7.56 (d, J = 8.2 Hz, 1H), 7.46 (s, 1H), 7.16 (s, 1H), 6.95 (d, J = 8.1 Hz, 1H), 6.81 (d, J = 8.1 Hz, 1H), 6.76-6.69 (m, 1H), 6.59 (d, J = 8.5 Hz, 1H). LC-MS (ES) m/z = 338.1 [M + H] + |
| 59 | $^1$H NMR (400 MHz, DMSO-$d_6$) δ 10.02 (s, 1H), 7.81 (t, J = 7.8 Hz, 1H), 7.47 (d, J = 7.6 Hz, 1H), 7.17 (d, J = 4.2 Hz, 2H), 7.18-7.10 (m, 1H), 7.10-7.03 (m, 1H), 6.76 (d, J = 8.1 Hz, 1H), 6.74-6.64 (m, 2H), 6.57 (dt, J = 9.0, 3.3 Hz, 1H), 4.12 (t, J = 4.3 Hz, 2H), 3.26 (t, J = 4.4 Hz, 2H). LC-MS (ES) m/z = 339.1 $[M + H]^+$ |
| 60 | $^1$H NMR (400 MHz, DMSO-$d_6$) δ 10.62 (s, 1H), 7.91 (t, J = 7.9 Hz, 1H), 7.67 (d, J = 7.5 Hz, 1H), 7.54 (d, J = 8.0 Hz, 1H), 7.33 (d, J = 10.7 Hz, 2H), 7.25 (t, J = 10.1 Hz, 1H), 7.08 (dd, J = 7.9, 2.7 Hz, 1H), 6.94 (d, J = 8.2 Hz, 1H), 6.75 (d, J = 8.7 Hz, 1H), 4.54 (s, 2H), 3.81 (s, 3H). LC-MS (ES) m/z = 387.1 $[M + H]^+$ |
| 61 | $^1$H NMR (400 MHz, DMSO-d6)- δ 12.42 (s, 1H), 10.12 (s, 1H), 8.22 (s, 1H), 8.02-7.99 (d, 8.4 Hz, 1H), 7.95-7.87 (m, 2H), 7.82 (d, J = 7.6 Hz, 1H), 7.23-7.18 (dd, J = 11.2 Hz, J = 8.8 Hz, 1H), 6.95 (d, J = 8.0 Hz, 1H), 6.82-6.79 (dd, J = 7.6 Hz, J = 2.8 Hz, 1H), 6.66-6.62 (m, 1H), 2.19 (s, 3H); LCMS (ES) m/z = 396.08 $[M + H]^+$ |
| 62 | 1H-NMR (400 MHz, DMSO-$d_6$) δ 10.08 (s, 1H), 7.90 (d, J = 8.8 Hz, 1H), 7.19-7.10 (m, 1H), 6.74 (dd, J = 7.6, 2.9 Hz, 1H), 6.63-6.55 (m, 2H), 3.56 (t, J = 4.8 Hz, 4H), 3.39 (t, J = 4.8 Hz, 4H); MS (ES) m/z: 316.1 (M + H) |
| 63 | $^1$H NMR (400 MHz, DMSO-$d_6$) δ 10.11 (s, 1H), 8.53 (d, J = 4 Hz, 1H), 8.34 (s, 1H), 8.03 (d, J = 8 Hz, 1H), 7.97-7.93(t, J = 7.6 Hz, 1H), 7.83 (d, J = 8 Hz, 1H), 7.78 (d, J = 7.6 Hz, 1H), 7.53 (t, J = 7.6 Hz, 1H), 7.20 (dd, J = 10.8 |

-continued

| Ex. | Spectral data |
|---|---|
| | Hz, & J = 8.8 Hz, 1H), 6.94 (d, J = 8.0 Hz, 1H), 6.79-6.77(m, 1H), 6.64-6.60 (m, 1H), 2.89-2.82 (m, 1H), 0.73-0.68 (m, 2H) 0.60-0.56 (m, 2H); LCMS (ES) m/z = 365.16 [M + H]$^+$ |
| 64 | $^1$H NMR (400 MHz, DMSO-$d_6$) δ10.04 (s, 1H), 7.78 (t, J = 8 Hz, 1H), 7.48 (d, J = 7.6 Hz, 1H), 7.31(dd, J = 2 Hz, J = 8.4 Hz 1H), 7.20-7.14 (m, 2H), 6.75-6.71 (m, 2H), 6.59-6.54 (m, 2H), 6.15(s, 1H), 4.10 (t, J = 4 Hz, 2H), 3.31 (s, 2H); LCMS (ES) m/z 339.10 [M + H]$^+$, (97.13%) |
| 65 | $^1$H NMR (400 MHz, DMSO-$d_6$) δ 10.05 (s, 1H), 7.79 (dd, J = 8.4, 5.6 Hz, 3H), 7.57 (d, J = 7.6 Hz, 1H), 7.16 (dd, J = 11.1, 8.8 Hz, 1H), 6.96 (d, J = 8.5 Hz, 2H), 6.80-6.70 (m, 2H), 6.58 (dt, J = 6.3, 3.2 Hz, 1H), 3.71 (t, J = 4.6 Hz, 4H), 3.15 (t, J = 4.7 Hz, 4H). LC-MS (ES) m/z = 367.1 [M + H]$^+$ |
| 66 | $^1$H NMR (400 MHz, DMSO-$d_6$) δ 10.10 (s, 1H), 8.17 (d, J = 2.2 Hz, 1H), 8.03-7.91 (m, 2H), 7.82 (d, J = 7.6 Hz, 1H), 7.68-7.61 (m, 1H), 7.18 (dd, J = 11.1, 8.8 Hz, 1H), 6.99 (d, J = 8.1 Hz, 1H), 6.77 (dd, J = 7.6, 2.9 Hz, 1H), 6.61 (dt, J = 8.8, 3.2 Hz, 1H). LC-MS (ES) m/z = 400.0 [M + H]$^+$ |
| 67 | $^1$H NMR (400 MHz, DMSO-$d_6$) δ 10.07 (s, 1H), 7.84 (t, J = 7.8 Hz, 1H), 7.61 (d, J = 7.7 Hz, 1H), 7.50-7.39 (m, 2H), 7.17 (t, J = 9.9 Hz, 1H), 6.95 (d, J = 8.2 Hz, 1H), 6.84 (d, J = 8.1 Hz, 1H), 6.75 (dd, J = 7.8, 2.9 Hz, 1H), 6.58 (d, J = 8.5 Hz, 1H), 6.04 (s, 2H). LC-MS (ES) m/z = 326.0 [M + H]$^+$ |
| 68 | $^1$H NMR (400 MHz, DMSO-$d_6$) δ 13.16 (s, 1H), 10.20 (s, 1H), 8.48 (s, 1H), 8.12-8.10 (d, J = 8.0 Hz, 1H), 7.96 (t, J = 7.6 Hz, 2H) 7.76 (d, J = 7.6 Hz, 1H), 7.56 (t, J = 7.6 Hz, 1H) 7.20 (dd, J = 11.2 Hz, J = 8.8 Hz, 1H), 6.94 (d, J = 8.4 Hz, 1H) 6.79 (dd, J = 7.6 Hz, J = 2.8 Hz, 1H), 6.64-6.60 (m, 1H); LCMS (ES) m/z = 326.11 [M + H]$^+$ |
| 69 | $^1$H NMR (400 MHz, DMSO-$d_6$) δ 10.11 (s, 1H), 10.01 (s, 1H), 8.79 (q, J = 4.6 Hz, 1H), 7.84 (s, 1H), 7.28 (s, 1H), 7.17 (dd, J = 11.0, 8.8 Hz, 1H), 7.12-6.95 (m, 3H), 6.76 (dd, J = 7.5, 2.9 Hz, 1H), 6.61 (dt, J = 8.8, 3.2 Hz, 1H), 2.79 (d, J = 4.4 Hz, 3H); LC-MS (ES) m/z = 373.0 [M + H]$^+$ |
| 70 | $^1$H NMR (400 MHz, DMSO-$d_6$) δ 10.02 (s, 1H), 8.80 (d, J = 4.9 Hz, 1H), 7.85 (s, 1H), 7.30 (s, 1H), 7.25 (dd, J = 11.2, 8.8 Hz, 1H), 7.14-6.95 (m, 4H), 6.76 (d, J = 8.7 Hz, 1H), 3.80 (s, 3H), 2.79 (d, J = 4.5 Hz, 3H); LC-MS (ES) m/z = 387.1 [M$^+$ H]$^+$ |
| 71 | 1H NMR (400 MHz, DMSO-d6) δ 10.13 (s, 1H), 9.18 (s, 1H), 8.24 (s, 1H), 8.05 (dd, J = 8.6, 1.6 Hz, 1H), 7.94 (t, J = 7.9 Hz, 1H), 7.85-7.78 (m, 2H), 7.19 (dd, J = 11.1, 8.8 Hz, 1H), 6.95 (d, J = 8.1 Hz, 1H), 6.78 (dd, J = 7.6, 2.8 Hz, 1H), 6.63 (dt, J = 8.9, 3.2 Hz, 1H); LC-MS (ES) m/z = 322.1 [M + H]$^+$ |
| 72 | $^1$H NMR (400 MHz, DMSO-$d_6$) δ 9.97 (s, 1H), 7.55 (t, J = 8.0 Hz, 1H), 7.10 (dd, J = 11.1, 8.8 Hz, 1H), 6.66 (dd, J = 7.6, 2.9 Hz, 1H), 6.53-6.44 (m, 2H), 6.12 (d, J = 7.8 Hz, 1H), 3.61 (t, J = 4.8 Hz, 4H), 3.30 (brs, 4H); LC-MS (ES) m/z = 291.1 [M + H] + |
| 73 | $^1$H NMR (400 MHz, DMSO-$d_6$) δ 10.08 (s, 1H), 8.23 (s, 1H), 8.11 (d, J = 9.9 Hz, 1H), 7.93-7.84 (m, 3H), 7.73-7.63 (m, 1H), 7.17 (t, J = 10.1 Hz, 1H), 6.88 (d, J = 8.2 Hz, 1H), 6.74 (d, J = 7.4 Hz, 1H), 6.60 (t, J = 10.2 Hz, 1H). LC-MS (ES) m/z = 349.0 [M + H]$^+$ |
| 74 | $^1$H NMR (400 MHz, DMSO-$d_6$) δ 10.02 (s, 1H), 7.88 (t, J = 7.8 Hz, 1H), 7.39 (q, J = 7.9 Hz, 1H), 7.18-7.07 (m, 2H), 6.94 (dd, J = 8.4, 3.4 Hz, 2H), 6.85 (t, J = 8.8 Hz, 1H), 6.67 (dd, J = 7.6, 3.1 Hz, 1H), 6.53 (dt, J = 9.3, 3.2 Hz, 1H), 3.71 (s, 3H). LC-MS (ES) m/z = 330.0 [M + H]$^+$ |
| 75 | $^1$H NMR (400 MHz, DMSO-$d_6$) δ 10.10 (s, 1H), 8.43 (d, J = 2.3 Hz, 1H), 8.25 (d, J = 7.9 Hz, 1H), 7.96 (q, J = 7.8 Hz, 2H), 7.85 (d, J = 7.5 Hz, 1H), 7.73 (t, J = 7.8 Hz, 1H), 7.18 (dd, J = 11.0, 8.8 Hz, 1H), 6.97 (d, J = 8.1 Hz, 1H), 6.77 (dd, J = 7.6, 2.8 Hz, 1H), 6.62 (dt, J = 8.8, 3.2 Hz, 1H), 3.24 (s, 3H). LC-MS (ES) m/z = 360.0 [M + H]$^+$ |
| 76 | $^1$H NMR (400 MHz, DMSO-$d_6$) δ 10.09 (s, 1H), 8.08 (t, J = 6.2 Hz, 2H), 7.96 (d, J = 6.6 Hz, 1H), 7.85 (d, J = 7.5 Hz, 2H), 7.78 (d, J = 6.9 Hz, 1H), 7.39 (d, J = 4.1 Hz, 2H), 7.18 (s, 1H), 7.01-6.93 (m, 1H), 6.78 (dd, J = 7.6, 3.9 Hz, 1H), 6.62 (dd, J = 8.9, 4.9 Hz, 1H). LC-MS (ES) m/z = 361.0 [M + H]$^+$ |
| 77 | $^1$H NMR (400 MHz, DMSO-$d_6$) δ 10.10 (s, 1H), 8.14 (d, J = 8.1 Hz, 2H), 7.97 (d, J = 7.4 Hz, 3H), 7.83 (d, J = 7.0 Hz, 1H), 7.18 (t, J = 10.1 Hz, 1H), 7.02 (d, J = 7.8 Hz, 1H), 6.77 (s, 1H), 6.62 (d, J = 8.7 Hz, 1H), 3.22 (s, 3H). LC-MS (ES) m/z = 360.0 [M + H]$^+$ |
| 78 | $^1$H NMR (400 MHz, DMSO-$d_6$) δ 10.10 (s, 1H), 8.75 (s, 1H), 8.41 (d, J = 8.3 Hz, 1H), 7.96 (t, J = 8.0 Hz, 1H), 7.79 (d, J = 7.3 Hz, 1H), 7.28 (d, J = 8.6 Hz, 1H), 7.18 (t, J = 9.8 Hz, 1H), 6.99 (d, J = 8.1 Hz, 1H), 6.78 (d, J = 7.5 Hz, 1H), 6.62 (d, J = 8.5 Hz, 1H). LC-MS (ES) m/z = 301.0 [M + H]$^+$ |
| 79 | $^1$H NMR (400 MHz, DMSO-$d_6$) δ 10.03 (d, J = 10.0 Hz, 2H), 8.13 (s, 1H), 7.91 (t, J = 8.0 Hz, 1H), 7.63 (d, J = 8.1 Hz, 1H), 7.57 (t, J = 9.4 Hz, 2H), 7.35 (t, J = 8.1 Hz, 1H), 7.16 (t, J = 10.3 Hz, 1H), 6.87 (d, J = 8.1 Hz, 1H), 6.77-6.70 (m, 1H), 6.64 - 6.57 (m, 1H), 2.04 (s, 3H). LC-MS (ES) m/z = 339.1 [M + H]$^+$ |
| 80 | $^1$H NMR (400 MHz, DMSO-$d_6$) δ 10.06 (s, 1H), 8.44 (s, 1H), 7.98 (d, J = 7.9 Hz, 2H), 7.92 (d, J = 7.9 Hz, 1H), 7.87 (d, J = 8.1 Hz, 2H), 7.77 (d, J = 7.7 Hz, 1H), 7.18 (t, J = 9.9 Hz, 1H), 6.94 (d, J = 8.1 Hz, 1H), 6.77 (d, J = 7.3 Hz, 1H), 6.61 (d, J = 8.8 Hz, 1H), 2.77 (d, J = 4.9 Hz, 3H). LC-MS |

-continued

| Ex. | Spectral data |
|---|---|
| | (ES)m/z = 339.1 [M + H]$^+$ |
| 81 | $^1$H NMR (400 MHz, DMSO-$d_6$) δ 10.05 (s, 1H), 8.48 (s, 1H), 8.37 (s, 1H), 8.02 (d, J = 7.6 Hz, 1H), 7.94 (t, J = 8.0 Hz, 1H), 7.83 (d, J = 7.2 Hz, 2H), 7.76 (d, J = 8.0 Hz, 1H), 7.51 (t, J = 7.6 Hz, 1H), 7.17 (t, J = 10.0 Hz, 1H), 6.92 (d, J = 8.0 Hz, 1H), 6.76 (d, J = 7.6 Hz, 1H), 6.61 (d, J = 8.4 Hz, 1H), 2.79 (d, J = 4.0 Hz, 3H). LC-MS (ES) m/z = 339.1 [M + H]$^+$ |
| 82 | LCMS (ES) m/z 316.0 [M + H]$^+$; $^1$H NMR (400 MHz, DMSO-$d_6$) δ 10.08 (s, 1H), 7.91 (dd, J = 8.3 Hz, 3H), 7.72 (d, J = 7.7 Hz, 1H), 7.50 (d, J = 8.6 Hz, 2H), 7.17 (dd, J = 8.8 Hz, 1H), 6.93 (d, J = 8.2 Hz, 1H), 6.75 (dd, J = 2.8 Hz, 1H), 6.60 (t, J = 3.2 Hz, 1H) |
| 83 | LCMS (ES) m/z 316.0 [M + H]$^+$; H NMR (400 MHz, DMSO-$d_6$) δ 10.03 (s, 1H), 7.93 (t, J = 7.9 Hz, 1H), 7.55-7.49 (m, 1H), 7.49-7.43 (m, 1H), 7.45-7.34 (m, 3H), 7.12 (t, J = 10.0 Hz, 1H), 7.00 (d, J = 8.3 Hz, 1H), 6.72 (dd, J = 2.9 Hz, 1H), 6.57 (t, J = 3.3 Hz, 1H) |
| 84 | LCMS (ES) m/z 318.0 [M + H]$^+$; $^1$H NMR (400 MHz, DMSO-$d_6$) δ 10.07 (s, 1H), 7.93 (t, J = 7.9 Hz, 1H), 7.76 (q, J = 8.7 Hz, 1H), 7.55-7.48 (m, 1H), 7.41-7.31 (m, 1H), 7.22-7.11 (m, 2H), 6.98 (d, J = 8.2 Hz, 1H), 6.74 (dd, J = 2.9 Hz, 1H), 6.60 (dd, J = 4.3 Hz, 1H) |
| 85 | LCMS (ES) m/z 334.2 [M + H]$^+$; $^1$H NMR (400 MHz, DMSO-$d_6$) δ 10.06 (s, 1H), 8.08 (dd, J = 7.3 Hz, 1H), 7.92 (dd, J = 8.8 Hz, 2H), 7.76 (d, J = 7.6 Hz, 1H), 7.48 (t, J = 9.0 Hz, 1H), 7.18 (dd, J = 8.8 Hz, 1H), 6.95 (d, J = 8.1 Hz, 1H), 6.76 (dd, J = 2.9 Hz, 1H), 6.60 (t, J = 3.2 Hz, 1H) |
| 86 | LCMS (ES) m/z 334.2 [M + H]$^+$; $^1$H NMR (400 MHz, DMSO-$d_6$) δ 10.04 (s, 1H), 7.96 (t, J = 7.9 Hz, 1H), 7.63 (q, J = 7.2 Hz, 2H), 7.55 (dd, J = 7.5 Hz, 1H), 7.29 (t, J = 8.0 Hz, 1H), 7.15 (dd, J = 8.8 Hz, 1H), 7.02 (d, J = 8.2 Hz, 1H), 6.75 (dd, J = 2.9 Hz, 1H), 6.60 (t, J = 3.2 Hz, 1H) |
| 87 | LCMS (ES) m/z 330.1 [M + H]$^+$; $^1$H NMR (400 MHz, DMSO-$d_6$) δ 10.03 (s, 1H), 7.88 (t, J = 7.9 Hz, 1H), 7.68 (t, J = 9.0 Hz, 1H), 7.48 (dd, J = 7.6 Hz, 1H), 7.15 (dd, J = 8.8 Hz, 1H), 6.94-6.82 (m, 3H), 6.74 (dd, J = 2.9 Hz, 1H), 6.59 (dt, J = 3.2 Hz, 1H), 3.79 (s, 3H) |
| 88 | LCMS (ES) m/z 318.0 [M + H]$^+$; $^1$H NMR (400 MHz, DMSO-$d_6$) δ 10.09 (s, 1H), 7.96 (t, J = 7.9 Hz, 1H), 7.59 (d, J = 7.5 Hz, 1H), 7.46 (t, J = 9.8 1H), 7.37 (dd, J = 9.9 Hz, 1H), 7.30 (d, J = 5.8 Hz, 1H), 7.18 (t, J = 10.1 Hz, 1H), 7.02 (d, J = 8.1 Hz, 1H), 6.77 (dd, J = 3.3 Hz, 1H), 6.62 (t, J = 7.1 Hz, 1H) |
| 89 | LCMS (ES) m/z 318.0 [M + H]$^+$; $^1$H NMR (400 MHz, DMSO-$d_6$) δ 10.11 (s, 1H), 7.95 (t, J = 7.8 Hz, 1H), 7.81 (d, J = 7.5 Hz, 1H), 7.61 (d, J = 6.7 Hz, 2H), 7.28 (t, J = 9.2 Hz, 1H), 7.19 (dd, J = 8.9 Hz, 1H), 7.00 (d, J = 8.1 Hz, 1H), 6.78 (dd, J = 2.9 Hz, 1H), 6.61 (dt, J = 3.2 Hz, 1H) |
| 90 | LCMS (ES) m/z 300.0 [M + H]$^+$; $^1$H NMR (400 MHz, DMSO-$d_6$) δ 10.07 (s, 1H), 7.93 (t, J = 7.9 Hz, 1H), 7.71 (t, J = 8.0 Hz, 1H), 7.54 (dd, J = 7.5 Hz, 1H), 7.49-7.39 (m, 1H), 7.34-7.22 (m, 2H), 7.16 (dd, J = 7.6 Hz, 1H), 6.98 (d, J = 8.2 Hz, 1H), 6.75 (dd, J = 2.4 Hz, 1H), 6.60 (dt, J = 2.4 Hz, 1H) |
| 91 | 1H NMR (400 MHz, DMSO-d6): δ 12.56 (br s, 1H), 8.19-8.24 (m, 1H), 8.04 (s, 1H), 7.64-7.91 (m, 3H), 7.53 (d, J = 8.4 Hz, 1H),7.27 (t, J = 9.2 Hz, 1H), 7.12 (d, J = 7.2 Hz, 1H), 6.87-6.90 (m, 1H), 6.76-6.78 (m, 1H), 3.81 (s, 3H); LCMS (ES) m/z = 336.1 [M + H] |
| 92 | $^1$H NMR (400 MHz, DMSO-$d_6$) δ 10.10 (s, 1H), 8.03-7.94 (m, 2H), 7.86 (t, J = 7.9 Hz, 1H), 7.77 (dd, J = 8.1, 1.6 Hz, 1H), 7.62 (dd, J = 7.5, 2.1 Hz, 1H), 7.16 (dd, J = 11.0, 8.8 Hz, 1H), 7.07 (d, J = 8.3 Hz, 1H), 6.76 (dd, J = 7.5, 2.9 Hz, 1H), 6.61 (dt, J = 8.9, 3.2 Hz, 1H). LC-MS (ES) m/z = 325.3 [M + H]$^+$ |
| 93 | $^1$H NMR (400 MHz, DMSO-$d_6$) δ 9.95 (s, 1H), 9.82 (s, 1H), 7.94 (t, J = 7.2 Hz, 1H), 7.51 (d, J = 7.6 Hz, 1H), 7.34 (t, J = 8.0 Hz, 1H), 7.07-6.99 (m, 4H), 6.97-6.90 (m, 3H), 2.57-2.48 (m, 1H), 0.87-0.82 (m, 4H). LC-MS (ES) m/z = 401.0 [M + H]$^+$ |
| 94 | $^1$H NMR (400 MHz, DMSO-$d_6$) δ 9.93 (s, 1H), 7.93 (t, J = 7.9 Hz, 1H), 7.59 (t, J = 6.5 Hz, 1H), 7.50 (dd, J = 7.5, 2.1 Hz, 1H), 7.39 (t, J = 8.0 Hz, 1H), 7.21-7.15 (m, 2H), 7.09 (d, J = 8.8 Hz, 1H), 7.07-6.91 (m, 4H), 4.16 (d, J = 6.4 Hz, 2H), 2.78 (s, 3H). LC-MS (ES) m/z = 389.0 [M + H]$^+$ |
| 95 | $^1$H NMR (400 MHz, DMSO-$d_6$) δ 9.83 (s, 1H), 7.96 (t, J = 7.9 Hz, 1H), 7.53 (d, J = 7.5 Hz, 1H), 7.35 (t, J = 8.1 Hz, 1H), 7.19 (q, J = 7.2 Hz, 2H), 7.17-7.09 (m, 1H), 7.09-7.01 (m, 3H), 6.91 (d, J = 8.2 Hz, 1H), 3.84 (s, 3H), 2.62 (d, J = 6.8 Hz, 1H), 0.90-0.78 (m, 4H). LC-MS (ES) m/z = 415.2 [M + H]$^+$ |
| 96 | $^1$H NMR (400 MHz, DMSO-$d_6$) δ 7.95 (t, J = 7.9 Hz, 1H), 7.59 (t, J = 6.5 Hz, 1H), 7.52 (dd, J = 7.5, 2.1 Hz, 1H), 7.39 (t, J = 8.0 Hz, 1H), 7.23-7.07 (m, 6H), 7.02 (d, J = 8.2 Hz, 1H), 4.16 (d, J = 6.3 Hz, 2H), 3.84 (s, 3H), 2.78 (s, 3H); LC-MS (ES) m/z = 403.3 [M + H]$^+$ |
| 97 | LCMS (ES) m/z 298.0 [M + H]$^+$; $^1$HNMR (400 MHz, DMSO-$d_6$) δ 10.06 (s, 1H), 9.52 (s, 1H), 7.87 (t, J = 7.9 Hz, 1H), 7.60 (d, J = 7.6 Hz, 1H), 7.33 (d, J = 7.8 Hz, 1H), 7.28 (t, J = 2.1 Hz, 1H), 7.25-7.12 (m, 2H), 6.88 (d, J = 8.1 Hz, 1H), 6.76 (dd, J = 5.2 Hz, 2H), 6.58 (dt, J = 3.2 Hz, 1H) |
| 98 | LCMS (ES) m/z 350.0 [M + H]$^+$; $^1$H NMR (400 MHz, DMSO-$d_6$) δ 10.11 (s, 1H), 8.11 (d, J = 7.9 Hz, 2H), 7.97 (td, J = 7.9 Hz, 1H), 7.80 (dd, J = 8.0 Hz, 3H), 7.18 (dd, J = 8.7 Hz, 1H), 7.00 (dd, J = 8.1 Hz, 1H), 6.77 (dd, J = 3.0 Hz, 1H), 6.61 (dt, J = 3.2 Hz, 1H) |
| 99 | LCMS (ES) m/z 312.1 [M + H]; $^1$H NMR (400 MHz, DMSO-$d_6$) δ 10.04 |

-continued

| Ex. | Spectral data |
|---|---|
| | (s, 1H), 7.84 (t, J = 7.9 Hz, 1H), 7.62 (d, J = 7.5 Hz, 1H), 7.54 (dd, J = 7.7 Hz, 1H), 7.40-7.31 (m, 1H), 7.19-7.07 (m, 2H), 6.97 (t, J = 7.5 Hz, 1H), 6.88 (d, J = 8.1 Hz, 1H), 6.72 (dd, J = 2.9 Hz, 1H), 6.57 (dt, J = 3.2 Hz, 1H), 3.81 (s, 3H) |
| 100 | LCMS (ES) m/z 384.0 $[M + H]^+$; $^1H$ NMR (400 MHz, DMSO-$d_6$) δ 10.11 (s, 1H), 8.31 (d, J = 2.2 Hz, 1H), 8.23 (dd, J = 8.5 Hz, 1H), 7.96 (t, J = 7.8 Hz, 1H), 7.86 (d, J = 7.5 Hz, 1H), 7.80 (d, J = 8.5 Hz, 1H), 7.18 (dd, J = 8.8 Hz, 1H), 7.00 (d, J = 8.1 Hz, 1H), 6.77 (dd, J = 7.5 1H), 6.62 (dt, J = 8.9 Hz, 1H) |
| 101 | LCMS (ES) m/z 384.0 $[M + H]^+$; $^1H$ NMR (400 MHz, DMSO-$d_6$) δ 10.11 (s, 1H), 8.31 (d, J = 2.2 Hz, 1H), 8.23 (dd, J = 8.5 Hz, 1H), 7.96 (t, J = 7.8 Hz, 1H), 7.86 (d, J = 7.5 Hz, 1H), 7.80 (d, J = 8.5 Hz, 1H), 7.18 (dd, J = 1.6 Hz, 1H), 7.00 (d, J = 8.1 Hz, 1H), 6.77 (dd, J = 2.8 Hz, 1H), 6.62 (dt, J = 3.2 Hz, 1H) |
| 102 | LCMS (ES) m/z 312.0 $[M + H]^+$; $^1H$ NMR (400 MHz, DMSO-$d_6$) δ 10.06 (s, 1H), 7.85 (d, J = 8.3 Hz, 3H), 7.61 (d, J = 7.6 Hz, 1H), 7.17 (dd, J = 8.6 Hz, 1H), 7.01-6.94 (m, 2H), 6.82 (d, J = 8.1 Hz, 1H), 6.75 (dd, J = 7.6 Hz, 1H), 6.59 (d, J = 8.9 Hz, 1H), 3.77 (s, 3H) |
| 103 | LCMS (ES) m/z 350.0 $[M + H]^+$; $^1H$ NMR (400 MHz, DMSO-$d_6$) δ 10.06 (s, 1H), 8.23 (d, J = 8.4 Hz, 2H), 7.95 (t, J = 7.9 Hz, 1H), 7.84 (d, J = 7.6 Hz, 1H), 7.75 (d, J = 7.8 Hz, 1H), 7.68 (t, J = 7.8 Hz, 1H), 6.78 (dd, J = Hz, 1H), 6.62 (q, J = 3.8 Hz, 1H), 6.77 (d, J = 7.2 Hz, 1H), 6.61 (dd, J = 8.4 Hz, 1H) |
| 104 | $^1H$ NMR (400 MHz, Chloroform-d) δ 8.19 (s, 1H), 8.12 (t, J = 8.4 Hz, 1H), 7.79 (dd, J = 8.0 Hz, 1H), 7.64 (t, J = 7.8 Hz, 1H), 7.5 (t, 2H), 7.11 (dd, J = 9.6 Hz, 1H), 6.8 (t, J = 4 Hz, 2H), 6.70 (d, J = 3.2 Hz, 1H), 5.85 (s, 1H); LCMS (ES) m/z 307.0 $[M + H]^+$ |
| 105 | $^1H$ NMR (400 MHz, DMSO-$d_6$) δ 13.01 (s, 1H), 8.05 (s, 1H), 7.95 (t, J = 7.9 Hz, 1H), 7.77 (d, J = 8.8 Hz, 1H), 7.53 (d, J = 7.6 Hz, 1H), 7.29 (s, 1H), 7.17 (t, J = 7.5 Hz, 2H), 7.12 (d, J = 7.4 Hz, 1H), 7.04 (d, J = 8.2 Hz, 1H), 6.95 (d, J = 8.8 Hz, 1H), 3.83 (s, 2H). LC-MS (ES) m/z = 336.1 $[M + H]^+$ |
| 106 | 1HNMR (400 MHz, DMSO-$d_6$): δ 9.94 (s, 1H), 9.81 (s, 1H), 7.92 (t, J = 8.0 Hz, 1H), 7.82 (d, J = 4.0 Hz, 1H), 7.49 (d, J = 6.4 Hz, 1H), 7.28 (t, J = 9.6 Hz, 1H), 6.93-7.08 (m, 5H), 2.06 (d, J = 5.6 Hz, 3H). LCMS (ES) m/z = 357.1 |
| 107 | 1HNMR (400 MHz, DMSO-$d_6$): δ 9.82 (s, 1H), 7.93 (t, J = 8.0 Hz, 1H), 7.83 (d, J = 3.6 Hz, 1H), 7.51 (d, J = 6.4 Hz, 1H), 7.02-7.30 (m, 4H), 6.98 (d, J = 18.0 Hz, 1H), 6.93 (d, J = 5.2 Hz, 1H), 3.84 (s, 3H), 2.07 (s, 3H). LCMS (ES) m/z = 371.3 [M + H] |
| 108 | 1H NMR(400 MHz, DMSO-$d_6$) δ 11.41 (s, 1H), 7.92 (t, J = 7.8 Hz, 1H), 7.48 (dd, J = 12.9, 7.2 Hz, 3H), 7.22 (dd, J = 8.6, 5.0 Hz, 1H), 7.18 (q, J = 8.2, 6.3 Hz, 2H), 7.02 (d, J = 8.2 Hz, 1H), 6.42-6.35 (m, 1H), 3.85 (s, 3H). LCMS (ES) m/z = 313.3 [M + H] |
| 109 | 1H NMR (400 MHz, DMSO-d6): δ 8.28 (s, 1H), 7.96 (t, J = 8.0 Hz, 1H), 7.54 (d, J = 6.0 Hz, 1H), 7.32-7.41 (m, 3H), 7.13-7.21 (m, 3H), 7.07 (d, J = 8.4 Hz, 1H), 3.84 (s, 3H); MS (ES) m/z: 371.1 (M + H) |
| 110 | 1HNMR (400 MHz, DMSO-$d_6$): δ 13.18 (s, 1H), 8.05 (d, J = 8.8 Hz, 2H), 7.93 (t, J = 7.6 Hz, 1H), 7.80-7.77 (m, 2H), 7.69 (d, J = 8.4 Hz, 1H), 7.29-7.24 (m, 1H), 7.14-7.11 (m, 1H), 6.95 (d, J = 8.0 Hz, 1H), 6.80-6.76 (m, 1H), 3.82 (s, 3H); LCMS (ES) m/z = 336.3 [M + H] |
| 111 | 1HNMR (400 MHz, DMSO-$d_6$): δ 9.73 (s, 1H), 7.83 (t, J = 7.6 Hz, 1H), 7.54 (d, J = 6.4 Hz, 1H), 7.39-7.43 (m, 1H), 7.19-7.29 (m, 3H), 6.87-6.91 (m, 2H), 6.64 (d, J = 8.0 Hz, 1H), 3.88 (s, 3H), 3.59 (s, 3H). LCMS (ES) m/z = 407.1 [M + H] |
| 112 | 1H NMR (400 MHz, DMSO-d6): δ 7.96 (t, J = 8.0 Hz, 1H), 7.89 (d, J = 2.8 Hz, 1H), 7.83 (s, 1H), 7.66-7.69 (m, 1H), 7.54 (d, J = 6.8 Hz, 1H), 7.15-7.25 (m, 3H), 7.13 (d, J = 8.4 Hz, 1H), 6.57 (d, J = 10 Hz, 1H), 3.85 (s, 3H); MS (ES) m/z: 363.3 (M + H) |
| 113 | 1HNMR (400 MHz, DMSO-$d_6$): δ 9.81 (bs, 2H), 7.91 (t, J = 7.2 Hz, 1H), 7.79 (s, 1H), 7.61 (d, J = 6.8 Hz, 2H), 7.37 (t, J = 8.0 Hz, 1H), 7.12-7.23 (m, 2H), 6.91 (d, J = 8.0 Hz, 1H), 6.73 (d, J = 5.2 Hz, 1H), 6.60 (d, J = 8.8 Hz, 1H), 2.50 (d, J = 20.4 Hz, 1H), 0.88 (s, 4H). LCMS (ES) m/z = 401.3 [M + H] |
| 114 | 1HNMR (400 MHz, DMSO-$d_6$): δ 10.08 (s, 1H), 9.66 (s, 1H), 7.93 (t, J = 8.0 Hz, 1H), 7.48 (t, J = 7.2 Hz, 2H), 7.41 (t, J = 7.2 Hz, 1H), 7.11-7.22 (m, 2H), 6.98 (d, J = 8.4 Hz, 1H), 6.73-6.75 (m, 1H), 6.57-6.60 (m, 1H), 2.60-2.64 (m, 1H), 0.79-0.90 (m, 4H). LCMS (ES) m/z = 419.3 [M + H] |

Example 115: Synthesis of 2,6-difluoro-3-((2-(4-morpholinophenyl)pyrimidin-4-yl)oxy)phenol

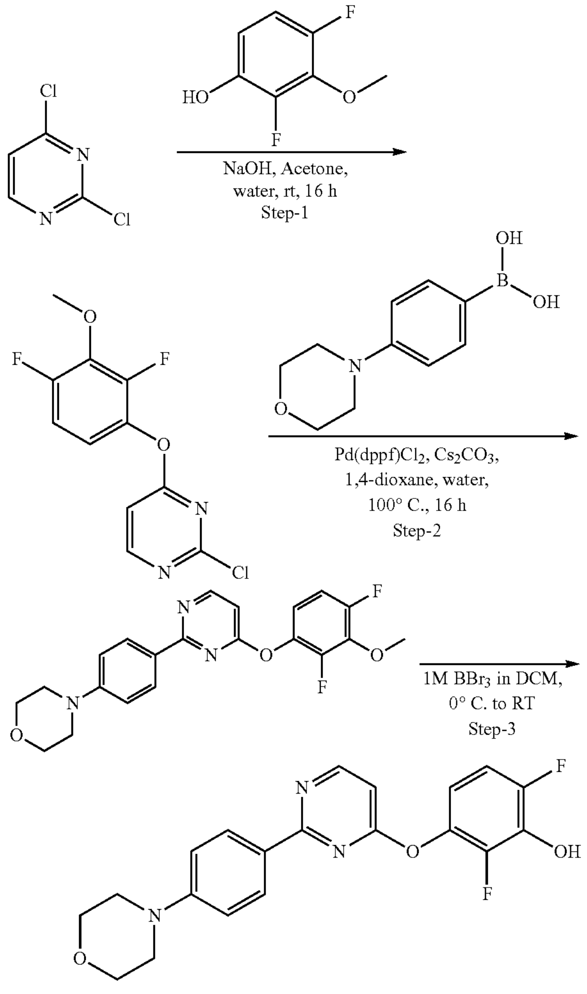

Step 1: Synthesis of 2-chloro-4-(2,4-difluoro-3-methoxyphenoxy)pyrimidine

To a stirred solution of 2,4-difluoro-3-methoxyphenol (0.53 g, 3.36 mmol) in acetone (5.0 mL) and water (2.0 mL) was added sodium hydroxide (0.13 g, 3.36 mmol) and stirred for 20 minutes followed by the addition of 2,4-dichloropyrimidine (0.5 g, 3.36 mmol), the reaction mixture was then stirred at ambient temperature for 3 hours. The reaction mixture was evaporated under vacuo and added ice cold water (10 mL), obtained solid was filtered, washed with water (20 mL) and dried to afford 2-chloro-4-(2,4-difluoro-3-methoxyphenoxy)pyrimidine (0.72 g, 80%) as a white solid. LCMS (ES) m/z calcd. for C11H7ClF2N2O2, 272.02; found, 273.0 (M+H).

Step 2: Synthesis of 4-(4-(4-(2,4-difluoro-3-methoxyphenoxy)pyrimidin-2-yl)phenyl)morpholine To a stirred solution of 2-chloro-4-(2,4-difluoro-3-methoxyphenoxy)pyrimidine (200 mg, 0.734 mmol) and [4-(morpholin-4-yl)phenyl]boronic acid (182 mg, 0.88 mmol) in 1,4-dioxane (5.00 mL) and water (1.00 mL), was added cesium carbonate (717 mg, 2.20 mmol). Reaction mixture was purged with Argon gas. To this was added Pd(dppf)$Cl_2$ (53.7 mg, 0.073 mmol) and then heated to 100° C. for 16 h. The reaction mixture was cooled to room temperature and quenched with water (10 mL), extracted with ethyl acetate (10 mL). The organic layer was dried over anhydrous sodium sulfate and concentrated under vacuo to obtain crude. The crude was purified by flash chromatography to afford 4-(4-(4-(2,4-difluoro-3-methoxyphenoxy)pyrimidin-2-yl)phenyl)morpholine (0.185 g, 63%) as a white solid. LCMS (ES) m/z calcd. for C21H19F2N3O3, 399.14; found, 400.2 (M+H).

Step 3: Synthesis of 2,6-difluoro-3-((2-(4-morpholinophenyl)pyrimidin-4-yl)oxy)phenol To a stirred suspended solution of 4-(4-(4-(2,4-difluoro-3-methoxyphenoxy)pyrimidin-2-yl)phenyl)morpholine (200 mg, 0.5 mmol) in dichloromethane (0.5 mL) was added borane tribromide (1.00 mL, 1.00 mmol) at 0° C. and then stirred at ambient temperature for 3 hours. The reaction mixture was carefully quenched with methanol at 0° C. and then evaporated under vacuo to obtain crude. The crude was purified using flash chromatography. The column purified compound was further purified by preparative HPLC to afford 2,6-difluoro-3-((2-(4-morpholinophenyl)pyrimidin-4-yl)oxy)phenol as a white solid (0.06 g, 34%). LCMS (ES) m/z calcd. For C20H17F2N3O3, 385.12; found, 386.1 (M+H). 1H NMR (400 MHz, DMSO-d6) δ: 10.54 (br, 1H), 8.7 (d, J=6.0 Hz, 1H), 7.98 (d, J=8.8 Hz, 2H), 7.17-7.12 (m, 1H), 7.0-7.97 (m, 3H), 6.92-6.90 (m, 1H), 3.73 (t, J=4.0 Hz, 4H), 3.22 (t, J=4.8 Hz, 4H).

Example 116: Synthesis of 4-(4-(4-(2,4-difluoro-3-hydroxyphenoxy)pyrimidin-2-yl)phenyl)thiomorpholine 1,1-dioxide

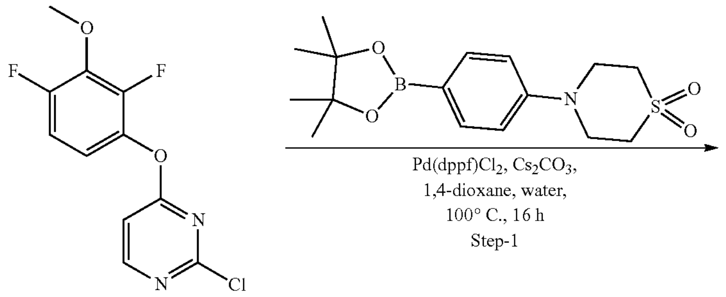

-continued

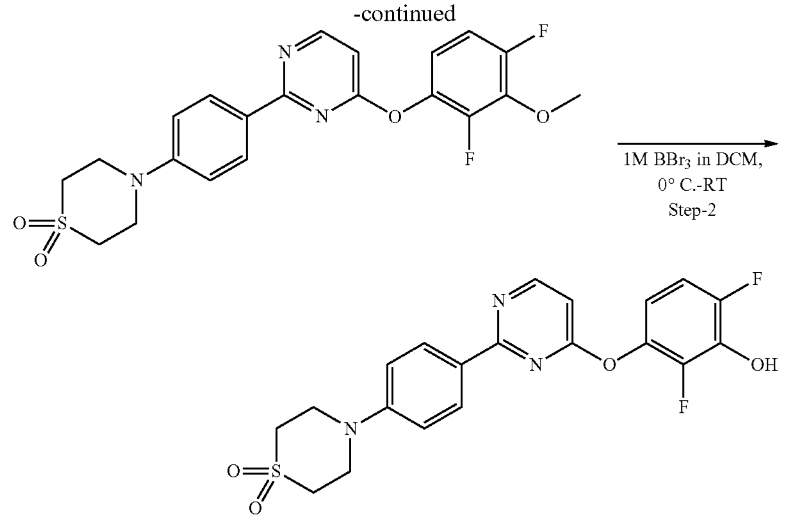

Step 1: Synthesis of 4-(4-(4-(2,4-difluoro-3-methoxyphenoxy)pyrimidin-2-yl)phenyl)thiomorpholine 1,1-dioxide To a stirred solution of 2-chloro-4-(2,4-difluoro-3-methoxyphenoxy)pyrimidine (0.3 g, 1.10 mmol) and 4-(4-(4,4,5,5-tetramethyl-1,3,2-dioxaborolan-2-yl)phenyl)thiomorpholine 1,1-dioxide (0.44 g, 1.32 mmol) in 1,4-dioxane (8.0 mL) and water (1.00 mL) was added cesium carbonate (1.08 g, 3.30 mmol). Reaction mixture was purged with Argon gas. To this was added Pd(dppf)$cl_2$ (80.5 mg, 0.11 mmol) and then heated to 100° C. for 16 h. The reaction mixture was cooled to room temperature and quenched with water (10 mL), extracted with ethyl acetate (10 mL). The organic layer was dried over anhydrous sodium sulfate and concentrated under vacuo to obtain crude. The crude was purified by flash chromatography to afford 4-(4-(4-(2,4-difluoro-3-methoxyphenoxy)pyrimidin-2-yl)phenyl)thiomorpholine 1,1-dioxide (0.36 g, 73%) as a white solid. LCMS (ES) m/z calcd. for C21H19F2N3O4S, 447.11; found, 448.1 (M+H).

Step 2: Synthesis of 4-(4-(4-(2,4-difluoro-3-hydroxyphenoxy)pyrimidin-2-yl)phenyl)thiomorpholine 1,1-dioxide To a stirred suspended solution of 4-(4-(4-(2,4-difluoro-3-methoxyphenoxy)pyrimidin-2-yl)phenyl)thiomorpholine 1,1-dioxide (350 mg, 0.782 mmol) in dichloromethane (0.5 mL) was added borane tribromide (1.56 mL, 1.56 mmol) at 0° C. and then stirred at ambient temperature for 3 hours. The reaction mixture was carefully quenched with methanol at 0° C. and then evaporated under vacuo to obtain crude. The crude was purified using flash chromatography. The column purified compound was further purified by preparative HPLC to afford 4-(4-(4-(2,4-difluoro-3-hydroxyphenoxy)pyrimidin-2-yl)phenyl)thiomorpholine 1,1-dioxide as a white solid (0.13 g, 40%). LCMS (ES) m/z calcd. for C20H17F2N3O4S, 433.09; found, 434.1 (M+H). $^1$H NMR (400 MHz, DMSO-d6) δ: 10.55 (br, 1H), 8.72 (d, J=5.6 Hz, 1H), 8.0 (d, J=8.8 Hz, 2H), 7.17-7.12 (m, 1H), 7.09 (d, J=9.2 Hz, 2H), 7.02 (d, J=5.6 Hz, 1H), 6.92-6.87 (m, 1H), 3.90 (br, 4H), 3.66 (br, 4H).

Example 117: Synthesis of 6-chloro-2-fluoro-3-((2-(4 morpholinophenyl)pyrimidin-4-yl)oxy)phenol

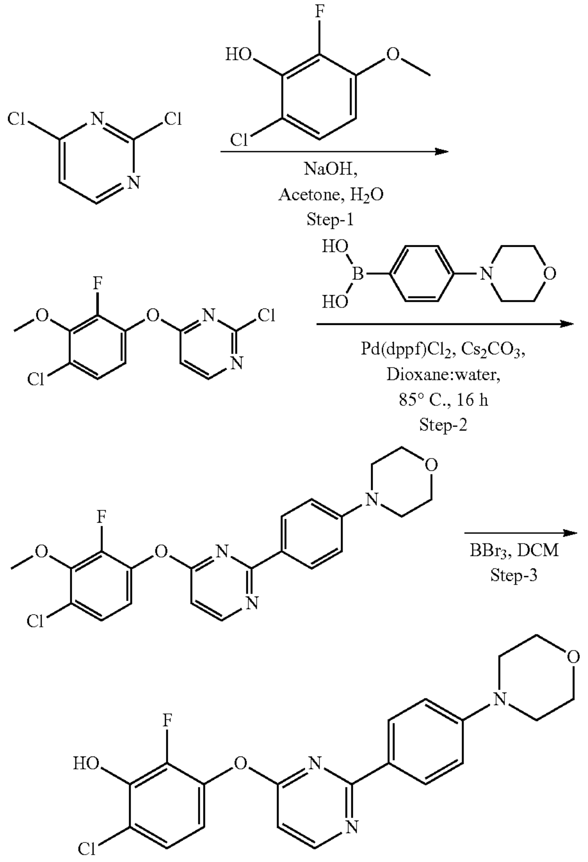

Step-1: Synthesis of 2-chloro-4-(4-chloro-2-fluoro-3-methoxyphenoxy) pyrimidine

A solution of 6-chloro-2-fluoro-3-methoxyphenol (400 mg, 2.27 mmol) and sodium hydroxide (90.6 mg, 2.27 mmol) in acetone (10.0 mL) and water (10.0 mL) was stirred at room temperature for 20 min. Then, 2,4-dichloropyrimidine (337 mg, 2.27 mmol) was added. The reaction mixture was stirred at room temperature for 3 h. After completion of the reaction, acetone was removed under vacuum. The residue was diluted with water (100.0 mL), the solid was filtered, washed with fresh water (approximately 100.0 mL) and dried under vacuum at 50° C. to afford 2-chloro-4-(4-chloro-2-fluoro-3-methoxyphenoxy) pyrimidine (455 mg, 69%) as an off-white solid. LCMS (ES) m/z calcd. for C11H7C12FN2O2, 287.99; found 289.0 (M+H).

Step-2: Synthesis Of 4-(4-(4-(4-chloro-2-fluoro-3-methoxyphenoxy)pyrimidin-2-yl)phenyl)morpholine To a stirred solution of 2-chloro-4-(4-chloro-2-fluoro-3-methoxyphenoxy) pyrimidine (400 mg, 1.38 mmol) and [4-(morpholin-4-yl)phenyl]boronic acid (286 mg, 1.38 mmol) in 1,4-dioxane (4.00 mL) and water (1.00 mL), was added cesium carbonate (768 mg, 2.36 mmol). Reaction mixture was purged with argon and then added Pd(dppf)$Cl_2$ (57.4 mg, 0.78.5 mmol). The reaction mixture was heated at 85° C. for 16 h. After completion of the reaction, the reaction mixture was cooled to ambient temperature and quenched with water (20.0 mL), extracted by ethyl acetate (2×20.0 mL). The organic layer was dried over anhydrous sodium sulfate and concentrated reduced under vacuum. Crude was purified by flash chromatography to afford 4-(4-(4-(4-chloro-2-fluoro-3-methoxyphenoxy)pyrimidin-2-yl)phenyl) morpholine (333.0 mg, 58%) as white solid. LCMS (ES) m/z calcd. for C21H19ClFN3O3, 415.11; found 416.1 (M+H). $^1$H-NMR (400 MHz, DMSO-d6): δ 8.74 (d, J=5.6 Hz, 1H), 7.98 (d, J=8.8 Hz, 2H), 7.47-7.45 (m, 1H), 7.29-7.25 (m, 1H), 7.07 (d, J=5.6 Hz, 1H), 7.0 (d, J=8.5 Hz, 2H), 3.90 (s, 3H), 3.72 (t, J=4.8 Hz, 4H), 3.21 (t, J=4.8 Hz, 4H).

Step-3: Synthesis of 6-chloro-2-fluoro-3-((2-(4-morpholinophenyl)pyrimidin-4-yl)oxy)phenol To a stirred solution of 4-(4-(4-(4-chloro-2-fluoro-3-methoxyphenoxy)pyrimidin-2-yl)phenyl)morpholine (300 mg, 0.721 mmol) in dichloromethane (5.00 mL), BBr3 (0.721 mL, 0.721 mmol) was added dropwise at 0° C. The reaction mixture was stirred for 3 h at RT. After completion of reaction, reaction mixture was quenched with 50.0 mL of saturated aqueous solution of sodium bicarbonate and extracted by ethyl acetate (2×25.0 mL). Combined organic layer was dried over anhydrous sodium sulphate and evaporated under reduced pressure. Crude was purified by column chromatography to afford 6-chloro-2-fluoro-3-((2-(4-morpholinophenyl)pyrimidin-4-yl)oxy)phenol as white solid. LCMS (ES) m/z calcd. for C20H17ClFN3O3, 401.09; found 402.1 (M+H). $^1$H-NMR (400 MHz, DMSO-d6): δ 10.75 (br s, 1H), 8.69 (d, J=5.6 Hz, 1H), 7.95 (d, J=8.8 Hz, 2H), 7.31-7.28 (m, 1H), 7.01-6.89 (m, 4H), 3.72 (t, J=4.4 Hz, 4H), 3.21 (t, J=4.0 Hz, 4H).

Example 118: Synthesis of 2,6-dichloro-3-((2-(4-morpholinophenyl) pyrimidin-4-yl) oxy) phenol

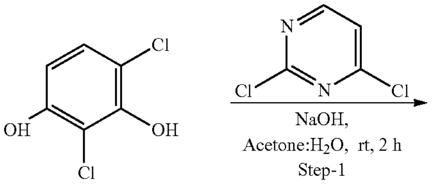

-continued

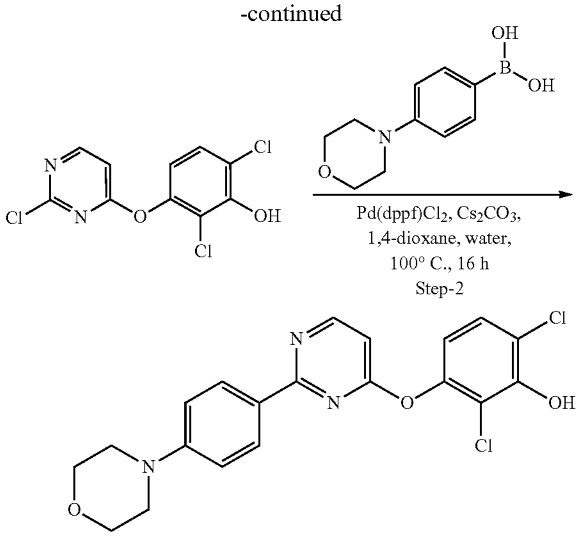

Step 1: Synthesis of 2,6-dichloro-3-((2-chloropyrimidin-4-yl)oxy)phenol

To a stirred solution of 2,4-dichlorobenzene-1,3-diol (0.5 g, 2.79 mmol) in acetone (3.0 mL):water (3.0 mL) was added sodium hydroxide (0.112 g, 2.79 mmol) and the reaction mixture was stirred for 20 min at room temperature. The 2,4-dichloropyrimidine was added portion wise to the reaction mixture and stirred at ambient temperature for 2 h. The reaction was monitored by TLC. After completion of the starting material, reaction mixture was evaporated and diluted with water (10 ml) and extracted with ethyl acetate (15 mL×2). The organic phase was washed with brine solution, dried over anhydrous sodium sulfate and concentrated under vacuo to result in crude. The crude product was purified by flash chromatography to afford 2,6-dichloro-3-((2-chloropyrimidin-4-yl) oxy) phenol as a white solid (0.18 g, 0.61 mmol). LCMS (ES) m/z calcd. for C10H5C13N2O2, 289.94; found, 291.0 (M+H).

Step 2: Synthesis of 2,6-dichloro-3-((2-(4-morpholinophenyl) pyrimidin-4-yl) oxy) phenol To a stirred solution of 2,6-dichloro-3-((2-chloropyrimidin-4-yl)oxy)phenol (0.18 g, 0.617 mmol), (4-morpholinophenyl)boronic acid (0.153 g, 0.741 mmol) in 1,4-dioxane (3.0 mL) and water (0.5 mL), was added cesium carbonate (0.6 g, 1.85 mmol). Reaction mixture was purged with argon gas for 20 min and was added Pd(dppf)$Cl_2$.DCM (0.045 g, 0.062 mmol). The reaction mixture was heated at 100° C. for 16 h. The progress of reaction was monitored by TLC. After completion of the starting material, reaction mixture was cooled to room temperature and quenched with water (10 mL), extracted by ethyl acetate (20 mL×2). The organic layer was dried over anhydrous sodium sulfate and concentrated under vacuo to result in crude which was purified by prep HPLC to afford 2,6-dichloro-3-((2-(4-morpholinophenyl)pyrimidin-4-yl)oxy)phenol (0.035 g, 0.083 mmol) as off white solid. LCMS (ES) m/z calcd. for C20H17C12N3O3, 417.06; found, 418.1, (M+H). $^1$H NMR (400 MHz, DMSO-d6) δ 10.50 (s, 1H), 8.68 (d, J=6.0 Hz, 1H), 7.94 (d, J=9.2 Hz, 2H), 7.47 (d, J=8.8 Hz, 1H), 6.99-6.94 (m, 4H), 3.71-3.69 (m, 4H), 3.20-3.18 (m, 4H).

Example A: NADH Detection Assay for Evaluation of HSD17ß13 Activity and Identification of Inhibitors The fluorescence based Leukotriene B3 (LTB3) assay monitors the fluorescence of NADH, which is generated from NAD+ during the dehydrogenation of the substrate LTB3. The reactions were performed in a 384-well plates (Greiner; #655076) in a 20 μl reaction volume containing the following reagents (final concentrations): 25 μM LTB3 (Cayman; #20109); 3 mM NAD+ (Sigma; #N0623); 125 nM HSD17B13 enzyme (in-house; *E. coli* expressed His-tagged, purified, soluble protein); 1 M potassium phosphate buffer, pH 7.4; and 1% DMSO. Reactions were initiated by co-addition of NAD+ and enzyme, and monitored for 1 hour at 26.5° C. Generation of NADH was measured as the fluorescence signal (Excitation at 340 nm and Emission at 445 nm) at 1 hour minus the baseline fluorescence at t=0. Fluorescence signals in the absence of LTB3 (negative control values), were subtracted from all values so that the results reflected substrate-dependent production of NADH. NADH standards were included to allow the conversion of relative fluorescence units into rates of enzyme activity. Enzyme activity in the presence of test compounds was expressed as a percentage of the uninhibited enzyme activity, and plotted versus inhibitor concentration. Non-linear regression was performed using a four-parameter logistic model and GraphPad Prism software (GraphPad Software, La Jolla, CA). Ten concentrations of inhibitor were tested (in the range of 30 μM-2.5 nM), and two independent assessments were performed at each concentration. The data are is shown in table 2 below:

TABLE 2

| Ex. | IC50 with LTB3 (μM) |
|---|---|
| 1 | A |
| 2 | B |
| 3 | B |
| 4 | A |
| 5 | D |
| 6 | D |
| 7 | D |
| 8 | B |
| 9 | C |
| 10 | D |
| 11 | C |
| 12 | A |
| 13 | B |
| 14 | D |
| 15 | A |
| 16 | D |
| 17 | A |
| 18 | A |
| 19 | NT |
| 20 | B |
| 21 | B |
| 22 | A |
| 23 | D |
| 25 | A |
| 26 | A |
| 27 | A |
| 28 | A |
| 29 | A |
| 30 | D |
| 31 | A |
| 32 | B |
| 33 | A |
| 34 | D |
| 35 | D |
| 36 | A |
| 37 | A |
| 38 | D |

TABLE 2-continued

| Ex. | IC50 with LTB3 (μM) |
|---|---|
| 39 | A |
| 40 | A |
| 41 | B |
| 42 | D |
| 43 | B |
| 44 | A |
| 45 | A |
| 46 | A |
| 47 | A |
| 48 | D |
| 49 | B |
| 50 | A |
| 51 | D |
| 52 | D |
| 53 | A |
| 54 | A |
| 55 | B |
| 56 | D |
| 57 | D |
| 58 | A |
| 59 | A |
| 60 | D |
| 61 | D |
| 62 | D |
| 63 | C |
| 64 | NT |
| 65 | NT |
| 66 | A |
| 67 | A |
| 68 | D |
| 69 | C |
| 70 | D |
| 71 | C |
| 72 | D |
| 73 | D |
| 74 | D |
| 75 | D |
| 76 | C |
| 77 | C |
| 78 | B |
| 79 | A |
| 80 | A |
| 81 | A |
| 82 | A |
| 83 | A |
| 84 | B |
| 85 | B |
| 86 | A |
| 87 | A |
| 88 | A |
| 89 | A |
| 90 | A |
| 91 | D |
| 92 | D |
| 93 | D |
| 94 | D |
| 95 | D |
| 96 | D |
| 97 | C |
| 98 | C |
| 99 | C |
| 100 | C |
| 101 | C |
| 102 | C |
| 103 | B |
| 104 | C |
| 105 | D |
| 106 | D |
| 107 | D |
| 108 | D |
| 109 | D |
| 110 | D |
| 111 | D |
| 112 | D |
| 113 | C |
| 114 | B |

A is less than or equal to 5 μM;

TABLE 2-continued

| Ex. | IC50 with LTB3 (μM) |
|---|---|

B is more than 5 μM and less than or equal to 10 μM;
C is more than 10 μM and less than or equal to 30 μM;
D is more than 30 μM.
NT: not tested

Example B: Estrone Detection Assay for Evaluation of HSD17ß13 Activity and Identification of Inhibitors The liquid chromatography/mass spectrometry (LC/MS) estrone detection assay monitors the conversion of estradiol to estrone by HSD17B13. This assay was undertaken in a 96wp format (Eppendorf deep well Plate 96/500) in an 80 μl reaction volume containing: 4 μM of Estradiol (E2; Cayman; Ser. No. 10/006,315), 6 mM NAD+(Sigma; #N0623) and 30 nM HSD17B13 enzyme (in-house; *E. coli* expressed His-tagged, purified, soluble protein) in a reaction containing 1M potassium phosphate buffer pH 7.4, with 0.5% vehicle (DMSO). Reactions were incubated for 2 hours at 26.5° C., and estradiol (E2) conversion to estrone (E1) was quantitated by LC-MS/MS based analyte detection for both E2 and E1 using LCMS grade reagents.

Reactions were terminated by the addition of two volumes of acetonitrile (MeCN; LCMS grade; CAS #75/05/8) containing deuterated (D4)-E1 used as internal standard (Clear Synth; #CS-T-54273; 500 ng/mL final concentration). Samples were applied to pre-prepared Bond Elut-C18 extraction cartridges (3 mL; Agilent; Ser. No. 12/102,028), washed and eluted in MeCN. Eluates were dried under nitrogen and re-suspended in 60% methanol (LCMS grade methanol; CAS #67/56/1) before submission for analysis. Aqueous linearity for E2 and E1 were included for quantification.

Analysis of samples was undertaken on a XBridge BEH C18 column (Waters; #186003033) using 0.1% Diethyl Amine in MeCN (mobile phase A; DEA CAS #109-89-7) and 0.1% Diethyl Amine in milli-Q water (mobile phase B) in a 3 min gradient allowing 25% B. Analytes were detected in negative mode using MRM analysis, with E2 having a RT of 1.85 min and E1 having a RT of 2 min. Activity of the enzyme, in the absence of NAD+, was used to evaluate specificity of conversion. Enzyme activity in the presence of test samples was expressed as a percentage of the uninhibited enzyme activity, and plotted versus inhibitor concentration. Non-linear regression was performed using a four-parameter logistic model and GraphPad Prism software (GraphPad Software, La Jolla, CA). All assessments were undertaken in duplicate evaluations and pooled during extraction process and subsequently injected as duplicates for LC-MS/MS analysis.

The data is shown in table 3 below:

TABLE 3

| $IC_{50}$ with Estradiol | |
|---|---|
| Ex. | $IC_{50}$ with Estradiol (μM) |
| 115 | A |
| 116 | A |
| 117 | B |
| 118 | C |

A is less than or equal to 0.1 μM;
B is more than 0.1 μM and less than or equal to 0.5 μM;

TABLE 3-continued

| $IC_{50}$ with Estradiol | |
|---|---|
| Ex. | $IC_{50}$ with Estradiol (μM) |

C is more than 0.5 μM and less than or equal to 1.0 μM;
D is more than 1.0 μM and less than or equal to 10 μM;
E is more than 10 μM;
NT: not tested

What is claimed is:

1. A compound of Formula (I), or a pharmaceutically acceptable salt, solvate, or stereoisomer thereof:

(I)

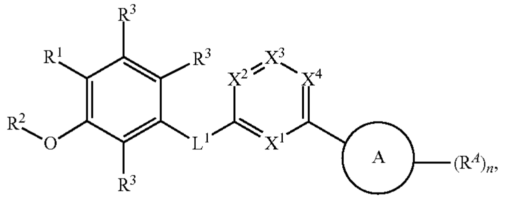

wherein:

$R^1$ is halogen;

$R^2$ is hydrogen;

each $R^3$ is independently hydrogen, deuterium, halogen, —CN, —OH, —$OR^a$, —SH, —$SR^a$, —S(═O)$R^a$, —S(═O)$_2R^a$, —$NO_2$, —$NR^cR^d$, —NHS(═O)$_2R^a$, —S(═O)$_2NR^cR^d$, —C(═O)$R^a$, —OC(═O)$R^a$, —C(═O)$OR^b$, —OC(═O)$OR^b$, —C(═O)$NR^cR^d$, —OC(═O)$NR^cR^d$, —$NR^b$C(═O)$NR^cR^d$, —$NR^b$C(═O)$R^a$, —$NR^b$C(═O)$OR^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$C(═O)$OR^b$, cycloalkyl, heterocycloalkyl, aryl, or heteroaryl;

$L^1$ is —O;

$X^1$ is N or C—$R^{X1}$;

$R^{X1}$ is deuterium, halogen, —CN, —OH, —$OR^a$, —SH, —$SR^a$, —S(═O)$R^a$, —S(═O)$_2R^a$, —$NO_2$, —$NR^cR^d$, —NHS(═O)$_2R^a$, —S(═O)$_2NR^cR^d$, —C(═O)$R^a$, —OC(═O)$R^a$, —C(═O)$OR^b$, —OC(═O)$OR^b$, —C(═O)$NR^cR^d$, —OC(═O)$NR^cR^d$, —$NR^b$C(═O)$NR^cR^d$, —$NR^b$C(═O)$R^a$, —$NR^b$C(═O)$OR^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$C(═O)$OR^b$, cycloalkyl, heterocycloalkyl, aryl, or heteroaryl;

$X^2$ is N or C—$R^{X2}$;

$R^{X2}$ is hydrogen, deuterium, halogen, —CN, —OH, —$OR^a$, —SH, —$SR^a$, —S(═O)$R^a$, —S(═O)$_2R^a$, —$NO_2$, —$NR^cR^d$, —NHS(═O)$_2R^a$, —S(═O)$_2NR^cR^d$, —C(═O)$R^a$, —OC(═O)$R^a$, —C(═O)$OR^b$, —OC(═O)$OR^b$, —C(═O)$NR^cR^d$, —OC(═O)$NR^cR^d$, —$NR^b$C(═O)$NR^cR^d$, —$NR^b$C(═O)$R^a$, —$NR^b$C(═O)$OR^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$C(═O)$OR^b$, cycloalkyl, heterocycloalkyl, aryl, or heteroaryl;

$X^3$ is N or C—$R^{X3}$;

$R^{X3}$ is hydrogen, deuterium, halogen, —CN, —OH, —$OR^a$, —SH, —$SR^a$, —S(═O)$R^a$, —S(═O)$_2R^a$, —$NO_2$, —$NR^cR^d$, —NHS(═O)$_2R^a$, —S(═O)$_2NR^cR^d$, —C(═O)$R^a$, —OC(═O)$R^a$, —C(═O)$OR^b$, —OC(═O)$OR^b$, —C(═O)$NR^cR^d$, —OC(═O)NR- $^c$R$^d$, —NR$^b$C(═O)NR$^c$R$^d$, —NR$^b$C(═O)R$^a$, —NR$^b$C(═O)OR$^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$C(═O)OR$^b$, cycloalkyl, heterocycloalkyl, aryl, or heteroaryl;

$X^4$ is N or C—R$^{X4}$;

R$^{X4}$ is hydrogen, deuterium, halogen, —CN, —OH, —OR$^a$, —SH, —SR$^a$, —S(═O)R$^a$, —S(═O)$_2$R$^a$, —$NO_2$, —NR$^c$R$^d$, —NHS(═O)$_2$R$^a$, —S(═O)$_2$NR$^c$R$^d$, —C(═O)R$^a$, —OC(═O)R$^a$, —C(═O)OR$^b$, —OC(═O)OR$^b$, —C(═O)NR$^c$R$^d$, —OC(═O)NR$^c$R$^d$, —NR$^b$C(═O)NR$^c$R$^d$, —NR$^b$C(═O)R$^a$, —NR$^b$C(═O)OR$^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$C(═O)OR$^b$, cycloalkyl, heterocycloalkyl, aryl, or heteroaryl;

Ring A is aryl, heteroaryl, cycloalkyl, or heterocycloalkyl;

each R$^A$ is independently deuterium, halogen, —Y—CN, —Y—OH, —Y—OR$^a$, —Y—SH, —Y—SR$^a$, —Y—S(═O)R$^a$, —Y—S(═O)$_2$R$^a$, —Y—$NO_2$, —Y—NR$^c$R$^d$, —Y—NR$^b$S(═O)$_2$R$^a$, —Y—NR$^b$S(═O)$_2$NR$^c$R$^d$, —Y—S(═O)$_2$NR$^c$R$^d$, —Y—C(═O)R$^a$, —Y—OC(═O)R$^a$, —Y—C(═O)OR$^b$, —Y—OC(═O)OR$^b$, —Y—C(═O)NR$^c$R$^d$, —Y—OC(═O)NR$^c$R$^d$, —Y—NR$^b$C(═O)NR$^c$R$^d$, —Y—NR$^b$C(═O)R$^a$, —Y—NR$^b$C(═O)OR$^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, —$C_1$-$C_6$C(═O)OR$^b$, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three deuterium, oxo, halogen, —CN, —OH, —OMe, —S(═O)Me, —S(═O)$_2$Me, —$NH_2$, —S(═O)$_2$$NH_2$, —C(═O)Me, —C(═O)OH, —C(═O)OMe, $C_1$-$C_6$alkyl, $C_1$-$C_6$haloalkyl, $C_1$-$C_6$hydroxyalkyl, or $C_1$-$C_6$aminoalkyl; or two R$^A$ on the same carbon are taken together to form an oxo;

each Y is independently a bond, $C_1$-$C_6$alkylene, or $C_1$-$C_6$haloalkylene;

n is 0-4;

each R$^a$ is independently $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one, two, or three deuterium, oxo, halogen, —CN, —OH, —OMe, —S(═O)Me, —S(═O)$_2$Me, —$NH_2$, —S(═O)$_2$$NH_2$, —C(═O)Me, —C(═O)OH, —C(═O)OMe, $C_1$-$C_6$alkyl, $C_1$-$C_6$haloalkyl, $C_1$-$C_6$hydroxyalkyl, or $C_1$-$C_6$aminoalkyl;

each R$^b$ is independently hydrogen, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one, two, or three deuterium, oxo, halogen, —CN, —OH, —OMe, —S(═O)Me, —S(═O)$_2$Me, —$NH_2$, —S(═O)$_2$$NH_2$, —C(═O)Me, —C(═O)OH, —C(═O)OMe, $C_1$-$C_6$alkyl, $C_1$-$C_6$haloalkyl, $C_1$-$C_6$hydroxyalkyl, or $C_1$-$C_6$aminoalkyl; and each R$^c$ and R$^d$ are independently hydrogen, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently optionally substituted with one, two, or three oxo, deuterium, halogen, —CN, —OH, —OMe, —S(═O)Me, —S(═O)$_2$Me, —$NH_2$, —S(═O)$_2$$NH_2$, —C(═O)Me, —C(═O)OH, —C(═O)OMe, $C_1$-$C_6$alkyl, $C_1$-$C_6$haloalkyl, $C_1$-$C_6$hydroxyalkyl, or $C_1$-$C_6$aminoalkyl;

or R$^c$ and R$^d$ are taken together with the atom to which they are attached to form a heterocycloalkyl optionally substituted with one, two, or three oxo, deuterium, halogen, —CN, —OH, —OMe, —S(═O)Me, —S(═O)$_2$Me, —$NH_2$, —S(═O)$_2$$NH_2$, —C(═O)Me, —C(═O)OH, —C(═O)OMe, $C_1$-$C_6$alkyl, $C_1$-$C_6$haloalkyl, $C_1$-$C_6$hydroxyalkyl, or $C_1$-$C_6$aminoalkyl;

provided that the compound of Formula (I) is not

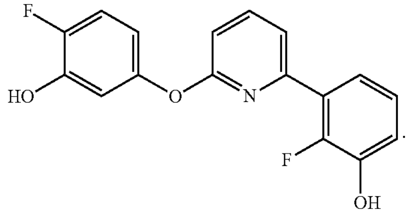 [SMILES: Oc1cc(Oc2cccc(-c3cccc(O)c3F)n2)ccc1F]

2. The compound of claim 1, or a pharmaceutically acceptable salt, solvate, or stereoisomer thereof, wherein: R$^1$ is fluoro.

3. The compound of claim 1, or a pharmaceutically acceptable salt, solvate, or stereoisomer thereof, wherein: each R$^3$ is independently hydrogen, deuterium, halogen, or $C_1$-$C_6$alkyl.

4. The compound of claim 1, or a pharmaceutically acceptable salt, solvate, or stereoisomer thereof, wherein: $X^1$ is N or $X^1$ is C—R$^{X1}$ and R$^{X1}$ is deuterium, halogen, —CN, —OH, —OR$^a$, or $C_1$-$C_6$alkyl.

5. The compound of claim 1, or a pharmaceutically acceptable salt, solvate, or stereoisomer thereof, wherein: $X^2$ is C—R$^{X2}$.

6. The compound of claim 5, or a pharmaceutically acceptable salt, solvate, or stereoisomer thereof, wherein: R$^{X2}$ is hydrogen, deuterium, halogen, —CN, —OH, —OR$^a$, or $C_1$-$C_6$alkyl.

7. The compound of claim 1, or a pharmaceutically acceptable salt, solvate, or stereoisomer thereof, wherein: $X^3$ is C—R$^{X3}$.

8. The compound of claim 7, or a pharmaceutically acceptable salt, solvate, or stereoisomer thereof, wherein: R$^{X3}$ is hydrogen, deuterium, halogen, —CN, —OH, —OR$^a$, or $C_1$-$C_6$alkyl.

9. The compound of claim 1, or a pharmaceutically acceptable salt, solvate, or stereoisomer thereof, wherein: $X^4$ is C—R$^{X4}$.

10. The compound of claim 9, or a pharmaceutically acceptable salt, solvate, or stereoisomer thereof, wherein:

$R^{X4}$ is hydrogen, deuterium, halogen, —CN, —OH, —$OR^a$, or $C_1$-$C_6$alkyl.

11. The compound of claim 1, or a pharmaceutically acceptable salt, solvate, or stereoisomer thereof, wherein:

Ring A is aryl or heteroaryl.

12. The compound of claim 1, or a pharmaceutically acceptable salt, solvate, or stereoisomer thereof, wherein:

each $R^A$ is independently deuterium, halogen, —Y—CN, —Y—OH, —Y—$OR^a$, —Y—$S(=O)_2R^a$, —Y—$NR^cR^d$, —Y—$NR^bS(=O)_2R^a$, —Y—$NR^bS(=O)_2NR^cR^d$, —Y—$S(=O)_2NR^cR^d$, —Y—$C(=O)R^a$, —Y—$C(=O)OR^b$, —Y—$C(=O)NR^cR^d$, —Y—$NR^bC(=O)R^a$, $C_1$-$C_6$alkyl, or $C_1$-$C_6$haloalkyl; wherein each alkyl is independently optionally substituted with one, two, or three deuterium, oxo, halogen, —CN, —OH, —OMe, —S(=O)Me, —$S(=O)_2Me$, —$NH_2$, —$S(=O)_2NH_2$, —C(=O)Me, —C(=O)OH, —C(=O)OMe, $C_1$-$C_6$alkyl, $C_1$-$C_6$haloalkyl, $C_1$-$C_6$hydroxyalkyl, or $C_1$-$C_6$aminoalkyl; or two $R^A$ on the same carbon are taken together to form an oxo.

13. The compound of claim 1, or a pharmaceutically acceptable salt, solvate, or stereoisomer thereof, wherein:

each $R^A$ is independently halogen or —Y—OH.

14. The compound of claim 1, or a pharmaceutically acceptable salt, solvate, or stereoisomer thereof, wherein:

each Y is independently a bond or $C_1$-$C_6$alkylene.

15. The compound of claim 1, or a pharmaceutically acceptable salt, solvate, or stereoisomer thereof, wherein:

n is 1-3.

16. The compound of claim 1 selected from the group consisting of:

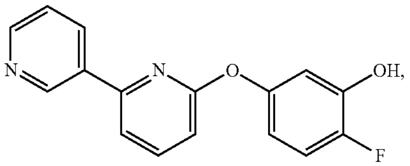

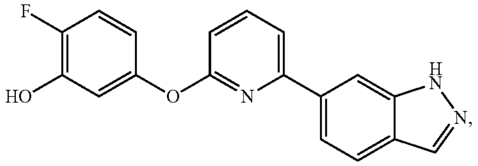

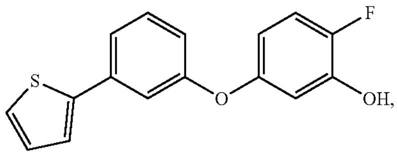

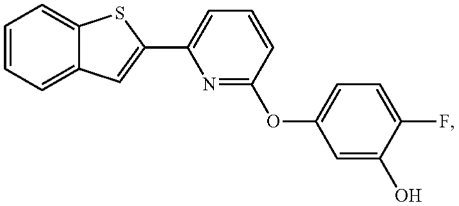

-continued

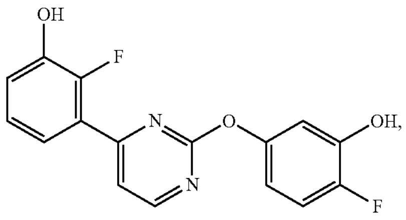

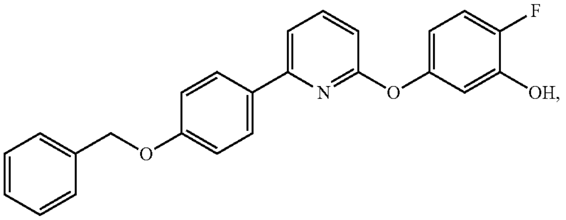

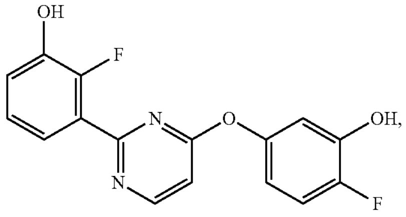

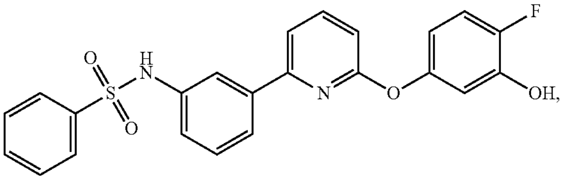

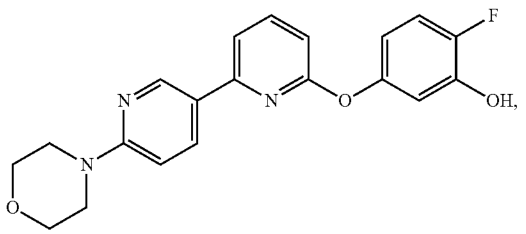

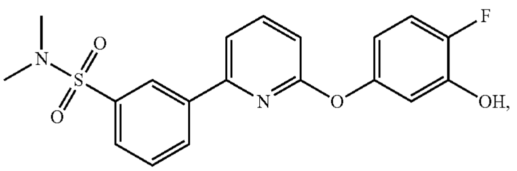

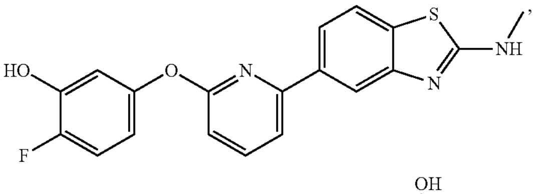

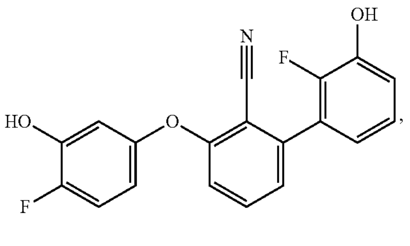

-continued
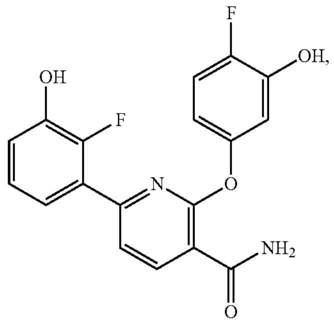
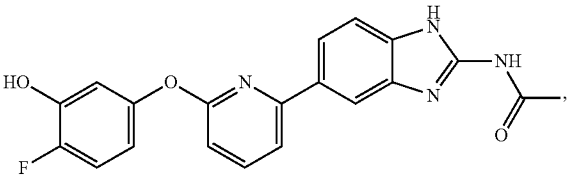
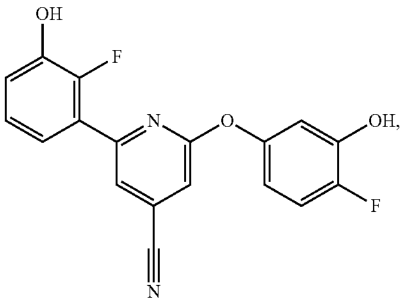
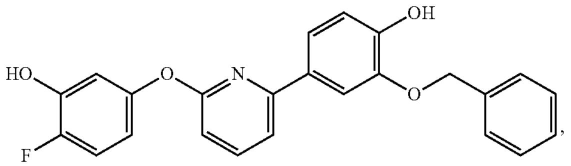
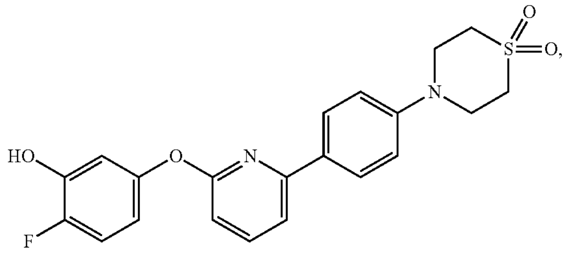
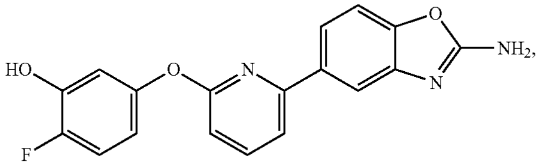
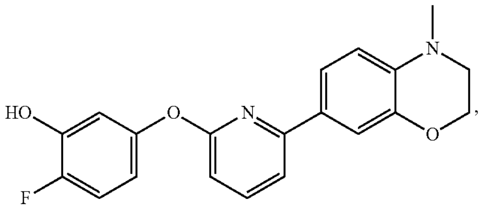
-continued
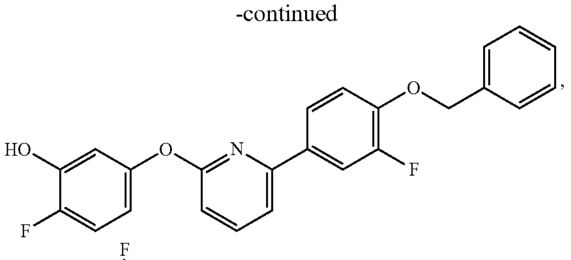
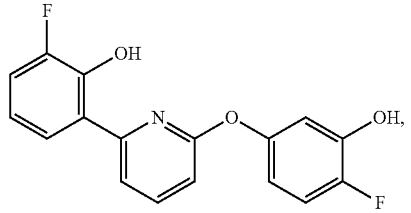
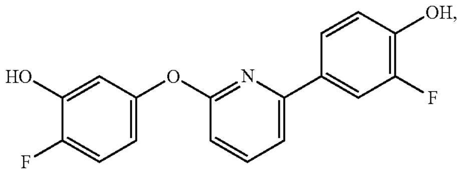
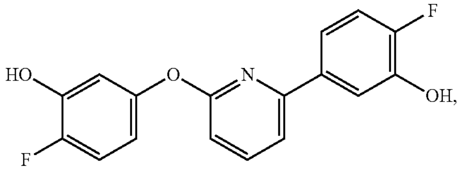
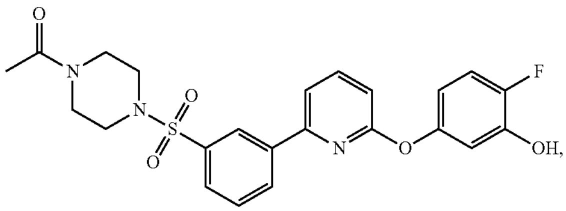
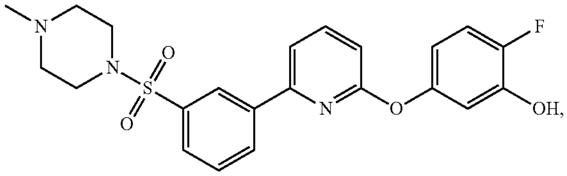
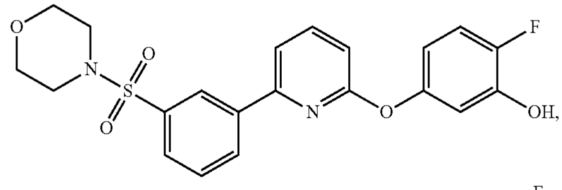
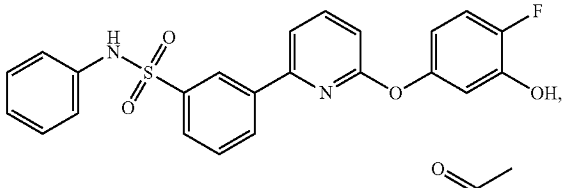
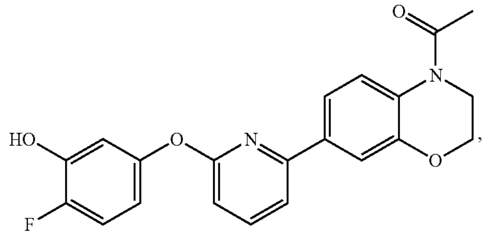

-continued
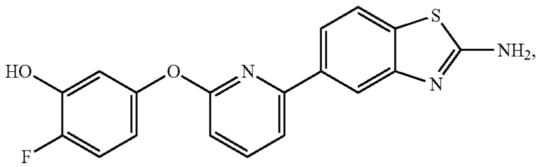,
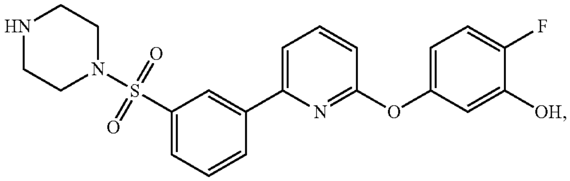,
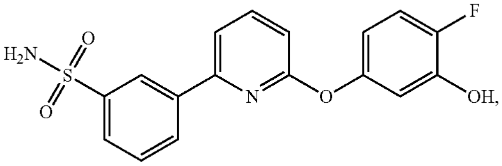,
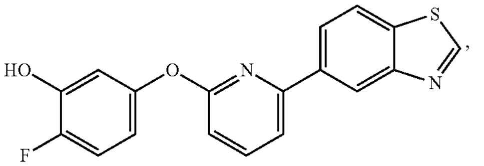,
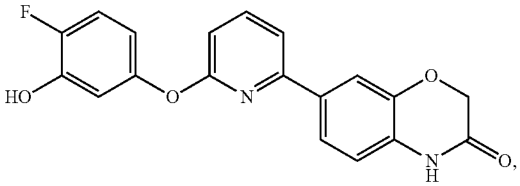,
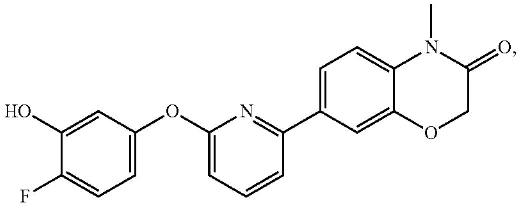,
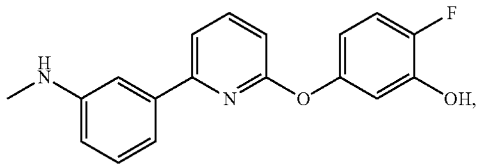,
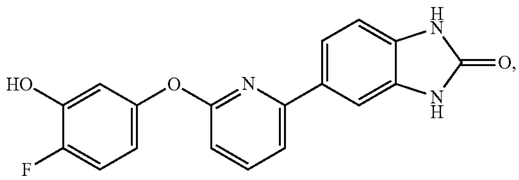,
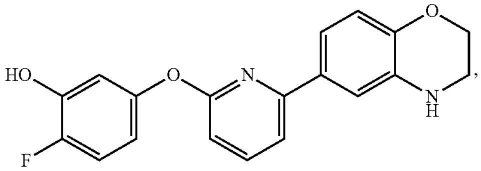,
-continued
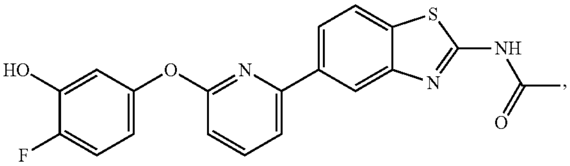,
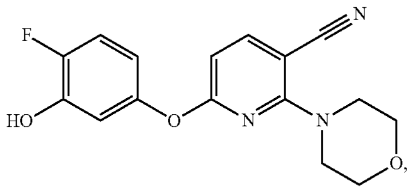,
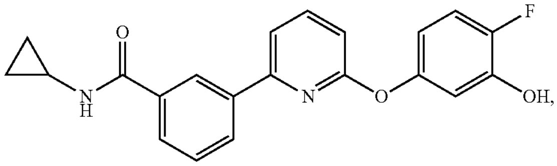,
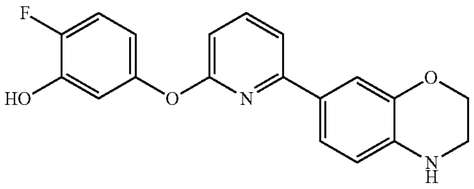,
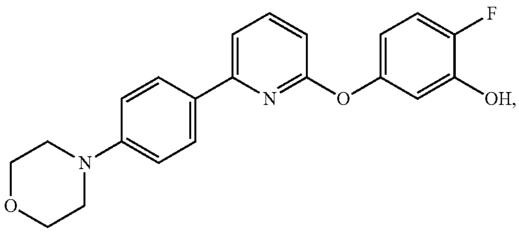,
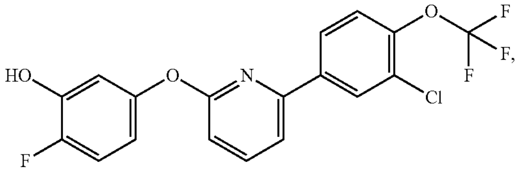,
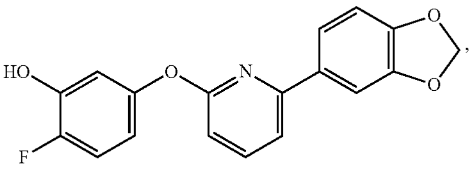,
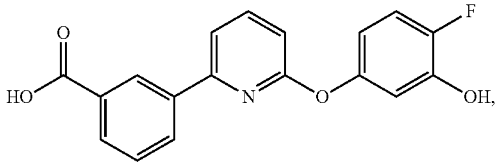, -continued
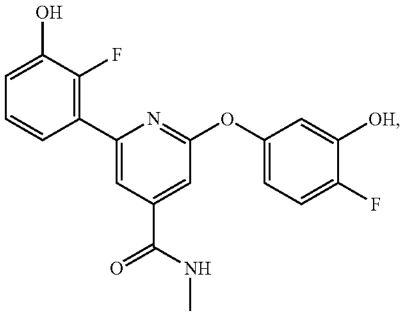
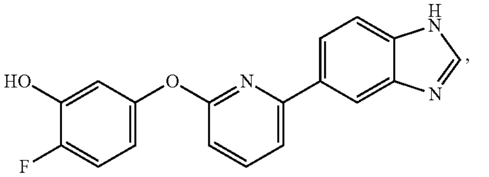
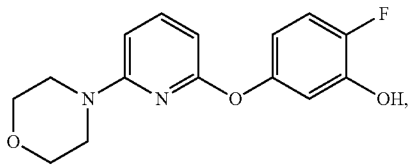
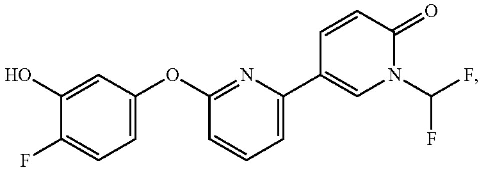
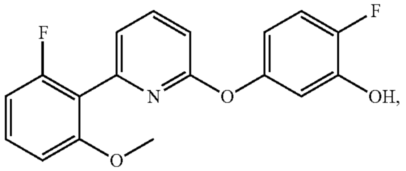
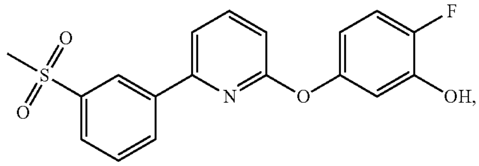
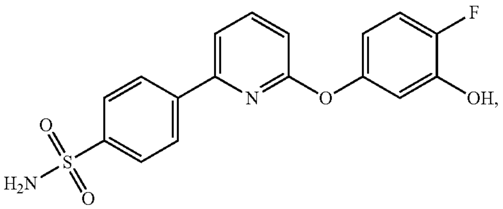
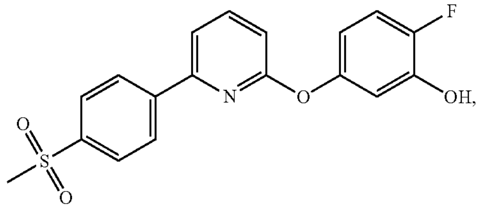
-continued
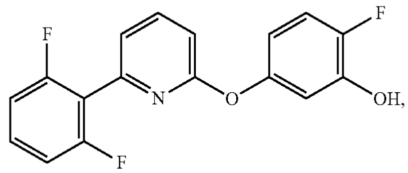
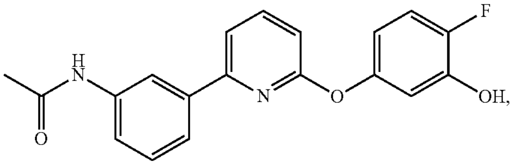
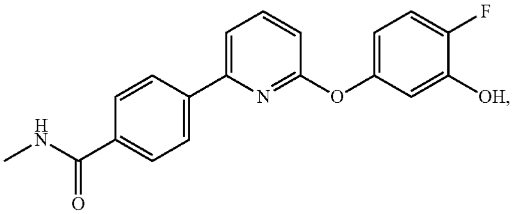
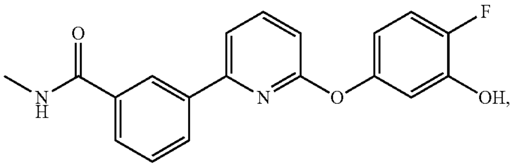
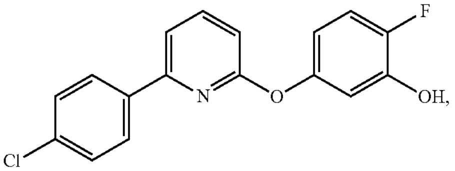
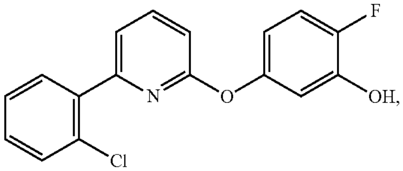
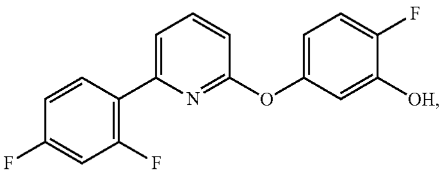
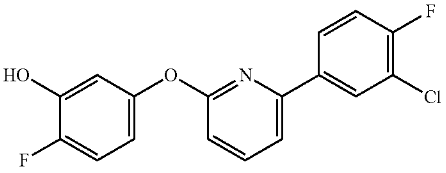
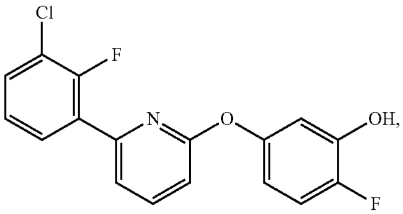

-continued
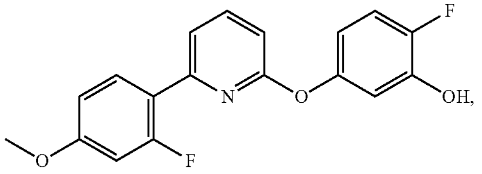
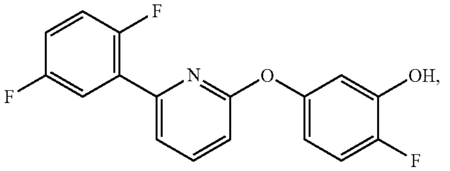
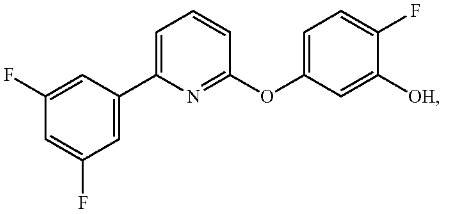
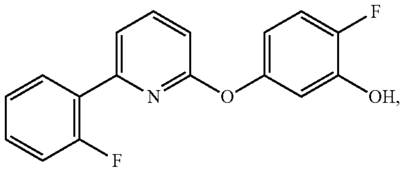
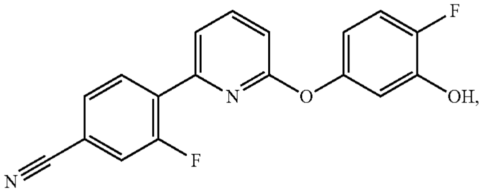
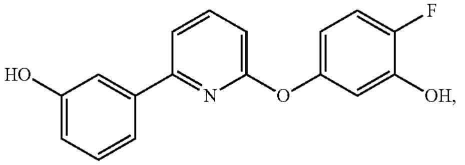
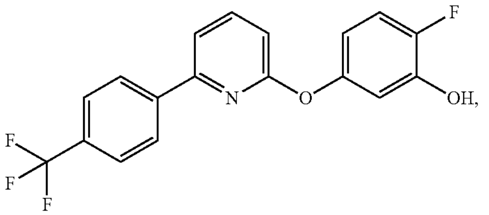
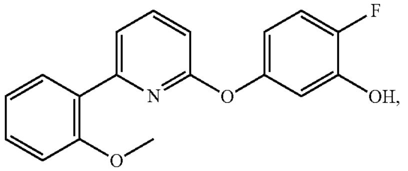
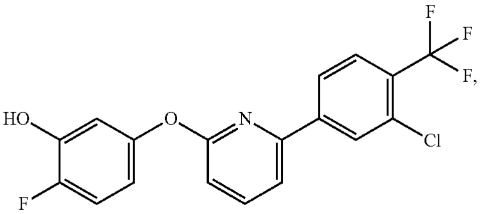
-continued
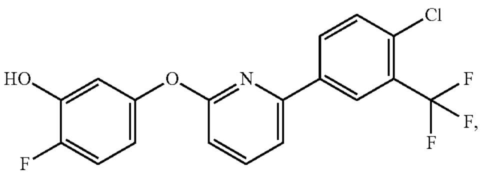
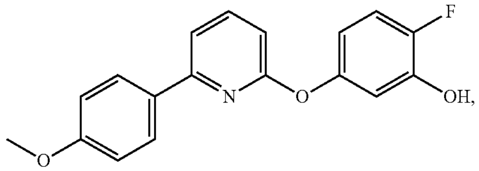
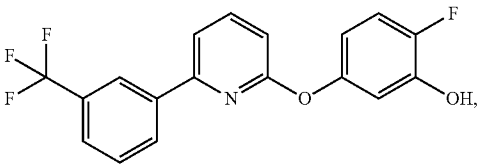
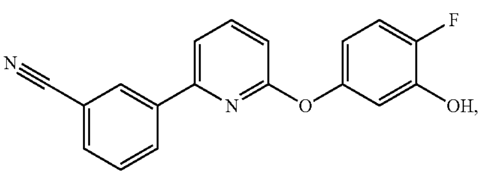
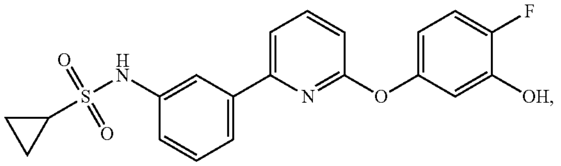
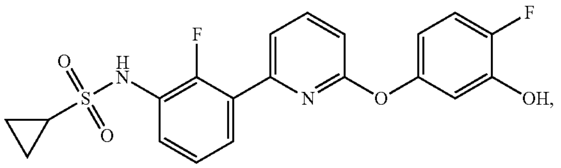
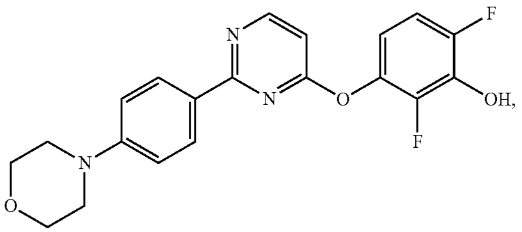
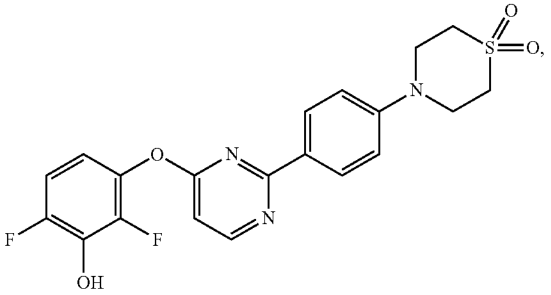

-continued

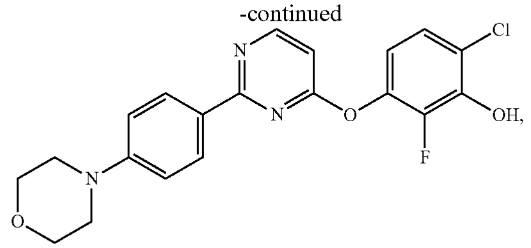

and

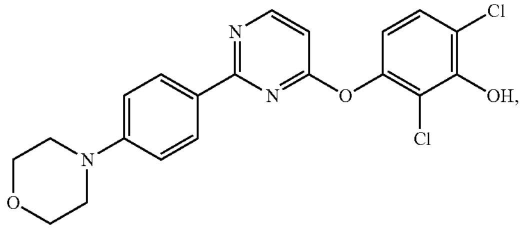 [SMILES: Oc1c(Cl)ccc(Oc2ccnc(-c3ccc(N4CCOCC4)cc3)n2)c1Cl]

or a pharmaceutically acceptable salt, solvate, or stereoisomer thereof.

17. A pharmaceutical composition comprising a compound of claim 1, or a pharmaceutically acceptable salt, solvate, or stereoisomer thereof, and a pharmaceutically acceptable carrier.

18. A method of treating a disease associated with HSD17B13 in a subject in need thereof, the method comprising administering to the subject a pharmaceutically effective amount a compound of claim 1, or a pharmaceutically acceptable salt, solvate, or stereoisomer thereof.

* * * * *